(12) United States Patent
Schurpf et al.

(10) Patent No.: US 11,643,459 B2
(45) Date of Patent: May 9, 2023

(54) TGFβ1-BINDING IMMUNOGLOBULINS AND USE THEREOF

(71) Applicant: Scholar Rock, Inc., Cambridge, MA (US)

(72) Inventors: Thomas Schurpf, Cambridge, MA (US); Gregory J. Carven, Maynard, MA (US); Abhishek Datta, Boston, MA (US); Kimberly Long, Boston, MA (US)

(73) Assignee: Scholar Rock, Inc., Cambridge, MA (US)

( * ) Notice: Subject to any disclaimer, the term of this patent is extended or adjusted under 35 U.S.C. 154(b) by 459 days.

(21) Appl. No.: 16/083,637

(22) PCT Filed: Mar. 10, 2017

(86) PCT No.: PCT/US2017/021972
§ 371 (c)(1),
(2) Date: Sep. 10, 2018

(87) PCT Pub. No.: WO2017/156500
PCT Pub. Date: Sep. 14, 2017

(65) Prior Publication Data
US 2019/0071493 A1  Mar. 7, 2019

Related U.S. Application Data

(60) Provisional application No. 62/452,866, filed on Jan. 31, 2017, provisional application No. 62/443,615, filed on Jan. 6, 2017, provisional application No. 62/307,353, filed on Mar. 11, 2016.

(51) Int. Cl.
| | | |
|---|---|---|
| *C07K 16/22* | (2006.01) |
| *A61P 21/00* | (2006.01) |
| *A61P 13/12* | (2006.01) |
| *A61P 35/00* | (2006.01) |
| *A61K 39/395* | (2006.01) |
| *A61K 39/00* | (2006.01) |

(52) U.S. Cl.
CPC ........ *C07K 16/22* (2013.01); *A61K 39/39558* (2013.01); *A61P 13/12* (2018.01); *A61P 21/00* (2018.01); *A61P 35/00* (2018.01); *A61K 2039/505* (2013.01); *C07K 2317/32* (2013.01); *C07K 2317/33* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,399,676 | B2 | 7/2016 | Schurpf et al. |
| 9,573,995 | B2 | 2/2017 | Schurpf et al. |
| 9,580,500 | B2 | 2/2017 | Schurpf et al. |
| 9,758,576 | B2 | 9/2017 | Schurpf et al. |
| 9,758,577 | B2 | 9/2017 | Schurpf et al. |
| 10,597,443 | B2 | 3/2020 | Schurpf et al. |
| 2005/0059113 | A1 | 3/2005 | Bedian et al. |
| 2012/0201781 | A1 | 8/2012 | Kamath |
| 2012/0315282 | A1 | 12/2012 | Bedinger et al. |
| 2015/0132319 | A1 | 5/2015 | Van Snick et al. |
| 2015/0284455 | A1 | 10/2015 | Springer et al. |
| 2017/0073406 | A1 | 3/2017 | Schurpf et al. |
| 2017/0210798 | A1 | 7/2017 | Schurpf et al. |
| 2018/0016332 | A1 | 1/2018 | Schurpf et al. |
| 2018/0022798 | A1 | 1/2018 | Schurpf et al. |
| 2018/0207267 | A1 | 7/2018 | Schurpf et al. |
| 2019/0085067 | A1 | 3/2019 | Schurpf et al. |
| 2019/0209682 | A1 | 7/2019 | Schurpf et al. |
| 2020/0024339 | A1 | 1/2020 | Springer et al. |
| 2020/0131259 | A1 | 4/2020 | Schurpf et al. |
| 2021/0284722 | A1 | 9/2021 | Schurpf et al. |

FOREIGN PATENT DOCUMENTS

| | | |
|---|---|---|
| CN | 1745102 A | 3/2006 |
| CN | 101163502 A | 4/2008 |
| CN | 101163719 A | 4/2008 |
| CN | 102807617 A | 12/2012 |
| CN | 103214577 A | 7/2013 |
| CN | 104271599 A | 1/2015 |
| EP | 2714741 A2 | 4/2014 |
| EP | 2718320 A2 | 4/2014 |
| EP | 2766033 A2 | 8/2014 |
| EP | 2832747 A1 | 2/2015 |
| EP | 3160997 A1 | 5/2017 |

(Continued)

OTHER PUBLICATIONS

Lonning et al. Current Pharmaceutical Biotechnology, 2011, 12, 2176-2189 (Year: 2011).*
Vargas et al. J. of Pharmacology and Toxicological Methods, vol. 58, p. 72-76 (2008). (Year: 2008).*
Cuende et al., Monoclonal antibodies against GARP/TGF-beta1 complexes inhibit the immunosuppressive activity of human regulatory T cells in vivo. Sci Transl Med. Apr. 22, 2015;7(284):284ra56. 13 pages.
International Search Report and Written Opinion for Application No. PCT/US201/012601, dated Apr. 17, 2018, pp. 1-16.
International Search Report and Written Opinion for Application No. PCT/US2017/021972, dated Jul. 7, 2017, 12 pages.

(Continued)

*Primary Examiner* — Ruixiang Li
(74) *Attorney, Agent, or Firm* — Finnegan, Henderson, Farabow, Garrett & Dunner, LLP

(57) ABSTRACT

Disclosed herein are immunoglobulins, such as antibodies, and antigen binding portions thereof, that specifically bind complexes of GARP-TGFβ1, LTBP1-TGFβ1, LTBP3-TGFβ1, and/or LRRC33-TGFβ1. The application also provides methods of use of these immunoglobulins for, for example, inhibiting TGFβ1 activity, and treating subjects suffering from TGFβ1-related disorders, such as cancer and fibrosis.

15 Claims, 30 Drawing Sheets

Specification includes a Sequence Listing.

(56) References Cited

FOREIGN PATENT DOCUMENTS

| | | |
|---|---|---|
| EP | 3221348 A1 | 9/2017 |
| WO | 1992/00330 A1 | 1/1992 |
| WO | 1997/13844 A1 | 4/1997 |
| WO | 2000/66631 A1 | 11/2000 |
| WO | 2005/023870 A1 | 3/2005 |
| WO | 2006/116002 A2 | 11/2006 |
| WO | WO 2008/118356 A2 | 10/2008 |
| WO | 2010/053814 A1 | 5/2010 |
| WO | 2011/102483 A1 | 8/2011 |
| WO | 2012/167143 A1 | 12/2012 |
| WO | WO 2013/068902 A1 | 5/2013 |
| WO | 2013/134365 A1 | 9/2013 |
| WO | 2014/152157 A2 | 9/2014 |
| WO | 2014/182676 A2 | 11/2014 |
| WO | 2015/015003 A1 | 2/2015 |
| WO | 2016/079157 A1 | 5/2016 |
| WO | 2016/141245 A1 | 9/2016 |
| WO | 2017/156500 A1 | 9/2017 |
| WO | 2018/013939 A1 | 1/2018 |
| WO | 2018/129329 A1 | 7/2018 |

OTHER PUBLICATIONS

Abdiche et al., High-throughput epitope binning assays on label-free array-based biosensors can yield exquisite epitope discrimination that facilitates the selection of monoclonal antibodies with functional activity. PLoS One. Mar. 20, 2014;9(3):e92451, 16 pages.

Anderton et al., Induction of heart valve lesions by small-molecule ALK5 inhibitors. Toxicol Pathol. Oct. 2011;39(6):916-24.

Bedinger et al., Development and characterization of human monoclonal antibodies that neutralize multiple TGFβ isoforms. MAbs. 2016;8(2);389-404.

Creative Biolabs, Monoclonal Antibody Epitope Binning. Retrieved online at: https://www.creative-biolabs.com/Monoclonal-Antibody-Epitope-Binning.html. 2 pages. Aug. 13, 2020.

Dennler et al., Direct binding of Smad3 and Smad4 to critical TGF beta-inducible elements in the promoter of human plasminogen activator inhibitor-type 1 gene. EMBO J. Jun. 1, 1998;17(11):3091-100.

Kulkarni et al., Transforming growth factor beta 1 null mutation in mice causes excessive inflammatory response and early death. Proc Natl Acad Sci U S A. Jan. 15, 1993;90(2):770-4.

Markovitz et al., The diversity of the immune response to the A2 domain of human factor VIII. Blood. Apr. 4, 2013;121(14):2785-95.

Stauber et al., Nonclinical Safety Evaluation of a Transforming Growth Factor beta Receptor I Kinase Inhibitor in Fischer 344 Rats and Beagle Dogs. J Clin Pract. 2014;4(3):1000196, 10 pages.

Biolegend, Ultra-LEAF™ Purified anti-mouse/human LAP (TGF-beta1) Antibody. Retrieved online at: https://www.biolegend.com/en-US/global-elements/pdf-popup/ultra-leaf-purified-anti-mouse-human-lap-tgf-beta1-antibody-9009?filename=Ultra-LEAF%20Purified%20anti-mousehuman%20LAP%20TGF-beta1%20Antibody.pdf&pdfgen=true. 3 pages, Aug. 27, 2014.

Denton et al., Recombinant human anti-transforming growth factor beta1 antibody therapy in systemic sclerosis: a multicenter, randomized, placebo-controlled phase I/II trial of CAT-192. Arthritis Rheum. Jan. 2007;56(1):323-33.

Dong et al., Force interacts with macromolecular structure in activation of TGF-beta. Nature. Feb. 2, 2017;542 (7639):55-59.

Oida et al., TGF-beta induces surface LAP expression on murine CD4 T cells independent of Foxp3 induction. PLoS One. Nov. 24, 2010;5(11):e15523, 8 pages.

U.S. Appl. 14/795,022, filed Jul. 9, 2015, U.S. Pat. No. 9,580,500, Issued.

U.S. Appl. No. 16/209,078, filed Dec. 4, 2018, 2019-0085067, Published.

Morris et al., Phase I study of GC1008 (fresolimumab): a human anti-transforming growth factor-beta (TGFβ) monoclonal antibody in patients with advanced malignant melanoma or renal cell carcinoma. PLoS One. Mar. 11, 2014;9(3):e90353. 11 pages.

R&D Systems, a bio-techne brand, Human LAP (TGF-beta1) Antibody, Antigen Affinity-purified Polyclonal Goat IgG, Catalog No. AF-246-NA. 2 pages, Nov. 9, 2015.

Voelker et al., Anti-TGF-beta1 Antibody Therapy in Patients with Diabetic Nephropathy. J Am Soc Nephrol. Mar. 2017;28(3):953-962.

Wang et al., GARP regulates the bioavailability and activation of TGFbeta. Mol Biol Cell. Mar. 2012;23(6):1129-39.

Bendig et al., Humanization of Rodent Monoclonal Antibodies by CDR Grafting.Methods: A Companion to Methods in Enzymology. 1995;8:83-93.

Gasset et al., A peptide mimetic of an anti-CD4 monoclonal antibody by rational design. Biochem Biophys Res Commun. 2003;307(1):198-205.

MacCallum et al., Antibody-antigen interactions: contact analysis and binding site topography. J Mol Biol. 1996;262(5):732-45.

Metelli et al., Immunoregulatory functions and the therapeutic implications of GARP-TGF-β in inflammation and cancer. J Hematol Oncol. 2018;11(1):24, 11 pages.

Paul, Fundamental Immunology, Third Edition. Raven Press, New York. pp. 292-295, (1993).

Rudikoff et al., Single amino acid substitution altering antigen-binding specificity. Proc Natl Acad Sci U S A. Mar. 1982;79(6):1979-83.

Vajdos et al., Comprehensive functional maps of the antigen-binding site of an anti-ErbB2 antibody obtained with shotgun scanning mutagenesis. J Mol Biol. 2002;320(2):415-28.

Wu et al., Humanization of a murine monoclonal antibody by simultaneous optimization of framework and CDR residues. J Mol Biol. 1999;294(1):151-62.

U.S. Appl. No. 14/439,284, filed Apr. 29, 2015, 2015-0284455, Abandoned.

U.S. Appl. No. 16/583,799, filed Sep. 26, 2019, 2020-0024339, Published.

U.S. Appl. No. 14/795,007, filed Jul. 9, 2015, U.S. Pat. No. 9,573,995, Issued.

U.S. Appl. No. 14/795,012, filed Jul. 9, 2015, U.S. Pat. No. 9,758,576, Issued.

U.S. Appl. No. 14/795,022, filed Jul. 9, 2015, U.S. Pat. No. 9,580,500, Issued.

U.S. Appl. No. 14/795,033, filed Jul. 9, 2015, U.S. Pat. No. 9,399,676, Issued.

U.S. Appl. No. 15/401,386, filed Jan. 9, 2017, 2017-0210798, Abandoned.

U.S. Appl. No. 15/404,663, filed Jan. 12, 2017, U.S. Pat. No. 10,597,443, Issued.

U.S. Appl. No. 15/187,278, filed Jun. 20, 2016, U.S. Pat. No. 9,758,577, Issued.

U.S. Appl. No. 15/659,974, filed Jul. 26, 2017, 2018-0016332, Abandoned.

U.S. Appl. No. 15/671,217, filed Aug. 8, 2017, 2018-0022798, Published.

U.S. Appl. No. 16/209,078, filed Dec. 4, 2018, U.S. Pat. No. 10,981,981, Issued.

U.S. Appl. No. 16/736,207, filed Jan. 7, 2020, 2020-0131259, Published.

U.S. Appl. No. 17/196,256, filed May 9, 2021, Pending.

U.S. Appl. No. 15/863,564, filed Jan. 5, 2018, 2018-0207267, Published.

U.S. Appl. No. 16/361,486, filed Mar. 22, 2019, 2019-0209682, Published.

GenBank Accession No. CAC10871, Immunoglobulin kappa chain variable region, partial [*Homo sapiens*] 2 pages, Mar. 22, 2001.

Guo et al., Detecting the activity of antibodies induced by recombinant TGFbeta1 vaccine. Zhonghua Gan Zang Bing Za Zhi. Mar. 2006;14(3):183-6.

Cane et al., TGFbeta1 neutralization displays therapeutic efficacy through both an immunomodulatory and a non-immune tumor-intrinsic mechanism. J Immunother Cancer Feb. 2021;9(2):e001798, 15 pages.

(56) References Cited

OTHER PUBLICATIONS

Fehrholz et al., Caffeine and rolipram affect Smad signalling and TGF-beta1 stimulated CTGF and transgelin expression in lung epithelial cells PLoS One. May 14, 2014;9(5):e97357, 11 pages.
GenBank ABD59021.1: anti-TREM-like transcript-1 antibody; Feb. 1, 2008, 4pgs.
Yanagawa et al. "Isoform-specific regulation of transforming growth factor-β mRNA expression in macrophages in response to adrenoceptor stimulation," Microbiol Immunol, 2016, 60(1):56-63.

* cited by examiner

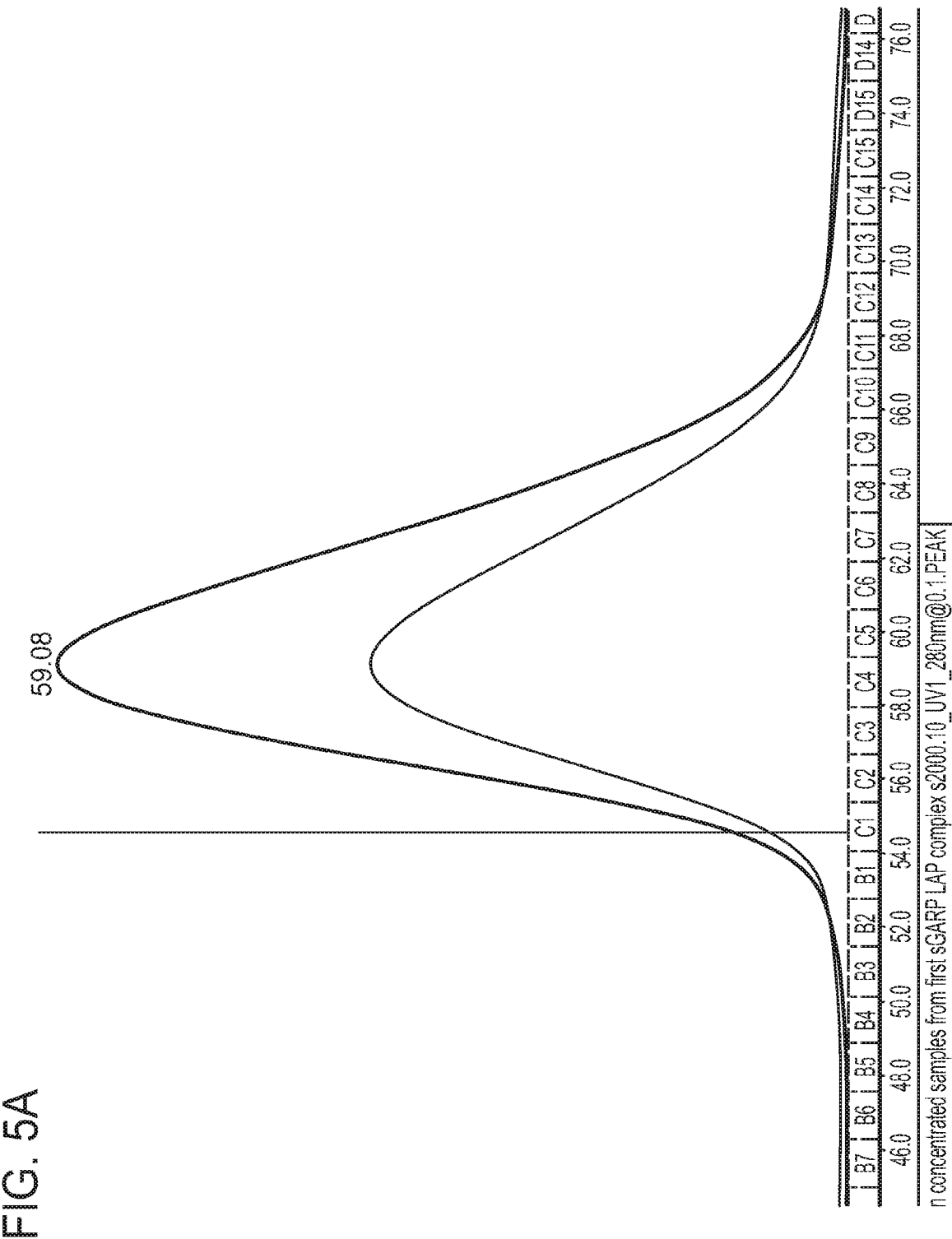

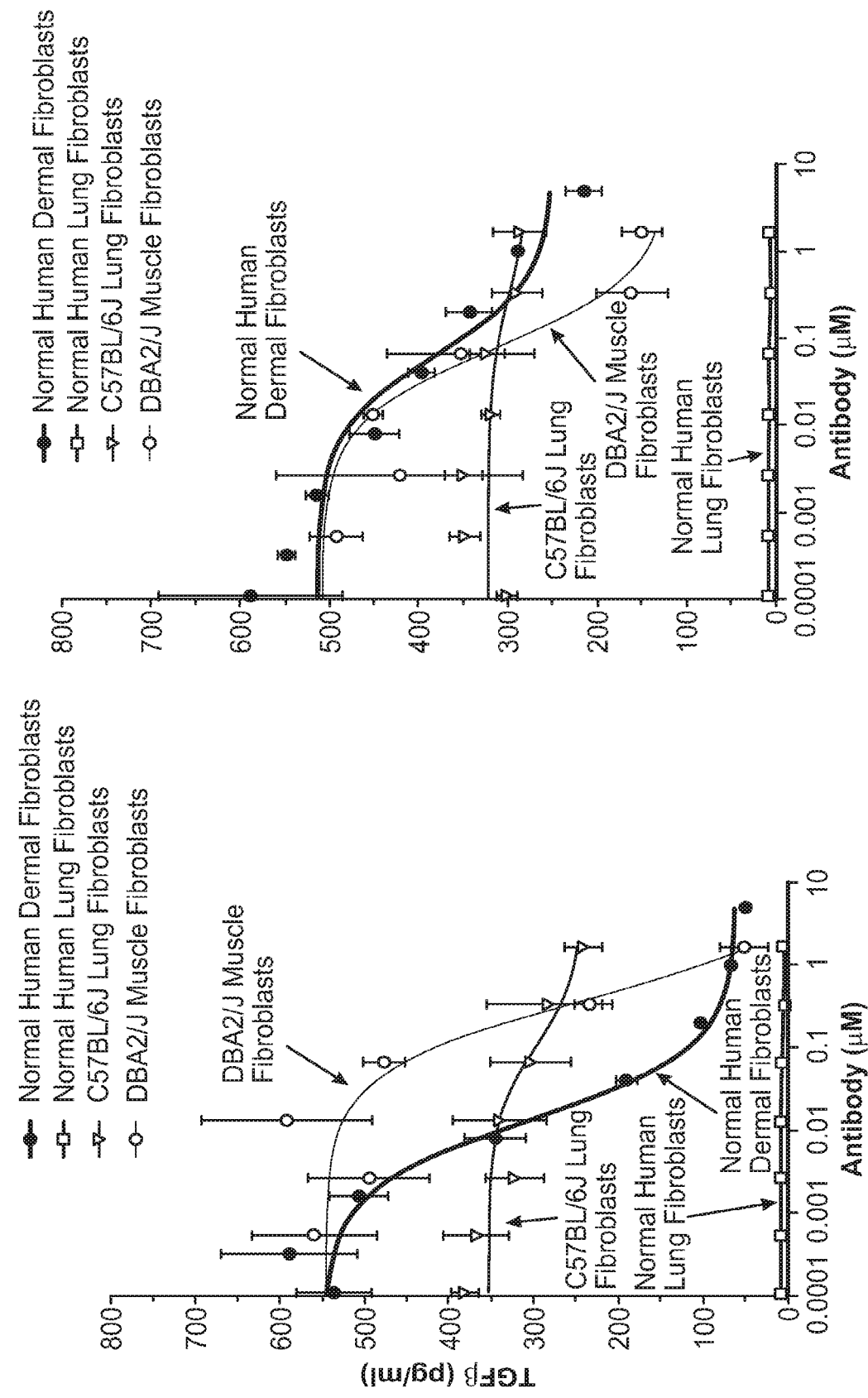

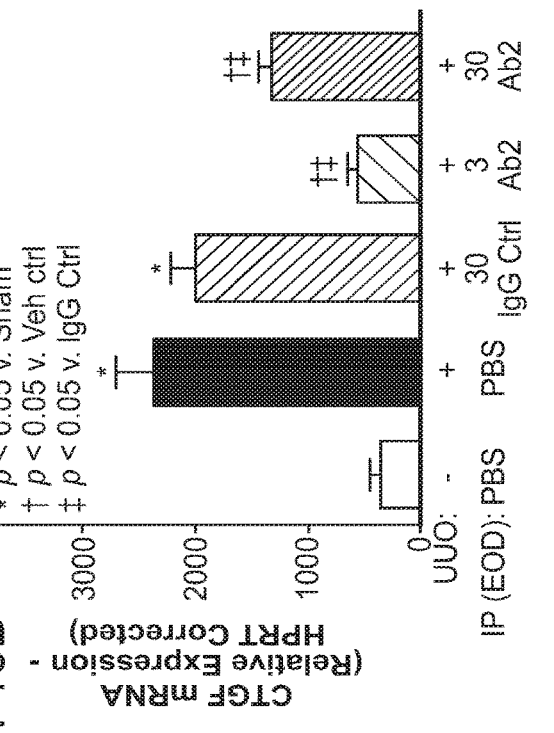
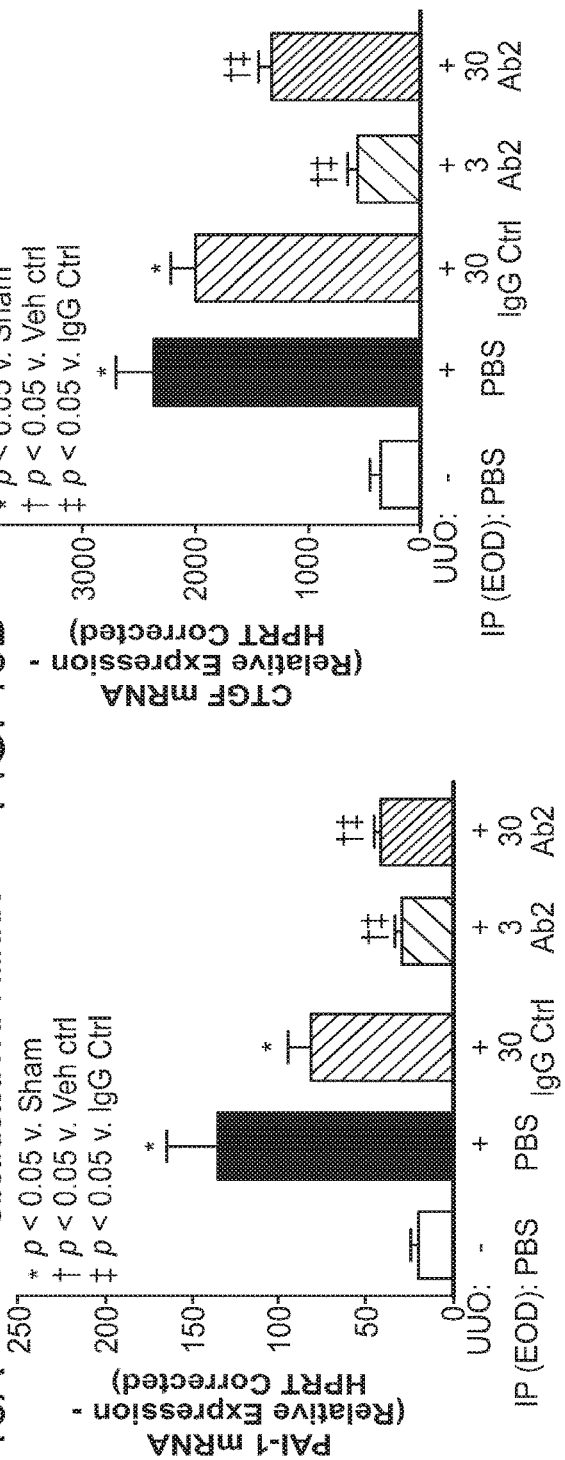
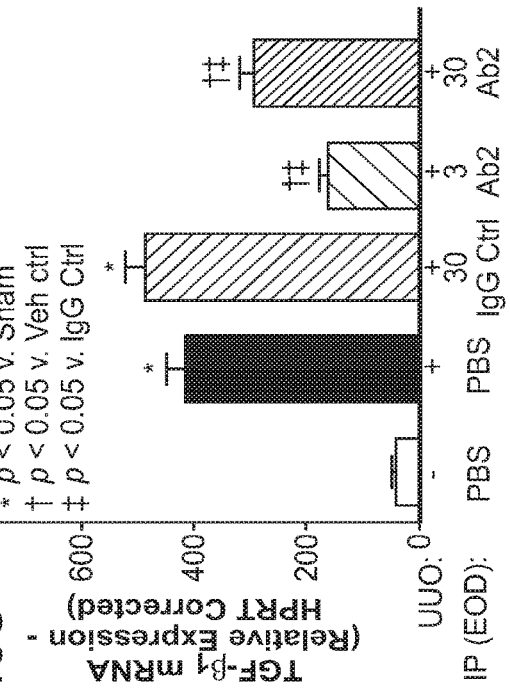

SEQUENCE LISTING

<160> NUMBER OF SEQ ID NOS: 94

<210> SEQ ID NO 1
<211> LENGTH: 5
<212> TYPE: PRT
<213> ORGANISM: Artificial Sequence
<220> FEATURE:
<223> OTHER INFORMATION: Synthetic: CDRH1

<400> SEQUENCE: 1

Ser Tyr Gly Met His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic: CDRH1

<400> SEQUENCE: 2

Ser Asp Trp Ile Gly
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic: CDRH2

<400> SEQUENCE: 3

Val Ile Ser Tyr Asp Gly Ser Asn Lys Tyr Tyr Ala Asp Ser Val Lys
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: Synthetic: CDRH2

<400> SEQUENCE: 4

Val Ile Tyr Pro Gly Asp Ser Asp Thr Arg Tyr Ser Ala Ser Phe Gln
1               5                   10                  15

Gly

<210> SEQ ID NO 5
<211> LENGTH: 14
<212> TYPE: PRT
<213> ORGANISM: Artificial Sequence
<220> FEATURE:
<223> OTHER INFORMATION: Synthetic: CDRH3

<400> SEQUENCE: 5

Asp Ile Arg Pro Tyr Gly Asp Tyr Ser Ala Ala Phe Asp Ile
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic: CDRH3

```
<400> SEQUENCE: 6

Ala Ala Gly Ile Ala Ala Ala Gly His Val Thr Ala Phe Asp Ile
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Synthetic: CDRL1

<400> SEQUENCE: 7

Thr Gly Ser Ser Gly Ser Ile Ala Ser Asn Tyr Val Gln
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Synthetic: CDRL1

<400> SEQUENCE: 8

Lys Ser Ser Gln Ser Val Leu Tyr Ser Ser Asn Asn Lys Asn Tyr Leu
1               5                   10                  15

Ala

<210> SEQ ID NO 9
<211> LENGTH: 7
<212> TYPE: PRT
<213> ORGANISM: Artificial Sequence
<220> FEATURE:
<223> OTHER INFORMATION: Synthetic: CDRL2

<400> SEQUENCE: 9

Glu Asp Asn Gln Arg Pro Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic: CDRL2

<400> SEQUENCE: 10

Trp Ala Ser Thr Arg Glu Ser
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic: CDRL3

<400> SEQUENCE: 11

Gln Ser Tyr Asp Ser Ser Asn His Gly Gly Val
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic: CDRL3
```

<400> SEQUENCE: 12

Gln Gln Tyr Tyr Ser Thr Pro Val Thr
1               5

<210> SEQ ID NO 13
<211> LENGTH: 123
<212> TYPE: PRT
<213> ORGANISM: Artificial Sequence
<220> FEATURE:
<223> OTHER INFORMATION: Synthetic: Ab1  Heavy chain variable region
      amino acid sequence

<400> SEQUENCE: 13

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Arg Pro Tyr Gly Asp Tyr Ser Ala Ala Phe Asp Ile
            100                 105                 110

Trp Gly Gln Gly Thr Leu Val Thr Val Ser Ser
        115                 120

<210> SEQ ID NO 14
<211> LENGTH: 112
<212> TYPE: PRT
<213> ORGANISM: Artificial Sequence
<220> FEATURE:
<223> OTHER INFORMATION: Synthetic: Ab1  Light chain variable region
      amino acid sequence

<400> SEQUENCE: 14

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Ser Ile Val
        35                  40                  45

Ile Phe Glu Asp Asn Gln Arg Pro Ser Gly Ala Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Gly Gly Val Phe Gly Gly Gly Thr Gln Leu Thr Val Leu
            100                 105                 110

<210> SEQ ID NO 15
<211> LENGTH: 449
<212> TYPE: PRT
<213> ORGANISM: Artificial Sequence
<220> FEATURE:

<223> OTHER INFORMATION: Synthetic: Ab1 Heavy chain amino acid sequence

<400> SEQUENCE: 15

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Arg Pro Tyr Gly Asp Tyr Ser Ala Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
            435                 440                 445

Gly

<210> SEQ ID NO 16
<211> LENGTH: 218
<212> TYPE: PRT
<213> ORGANISM: Artificial Sequence
<220> FEATURE:
<223> OTHER INFORMATION: Synthetic: Ab1  Light chain amino acid sequence

<400> SEQUENCE: 16

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Ser Ile Val
        35                  40                  45

Ile Phe Glu Asp Asn Gln Arg Pro Ser Gly Ala Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Gly Gly Val Phe Gly Gly Gly Thr Gln Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 17
<211> LENGTH: 124
<212> TYPE: PRT
<213> ORGANISM: Artificial Sequence
<220> FEATURE:
<223> OTHER INFORMATION: Synthetic: Ab2  Heavy chain variable region
      amino acid sequence

<400> SEQUENCE: 17

Glu Val Gln Leu Val Gln Ser Gly Ala Glu Met Lys Lys Pro Gly Glu
1               5                   10                  15

Ser Leu Lys Ile Ser Cys Lys Gly Ser Gly Tyr Asn Phe Ala Ser Asp
            20                  25                  30
```

```
Trp Ile Gly Trp Val Arg Gln Thr Pro Gly Lys Gly Leu Glu Trp Met
            35                  40                  45

Gly Val Ile Tyr Pro Gly Asp Ser Asp Thr Arg Tyr Ser Ala Ser Phe
        50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Ser Ala Ala Gly Ile Ala Ala Ala Gly His Val Thr Ala Phe Asp
            100                 105                 110

Ile Trp Gly Gln Gly Thr Met Val Thr Val Ser Ser
        115                 120
```

<210> SEQ ID NO 18
<211> LENGTH: 113
<212> TYPE: PRT
<213> ORGANISM: Artificial Sequence
<220> FEATURE:
<223> OTHER INFORMATION: Synthetic: Ab2 Light chain variable region
      amino acid sequence

<400> SEQUENCE: 18

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Val Thr Phe Gly Gln Gly Thr Lys Leu Glu Ile
            100                 105                 110

Lys
```

<210> SEQ ID NO 19
<211> LENGTH: 450
<212> TYPE: PRT
<213> ORGANISM: Artificial Sequence
<220> FEATURE:
<223> OTHER INFORMATION: Synthetic: Ab2 Heavy chain amino acid sequence

<400> SEQUENCE: 19

```
Glu Val Gln Leu Val Gln Ser Gly Ala Glu Met Lys Lys Pro Gly Glu
1               5                   10                  15

Ser Leu Lys Ile Ser Cys Lys Gly Ser Gly Tyr Asn Phe Ala Ser Asp
            20                  25                  30

Trp Ile Gly Trp Val Arg Gln Thr Pro Gly Lys Gly Leu Glu Trp Met
        35                  40                  45

Gly Val Ile Tyr Pro Gly Asp Ser Asp Thr Arg Tyr Ser Ala Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
```

```
                85                  90                  95
Ala Ser Ala Ala Gly Ile Ala Ala Gly His Val Thr Ala Phe Asp
            100                 105                 110
Ile Trp Gly Gln Gly Thr Met Val Thr Val Ser Ser Ala Ser Thr Lys
            115                 120                 125
Gly Pro Ser Val Phe Pro Leu Ala Pro Cys Ser Arg Ser Thr Ser Glu
130                 135                 140
Ser Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Ser Leu Gly Thr Lys Thr Tyr Thr Cys Asn
                195                 200                 205
Val Asp His Lys Pro Ser Asn Thr Lys Val Asp Lys Arg Val Glu Ser
            210                 215                 220
Lys Tyr Gly Pro Pro Cys Pro Pro Cys Pro Ala Pro Glu Phe Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser Gln
                260                 265                 270
Glu Asp Pro Glu Val Gln Phe Asn Trp Tyr Val Asp Gly Val Glu Val
            275                 280                 285
His Asn Ala Lys Thr Lys Pro Arg Glu Glu Gln Phe Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Gly Leu Pro Ser Ser Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Gln Glu Glu Met Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Arg Leu Thr Val
                405                 410                 415
Asp Lys Ser Arg Trp Gln Glu Gly Asn Val Phe Ser Cys Ser Val Met
                420                 425                 430
His Glu Ala Leu His Asn His Tyr Thr Gln Lys Ser Leu Ser Leu Ser
            435                 440                 445
Leu Gly
450

<210> SEQ ID NO 20
<211> LENGTH: 220
<212> TYPE: PRT
<213> ORGANISM: Artificial Sequence
<220> FEATURE:
<223> OTHER INFORMATION: Synthetic: Ab2  Light chain amino acid sequence
```

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Val Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 21
<211> LENGTH: 361
<212> TYPE: PRT
<213> ORGANISM: Artificial Sequence
<220> FEATURE:
<223> OTHER INFORMATION: Synthetic: TGF-Beta-1

<400> SEQUENCE: 21

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys

```
            130                 135                 140
Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
                260                 265                 270

Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
        290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360

<210> SEQ ID NO 22
<211> LENGTH: 395
<212> TYPE: PRT
<213> ORGANISM: Artificial Sequence
<220> FEATURE:
<223> OTHER INFORMATION: Synthetic: TGF-Beta-2

<400> SEQUENCE: 22

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
        35                  40                  45

Ile Ser Ile Tyr Asn Ser Thr Arg Asp Leu Leu Gln Glu Lys Ala Ser
    50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
```

```
                    130                 135                 140
Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Lys Arg Ala Leu Asp Ala Ala
        275                 280                 285

Tyr Cys Phe Arg Asn Val Gln Asp Asn Cys Cys Leu Arg Pro Leu Tyr
    290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                325                 330                 335

Ser Asp Thr Gln His Ser Arg Val Leu Ser Leu Tyr Asn Thr Ile Asn
            340                 345                 350

Pro Glu Ala Ser Ala Ser Pro Cys Cys Val Ser Gln Asp Leu Glu Pro
        355                 360                 365

Leu Thr Ile Leu Tyr Tyr Ile Gly Lys Thr Pro Lys Ile Glu Gln Leu
    370                 375                 380

Ser Asn Met Ile Val Lys Ser Cys Lys Cys Ser
385                 390                 395

<210> SEQ ID NO 23
<211> LENGTH: 392
<212> TYPE: PRT
<213> ORGANISM: Artificial Sequence
<220> FEATURE:
<223> OTHER INFORMATION: Synthetic: TGF-Beta-3

<400> SEQUENCE: 23

Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
                20                  25                  30

Leu Thr Ser Pro Pro Glu Pro Thr Val Met Thr His Val Pro Tyr Gln
            35                  40                  45

Val Leu Ala Leu Tyr Asn Ser Thr Arg Glu Leu Leu Glu Glu Met His
        50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
```

```
            100                 105                 110
Arg Phe Asn Val Ser Ser Val Glu Lys Asn Arg Thr Asn Leu Phe Arg
            115                 120                 125

Ala Glu Phe Arg Val Leu Arg Val Pro Asn Pro Ser Ser Lys Arg Asn
        130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Lys Arg Ala Leu Asp Thr Asn Tyr Cys Phe
        275                 280                 285

Arg Asn Leu Glu Glu Asn Cys Cys Val Arg Pro Leu Tyr Ile Asp Phe
    290                 295                 300

Arg Gln Asp Leu Gly Trp Lys Trp Val His Glu Pro Lys Gly Tyr Tyr
305                 310                 315                 320

Ala Asn Phe Cys Ser Gly Pro Cys Pro Tyr Leu Arg Ser Ala Asp Thr
                325                 330                 335

Thr His Ser Thr Val Leu Gly Leu Tyr Asn Thr Leu Asn Pro Glu Ala
            340                 345                 350

Ser Ala Ser Pro Cys Cys Val Pro Gln Asp Leu Glu Pro Leu Thr Ile
        355                 360                 365

Leu Tyr Tyr Val Gly Arg Thr Pro Lys Val Glu Gln Leu Ser Asn Met
    370                 375                 380

Val Val Lys Ser Cys Lys Cys Ser
385                 390

<210> SEQ ID NO 24
<211> LENGTH: 361
<212> TYPE: PRT
<213> ORGANISM: Artificial Sequence
<220> FEATURE:
<223> OTHER INFORMATION: Synthetic: proTGF-Beta-1

<400> SEQUENCE: 24

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
        50                  55                  60

Glu Pro Glu Pro Glu Pro Glu Ala Asp Tyr Tyr Ala Lys Glu Val Thr
```

```
                65                  70                  75                  80
Arg Val Leu Met Val Glu Thr His Asn Glu Ile Tyr Asp Lys Phe Lys
                    85                  90                  95

Gln Ser Thr His Ser Ile Tyr Met Phe Phe Asn Thr Ser Glu Leu Arg
                100                 105                 110

Glu Ala Val Pro Glu Pro Val Leu Leu Ser Arg Ala Glu Leu Arg Leu
                115                 120                 125

Leu Arg Leu Lys Leu Lys Val Glu Gln His Val Glu Leu Tyr Gln Lys
            130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
                180                 185                 190

His Cys Ser Cys Asp Ser Arg Asp Asn Thr Leu Gln Val Asp Ile Asn
            195                 200                 205

Gly Phe Thr Thr Gly Arg Arg Gly Asp Leu Ala Thr Ile His Gly Met
            210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
                260                 265                 270

Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
            290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
                340                 345                 350

Met Ile Val Arg Ser Cys Lys Cys Ser
            355                 360

<210> SEQ ID NO 25
<211> LENGTH: 361
<212> TYPE: PRT
<213> ORGANISM: Artificial Sequence
<220> FEATURE:
<223> OTHER INFORMATION: Synthetic: proTGF-Beta-1 C4S

<400> SEQUENCE: 25

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
50              55                  60

Glu Pro Glu Pro Glu Pro Glu Ala Asp Tyr Tyr Ala Lys Glu Val Thr
```

```
            65                  70                  75                  80
Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360

<210> SEQ ID NO 26
<211> LENGTH: 360
<212> TYPE: PRT
<213> ORGANISM: Artificial Sequence
<220> FEATURE:
<223> OTHER INFORMATION: Synthetic: proTGF-Beta-1 D2G

<400> SEQUENCE: 26

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
```

```
                65                  70                  75                  80
Arg Val Leu Met Val Glu Thr His Asn Glu Ile Tyr Asp Lys Phe Lys
                    85                  90                  95

Gln Ser Thr His Ser Ile Tyr Met Phe Phe Asn Thr Ser Glu Leu Arg
                    100                 105                 110

Glu Ala Val Pro Glu Pro Val Leu Leu Ser Arg Ala Glu Leu Arg Leu
                    115                 120                 125

Leu Arg Leu Lys Leu Lys Val Glu Gln His Val Glu Leu Tyr Gln Lys
            130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                    165                 170                 175

Gln Trp Leu Ser Arg Gly Gly Glu Ile Glu Gly Phe Arg Leu Ser Ala
                    180                 185                 190

His Cys Ser Cys Asp Ser Arg Asp Asn Thr Leu Gln Val Asp Ile Asn
                    195                 200                 205

Gly Phe Thr Thr Gly Arg Arg Gly Asp Leu Ala Thr Ile His Gly Met
            210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
                    245                 250                 255

Ser Ser Thr Glu Lys Asn Cys Cys Val Arg Gln Leu Tyr Ile Asp Phe
                    260                 265                 270

Arg Lys Asp Leu Gly Trp Lys Trp Ile His Glu Pro Lys Gly Tyr His
                    275                 280                 285

Ala Asn Phe Cys Leu Gly Pro Cys Pro Tyr Ile Trp Ser Leu Asp Thr
            290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                    325                 330                 335

Val Tyr Tyr Val Gly Arg Lys Pro Lys Val Glu Gln Leu Ser Asn Met
                    340                 345                 350

Ile Val Arg Ser Cys Lys Cys Ser
            355                 360

<210> SEQ ID NO 27
<211> LENGTH: 360
<212> TYPE: PRT
<213> ORGANISM: Artificial Sequence
<220> FEATURE:
<223> OTHER INFORMATION: Synthetic: proTGF-Beta-1 C4S D2G

<400> SEQUENCE: 27

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
                35                  40                  45

Leu Ala Leu Tyr Asn Ser Thr Arg Asp Arg Val Ala Gly Glu Ser Ala
        50                  55                  60

Glu Pro Glu Pro Glu Pro Glu Ala Asp Tyr Tyr Ala Lys Glu Val Thr
```

```
                65                  70                  75                  80
Arg Val Leu Met Val Glu Thr His Asn Glu Ile Tyr Asp Lys Phe Lys
                    85                  90                  95

Gln Ser Thr His Ser Ile Tyr Met Phe Phe Asn Thr Ser Glu Leu Arg
                100                 105                 110

Glu Ala Val Pro Glu Pro Val Leu Leu Ser Arg Ala Glu Leu Arg Leu
                115                 120                 125

Leu Arg Leu Lys Leu Lys Val Glu Gln His Val Glu Leu Tyr Gln Lys
            130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
                180                 185                 190

His Cys Ser Cys Asp Ser Arg Asp Asn Thr Leu Gln Val Asp Ile Asn
                195                 200                 205

Gly Phe Thr Thr Gly Arg Arg Gly Asp Leu Ala Thr Ile His Gly Met
            210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
                260                 265                 270

Arg Lys Asp Leu Gly Trp Lys Trp Ile His Glu Pro Lys Gly Tyr His
            275                 280                 285

Ala Asn Phe Cys Leu Gly Pro Cys Pro Tyr Ile Trp Ser Leu Asp Thr
290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
                340                 345                 350

Ile Val Arg Ser Cys Lys Cys Ser
            355                 360

<210> SEQ ID NO 28
<211> LENGTH: 395
<212> TYPE: PRT
<213> ORGANISM: Artificial Sequence
<220> FEATURE:
<223> OTHER INFORMATION: Synthetic: proTGF-Beta-2

<400> SEQUENCE: 28

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
                20                  25                  30

Ser Pro Pro Glu Asp Tyr Pro Glu Pro Glu Glu Val Pro Pro Glu Val
            35                  40                  45

Ile Ser Ile Tyr Asn Ser Thr Arg Asp Leu Leu Gln Glu Lys Ala Ser
        50                  55                  60

Arg Arg Ala Ala Ala Cys Glu Arg Glu Arg Ser Asp Glu Glu Tyr Tyr
```

```
                65                  70                  75                  80
Ala Lys Glu Val Tyr Lys Ile Asp Met Pro Pro Phe Phe Pro Ser Glu
                            85                  90                  95

Asn Ala Ile Pro Pro Thr Phe Tyr Arg Pro Tyr Phe Arg Ile Val Arg
                        100                 105                 110

Phe Asp Val Ser Ala Met Glu Lys Asn Ala Ser Asn Leu Val Lys Ala
                    115                 120                 125

Glu Phe Arg Val Phe Arg Leu Gln Asn Pro Lys Ala Arg Val Pro Glu
                130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                    165                 170                 175

Gly Glu Trp Leu Ser Phe Asp Val Thr Asp Ala Val His Glu Trp Leu
                180                 185                 190

His His Lys Asp Arg Asn Leu Gly Phe Lys Ile Ser Leu His Cys Pro
            195                 200                 205

Cys Cys Thr Phe Val Pro Ser Asn Asn Tyr Ile Ile Pro Asn Lys Ser
        210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                    245                 250                 255

Gly Lys Thr Pro His Leu Leu Leu Met Leu Leu Pro Ser Tyr Arg Leu
                260                 265                 270

Glu Ser Gln Gln Thr Asn Arg Arg Lys Lys Arg Ala Leu Asp Ala Ala
            275                 280                 285

Tyr Cys Phe Arg Asn Val Gln Asp Asn Cys Cys Leu Arg Pro Leu Tyr
        290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                    325                 330                 335

Ser Asp Thr Gln His Ser Arg Val Leu Ser Leu Tyr Asn Thr Ile Asn
                340                 345                 350

Pro Glu Ala Ser Ala Ser Pro Cys Cys Val Ser Gln Asp Leu Glu Pro
            355                 360                 365

Leu Thr Ile Leu Tyr Tyr Ile Gly Lys Thr Pro Lys Ile Glu Gln Leu
        370                 375                 380

Ser Asn Met Ile Val Lys Ser Cys Lys Cys Ser
385                 390                 395

<210> SEQ ID NO 29
<211> LENGTH: 395
<212> TYPE: PRT
<213> ORGANISM: Artificial Sequence
<220> FEATURE:
<223> OTHER INFORMATION: Synthetic: proTGF-Beta-2 C5S

<400> SEQUENCE: 29

Ser Leu Ser Thr Ser Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
                20                  25                  30

Ser Pro Pro Glu Asp Tyr Pro Glu Pro Glu Glu Val Pro Pro Glu Val
```

```
                35                  40                  45
Ile Ser Ile Tyr Asn Ser Thr Arg Asp Leu Leu Gln Glu Lys Ala Ser
 50                  55                  60

Arg Arg Ala Ala Ala Cys Glu Arg Glu Arg Ser Asp Glu Glu Tyr Tyr
 65                  70                  75                  80

Ala Lys Glu Val Tyr Lys Ile Asp Met Pro Phe Phe Pro Ser Glu
                 85                  90                  95

Asn Ala Ile Pro Pro Thr Phe Tyr Arg Pro Tyr Phe Arg Ile Val Arg
                100                 105                 110

Phe Asp Val Ser Ala Met Glu Lys Asn Ala Ser Asn Leu Val Lys Ala
                115                 120                 125

Glu Phe Arg Val Phe Arg Leu Gln Asn Pro Lys Ala Arg Val Pro Glu
                130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
                180                 185                 190

His His Lys Asp Arg Asn Leu Gly Phe Lys Ile Ser Leu His Cys Pro
                195                 200                 205

Cys Cys Thr Phe Val Pro Ser Asn Asn Tyr Ile Ile Pro Asn Lys Ser
210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
                260                 265                 270

Glu Ser Gln Gln Thr Asn Arg Arg Lys Lys Arg Ala Leu Asp Ala Ala
                275                 280                 285

Tyr Cys Phe Arg Asn Val Gln Asp Asn Cys Cys Leu Arg Pro Leu Tyr
290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                325                 330                 335

Ser Asp Thr Gln His Ser Arg Val Leu Ser Leu Tyr Asn Thr Ile Asn
                340                 345                 350

Pro Glu Ala Ser Ala Ser Pro Cys Cys Val Ser Gln Asp Leu Glu Pro
                355                 360                 365

Leu Thr Ile Leu Tyr Tyr Ile Gly Lys Thr Pro Lys Ile Glu Gln Leu
                370                 375                 380

Ser Asn Met Ile Val Lys Ser Cys Lys Cys Ser
385                 390                 395

<210> SEQ ID NO 30
<211> LENGTH: 394
<212> TYPE: PRT
<213> ORGANISM: Artificial Sequence
<220> FEATURE:
<223> OTHER INFORMATION: Synthetic: proTGF-Beta-2 C5S D2G

<400> SEQUENCE: 30

Ser Leu Ser Thr Ser Ser Thr Leu Asp Met Asp Gln Phe Met Arg Lys
```

```
              1               5              10              15
            Arg Ile Glu Ala Ile Arg Gly Gln Ile Leu Ser Lys Leu Lys Leu Thr
                             20                  25                  30
            Ser Pro Pro Glu Asp Tyr Pro Glu Pro Glu Val Pro Pro Glu Val
                35                  40                  45
            Ile Ser Ile Tyr Asn Ser Thr Arg Asp Leu Leu Gln Glu Lys Ala Ser
                50                  55                  60
            Arg Arg Ala Ala Ala Cys Glu Arg Glu Arg Ser Asp Glu Glu Tyr Tyr
             65                  70                  75                  80
            Ala Lys Glu Val Tyr Lys Ile Asp Met Pro Pro Phe Phe Pro Ser Glu
                            85                   90                  95
            Asn Ala Ile Pro Pro Thr Phe Tyr Arg Pro Tyr Phe Arg Ile Val Arg
                           100                 105                 110
            Phe Asp Val Ser Ala Met Glu Lys Asn Ala Ser Asn Leu Val Lys Ala
                           115                 120                 125
            Glu Phe Arg Val Phe Arg Leu Gln Asn Pro Lys Ala Arg Val Pro Glu
                           130                 135                 140
            Gln Arg Ile Glu Leu Tyr Gln Ile Leu Lys Ser Lys Asp Leu Thr Ser
            145                 150                 155                 160
            Pro Thr Gln Arg Tyr Ile Asp Ser Lys Val Val Lys Thr Arg Ala Glu
                           165                 170                 175
            Gly Glu Trp Leu Ser Phe Asp Val Thr Asp Ala Val His Glu Trp Leu
                           180                 185                 190
            His His Lys Asp Arg Asn Leu Gly Phe Lys Ile Ser Leu His Cys Pro
                           195                 200                 205
            Cys Cys Thr Phe Val Pro Ser Asn Asn Tyr Ile Ile Pro Asn Lys Ser
                           210                 215                 220
            Glu Glu Leu Glu Ala Arg Phe Ala Gly Ile Asp Gly Thr Ser Thr Tyr
            225                 230                 235                 240
            Thr Ser Gly Asp Gln Lys Thr Ile Lys Ser Thr Arg Lys Lys Asn Ser
                           245                 250                 255
            Gly Lys Thr Pro His Leu Leu Leu Met Leu Leu Pro Ser Tyr Arg Leu
                           260                 265                 270
            Glu Ser Gln Gln Thr Asn Arg Arg Lys Gly Ala Leu Asp Ala Ala Tyr
                           275                 280                 285
            Cys Phe Arg Asn Val Gln Asp Asn Cys Cys Leu Arg Pro Leu Tyr Ile
                           290                 295                 300
            Asp Phe Lys Arg Asp Leu Gly Trp Lys Trp Ile His Glu Pro Lys Gly
            305                 310                 315                 320
            Tyr Asn Ala Asn Phe Cys Ala Gly Ala Cys Pro Tyr Leu Trp Ser Ser
                           325                 330                 335
            Asp Thr Gln His Ser Arg Val Leu Ser Leu Tyr Asn Thr Ile Asn Pro
                           340                 345                 350
            Glu Ala Ser Ala Ser Pro Cys Cys Val Ser Gln Asp Leu Glu Pro Leu
                           355                 360                 365
            Thr Ile Leu Tyr Tyr Ile Gly Lys Thr Pro Lys Ile Glu Gln Leu Ser
                           370                 375                 380
            Asn Met Ile Val Lys Ser Cys Lys Cys Ser
            385                 390

<210> SEQ ID NO 31
<211> LENGTH: 394
<212> TYPE: PRT
<213> ORGANISM: Artificial Sequence
```

<220> FEATURE:
<223> OTHER INFORMATION: Synthetic: proTGF-Beta-2 D2G

<400> SEQUENCE: 31

```
Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
        35                  40                  45

Ile Ser Ile Tyr Asn Ser Thr Arg Asp Leu Leu Gln Glu Lys Ala Ser
50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Gly Ala Leu Asp Ala Ala Tyr
        275                 280                 285

Cys Phe Arg Asn Val Gln Asp Asn Cys Cys Leu Arg Pro Leu Tyr Ile
290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
        355                 360                 365

Thr Ile Leu Tyr Tyr Ile Gly Lys Thr Pro Lys Ile Glu Gln Leu Ser
370                 375                 380

Asn Met Ile Val Lys Ser Cys Lys Cys Ser
385                 390
```

<210> SEQ ID NO 32
<211> LENGTH: 392
<212> TYPE: PRT
<213> ORGANISM: Artificial Sequence
<220> FEATURE:
<223> OTHER INFORMATION: Synthetic: proTGF-Beta-3

<400> SEQUENCE: 32

```
Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Lys Arg Ala Leu Asp Thr Asn Tyr Cys Phe
        275                 280                 285

Arg Asn Leu Glu Glu Asn Cys Cys Val Arg Pro Leu Tyr Ile Asp Phe
    290                 295                 300

Arg Gln Asp Leu Gly Trp Lys Trp Val His Glu Pro Lys Gly Tyr Tyr
305                 310                 315                 320

Ala Asn Phe Cys Ser Gly Pro Cys Pro Tyr Leu Arg Ser Ala Asp Thr
                325                 330                 335

Thr His Ser Thr Val Leu Gly Leu Tyr Asn Thr Leu Asn Pro Glu Ala
            340                 345                 350

Ser Ala Ser Pro Cys Cys Val Pro Gln Asp Leu Glu Pro Leu Thr Ile
        355                 360                 365
```

```
Leu Tyr Tyr Val Gly Arg Thr Pro Lys Val Glu Gln Leu Ser Asn Met
        370                 375                 380

Val Val Lys Ser Cys Lys Cys Ser
385                 390

<210> SEQ ID NO 33
<211> LENGTH: 392
<212> TYPE: PRT
<213> ORGANISM: Artificial Sequence
<220> FEATURE:
<223> OTHER INFORMATION: Synthetic: proTGF-Beta-3 C7S

<400> SEQUENCE: 33

Ser Leu Ser Leu Ser Thr Ser Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Lys Arg Ala Leu Asp Thr Asn Tyr Cys Phe
        275                 280                 285

Arg Asn Leu Glu Glu Asn Cys Cys Val Arg Pro Leu Tyr Ile Asp Phe
    290                 295                 300

Arg Gln Asp Leu Gly Trp Lys Trp Val His Glu Pro Lys Gly Tyr Tyr
305                 310                 315                 320

Ala Asn Phe Cys Ser Gly Pro Cys Pro Tyr Leu Arg Ser Ala Asp Thr
                325                 330                 335
```

```
Thr His Ser Thr Val Leu Gly Leu Tyr Asn Thr Leu Asn Pro Glu Ala
            340                 345                 350

Ser Ala Ser Pro Cys Cys Val Pro Gln Asp Leu Glu Pro Leu Thr Ile
            355                 360                 365

Leu Tyr Tyr Val Gly Arg Thr Pro Lys Val Glu Gln Leu Ser Asn Met
370                 375                 380

Val Val Lys Ser Cys Lys Cys Ser
385                 390

<210> SEQ ID NO 34
<211> LENGTH: 391
<212> TYPE: PRT
<213> ORGANISM: Artificial Sequence
<220> FEATURE:
<223> OTHER INFORMATION: Synthetic: proTGF-Beta-3 C7S D2G

<400> SEQUENCE: 34

Ser Leu Ser Leu Ser Thr Ser Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Gly Ala Leu Asp Thr Asn Tyr Cys Phe Arg
        275                 280                 285

Asn Leu Glu Glu Asn Cys Cys Val Arg Pro Leu Tyr Ile Asp Phe Arg
    290                 295                 300
```

-continued

Gln Asp Leu Gly Trp Lys Trp Val His Glu Pro Lys Gly Tyr Tyr Ala
305                 310                 315                 320

Asn Phe Cys Ser Gly Pro Cys Pro Tyr Leu Arg Ser Ala Asp Thr Thr
            325                 330                 335

His Ser Thr Val Leu Gly Leu Tyr Asn Thr Leu Asn Pro Glu Ala Ser
        340                 345                 350

Ala Ser Pro Cys Cys Val Pro Gln Asp Leu Glu Pro Leu Thr Ile Leu
    355                 360                 365

Tyr Tyr Val Gly Arg Thr Pro Lys Val Glu Gln Leu Ser Asn Met Val
370                 375                 380

Val Lys Ser Cys Lys Cys Ser
385                 390

<210> SEQ ID NO 35
<211> LENGTH: 391
<212> TYPE: PRT
<213> ORGANISM: Artificial Sequence
<220> FEATURE:
<223> OTHER INFORMATION: Synthetic: proTGF-Beta-3 D2G

<400> SEQUENCE: 35

Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

```
Gln Gly Gly Gln Arg Lys Gly Ala Leu Asp Thr Asn Tyr Cys Phe Arg
            275                 280                 285

Asn Leu Glu Glu Asn Cys Cys Val Arg Pro Leu Tyr Ile Asp Phe Arg
        290                 295                 300

Gln Asp Leu Gly Trp Lys Trp Val His Glu Pro Lys Gly Tyr Tyr Ala
305                 310                 315                 320

Asn Phe Cys Ser Gly Pro Cys Pro Tyr Leu Arg Ser Ala Asp Thr Thr
            325                 330                 335

His Ser Thr Val Leu Gly Leu Tyr Asn Thr Leu Asn Pro Glu Ala Ser
            340                 345                 350

Ala Ser Pro Cys Cys Val Pro Gln Asp Leu Glu Pro Leu Thr Ile Leu
            355                 360                 365

Tyr Tyr Val Gly Arg Thr Pro Lys Val Glu Gln Leu Ser Asn Met Val
        370                 375                 380

Val Lys Ser Cys Lys Cys Ser
385                 390

<210> SEQ ID NO 36
<211> LENGTH: 361
<212> TYPE: PRT
<213> ORGANISM: Mus musculus
<220> FEATURE:
<221> NAME/KEY: misc_feature
<222> LOCATION: (1)..(361)
<223> OTHER INFORMATION: proTGF-Beta-1

<400> SEQUENCE: 36

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220
```

```
Asn Arg Pro Phe Leu Leu Leu Met Ala Thr Pro Leu Glu Arg Ala Gln
225                 230                 235                 240

His Leu His Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
                260                 265                 270

Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
        290                 295                 300

Thr Gln Tyr Ser Lys Val Leu Ala Leu Tyr Asn Gln His Asn Pro Gly
305                 310                 315                 320

Ala Ser Ala Ser Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
                340                 345                 350

Met Ile Val Arg Ser Cys Lys Cys Ser
                355                 360

<210> SEQ ID NO 37
<211> LENGTH: 361
<212> TYPE: PRT
<213> ORGANISM: Macaca fascicularis
<220> FEATURE:
<221> NAME/KEY: misc_feature
<222> LOCATION: (1)..(361)
<223> OTHER INFORMATION: proTGF-Beta-1

<400> SEQUENCE: 37

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
```

```
                    210                 215                 220
Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                    245                 250                 255

Phe Ser Ser Thr Glu Lys Asn Cys Cys Val Arg Gln Leu Tyr Ile Asp
                260                 265                 270

Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
        290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
            355                 360

<210> SEQ ID NO 38
<211> LENGTH: 249
<212> TYPE: PRT
<213> ORGANISM: Mus musculus
<220> FEATURE:
<221> NAME/KEY: misc_feature
<222> LOCATION: (1)..(249)
<223> OTHER INFORMATION: TGF-Beta-1 LAP C4S

<400> SEQUENCE: 38

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205
```

```
Gly Ile Ser Pro Lys Arg Arg Gly Asp Leu Gly Thr Ile His Asp Met
            210                 215                 220

Asn Arg Pro Phe Leu Leu Leu Met Ala Thr Pro Leu Glu Arg Ala Gln
225                 230                 235                 240

His Leu His Ser Ser Arg His Arg Arg
                245

<210> SEQ ID NO 39
<211> LENGTH: 249
<212> TYPE: PRT
<213> ORGANISM: Macaca fascicularis
<220> FEATURE:
<221> NAME/KEY: misc_feature
<222> LOCATION: (1)..(249)
<223> OTHER INFORMATION: TGF-Beta-1 LAP C4S

<400> SEQUENCE: 39

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg
                245

<210> SEQ ID NO 40
<211> LENGTH: 360
<212> TYPE: PRT
<213> ORGANISM: Mus musculus
<220> FEATURE:
<221> NAME/KEY: misc_feature
<222> LOCATION: (1)..(360)
<223> OTHER INFORMATION: proTGF-Beta-1 C4S D2G
```

<400> SEQUENCE: 40

```
Leu Ser Thr Ser Lys Thr Ile Asp Met Glu Leu Val Lys Arg Lys Arg
1               5                   10                  15
Ile Glu Ala Ile Arg Gly Gln Ile Leu Ser Lys Leu Arg Leu Ala Ser
            20                  25                  30
Pro Pro Ser Gln Gly Glu Val Pro Gly Pro Leu Pro Glu Ala Val
        35                  40                  45
Leu Ala Leu Tyr Asn Ser Thr Arg Asp Arg Val Ala Gly Glu Ser Ala
    50                  55                  60
Asp Pro Glu Pro Glu Pro Glu Ala Asp Tyr Tyr Ala Lys Glu Val Thr
65                  70                  75                  80
Arg Val Leu Met Val Asp Arg Asn Asn Ala Ile Tyr Glu Lys Thr Lys
                85                  90                  95
Asp Ile Ser His Ser Ile Tyr Met Phe Phe Asn Thr Ser Asp Ile Arg
                100                 105                 110
Glu Ala Val Pro Glu Pro Pro Leu Leu Ser Arg Ala Glu Leu Arg Leu
            115                 120                 125
Gln Arg Leu Lys Ser Ser Val Glu Gln His Val Glu Leu Tyr Gln Lys
        130                 135                 140
Tyr Ser Asn Asn Ser Trp Arg Tyr Leu Gly Asn Arg Leu Leu Thr Pro
145                 150                 155                 160
Thr Asp Thr Pro Glu Trp Leu Ser Phe Asp Val Thr Gly Val Val Arg
                165                 170                 175
Gln Trp Leu Asn Gln Gly Asp Gly Ile Gln Gly Phe Arg Phe Ser Ala
            180                 185                 190
His Cys Ser Cys Asp Ser Lys Asp Asn Lys Leu His Val Glu Ile Asn
        195                 200                 205
Gly Ile Ser Pro Lys Arg Arg Gly Asp Leu Gly Thr Ile His Asp Met
    210                 215                 220
Asn Arg Pro Phe Leu Leu Leu Met Ala Thr Pro Leu Glu Arg Ala Gln
225                 230                 235                 240
His Leu His Ser Ser Arg His Gly Ala Leu Asp Thr Asn Tyr Cys Phe
                245                 250                 255
Ser Ser Thr Glu Lys Asn Cys Cys Val Arg Gln Leu Tyr Ile Asp Phe
            260                 265                 270
Arg Lys Asp Leu Gly Trp Lys Trp Ile His Glu Pro Lys Gly Tyr His
        275                 280                 285
Ala Asn Phe Cys Leu Gly Pro Cys Pro Tyr Ile Trp Ser Leu Asp Thr
    290                 295                 300
Gln Tyr Ser Lys Val Leu Ala Leu Tyr Asn Gln His Asn Pro Gly Ala
305                 310                 315                 320
Ser Ala Ser Pro Cys Cys Val Pro Gln Ala Leu Glu Pro Leu Pro Ile
                325                 330                 335
Val Tyr Tyr Val Gly Arg Lys Pro Lys Val Glu Gln Leu Ser Asn Met
            340                 345                 350
Ile Val Arg Ser Cys Lys Cys Ser
        355                 360
```

<210> SEQ ID NO 41
<211> LENGTH: 361
<212> TYPE: PRT
<213> ORGANISM: Mus musculus
<220> FEATURE:
<221> NAME/KEY: misc_feature
<222> LOCATION: (1)..(361)
<223> OTHER INFORMATION: proTGF-Beta-1 C4S

<400> SEQUENCE: 41

```
Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240

His Leu His Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ser Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360
```

<210> SEQ ID NO 42
<211> LENGTH: 361
<212> TYPE: PRT
<213> ORGANISM: Macaca fascicularis
<220> FEATURE:
<221> NAME/KEY: misc_feature
<222> LOCATION: (1)..(361)
<223> OTHER INFORMATION: proTGF-Beta-1 C4S

<400> SEQUENCE: 42

```
Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360
```

<210> SEQ ID NO 43
<211> LENGTH: 360

```
<212> TYPE: PRT
<213> ORGANISM: Macaca fascicularis
<220> FEATURE:
<221> NAME/KEY: misc_feature
<222> LOCATION: (1)..(360)
<223> OTHER INFORMATION: proTGF-Beta-1 C4S D2G

<400> SEQUENCE: 43
```

| | | | | | | | | | | | | | | | |
|---|---|---|---|---|---|---|---|---|---|---|---|---|---|---|---|
|Leu|Ser|Thr|Ser|Lys|Thr|Ile|Asp|Met|Glu|Leu|Val|Lys|Arg|Lys|Arg|
|1| | | |5| | | | |10| | | | |15| |

| | | | | | | | | | | | | | | | |
|---|---|---|---|---|---|---|---|---|---|---|---|---|---|---|---|
|Ile|Glu|Ala|Ile|Arg|Gly|Gln|Ile|Leu|Ser|Lys|Leu|Arg|Leu|Ala|Ser|
| | | |20| | | | |25| | | | |30| | |

| | | | | | | | | | | | | | | | |
|---|---|---|---|---|---|---|---|---|---|---|---|---|---|---|---|
|Pro|Pro|Ser|Gln|Gly|Glu|Val|Pro|Gly|Pro|Leu|Pro|Glu|Ala|Val|
| | |35| | | | |40| | | | |45| | | |

| | | | | | | | | | | | | | | | |
|---|---|---|---|---|---|---|---|---|---|---|---|---|---|---|---|
|Leu|Ala|Leu|Tyr|Asn|Ser|Thr|Arg|Asp|Arg|Val|Ala|Gly|Glu|Ser|Ala|
|50| | | | |55| | | | |60| | | | | |

| | | | | | | | | | | | | | | | |
|---|---|---|---|---|---|---|---|---|---|---|---|---|---|---|---|
|Glu|Pro|Glu|Pro|Glu|Pro|Glu|Ala|Asp|Tyr|Tyr|Ala|Lys|Glu|Val|Thr|
|65| | | | |70| | | | |75| | | | |80|

| | | | | | | | | | | | | | | | |
|---|---|---|---|---|---|---|---|---|---|---|---|---|---|---|---|
|Arg|Val|Leu|Met|Val|Glu|Thr|His|Asn|Glu|Ile|Tyr|Asp|Lys|Phe|Lys|
| | | | |85| | | | |90| | | | |95| |

| | | | | | | | | | | | | | | | |
|---|---|---|---|---|---|---|---|---|---|---|---|---|---|---|---|
|Gln|Ser|Thr|His|Ser|Ile|Tyr|Met|Phe|Phe|Asn|Thr|Ser|Glu|Leu|Arg|
| | | |100| | | | |105| | | | |110| | |

| | | | | | | | | | | | | | | | |
|---|---|---|---|---|---|---|---|---|---|---|---|---|---|---|---|
|Glu|Ala|Val|Pro|Glu|Pro|Val|Leu|Leu|Ser|Arg|Ala|Glu|Leu|Arg|Leu|
| | |115| | | | |120| | | | |125| | | |

| | | | | | | | | | | | | | | | |
|---|---|---|---|---|---|---|---|---|---|---|---|---|---|---|---|
|Leu|Arg|Leu|Lys|Leu|Lys|Val|Glu|Gln|His|Val|Glu|Leu|Tyr|Gln|Lys|
| |130| | | | |135| | | | |140| | | | |

| | | | | | | | | | | | | | | | |
|---|---|---|---|---|---|---|---|---|---|---|---|---|---|---|---|
|Tyr|Ser|Asn|Asn|Ser|Trp|Arg|Tyr|Leu|Ser|Asn|Arg|Leu|Leu|Ala|Pro|
|145| | | | |150| | | | |155| | | | |160|

| | | | | | | | | | | | | | | | |
|---|---|---|---|---|---|---|---|---|---|---|---|---|---|---|---|
|Ser|Asp|Ser|Pro|Glu|Trp|Leu|Ser|Phe|Asp|Val|Thr|Gly|Val|Val|Arg|
| | | | |165| | | | |170| | | | |175| |

| | | | | | | | | | | | | | | | |
|---|---|---|---|---|---|---|---|---|---|---|---|---|---|---|---|
|Gln|Trp|Leu|Ser|Arg|Gly|Gly|Glu|Ile|Glu|Gly|Phe|Arg|Leu|Ser|Ala|
| | | | |180| | | | |185| | | | |190| | |

| | | | | | | | | | | | | | | | |
|---|---|---|---|---|---|---|---|---|---|---|---|---|---|---|---|
|His|Cys|Ser|Cys|Asp|Ser|Lys|Asp|Asn|Thr|Leu|Gln|Val|Asp|Ile|Asn|
| | | |195| | | | |200| | | | |205| | | |

| | | | | | | | | | | | | | | | |
|---|---|---|---|---|---|---|---|---|---|---|---|---|---|---|---|
|Gly|Phe|Thr|Thr|Gly|Arg|Arg|Gly|Asp|Leu|Ala|Thr|Ile|His|Gly|Met|
| | |210| | | | |215| | | | |220| | | | |

| | | | | | | | | | | | | | | | |
|---|---|---|---|---|---|---|---|---|---|---|---|---|---|---|---|
|Asn|Arg|Pro|Phe|Leu|Leu|Leu|Met|Ala|Thr|Pro|Leu|Glu|Arg|Ala|Gln|
|225| | | | |230| | | | |235| | | | |240|

| | | | | | | | | | | | | | | | |
|---|---|---|---|---|---|---|---|---|---|---|---|---|---|---|---|
|His|Leu|Gln|Ser|Ser|Arg|His|Gly|Ala|Leu|Asp|Thr|Asn|Tyr|Cys|Phe|
| | | | |245| | | | |250| | | | |255| |

| | | | | | | | | | | | | | | | |
|---|---|---|---|---|---|---|---|---|---|---|---|---|---|---|---|
|Ser|Ser|Thr|Glu|Lys|Asn|Cys|Cys|Val|Arg|Gln|Leu|Tyr|Ile|Asp|Phe|
| | | |260| | | | |265| | | | |270| | | |

| | | | | | | | | | | | | | | | |
|---|---|---|---|---|---|---|---|---|---|---|---|---|---|---|---|
|Arg|Lys|Asp|Leu|Gly|Trp|Lys|Trp|Ile|His|Glu|Pro|Lys|Gly|Tyr|His|
| | |275| | | | |280| | | | |285| | | | |

| | | | | | | | | | | | | | | | |
|---|---|---|---|---|---|---|---|---|---|---|---|---|---|---|---|
|Ala|Asn|Phe|Cys|Leu|Gly|Pro|Cys|Pro|Tyr|Ile|Trp|Ser|Leu|Asp|Thr|
| |290| | | | |295| | | | |300| | | | | |

| | | | | | | | | | | | | | | | |
|---|---|---|---|---|---|---|---|---|---|---|---|---|---|---|---|
|Gln|Tyr|Ser|Lys|Val|Leu|Ala|Leu|Tyr|Asn|Gln|His|Asn|Pro|Gly|Ala|
|305| | | | |310| | | | |315| | | | |320|

| | | | | | | | | | | | | | | | |
|---|---|---|---|---|---|---|---|---|---|---|---|---|---|---|---|
|Ser|Ala|Ala|Pro|Cys|Cys|Val|Pro|Gln|Ala|Leu|Glu|Pro|Leu|Pro|Ile|
| | | | |325| | | | |330| | | | |335| |

| | | | | | | | | | | | | | | | |
|---|---|---|---|---|---|---|---|---|---|---|---|---|---|---|---|
|Val|Tyr|Tyr|Val|Gly|Arg|Lys|Pro|Lys|Val|Glu|Gln|Leu|Ser|Asn|Met|
| | | |340| | | | |345| | | | |350| | | |

| | | | | | |
|---|---|---|---|---|---|
|Ile|Val|Arg|Ser|Cys|Lys|Cys|Ser|
| | |355| | | | |360|

<210> SEQ ID NO 44
<211> LENGTH: 1260
<212> TYPE: PRT
<213> ORGANISM: Macaca fascicularis
<220> FEATURE:
<221> NAME/KEY: misc_feature
<222> LOCATION: (1)..(1260)
<223> OTHER INFORMATION: LTBP3

<400> SEQUENCE: 44

```
Gly Pro Ala Gly Glu Arg Gly Ala Gly Gly Gly Ala Leu Ala Arg
1               5                   10                  15

Glu Arg Phe Lys Val Val Phe Ala Pro Val Ile Cys Lys Arg Thr Cys
            20                  25                  30

Leu Lys Gly Gln Cys Arg Asp Ser Cys Gln Gln Gly Ser Asn Met Thr
        35                  40                  45

Leu Ile Gly Glu Asn Gly His Ser Thr Asp Thr Leu Thr Gly Ser Gly
    50                  55                  60

Phe Arg Val Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Gly Gly Ala Gly Gly Thr Gly Gly Ser Gly
            100                 105                 110

Pro Gly Leu Ser Arg Ala Gly Ala Leu Ser Thr Gly Ala Leu Pro Pro
        115                 120                 125

Leu Ala Pro Glu Gly Asp Ser Val Ala Ser Lys His Ala Ile Tyr Ala
    130                 135                 140

Val Gln Val Ile Ala Asp Pro Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Pro Val Val Asn Val Arg Val His His Pro
            180                 185                 190

Pro Glu Ala Ser Val Gln Val His Arg Ile Glu Ser Ser Asn Ala Glu
        195                 200                 205

Gly Ala Ala Pro Ser Gln His Leu Leu Pro His Pro Lys Pro Ser His
    210                 215                 220

Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
            260                 265                 270

Cys His Lys Cys Pro Gln Leu Gln Tyr Thr Gly Val Gln Lys Pro Gly
        275                 280                 285

Pro Val Arg Gly Glu Val Gly Ala Asp Cys Pro Gln Gly Tyr Lys Arg
    290                 295                 300

Leu Asn Ser Thr His Cys Gln Asp Ile Asn Glu Cys Ala Met Pro Gly
305                 310                 315                 320

Val Cys Arg His Gly Asp Cys Leu Asn Asn Pro Gly Ser Tyr Arg Cys
                325                 330                 335

Val Cys Pro Pro Gly His Ser Leu Gly Pro Ser Arg Thr Gln Cys Ile
            340                 345                 350

Ala Asp Lys Pro Glu Glu Lys Ser Leu Cys Phe Arg Leu Val Ser Pro
        355                 360                 365
```

```
Glu His Gln Cys Gln His Pro Leu Thr Thr Arg Leu Thr Arg Gln Leu
    370                 375                 380

Cys Cys Cys Ser Val Gly Lys Ala Trp Gly Ala Arg Cys Gln Arg Cys
385                 390                 395                 400

Pro Ala Asp Gly Thr Ala Ala Phe Lys Glu Ile Cys Pro Ala Gly Lys
                405                 410                 415

Gly Tyr His Ile Leu Thr Ser His Gln Thr Leu Thr Ile Gln Gly Glu
            420                 425                 430

Ser Asp Phe Ser Leu Phe Leu His Pro Asp Gly Pro Pro Lys Pro Gln
        435                 440                 445

Gln Leu Pro Glu Ser Pro Ser Gln Ala Pro Pro Glu Asp Thr Glu
    450                 455                 460

Glu Glu Arg Gly Val Thr Thr Asp Ser Pro Val Ser Glu Glu Arg Ser
465                 470                 475                 480

Val Gln Gln Ser His Pro Thr Ala Thr Thr Ser Pro Ala Arg Pro Tyr
                485                 490                 495

Pro Glu Leu Ile Ser Arg Pro Ser Pro Pro Thr Met Arg Trp Phe Leu
            500                 505                 510

Pro Asp Leu Pro Pro Ser Arg Ser Ala Val Glu Ile Ala Pro Thr Gln
        515                 520                 525

Val Thr Glu Thr Asp Glu Cys Arg Leu Asn Gln Asn Ile Cys Gly His
    530                 535                 540

Gly Glu Cys Val Pro Gly Pro Pro Asp Tyr Ser Cys His Cys Asn Pro
545                 550                 555                 560

Gly Tyr Arg Ser His Pro Gln His Arg Tyr Cys Val Asp Val Asn Glu
                565                 570                 575

Cys Glu Ala Glu Pro Cys Gly Pro Gly Arg Gly Ile Cys Met Asn Thr
            580                 585                 590

Gly Gly Ser Tyr Asn Cys His Cys Asn Arg Gly Tyr Arg Leu His Val
        595                 600                 605

Gly Ala Gly Gly Arg Ser Cys Val Asp Leu Asn Glu Cys Ala Lys Pro
    610                 615                 620

His Leu Cys Gly Asp Gly Gly Phe Cys Ile Asn Phe Pro Gly His Tyr
625                 630                 635                 640

Lys Cys Asn Cys Tyr Pro Gly Tyr Arg Leu Lys Ala Ser Arg Pro Pro
                645                 650                 655

Val Cys Glu Asp Ile Asp Glu Cys Arg Asp Pro Ser Ser Cys Pro Asp
            660                 665                 670

Gly Lys Cys Glu Asn Lys Pro Gly Ser Phe Lys Cys Ile Ala Cys Gln
        675                 680                 685

Pro Gly Tyr Arg Ser Gln Gly Gly Gly Ala Cys Arg Asp Val Asn Glu
    690                 695                 700

Cys Ala Glu Gly Ser Pro Cys Ser Pro Gly Trp Cys Glu Asn Leu Pro
705                 710                 715                 720

Gly Ser Phe Arg Cys Thr Cys Ala Gln Gly Tyr Ala Pro Ala Pro Asp
                725                 730                 735

Gly Arg Ser Cys Val Asp Val Asp Glu Cys Glu Ala Gly Asp Val Cys
            740                 745                 750

Asp Asn Gly Ile Cys Thr Asn Thr Pro Gly Ser Phe Gln Cys Gln Cys
        755                 760                 765

Leu Ser Gly Tyr His Leu Ser Arg Asp Arg Ser His Cys Glu Asp Ile
    770                 775                 780
```

```
Asp Glu Cys Asp Phe Pro Ala Ala Cys Ile Gly Asp Cys Ile Asn
785                 790                 795                 800

Thr Asn Gly Ser Tyr Arg Cys Leu Cys Pro Gln Gly His Arg Leu Val
            805                 810                 815

Gly Gly Arg Lys Cys Gln Asp Ile Asp Glu Cys Thr Gln Asp Pro Gly
            820                 825                 830

Leu Cys Leu Pro His Gly Ala Cys Lys Asn Leu Gln Gly Ser Tyr Val
        835                 840                 845

Cys Val Cys Asp Glu Gly Phe Thr Pro Thr Gln Asp Gln His Gly Cys
    850                 855                 860

Glu Glu Val Glu Gln Pro His His Lys Lys Glu Cys Tyr Leu Asn Phe
865                 870                 875                 880

Asp Asp Thr Val Phe Cys Asp Ser Val Leu Ala Thr Asn Val Thr Gln
                885                 890                 895

Gln Glu Cys Cys Cys Ser Leu Gly Ala Gly Trp Gly Asp His Cys Glu
                900                 905                 910

Ile Tyr Pro Cys Pro Val Tyr Ser Ser Ala Glu Phe His Ser Leu Cys
            915                 920                 925

Pro Asp Gly Lys Gly Tyr Thr Gln Asp Asn Asn Ile Val Asn Tyr Gly
    930                 935                 940

Ile Pro Ala His Arg Asp Ile Asp Glu Cys Met Leu Phe Gly Ala Glu
945                 950                 955                 960

Ile Cys Lys Glu Gly Lys Cys Val Asn Thr Gln Pro Gly Tyr Glu Cys
                965                 970                 975

Tyr Cys Lys Gln Gly Phe Tyr Tyr Asp Gly Asn Leu Leu Glu Cys Val
            980                 985                 990

Asp Val Asp Glu Cys Leu Asp Glu Ser Asn Cys Arg Asn Gly Val Cys
        995                 1000                1005

Glu Asn Thr Arg Gly Gly Tyr Arg Cys Ala Cys Thr Pro Pro Ala
1010                1015                1020

Glu Tyr Ser Pro Ala Gln Arg Gln Cys Leu Ser Pro Glu Glu Met
1025                1030                1035

Asp Val Asp Glu Cys Gln Asp Pro Ala Ala Cys Arg Pro Gly Arg
1040                1045                1050

Cys Val Asn Leu Pro Gly Ser Tyr Arg Cys Glu Cys Arg Pro Pro
1055                1060                1065

Trp Val Pro Gly Pro Ser Gly Arg Asp Cys Gln Leu Pro Glu Ser
1070                1075                1080

Pro Ala Glu Arg Ala Pro Glu Arg Arg Asp Val Cys Trp Ser Gln
1085                1090                1095

Arg Gly Glu Asp Gly Met Cys Ala Gly Pro Gln Ala Gly Pro Ala
1100                1105                1110

Leu Thr Phe Asp Asp Cys Cys Cys Arg Gln Gly Arg Gly Trp Gly
1115                1120                1125

Ala Gln Cys Arg Pro Cys Pro Pro Arg Gly Ala Gly Ser Gln Cys
1130                1135                1140

Pro Thr Ser Gln Ser Glu Ser Asn Ser Phe Trp Asp Thr Ser Pro
1145                1150                1155

Leu Leu Leu Gly Lys Pro Arg Arg Asp Glu Asp Ser Ser Glu Glu
1160                1165                1170

Asp Ser Asp Glu Cys Arg Cys Val Ser Gly Arg Cys Val Pro Arg
1175                1180                1185

Pro Gly Gly Ala Val Cys Glu Cys Pro Gly Gly Phe Gln Leu Asp
```

1190                1195                1200

Ala Ser Arg Ala Arg Cys Val Asp Ile Asp Glu Cys Arg Glu Leu
            1205                1210                1215

Asn Gln Arg Gly Leu Leu Cys Lys Ser Glu Arg Cys Val Asn Thr
        1220                1225                1230

Ser Gly Ser Phe Arg Cys Val Cys Lys Ala Gly Phe Ala Arg Ser
    1235                1240                1245

Arg Pro His Gly Ala Cys Val Pro Gln Arg Arg
    1250                1255                1260

<210> SEQ ID NO 45
<211> LENGTH: 1228
<212> TYPE: PRT
<213> ORGANISM: Mus musculus
<220> FEATURE:
<221> NAME/KEY: misc_feature
<222> LOCATION: (1)..(1228)
<223> OTHER INFORMATION: LTBP3

<400> SEQUENCE: 45

Gly Pro Ala Gly Glu Arg Gly Thr Gly Gly Gly Ala Leu Ala Arg
1               5                   10                  15

Glu Arg Phe Lys Val Val Phe Ala Pro Val Ile Cys Lys Arg Thr Cys
            20                  25                  30

Leu Lys Gly Gln Cys Arg Asp Ser Cys Gln Gln Gly Ser Asn Met Thr
        35                  40                  45

Leu Ile Gly Glu Asn Gly His Ser Thr Asp Thr Leu Thr Gly Ser Ala
    50                  55                  60

Phe Arg Val Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Ala Gly Thr Gly Ala Gly Thr Gly Ser Ser Gly
            100                 105                 110

Pro Gly Leu Ala Arg Thr Gly Ala Met Ser Thr Gly Pro Leu Pro Pro
        115                 120                 125

Leu Ala Pro Glu Gly Glu Ser Val Ala Ser Lys His Ala Ile Tyr Ala
    130                 135                 140

Val Gln Val Ile Ala Asp Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Val Val Asn Val Arg Val His His Pro
            180                 185                 190

Pro Glu Ala Ser Val Gln Val His Arg Ile Glu Gly Pro Asn Ala Glu
        195                 200                 205

Gly Pro Ala Ser Ser Gln His Leu Leu Pro His Pro Lys Pro Pro His
    210                 215                 220

Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
            260                 265                 270

Cys His Lys Cys Pro Gln Leu Gln Tyr Thr Gly Val Gln Lys Pro Val
        275                 280                 285

```
Pro Val Arg Gly Glu Val Gly Ala Asp Cys Pro Gln Gly Tyr Lys Arg
    290             295                 300
Leu Asn Ser Thr His Cys Gln Asp Ile Asn Glu Cys Ala Met Pro Gly
305             310                 315                 320
Asn Val Cys His Gly Asp Cys Leu Asn Asn Pro Gly Ser Tyr Arg Cys
                325                 330                 335
Val Cys Pro Pro Gly His Ser Leu Gly Pro Leu Ala Ala Gln Cys Ile
            340                 345                 350
Ala Asp Lys Pro Glu Glu Lys Ser Leu Cys Phe Arg Leu Val Ser Thr
        355                 360                 365
Glu His Gln Cys Gln His Pro Leu Thr Thr Arg Leu Thr Arg Gln Leu
    370                 375                 380
Cys Cys Cys Ser Val Gly Lys Ala Trp Gly Ala Arg Cys Gln Arg Cys
385                 390                 395                 400
Pro Ala Asp Gly Thr Ala Ala Phe Lys Glu Ile Cys Pro Gly Lys Gly
                405                 410                 415
Tyr His Ile Leu Thr Ser His Gln Thr Leu Thr Ile Gln Gly Glu Ser
            420                 425                 430
Asp Phe Ser Leu Phe Leu His Pro Asp Gly Pro Pro Lys Pro Gln Gln
        435                 440                 445
Leu Pro Glu Ser Pro Ser Arg Ala Pro Pro Leu Glu Asp Thr Glu Glu
    450                 455                 460
Glu Arg Gly Val Thr Met Asp Pro Pro Val Ser Glu Glu Arg Ser Val
465                 470                 475                 480
Gln Gln Ser His Pro Thr Thr Thr Thr Ser Pro Pro Arg Pro Tyr Pro
                485                 490                 495
Glu Leu Ile Ser Arg Pro Ser Pro Pro Thr Phe His Arg Phe Leu Pro
            500                 505                 510
Asp Leu Pro Pro Ser Arg Ser Ala Val Glu Ile Ala Pro Thr Gln Val
        515                 520                 525
Thr Glu Thr Asp Glu Cys Arg Leu Asn Gln Asn Ile Cys Gly His Gly
    530                 535                 540
Gln Cys Val Pro Gly Pro Ser Asp Tyr Ser Cys His Cys Asn Ala Gly
545                 550                 555                 560
Tyr Arg Ser His Pro Gln His Arg Tyr Cys Val Asp Val Asn Glu Cys
                565                 570                 575
Glu Ala Glu Pro Cys Gly Pro Gly Lys Gly Ile Cys Met Asn Thr Gly
            580                 585                 590
Gly Ser Tyr Asn Cys His Cys Asn Arg Gly Tyr Arg Leu His Val Gly
        595                 600                 605
Ala Gly Gly Arg Ser Cys Val Asp Leu Asn Glu Cys Ala Lys Pro His
    610                 615                 620
Leu Cys Gly Asp Gly Gly Phe Cys Ile Asn Phe Pro Gly His Tyr Lys
625                 630                 635                 640
Cys Asn Cys Tyr Pro Gly Tyr Arg Leu Lys Ala Ser Arg Pro Pro Ile
                645                 650                 655
Cys Glu Asp Ile Asp Glu Cys Arg Asp Pro Ser Thr Cys Pro Asp Gly
            660                 665                 670
Lys Cys Glu Asn Lys Pro Gly Ser Phe Lys Cys Ile Ala Cys Gln Pro
        675                 680                 685
Gly Tyr Arg Ser Gln Gly Gly Gly Ala Cys Arg Asp Val Asn Glu Cys
    690                 695                 700
```

```
Ser Glu Gly Thr Pro Cys Ser Pro Gly Trp Cys Glu Asn Leu Pro Gly
705                 710                 715                 720

Ser Tyr Arg Cys Thr Cys Ala Gln Tyr Glu Pro Ala Gln Asp Gly Leu
            725                 730                 735

Ser Cys Ile Asp Val Asp Glu Cys Ala Gly Lys Val Cys Gln Asp
        740                 745                 750

Gly Ile Cys Thr Asn Thr Pro Gly Ser Phe Gln Cys Gln Cys Leu Ser
            755                 760                 765

Gly Tyr His Leu Ser Arg Asp Arg Ser Arg Cys Glu Asp Ile Asp Glu
        770                 775                 780

Cys Asp Phe Pro Ala Ala Cys Ile Gly Gly Asp Cys Ile Asn Thr Asn
785                 790                 795                 800

Gly Ser Tyr Arg Cys Leu Cys Pro Leu Gly His Arg Leu Val Gly Gly
            805                 810                 815

Arg Lys Cys Lys Lys Asp Ile Asp Glu Cys Ser Gln Asp Pro Gly Leu
        820                 825                 830

Cys Leu Pro His Ala Cys Glu Asn Leu Gln Gly Ser Tyr Val Cys Val
        835                 840                 845

Cys Asp Glu Gly Phe Thr Leu Thr Gln Asp Gln His Gly Cys Glu Glu
        850                 855                 860

Val Glu Gln Pro His His Lys Lys Glu Cys Tyr Leu Asn Phe Asp Asp
865                 870                 875                 880

Thr Val Phe Cys Asp Ser Val Leu Ala Thr Asn Val Thr Gln Gln Glu
                885                 890                 895

Cys Cys Cys Ser Leu Gly Ala Gly Trp Gly Asp His Cys Glu Ile Tyr
            900                 905                 910

Pro Cys Pro Val Tyr Ser Ser Ala Glu Phe His Ser Leu Val Pro Asp
        915                 920                 925

Gly Lys Arg Leu His Ser Gly Gln Gln His Cys Glu Leu Cys Ile Pro
        930                 935                 940

Ala His Arg Asp Ile Asp Glu Cys Ile Leu Phe Gly Ala Glu Ile Cys
945                 950                 955                 960

Lys Glu Gly Lys Cys Val Asn Thr Gln Pro Gly Tyr Glu Cys Tyr Cys
            965                 970                 975

Lys Gln Gly Phe Tyr Tyr Asp Gly Asn Leu Leu Glu Cys Val Asp Val
        980                 985                 990

Asp Glu Cys Leu Asp Glu Ser Asn  Cys Arg Asn Gly Val  Cys Glu Asn
            995                 1000                1005

Thr Arg Gly Gly Tyr Arg Cys  Ala Cys Thr Pro  Ala Glu Tyr
    1010                1015                1020

Ser Pro Ala Gln Ala Gln Cys  Leu Ile Pro Glu Arg  Trp Ser Thr
    1025                1030                1035

Pro Gln Arg Asp Val Lys Cys  Ala Gly Ala Ser Glu  Glu Arg Thr
    1040                1045                1050

Ala Cys Val Trp Gly Pro Trp  Ala Gly Pro Ala Leu  Thr Phe Asp
    1055                1060                1065

Asp Cys Cys Cys Arg Gln Pro  Arg Leu Gly Thr Gln  Cys Arg Pro
    1070                1075                1080

Cys Pro Pro Arg Gly Thr Gly  Ser Gln Cys Pro Thr  Ser Gln Ser
    1085                1090                1095

Glu Ser Asn Ser Phe Trp Asp  Thr Ser Pro Leu Leu  Leu Gly Lys
    1100                1105                1110

Ser Pro Arg Asp Glu Asp Ser  Ser Glu Glu Asp Ser  Asp Glu Cys
```

-continued

```
                1115                1120                1125

Arg Cys Val Ser Gly Arg Cys Val Pro Arg Pro Gly Gly Ala Val
    1130                1135                1140

Cys Glu Cys Pro Gly Gly Phe Gln Leu Asp Ala Ser Arg Ala Arg
    1145                1150                1155

Cys Val Asp Ile Asp Glu Cys Arg Glu Leu Asn Gln Arg Gly Leu
    1160                1165                1170

Leu Cys Lys Ser Glu Arg Cys Val Asn Thr Ser Gly Ser Phe Arg
    1175                1180                1185

Cys Val Cys Lys Ala Gly Phe Thr Arg Ser Arg Pro His Gly Pro
    1190                1195                1200

Ala Cys Leu Ser Ala Ala Ala Asp Asp Ala Ala Ile Ala His Thr
    1205                1210                1215

Ser Val Ile Asp His Arg Gly Tyr Phe His
    1220                1225

<210> SEQ ID NO 46
<211> LENGTH: 1373
<212> TYPE: PRT
<213> ORGANISM: Macaca fascicularis
<220> FEATURE:
<221> NAME/KEY: misc_feature
<222> LOCATION: (1)..(1373)
<223> OTHER INFORMATION: LTBP1S

<400> SEQUENCE: 46

Asn His Thr Gly Arg Ile Lys Val Val Phe Thr Pro Ser Ile Cys Lys
1               5                   10                  15

Val Thr Cys Thr Lys Gly Ser Cys Gln Asn Ser Cys Glu Lys Gly Asn
                20                  25                  30

Thr Thr Thr Leu Ile Ser Glu Asn Gly His Ala Ala Asp Thr Leu Thr
            35                  40                  45

Ala Thr Asn Phe Arg Val Val Leu Cys His Leu Pro Cys Met Asn Gly
        50                  55                  60

Gly Gln Cys Ser Ser Arg Asp Lys Cys Gln Cys Pro Pro Asn Phe Thr
65                  70                  75                  80

Gly Lys Leu Cys Gln Ile Pro Val His Gly Ala Ser Val Pro Lys Leu
                85                  90                  95

Tyr Gln His Ser Gln Gln Pro Gly Lys Ala Leu Gly Thr His Val Ile
                100                 105                 110

His Ser Thr His Thr Leu Pro Leu Thr Val Thr Ser Gln Gln Gly Val
            115                 120                 125

Lys Val Lys Phe Pro Pro Asn Ile Val Asn Ile His Val Lys His Pro
        130                 135                 140

Pro Glu Ala Ser Val Gln Ile His Gln Val Ser Arg Ile Asp Gly Pro
145                 150                 155                 160

Thr Gly Gln Lys Thr Lys Glu Ala Gln Pro Gly Gln Ser Gln Val Ser
                165                 170                 175

Tyr Gln Gly Leu Pro Val Gln Lys Thr Gln Thr Ile His Ser Thr Tyr
                180                 185                 190

Ser His Gln Gln Val Ile Pro His Val Tyr Pro Val Ala Ala Lys Thr
            195                 200                 205

Gln Leu Gly Arg Cys Phe Gln Glu Thr Ile Gly Ser Gln Cys Gly Lys
        210                 215                 220

Ala Leu Pro Gly Leu Ser Lys Gln Glu Asp Cys Cys Gly Thr Val Gly
225                 230                 235                 240
```

```
Thr Ser Trp Gly Phe Asn Lys Cys Gln Lys Cys Pro Lys Lys Pro Ser
            245                 250                 255

Tyr His Gly Tyr Asn Gln Met Met Glu Cys Leu Pro Gly Tyr Lys Arg
            260                 265                 270

Val Asn Asn Thr Phe Cys Gln Asp Ile Asn Glu Cys Gln Leu Gln Gly
            275                 280                 285

Val Cys Pro Asn Gly Glu Cys Leu Asn Thr Met Gly Ser Tyr Arg Cys
            290                 295                 300

Thr Cys Lys Ile Gly Phe Gly Pro Asp Pro Thr Phe Ser Ser Cys Val
305                 310                 315                 320

Pro Asp Pro Pro Val Ile Ser Glu Glu Lys Gly Pro Cys Tyr Arg Leu
            325                 330                 335

Val Ser Ser Gly Arg Gln Cys Met His Pro Leu Ser Val His Leu Thr
            340                 345                 350

Lys Gln Leu Cys Cys Cys Ser Val Gly Lys Ala Trp Gly Pro His Cys
            355                 360                 365

Glu Lys Cys Pro Leu Pro Gly Thr Ala Ala Phe Lys Glu Ile Cys Pro
            370                 375                 380

Gly Gly Met Gly Tyr Thr Val Ser Gly Val His Arg Arg Arg Pro Ile
385                 390                 395                 400

His His His Val Gly Lys Gly Pro Val Phe Val Lys Pro Lys Asn Thr
            405                 410                 415

Gln Pro Val Ala Lys Ser Thr His Pro Pro Leu Pro Ala Lys Glu
            420                 425                 430

Glu Pro Val Glu Ala Leu Thr Phe Ser Arg Glu His Gly Pro Gly Val
            435                 440                 445

Ala Glu Pro Glu Val Ala Thr Ala Pro Pro Glu Lys Glu Ile Pro Ser
            450                 455                 460

Leu Asp Gln Glu Lys Thr Lys Leu Glu Pro Gly Gln Pro Gln Leu Ser
465                 470                 475                 480

Pro Gly Ile Ser Thr Ile His Leu His Pro Gln Phe Pro Val Val Ile
            485                 490                 495

Glu Lys Thr Ser Pro Pro Val Pro Val Glu Val Ala Pro Glu Ala Ser
            500                 505                 510

Thr Ser Ser Ala Ser Gln Val Ile Ala Pro Thr Gln Val Thr Glu Ile
            515                 520                 525

Asn Glu Cys Thr Val Asn Pro Asp Ile Cys Gly Ala Gly His Cys Ile
530                 535                 540

Asn Leu Pro Val Arg Tyr Thr Cys Ile Cys Tyr Glu Gly Tyr Lys Phe
545                 550                 555                 560

Ser Glu Gln Gln Arg Lys Cys Val Asp Ile Asp Glu Cys Thr Gln Val
            565                 570                 575

Gln His Leu Cys Ser Gln Gly Arg Cys Glu Asn Thr Glu Gly Ser Phe
            580                 585                 590

Leu Cys Ile Cys Pro Ala Gly Phe Met Ala Ser Glu Glu Gly Thr Asn
            595                 600                 605

Cys Ile Asp Val Asp Glu Cys Leu Arg Pro Asp Val Cys Gly Glu Gly
            610                 615                 620

His Cys Val Asn Thr Val Gly Ala Phe Arg Cys Glu Tyr Cys Asp Ser
625                 630                 635                 640

Gly Tyr Arg Met Thr Gln Arg Gly Arg Cys Glu Asp Ile Asp Glu Cys
            645                 650                 655
```

-continued

Leu Asn Pro Ser Thr Cys Pro Asp Glu Gln Cys Val Asn Ser Pro Gly
            660                 665                 670

Ser Tyr Gln Cys Val Pro Cys Thr Glu Gly Phe Arg Gly Trp Asn Gly
        675                 680                 685

Gln Cys Leu Asp Val Asp Glu Cys Leu Glu Pro Asn Val Cys Thr Asn
    690                 695                 700

Gly Asp Cys Ser Asn Leu Glu Gly Ser Tyr Met Cys Ser Cys His Lys
705                 710                 715                 720

Gly Tyr Thr Arg Thr Pro Asp His Lys His Cys Lys Asp Ile Asp Glu
                725                 730                 735

Cys Gln Gln Gly Asn Leu Cys Val Asn Gly Gln Cys Lys Asn Thr Glu
            740                 745                 750

Gly Ser Phe Arg Cys Thr Cys Gly Gln Gly Tyr Gln Leu Ser Ala Ala
        755                 760                 765

Lys Asp Gln Cys Glu Asp Ile Asp Glu Cys Gln His His Leu Cys
    770                 775                 780

Ala His Gly Gln Cys Arg Asn Thr Glu Gly Ser Phe Gln Cys Val Cys
785                 790                 795                 800

Asp Gln Gly Tyr Arg Ala Ser Gly Leu Gly Asp His Cys Glu Asp Ile
                805                 810                 815

Asn Glu Cys Leu Glu Asp Lys Ser Val Cys Gln Arg Gly Asp Cys Ile
            820                 825                 830

Asn Thr Ala Gly Ser Tyr Asp Cys Thr Cys Pro Asp Gly Phe Gln Leu
        835                 840                 845

Asp Asp Asn Lys Thr Cys Gln Asp Ile Asn Glu Cys Glu His Pro Gly
850                 855                 860

Leu Cys Gly Pro Gln Gly Glu Cys Leu Asn Thr Glu Gly Ser Phe His
865                 870                 875                 880

Cys Val Cys Gln Gln Gly Phe Ser Ile Ser Ala Asp Gly Arg Thr Cys
                885                 890                 895

Glu Asp Ile Asp Glu Cys Val Asn Asn Thr Val Cys Asp Ser His Gly
            900                 905                 910

Phe Cys Asp Asn Thr Ala Gly Ser Phe Arg Cys Leu Cys Tyr Gln Gly
        915                 920                 925

Phe Gln Ala Pro Gln Asp Gly Gln Gly Cys Val Asp Val Asn Glu Cys
    930                 935                 940

Glu Leu Leu Ser Gly Val Cys Gly Glu Ala Phe Cys Glu Asn Val Glu
945                 950                 955                 960

Gly Ser Phe Leu Cys Val Cys Ala Asp Glu Asn Gln Glu Tyr Ser Pro
                965                 970                 975

Met Thr Gly Gln Cys Arg Ser Arg Thr Ser Thr Asp Leu Asp Val Glu
            980                 985                 990

Gln Pro Lys Glu Glu Lys Lys Glu Cys Tyr Tyr Asn Leu Asn Asp Ala
        995                 1000                1005

Ser Leu Cys Asp Asn Val Leu Ala Pro Asn Val Thr Lys Gln Glu
    1010                1015                1020

Cys Cys Cys Thr Ser Gly Ala Gly Trp Gly Asp Asn Cys Glu Ile
    1025                1030                1035

Phe Pro Cys Pro Val Leu Gly Thr Ala Glu Phe Thr Glu Met Cys
    1040                1045                1050

Pro Lys Gly Lys Gly Phe Val Pro Ala Gly Glu Ser Ser Ser Glu
    1055                1060                1065

Ala Gly Gly Glu Asn Tyr Lys Asp Ala Asp Glu Cys Leu Leu Phe

```
                1070                1075                1080

Gly Gln Glu Ile Cys Lys Asn Gly Phe Cys Leu Asn Thr Arg Pro
    1085                1090                1095

Gly Tyr Glu Cys Tyr Cys Lys Gln Gly Thr Tyr Tyr Asp Pro Val
    1100                1105                1110

Lys Leu Gln Cys Phe Asp Met Asp Glu Cys Gln Asp Pro Ser Ser
    1115                1120                1125

Cys Ile Asp Gly Gln Cys Val Asn Thr Glu Gly Ser Tyr Asn Cys
    1130                1135                1140

Phe Cys Thr His Pro Met Val Leu Asp Ala Ser Glu Lys Arg Cys
    1145                1150                1155

Ile Arg Pro Ala Glu Ser Asn Glu Gln Ile Glu Glu Thr Asp Val
    1160                1165                1170

Tyr Gln Asp Leu Cys Trp Glu His Leu Ser Asp Glu Tyr Val Cys
    1175                1180                1185

Ser Arg Pro Leu Val Gly Lys Gln Thr Thr Tyr Thr Glu Cys Cys
    1190                1195                1200

Cys Leu Tyr Gly Glu Ala Trp Gly Met Gln Cys Ala Leu Cys Pro
    1205                1210                1215

Met Lys Asp Ser Asp Asp Tyr Ala Gln Leu Cys Asn Ile Pro Val
    1220                1225                1230

Thr Gly Arg Arg Gln Pro Tyr Gly Arg Asp Ala Leu Val Asp Phe
    1235                1240                1245

Ser Glu Gln Tyr Ala Pro Glu Ala Asp Pro Tyr Phe Ile Gln Asp
    1250                1255                1260

Arg Phe Leu Asn Ser Phe Glu Glu Leu Gln Ala Glu Glu Cys Gly
    1265                1270                1275

Ile Leu Asn Gly Cys Glu Asn Gly Arg Cys Val Arg Val Gln Glu
    1280                1285                1290

Gly Tyr Thr Cys Asp Cys Phe Asp Gly Tyr His Leu Asp Thr Ala
    1295                1300                1305

Lys Met Thr Cys Val Asp Val Asn Glu Cys Asp Glu Leu Asn Asn
    1310                1315                1320

Arg Met Ser Leu Cys Lys Asn Ala Lys Cys Ile Asn Thr Glu Gly
    1325                1330                1335

Ser Tyr Lys Cys Leu Cys Leu Pro Gly Tyr Val Pro Ser Asp Lys
    1340                1345                1350

Pro Asn Tyr Cys Thr Pro Leu Asn Thr Ala Leu Asn Leu Glu Lys
    1355                1360                1365

Asp Ser Asp Leu Glu
    1370

<210> SEQ ID NO 47
<211> LENGTH: 1374
<212> TYPE: PRT
<213> ORGANISM: Mus musculus
<220> FEATURE:
<221> NAME/KEY: misc_feature
<222> LOCATION: (1)..(1374)
<223> OTHER INFORMATION: LTBP1S

<400> SEQUENCE: 47

Asn His Thr Gly Arg Ile Lys Val Val Phe Thr Pro Ser Ile Cys Lys
1               5                   10                  15

Val Thr Cys Thr Lys Gly Asn Cys Gln Asn Ser Cys Gln Lys Gly Asn
            20                  25                  30
```

```
Thr Thr Thr Leu Ile Ser Glu Asn Gly His Ala Ala Asp Thr Leu Thr
         35                  40                  45

Ala Thr Asn Phe Arg Val Val Ile Cys His Leu Pro Cys Met Asn Gly
     50                  55                  60

Gly Gln Cys Ser Ser Arg Asp Lys Cys Gln Cys Pro Pro Asn Phe Thr
 65                  70                  75                  80

Gly Lys Leu Cys Gln Ile Pro Val Leu Gly Ala Ser Met Pro Lys Leu
                 85                  90                  95

Tyr Gln His Ala Gln Gln Gly Lys Ala Leu Gly Ser His Val Ile
                100                 105                 110

His Ser Thr His Thr Leu Pro Leu Thr Met Thr Ser Gln Gln Gly Val
            115                 120                 125

Lys Val Lys Phe Pro Pro Asn Ile Val Asn Ile His Val Lys His Pro
        130                 135                 140

Pro Glu Ala Ser Val Gln Ile His Gln Val Ser Arg Ile Asp Ser Pro
145                 150                 155                 160

Gly Gly Gln Lys Val Lys Glu Ala Gln Pro Gly Gln Ser Gln Val Ser
                165                 170                 175

Tyr Gln Gly Leu Pro Val Gln Lys Thr Gln Thr Val His Ser Thr Tyr
            180                 185                 190

Ser His Gln Gln Leu Ile Pro His Val Tyr Pro Val Ala Ala Lys Thr
        195                 200                 205

Gln Leu Gly Arg Cys Phe Gln Glu Thr Ile Gly Ser Gln Cys Gly Lys
    210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Gln Ser
                245                 250                 255

Tyr His Gly Tyr Thr Gln Met Met Glu Cys Leu Gln Gly Tyr Lys Arg
            260                 265                 270

Val Asn Asn Thr Phe Cys Gln Asp Ile Asn Glu Cys Gln Leu Gln Gly
        275                 280                 285

Val Cys Pro Asn Gly Glu Cys Leu Asn Thr Met Gly Ser Tyr Arg Cys
    290                 295                 300

Ser Cys Lys Met Gly Phe Gly Pro Asp Pro Thr Phe Ser Ser Cys Val
305                 310                 315                 320

Pro Asp Pro Pro Val Ile Ser Glu Glu Lys Gly Pro Cys Tyr Arg Leu
                325                 330                 335

Val Ser Pro Gly Arg His Cys Met His Pro Leu Ser Val His Leu Thr
            340                 345                 350

Lys Gln Ile Cys Cys Cys Ser Val Gly Lys Ala Trp Gly Pro His Cys
        355                 360                 365

Glu Lys Cys Pro Leu Pro Gly Thr Ala Ala Phe Lys Glu Ile Cys Pro
    370                 375                 380

Gly Gly Met Gly Tyr Thr Val Ser Gly Val His Arg Arg Pro Ile
385                 390                 395                 400

His Gln His Ile Gly Lys Glu Ala Val Tyr Val Lys Pro Lys Asn Thr
                405                 410                 415

Gln Pro Val Ala Lys Ser Thr His Pro Pro Leu Pro Ala Lys Glu
            420                 425                 430

Glu Pro Val Glu Ala Leu Thr Ser Ser Trp Glu His Gly Pro Arg Gly
        435                 440                 445
```

-continued

Ala Glu Pro Glu Val Val Thr Ala Pro Pro Glu Lys Glu Ile Pro Ser
450                 455                 460

Leu Asp Gln Glu Lys Thr Arg Leu Glu Pro Gly Gln Pro Gln Leu Ser
465                 470                 475                 480

Pro Gly Val Ser Thr Ile His Leu His Pro Gln Phe Pro Val Val Val
                485                 490                 495

Glu Lys Thr Ser Pro Pro Val Pro Val Glu Val Ala Pro Glu Ala Ser
                500                 505                 510

Thr Ser Ser Ala Ser Gln Val Ile Ala Pro Thr Gln Val Thr Glu Ile
            515                 520                 525

Asn Glu Cys Thr Val Asn Pro Asp Ile Cys Gly Ala Gly His Cys Ile
530                 535                 540

Asn Leu Pro Val Arg Tyr Thr Cys Ile Cys Tyr Glu Gly Tyr Lys Phe
545                 550                 555                 560

Ser Glu Gln Leu Arg Lys Cys Val Asp Ile Asp Glu Cys Ala Gln Val
                565                 570                 575

Arg His Leu Cys Ser Gln Gly Arg Cys Glu Asn Thr Glu Gly Ser Phe
            580                 585                 590

Leu Cys Val Cys Pro Ala Gly Phe Met Ala Ser Glu Glu Gly Thr Asn
        595                 600                 605

Cys Ile Asp Val Asp Glu Cys Leu Arg Pro Asp Met Cys Arg Asp Gly
610                 615                 620

Arg Cys Ile Asn Thr Ala Gly Ala Phe Arg Cys Glu Tyr Cys Asp Ser
625                 630                 635                 640

Gly Tyr Arg Met Ser Arg Arg Gly Tyr Cys Glu Asp Ile Asp Glu Cys
                645                 650                 655

Leu Lys Pro Ser Thr Cys Pro Glu Glu Gln Cys Val Asn Thr Pro Gly
            660                 665                 670

Ser Tyr Gln Cys Val Pro Cys Thr Glu Gly Phe Arg Gly Trp Asn Gly
        675                 680                 685

Gln Cys Leu Asp Val Asp Glu Cys Leu Gln Pro Lys Val Cys Thr Asn
690                 695                 700

Gly Ser Cys Thr Asn Leu Glu Gly Ser Tyr Met Cys Ser Cys His Arg
705                 710                 715                 720

Gly Tyr Ser Pro Thr Pro Asp His Arg His Cys Gln Asp Ile Asp Glu
                725                 730                 735

Cys Gln Gln Gly Asn Leu Cys Met Asn Gly Gln Cys Arg Asn Thr Asp
            740                 745                 750

Gly Ser Phe Arg Cys Thr Cys Gly Gln Gly Tyr Gln Leu Ser Ala Ala
        755                 760                 765

Lys Asp Gln Cys Glu Asp Ile Asp Glu Cys Glu His His Leu Cys
770                 775                 780

Ser His Gly Gln Cys Arg Asn Thr Glu Gly Ser Phe Gln Cys Val Cys
785                 790                 795                 800

Asn Gln Gly Tyr Arg Ala Ser Val Leu Gly Asp His Cys Glu Asp Ile
                805                 810                 815

Asn Glu Cys Leu Glu Asp Ser Ser Val Cys Gln Gly Gly Asp Cys Ile
            820                 825                 830

Asn Thr Ala Gly Ser Tyr Asp Cys Thr Cys Pro Asp Gly Phe Gln Leu
        835                 840                 845

Asn Asp Asn Lys Gly Cys Gln Asp Ile Asn Glu Cys Ala Gln Pro Gly
850                 855                 860

Leu Cys Gly Ser His Gly Glu Cys Leu Asn Thr Gln Gly Ser Phe His

```
865                 870                 875                 880
Cys Val Cys Glu Gln Gly Phe Ser Ile Ser Ala Asp Gly Arg Thr Cys
                885                 890                 895
Glu Asp Ile Asp Glu Cys Val Asn Asn Thr Val Cys Asp Ser His Gly
                900                 905                 910
Phe Cys Asp Asn Thr Ala Gly Ser Phe Arg Cys Leu Cys Tyr Gln Gly
                915                 920                 925
Phe Gln Ala Pro Gln Asp Gly Gln Gly Cys Val Asp Val Asn Glu Cys
930                 935                 940
Glu Leu Leu Ser Gly Val Cys Gly Glu Ala Phe Cys Glu Asn Val Glu
945                 950                 955                 960
Gly Ser Phe Leu Cys Val Cys Ala Asp Glu Asn Gln Glu Tyr Ser Pro
                965                 970                 975
Met Thr Gly Gln Cys Arg Ser Arg Val Thr Glu Asp Ser Gly Val Asp
                980                 985                 990
Arg Gln Pro Arg Glu Glu Lys Lys Glu Cys Tyr Tyr Asn Leu Asn Asp
                995                 1000                1005
Ala Ser Leu Cys Asp Asn Val Leu Ala Pro Asn Val Thr Lys Gln
1010                1015                1020
Glu Cys Cys Cys Thr Ser Gly Ala Gly Trp Gly Asp Asn Cys Glu
1025                1030                1035
Ile Phe Pro Cys Pro Val Gln Gly Thr Ala Glu Phe Thr Glu Met
1040                1045                1050
Cys Pro Arg Gly Lys Gly Leu Val Pro Ala Gly Glu Ser Ser Tyr
1055                1060                1065
Asp Thr Gly Gly Glu Asn Tyr Lys Asp Ala Asp Glu Cys Leu Leu
1070                1075                1080
Phe Gly Glu Glu Ile Cys Lys Asn Gly Tyr Cys Leu Asn Thr Gln
1085                1090                1095
Pro Gly Tyr Glu Cys Tyr Cys Lys Gln Gly Thr Tyr Tyr Asp Pro
1100                1105                1110
Val Lys Leu Gln Cys Phe Asp Met Asp Glu Cys Gln Asp Pro Asn
1115                1120                1125
Ser Cys Ile Asp Gly Gln Cys Val Asn Thr Glu Gly Ser Tyr Asn
1130                1135                1140
Cys Phe Cys Thr His Pro Met Val Leu Asp Ala Ser Glu Lys Arg
1145                1150                1155
Cys Val Gln Pro Thr Glu Ser Asn Glu Gln Ile Glu Glu Thr Asp
1160                1165                1170
Val Tyr Gln Asp Leu Cys Trp Glu His Leu Ser Glu Glu Tyr Val
1175                1180                1185
Cys Ser Arg Pro Leu Val Gly Lys Gln Thr Thr Tyr Thr Glu Cys
1190                1195                1200
Cys Cys Leu Tyr Gly Glu Ala Trp Gly Met Gln Cys Ala Leu Cys
1205                1210                1215
Pro Met Lys Asp Ser Asp Asp Tyr Ala Gln Leu Cys Asn Ile Pro
1220                1225                1230
Val Thr Gly Arg Arg Arg Pro Tyr Gly Arg Asp Ala Leu Val Asp
1235                1240                1245
Phe Ser Glu Gln Tyr Gly Pro Glu Thr Asp Pro Tyr Phe Ile Gln
1250                1255                1260
Asp Arg Phe Leu Asn Ser Phe Glu Glu Leu Gln Ala Glu Glu Cys
1265                1270                1275
```

-continued

```
Gly Ile Leu Asn Gly Cys Glu Asn Gly Arg Cys Val Arg Val Gln
    1280            1285               1290

Glu Gly Tyr Thr Cys Asp Cys Phe Asp Gly Tyr His Leu Asp Met
    1295            1300               1305

Ala Lys Met Thr Cys Val Asp Val Asn Glu Cys Ser Glu Leu Asn
    1310            1315               1320

Asn Arg Met Ser Leu Cys Lys Asn Ala Lys Cys Ile Asn Thr Glu
    1325            1330               1335

Gly Ser Tyr Lys Cys Leu Cys Leu Pro Gly Tyr Ile Pro Ser Asp
    1340            1345               1350

Lys Pro Asn Tyr Cys Thr Pro Leu Asn Ser Ala Leu Asn Leu Asp
    1355            1360               1365

Lys Glu Ser Asp Leu Glu
    1370

<210> SEQ ID NO 48
<211> LENGTH: 646
<212> TYPE: PRT
<213> ORGANISM: Mus musculus
<220> FEATURE:
<221> NAME/KEY: misc_feature
<222> LOCATION: (1)..(646)
<223> OTHER INFORMATION: GARP

<400> SEQUENCE: 48

Ile Ser Gln Arg Arg Glu Gln Val Pro Cys Arg Thr Val Asn Lys Glu
1               5                   10                  15

Ala Leu Cys His Gly Leu Gly Leu Leu Gln Val Pro Ser Val Leu Ser
                20                  25                  30

Leu Asp Ile Gln Ala Leu Tyr Leu Ser Gly Asn Gln Leu Gln Ser Ile
            35                  40                  45

Leu Val Ser Pro Leu Gly Phe Tyr Thr Ala Leu Arg His Leu Asp Leu
        50                  55                  60

Ser Asp Asn Gln Ile Ser Phe Leu Gln Ala Gly Val Phe Gln Ala Leu
65                  70                  75                  80

Pro Tyr Leu Glu His Leu Asn Leu Ala His Asn Arg Leu Ala Thr Gly
                85                  90                  95

Met Ala Leu Asn Ser Gly Gly Leu Gly Arg Leu Pro Leu Leu Val Ser
                100                 105                 110

Leu Asp Leu Ser Gly Asn Ser Leu His Gly Asn Leu Val Glu Arg Leu
            115                 120                 125

Leu Gly Glu Thr Pro Arg Leu Arg Thr Leu Ser Leu Ala Glu Asn Ser
        130                 135                 140

Leu Thr Arg Leu Ala Arg His Thr Phe Trp Gly Met Pro Ala Val Glu
145                 150                 155                 160

Gln Leu Asp Leu His Ser Asn Val Leu Met Asp Ile Glu Asp Gly Ala
                165                 170                 175

Phe Glu Ala Leu Pro His Leu Thr His Leu Asn Leu Ser Arg Asn Ser
                180                 185                 190

Leu Thr Cys Ile Ser Asp Phe Ser Leu Gln Gln Leu Gln Val Leu Asp
            195                 200                 205

Leu Ser Cys Asn Ser Ile Glu Ala Phe Gln Thr Ala Pro Glu Pro Gln
        210                 215                 220

Ala Gln Phe Gln Leu Ala Trp Leu Asp Leu Arg Glu Asn Lys Leu Leu
225                 230                 235                 240
```

-continued

```
His Phe Pro Asp Leu Ala Val Phe Pro Arg Leu Ile Tyr Leu Asn Val
            245                 250                 255
Ser Asn Asn Leu Ile Gln Leu Pro Ala Gly Leu Pro Arg Gly Ser Glu
            260                 265                 270
Asp Leu His Ala Pro Ser Glu Gly Trp Ser Ala Ser Pro Leu Ser Asn
            275                 280                 285
Pro Ser Arg Asn Ala Ser Thr His Pro Leu Ser Gln Leu Leu Asn Leu
290                 295                 300
Asp Leu Ser Tyr Asn Glu Ile Glu Leu Val Pro Ala Ser Phe Leu Glu
305                 310                 315                 320
His Leu Thr Ser Leu Arg Phe Leu Asn Leu Ser Arg Asn Cys Leu Arg
            325                 330                 335
Ser Phe Glu Ala Arg Gln Val Asp Ser Leu Pro Cys Leu Val Leu Leu
            340                 345                 350
Asp Leu Ser His Asn Val Leu Glu Ala Leu Glu Leu Gly Thr Lys Val
            355                 360                 365
Leu Gly Ser Leu Gln Thr Leu Leu Leu Gln Asp Asn Ala Leu Gln Glu
            370                 375                 380
Leu Pro Pro Tyr Thr Phe Ala Ser Leu Ala Ser Leu Gln Arg Leu Asn
385                 390                 395                 400
Leu Gln Gly Asn Gln Val Ser Pro Cys Gly Gly Pro Ala Glu Pro Gly
            405                 410                 415
Pro Pro Gly Cys Val Asp Phe Ser Gly Ile Pro Thr Leu His Val Leu
            420                 425                 430
Asn Met Ala Gly Asn Ser Met Gly Met Leu Arg Ala Gly Ser Phe Leu
            435                 440                 445
His Thr Pro Leu Thr Glu Leu Asp Leu Ser Thr Asn Pro Gly Leu Asp
            450                 455                 460
Val Ala Thr Gly Ala Leu Val Gly Leu Glu Ala Ser Leu Glu Val Leu
465                 470                 475                 480
Glu Leu Gln Gly Asn Gly Leu Thr Val Leu Arg Val Asp Leu Pro Cys
            485                 490                 495
Phe Leu Arg Leu Lys Arg Leu Asn Leu Ala Glu Asn Gln Leu Ser His
            500                 505                 510
Leu Pro Ala Trp Thr Arg Ala Val Ser Leu Glu Val Leu Asp Leu Arg
            515                 520                 525
Asn Asn Ser Phe Ser Leu Leu Pro Gly Asn Ala Met Gly Gly Leu Glu
            530                 535                 540
Thr Ser Leu Arg Arg Leu Tyr Leu Gln Gly Asn Pro Leu Ser Cys Cys
545                 550                 555                 560
Gly Asn Gly Trp Leu Ala Ala Gln Leu His Gln Gly Arg Val Asp Val
            565                 570                 575
Asp Ala Thr Gln Asp Leu Ile Cys Arg Phe Gly Ser Gln Glu Glu Leu
            580                 585                 590
Ser Leu Ser Leu Val Arg Pro Glu Asp Cys Glu Lys Gly Gly Leu Lys
            595                 600                 605
Asn Val Asn Leu Ile Leu Leu Leu Ser Phe Thr Leu Val Ser Ala Ile
            610                 615                 620
Val Leu Thr Thr Leu Ala Thr Ile Cys Phe Leu Arg Arg Gln Lys Leu
625                 630                 635                 640
Ser Gln Gln Tyr Lys Ala
            645
```

```
<210> SEQ ID NO 49
<211> LENGTH: 611
<212> TYPE: PRT
<213> ORGANISM: Mus musculus
<220> FEATURE:
<221> NAME/KEY: misc_feature
<222> LOCATION: (1)..(611)
<223> OTHER INFORMATION: sGARP

<400> SEQUENCE: 49

Ile Ser Gln Arg Arg Glu Gln Val Pro Cys Arg Thr Val Asn Lys Glu
1               5                   10                  15

Ala Leu Cys His Gly Leu Gly Leu Leu Gln Val Pro Ser Val Leu Ser
            20                  25                  30

Leu Asp Ile Gln Ala Leu Tyr Leu Ser Gly Asn Gln Leu Gln Ser Ile
        35                  40                  45

Leu Val Ser Pro Leu Gly Phe Tyr Thr Ala Leu Arg His Leu Asp Leu
    50                  55                  60

Ser Asp Asn Gln Ile Ser Phe Leu Gln Ala Gly Val Phe Gln Ala Leu
65                  70                  75                  80

Pro Tyr Leu Glu His Leu Asn Leu Ala His Asn Arg Leu Ala Thr Gly
                85                  90                  95

Met Ala Leu Asn Ser Gly Gly Leu Gly Arg Leu Pro Leu Leu Val Ser
            100                 105                 110

Leu Asp Leu Ser Gly Asn Ser Leu His Gly Asn Leu Val Glu Arg Leu
        115                 120                 125

Leu Gly Glu Thr Pro Arg Leu Arg Thr Leu Ser Leu Ala Glu Asn Ser
    130                 135                 140

Leu Thr Arg Leu Ala Arg His Thr Phe Trp Gly Met Pro Ala Val Glu
145                 150                 155                 160

Gln Leu Asp Leu His Ser Asn Val Leu Met Asp Ile Glu Asp Gly Ala
                165                 170                 175

Phe Glu Ala Leu Pro His Leu Thr His Leu Asn Leu Ser Arg Asn Ser
            180                 185                 190

Leu Thr Cys Ile Ser Asp Phe Ser Leu Gln Gln Leu Gln Val Leu Asp
        195                 200                 205

Leu Ser Cys Asn Ser Ile Glu Ala Phe Gln Thr Ala Pro Glu Pro Gln
    210                 215                 220

Ala Gln Phe Gln Leu Ala Trp Leu Asp Leu Arg Glu Asn Lys Leu Leu
225                 230                 235                 240

His Phe Pro Asp Leu Ala Val Phe Pro Arg Leu Ile Tyr Leu Asn Val
                245                 250                 255

Ser Asn Asn Leu Ile Gln Leu Pro Ala Gly Leu Pro Arg Gly Ser Glu
            260                 265                 270

Asp Leu His Ala Pro Ser Glu Gly Trp Ser Ala Ser Pro Leu Ser Asn
        275                 280                 285

Pro Ser Arg Asn Ala Ser Thr His Pro Leu Ser Gln Leu Leu Asn Leu
    290                 295                 300

Asp Leu Ser Tyr Asn Glu Ile Glu Leu Val Pro Ala Ser Phe Leu Glu
305                 310                 315                 320

His Leu Thr Ser Leu Arg Phe Leu Asn Leu Ser Arg Asn Cys Leu Arg
                325                 330                 335

Ser Phe Glu Ala Arg Gln Val Asp Ser Leu Pro Cys Leu Val Leu Leu
            340                 345                 350

Asp Leu Ser His Asn Val Leu Glu Ala Leu Glu Leu Gly Thr Lys Val
        355                 360                 365
```

```
Leu Gly Ser Leu Gln Thr Leu Leu Gln Asp Asn Ala Leu Gln Glu
        370                 375                 380

Leu Pro Pro Tyr Thr Phe Ala Ser Leu Ala Ser Leu Gln Arg Leu Asn
385                 390                 395                 400

Leu Gln Gly Asn Gln Val Ser Pro Cys Gly Gly Pro Ala Glu Pro Gly
                405                 410                 415

Pro Pro Gly Cys Val Asp Phe Ser Gly Ile Pro Thr Leu His Val Leu
            420                 425                 430

Asn Met Ala Gly Asn Ser Met Gly Met Leu Arg Ala Gly Ser Phe Leu
            435                 440                 445

His Thr Pro Leu Thr Glu Leu Asp Leu Ser Thr Asn Pro Gly Leu Asp
        450                 455                 460

Val Ala Thr Gly Ala Leu Val Gly Leu Glu Ala Ser Leu Glu Val Leu
465                 470                 475                 480

Glu Leu Gln Gly Asn Gly Leu Thr Val Leu Arg Val Asp Leu Pro Cys
                485                 490                 495

Phe Leu Arg Leu Lys Arg Leu Asn Leu Ala Glu Asn Gln Leu Ser His
            500                 505                 510

Leu Pro Ala Trp Thr Arg Ala Val Ser Leu Glu Val Leu Asp Leu Arg
        515                 520                 525

Asn Asn Ser Phe Ser Leu Leu Pro Gly Asn Ala Met Gly Gly Leu Glu
        530                 535                 540

Thr Ser Leu Arg Arg Leu Tyr Leu Gln Gly Asn Pro Leu Ser Cys Cys
545                 550                 555                 560

Gly Asn Gly Trp Leu Ala Ala Gln Leu His Gln Gly Arg Val Asp Val
                565                 570                 575

Asp Ala Thr Gln Asp Leu Ile Cys Arg Phe Gly Ser Gln Glu Glu Leu
            580                 585                 590

Ser Leu Ser Leu Val Arg Pro Glu Asp Cys Glu Lys Gly Gly Leu Lys
        595                 600                 605

Asn Val Asn
    610

<210> SEQ ID NO 50
<211> LENGTH: 1375
<212> TYPE: PRT
<213> ORGANISM: Artificial Sequence
<220> FEATURE:
<223> OTHER INFORMATION: Synthetic: LTBP1S

<400> SEQUENCE: 50

Asn His Thr Gly Arg Ile Lys Val Val Phe Thr Pro Ser Ile Cys Lys
1               5                   10                  15

Val Thr Cys Thr Lys Gly Ser Cys Gln Asn Ser Cys Glu Lys Gly Asn
                20                  25                  30

Thr Thr Thr Leu Ile Ser Glu Asn Gly His Ala Ala Asp Thr Leu Thr
            35                  40                  45

Ala Thr Asn Phe Arg Val Val Ile Cys His Leu Pro Cys Met Asn Gly
        50                  55                  60

Gly Gln Cys Ser Ser Arg Asp Lys Cys Gln Cys Pro Pro Asn Phe Thr
65                  70                  75                  80

Gly Lys Leu Cys Gln Ile Pro Val His Gly Ala Ser Val Pro Lys Leu
                85                  90                  95

Tyr Gln His Ser Gln Gln Pro Gly Lys Ala Leu Gly Thr His Val Ile
                100                 105                 110
```

```
His Ser Thr His Thr Leu Pro Leu Thr Val Thr Ser Gln Gln Gly Val
        115                 120                 125

Lys Val Lys Phe Pro Pro Asn Ile Val Asn Ile His Val Lys His Pro
130                 135                 140

Pro Glu Ala Ser Val Gln Ile His Gln Val Ser Arg Ile Asp Gly Pro
145                 150                 155                 160

Thr Gly Gln Lys Thr Lys Glu Ala Gln Pro Gly Gln Ser Gln Val Ser
                165                 170                 175

Tyr Gln Gly Leu Pro Val Gln Lys Thr Gln Thr Ile His Ser Thr Tyr
                180                 185                 190

Ser His Gln Gln Val Ile Pro His Val Tyr Pro Val Ala Ala Lys Thr
                195                 200                 205

Gln Leu Gly Arg Cys Phe Gln Glu Thr Ile Gly Ser Gln Cys Gly Lys
                210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Pro Ser
                    245                 250                 255

Tyr His Gly Tyr Asn Gln Met Met Glu Cys Leu Pro Gly Tyr Lys Arg
                260                 265                 270

Val Asn Asn Thr Phe Cys Gln Asp Ile Asn Glu Cys Gln Leu Gln Gly
                275                 280                 285

Val Cys Pro Asn Gly Glu Cys Leu Asn Thr Met Gly Ser Tyr Arg Cys
                290                 295                 300

Thr Cys Lys Ile Gly Phe Gly Pro Asp Pro Thr Phe Ser Ser Cys Val
305                 310                 315                 320

Pro Asp Pro Pro Val Ile Ser Glu Glu Lys Gly Pro Cys Tyr Arg Leu
                325                 330                 335

Val Ser Ser Gly Arg Gln Cys Met His Pro Leu Ser Val His Leu Thr
                340                 345                 350

Lys Gln Leu Cys Cys Cys Ser Val Gly Lys Ala Trp Gly Pro His Cys
                355                 360                 365

Glu Lys Cys Pro Leu Pro Gly Thr Ala Ala Phe Lys Glu Ile Cys Pro
                370                 375                 380

Gly Gly Met Gly Tyr Thr Val Ser Gly Val His Arg Arg Arg Pro Ile
385                 390                 395                 400

His His His Val Gly Lys Gly Pro Val Phe Val Lys Pro Lys Asn Thr
                405                 410                 415

Gln Pro Val Ala Lys Ser Thr His Pro Pro Leu Pro Ala Lys Glu
                420                 425                 430

Glu Pro Val Glu Ala Leu Thr Phe Ser Arg Glu His Gly Pro Gly Val
                435                 440                 445

Ala Glu Pro Glu Val Ala Thr Ala Pro Pro Glu Lys Glu Ile Pro Ser
450                 455                 460

Leu Asp Gln Glu Lys Thr Lys Leu Glu Pro Gly Gln Pro Gln Leu Ser
465                 470                 475                 480

Pro Gly Ile Ser Thr Ile His Leu His Pro Gln Phe Pro Val Val Ile
                485                 490                 495

Glu Lys Thr Ser Pro Pro Val Pro Val Glu Val Ala Pro Glu Ala Ser
                500                 505                 510

Thr Ser Ser Ala Ser Gln Val Ile Ala Pro Thr Gln Val Thr Glu Ile
                515                 520                 525
```

-continued

```
Asn Glu Cys Thr Val Asn Pro Asp Ile Cys Gly Ala Gly His Cys Ile
    530                 535                 540

Asn Leu Pro Val Arg Tyr Thr Cys Ile Cys Tyr Glu Gly Tyr Arg Phe
545                 550                 555                 560

Ser Glu Gln Gln Arg Lys Cys Val Asp Ile Asp Glu Cys Thr Gln Val
                565                 570                 575

Gln His Leu Cys Ser Gln Gly Arg Cys Glu Asn Thr Glu Gly Ser Phe
            580                 585                 590

Leu Cys Ile Cys Pro Ala Gly Phe Met Ala Ser Glu Glu Gly Thr Asn
        595                 600                 605

Cys Ile Asp Val Asp Glu Cys Leu Arg Pro Asp Val Cys Gly Glu Gly
    610                 615                 620

His Cys Val Asn Thr Val Gly Ala Phe Arg Cys Glu Tyr Cys Asp Ser
625                 630                 635                 640

Gly Tyr Arg Met Thr Gln Arg Gly Arg Cys Glu Asp Ile Asp Glu Cys
                645                 650                 655

Leu Asn Pro Ser Thr Cys Pro Asp Glu Gln Cys Val Asn Ser Pro Gly
            660                 665                 670

Ser Tyr Gln Cys Val Pro Cys Thr Glu Gly Phe Arg Gly Trp Asn Gly
        675                 680                 685

Gln Cys Leu Asp Val Asp Glu Cys Leu Glu Pro Asn Val Cys Ala Asn
    690                 695                 700

Gly Asp Cys Ser Asn Leu Glu Gly Ser Tyr Met Cys Ser Cys His Lys
705                 710                 715                 720

Gly Tyr Thr Arg Thr Pro Asp His Lys His Cys Arg Asp Ile Asp Glu
                725                 730                 735

Cys Gln Gln Gly Asn Leu Cys Val Asn Gly Gln Cys Lys Asn Thr Glu
            740                 745                 750

Gly Ser Phe Arg Cys Thr Cys Gly Gln Gly Tyr Gln Leu Ser Ala Ala
        755                 760                 765

Lys Asp Gln Cys Glu Asp Ile Asp Glu Cys Gln His Arg His Leu Cys
    770                 775                 780

Ala His Gly Gln Cys Arg Asn Thr Glu Gly Ser Phe Gln Cys Val Cys
785                 790                 795                 800

Asp Gln Gly Tyr Arg Ala Ser Gly Leu Gly Asp His Cys Glu Asp Ile
                805                 810                 815

Asn Glu Cys Leu Glu Asp Lys Ser Val Cys Gln Arg Gly Asp Cys Ile
            820                 825                 830

Asn Thr Ala Gly Ser Tyr Asp Cys Thr Cys Pro Asp Gly Phe Gln Leu
        835                 840                 845

Asp Asp Asn Lys Thr Cys Gln Asp Ile Asn Glu Cys Glu His Pro Gly
    850                 855                 860

Leu Cys Gly Pro Gln Gly Glu Cys Leu Asn Thr Glu Gly Ser Phe His
865                 870                 875                 880

Cys Val Cys Gln Gln Gly Phe Ser Ile Ser Ala Asp Gly Arg Thr Cys
                885                 890                 895

Glu Asp Ile Asp Glu Cys Val Asn Asn Thr Val Cys Asp Ser His Gly
            900                 905                 910

Phe Cys Asp Asn Thr Ala Gly Ser Phe Arg Cys Leu Cys Tyr Gln Gly
        915                 920                 925

Phe Gln Ala Pro Gln Asp Gly Gln Gly Cys Val Asp Val Asn Glu Cys
    930                 935                 940

Glu Leu Leu Ser Gly Val Cys Gly Glu Ala Phe Cys Glu Asn Val Glu
```

-continued

```
945                 950                 955                 960
Gly Ser Phe Leu Cys Val Cys Ala Asp Glu Asn Gln Glu Tyr Ser Pro
                965                 970                 975
Met Thr Gly Gln Cys Arg Ser Arg Thr Ser Thr Asp Leu Asp Val Asp
            980                 985                 990
Val Asp Gln Pro Lys Glu Glu Lys Lys Glu Cys Tyr Tyr Asn Leu Asn
        995                 1000                1005
Asp Ala Ser Leu Cys Asp Asn Val Leu Ala Pro Asn Val Thr Lys
    1010                1015                1020
Gln Glu Cys Cys Cys Thr Ser Gly Val Gly Trp Gly Asp Asn Cys
    1025                1030                1035
Glu Ile Phe Pro Cys Pro Val Leu Gly Thr Ala Glu Phe Thr Glu
    1040                1045                1050
Met Cys Pro Lys Gly Lys Gly Phe Val Pro Ala Gly Glu Ser Ser
    1055                1060                1065
Ser Glu Ala Gly Gly Glu Asn Tyr Lys Asp Ala Glu Cys Leu
    1070                1075                1080
Leu Phe Gly Gln Glu Ile Cys Lys Asn Gly Phe Cys Leu Asn Thr
    1085                1090                1095
Arg Pro Gly Tyr Glu Cys Tyr Cys Lys Gln Gly Thr Tyr Tyr Asp
    1100                1105                1110
Pro Val Lys Leu Gln Cys Phe Asp Met Asp Glu Cys Gln Asp Pro
    1115                1120                1125
Ser Ser Cys Ile Asp Gly Gln Cys Val Asn Thr Glu Gly Ser Tyr
    1130                1135                1140
Asn Cys Phe Cys Thr His Pro Met Val Leu Asp Ala Ser Glu Lys
    1145                1150                1155
Arg Cys Ile Arg Pro Ala Glu Ser Asn Glu Gln Ile Glu Glu Thr
    1160                1165                1170
Asp Val Tyr Gln Asp Leu Cys Trp Glu His Leu Ser Asp Glu Tyr
    1175                1180                1185
Val Cys Ser Arg Pro Leu Val Gly Lys Gln Thr Thr Tyr Thr Glu
    1190                1195                1200
Cys Cys Cys Leu Tyr Gly Glu Ala Trp Gly Met Gln Cys Ala Leu
    1205                1210                1215
Cys Pro Leu Lys Asp Ser Asp Tyr Ala Gln Leu Cys Asn Ile
    1220                1225                1230
Pro Val Thr Gly Arg Arg Gln Pro Tyr Gly Arg Asp Ala Leu Val
    1235                1240                1245
Asp Phe Ser Glu Gln Tyr Thr Pro Glu Ala Asp Pro Tyr Phe Ile
    1250                1255                1260
Gln Asp Arg Phe Leu Asn Ser Phe Glu Glu Leu Gln Ala Glu Glu
    1265                1270                1275
Cys Gly Ile Leu Asn Gly Cys Glu Asn Gly Arg Cys Val Arg Val
    1280                1285                1290
Gln Glu Gly Tyr Thr Cys Asp Cys Phe Asp Gly Tyr His Leu Asp
    1295                1300                1305
Thr Ala Lys Met Thr Cys Val Asp Val Asn Glu Cys Asp Glu Leu
    1310                1315                1320
Asn Asn Arg Met Ser Leu Cys Lys Asn Ala Lys Cys Ile Asn Thr
    1325                1330                1335
Asp Gly Ser Tyr Lys Cys Leu Cys Leu Pro Gly Tyr Val Pro Ser
    1340                1345                1350
```

Asp Lys Pro Asn Tyr Cys Thr Pro Leu Asn Thr Ala Leu Asn Leu
    1355                1360                1365

Glu Lys Asp Ser Asp Leu Glu
    1370            1375

<210> SEQ ID NO 51
<211> LENGTH: 1260
<212> TYPE: PRT
<213> ORGANISM: Artificial Sequence
<220> FEATURE:
<223> OTHER INFORMATION: Synthetic: LTBP3

<400> SEQUENCE: 51

Gly Pro Ala Gly Glu Arg Gly Ala Gly Gly Gly Ala Leu Ala Arg
1               5                   10                  15

Glu Arg Phe Lys Val Val Phe Ala Pro Val Ile Cys Lys Arg Thr Cys
                20                  25                  30

Leu Lys Gly Gln Cys Arg Asp Ser Cys Gln Gln Gly Ser Asn Met Thr
            35                  40                  45

Leu Ile Gly Glu Asn Gly His Ser Thr Asp Thr Leu Thr Gly Ser Gly
        50                  55                  60

Phe Arg Val Val Val Cys Pro Leu Pro Cys Met Asn Gly Gly Gln Cys
65              70                  75                  80

Ser Ser Arg Asn Gln Cys Leu Cys Pro Pro Asp Phe Thr Gly Arg Phe
                85                  90                  95

Cys Gln Val Pro Ala Gly Gly Ala Gly Gly Thr Gly Gly Ser Gly
                100                 105                 110

Pro Gly Leu Ser Arg Thr Gly Ala Leu Ser Thr Gly Ala Leu Pro Pro
            115                 120                 125

Leu Ala Pro Glu Gly Asp Ser Val Ala Ser Lys His Ala Ile Tyr Ala
        130                 135                 140

Val Gln Val Ile Ala Asp Pro Pro Gly Pro Gly Glu Gly Pro Pro Ala
145             150                 155                 160

Gln His Ala Ala Phe Leu Val Pro Leu Gly Pro Gly Gln Ile Ser Ala
                165                 170                 175

Glu Val Gln Ala Pro Pro Pro Val Val Asn Val Arg Val His His Pro
                180                 185                 190

Pro Glu Ala Ser Val Gln Val His Arg Ile Glu Ser Ser Asn Ala Glu
            195                 200                 205

Ser Ala Ala Pro Ser Gln His Leu Leu Pro His Pro Lys Pro Ser His
        210                 215                 220

Pro Arg Pro Pro Thr Gln Lys Pro Leu Gly Arg Cys Phe Gln Asp Thr
225             230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
                260                 265                 270

Cys His Lys Cys Pro Gln Leu Gln Tyr Thr Gly Val Gln Lys Pro Gly
            275                 280                 285

Pro Val Arg Gly Glu Val Gly Ala Asp Cys Pro Gln Gly Tyr Lys Arg
        290                 295                 300

Leu Asn Ser Thr His Cys Gln Asp Ile Asn Glu Cys Ala Met Pro Gly
305             310                 315                 320

Val Cys Arg His Gly Asp Cys Leu Asn Asn Pro Gly Ser Tyr Arg Cys
                325                 330                 335

```
Val Cys Pro Pro Gly His Ser Leu Gly Pro Ser Arg Thr Gln Cys Ile
                340                 345                 350

Ala Asp Lys Pro Glu Glu Lys Ser Leu Cys Phe Arg Leu Val Ser Pro
                355                 360                 365

Glu His Gln Cys Gln His Pro Leu Thr Thr Arg Leu Thr Arg Gln Leu
        370                 375                 380

Cys Cys Cys Ser Val Gly Lys Ala Trp Gly Ala Arg Cys Gln Arg Cys
385                 390                 395                 400

Pro Thr Asp Gly Thr Ala Ala Phe Lys Glu Ile Cys Pro Ala Gly Lys
                405                 410                 415

Gly Tyr His Ile Leu Thr Ser His Gln Thr Leu Thr Ile Gln Gly Glu
                420                 425                 430

Ser Asp Phe Ser Leu Phe Leu His Pro Asp Gly Pro Pro Lys Pro Gln
            435                 440                 445

Gln Leu Pro Glu Ser Pro Ser Gln Ala Pro Pro Glu Asp Thr Glu
        450                 455                 460

Glu Glu Arg Gly Val Thr Thr Asp Ser Pro Val Ser Glu Glu Arg Ser
465                 470                 475                 480

Val Gln Gln Ser His Pro Thr Ala Thr Thr Pro Ala Arg Pro Tyr
                485                 490                 495

Pro Glu Leu Ile Ser Arg Pro Ser Pro Pro Thr Met Arg Trp Phe Leu
                500                 505                 510

Pro Asp Leu Pro Pro Ser Arg Ser Ala Val Glu Ile Ala Pro Thr Gln
            515                 520                 525

Val Thr Glu Thr Asp Glu Cys Arg Leu Asn Gln Asn Ile Cys Gly His
            530                 535                 540

Gly Glu Cys Val Pro Gly Pro Pro Asp Tyr Ser Cys His Cys Asn Pro
545                 550                 555                 560

Gly Tyr Arg Ser His Pro Gln His Arg Tyr Cys Val Asp Val Asn Glu
                565                 570                 575

Cys Glu Ala Glu Pro Cys Gly Pro Gly Arg Gly Ile Cys Met Asn Thr
            580                 585                 590

Gly Gly Ser Tyr Asn Cys His Cys Asn Arg Gly Tyr Arg Leu His Val
                595                 600                 605

Gly Ala Gly Gly Arg Ser Cys Val Asp Leu Asn Glu Cys Ala Lys Pro
            610                 615                 620

His Leu Cys Gly Asp Gly Gly Phe Cys Ile Asn Phe Pro Gly His Tyr
625                 630                 635                 640

Lys Cys Asn Cys Tyr Pro Gly Tyr Arg Leu Lys Ala Ser Arg Pro Pro
                645                 650                 655

Val Cys Glu Asp Ile Asp Glu Cys Arg Asp Pro Ser Ser Cys Pro Asp
                660                 665                 670

Gly Lys Cys Glu Asn Lys Pro Gly Ser Phe Lys Cys Ile Ala Cys Gln
            675                 680                 685

Pro Gly Tyr Arg Ser Gln Gly Gly Ala Cys Arg Asp Val Asn Glu
        690                 695                 700

Cys Ala Glu Gly Ser Pro Cys Ser Pro Gly Trp Cys Glu Asn Leu Pro
705                 710                 715                 720

Gly Ser Phe Arg Cys Thr Cys Ala Gln Gly Tyr Ala Pro Ala Pro Asp
                725                 730                 735

Gly Arg Ser Cys Leu Asp Val Asp Glu Cys Glu Ala Gly Asp Val Cys
                740                 745                 750
```

```
Asp Asn Gly Ile Cys Ser Asn Thr Pro Gly Ser Phe Gln Cys Gln Cys
        755                 760                 765

Leu Ser Gly Tyr His Leu Ser Arg Asp Arg Ser His Cys Glu Asp Ile
    770                 775                 780

Asp Glu Cys Asp Phe Pro Ala Ala Cys Ile Gly Gly Asp Cys Ile Asn
785                 790                 795                 800

Thr Asn Gly Ser Tyr Arg Cys Leu Cys Pro Gln Gly His Arg Leu Val
            805                 810                 815

Gly Gly Arg Lys Cys Gln Asp Ile Asp Glu Cys Ser Gln Asp Pro Ser
        820                 825                 830

Leu Cys Leu Pro His Gly Ala Cys Lys Asn Leu Gln Gly Ser Tyr Val
        835                 840                 845

Cys Val Cys Asp Glu Gly Phe Thr Pro Thr Gln Asp Gln His Gly Cys
        850                 855                 860

Glu Glu Val Glu Gln Pro His His Lys Lys Glu Cys Tyr Leu Asn Phe
865                 870                 875                 880

Asp Asp Thr Val Phe Cys Asp Ser Val Leu Ala Thr Asn Val Thr Gln
                885                 890                 895

Gln Glu Cys Cys Cys Ser Leu Gly Ala Gly Trp Gly Asp His Cys Glu
            900                 905                 910

Ile Tyr Pro Cys Pro Val Tyr Ser Ser Ala Glu Phe His Ser Leu Cys
        915                 920                 925

Pro Asp Gly Lys Gly Tyr Thr Gln Asp Asn Asn Ile Val Asn Tyr Gly
        930                 935                 940

Ile Pro Ala His Arg Asp Ile Asp Glu Cys Met Leu Phe Gly Ser Glu
945                 950                 955                 960

Ile Cys Lys Glu Gly Lys Cys Val Asn Thr Gln Pro Gly Tyr Glu Cys
            965                 970                 975

Tyr Cys Lys Gln Gly Phe Tyr Tyr Asp Gly Asn Leu Leu Glu Cys Val
                980                 985                 990

Asp Val Asp Glu Cys Leu Asp Glu  Ser Asn Cys Arg Asn  Gly Val Cys
            995                 1000                1005

Glu Asn  Thr Arg Gly Gly Tyr  Arg Cys Ala Cys Thr  Pro Pro Ala
    1010                1015                1020

Glu Tyr  Ser Pro Ala Gln Arg  Gln Cys Leu Ser Pro  Glu Glu Met
    1025                1030                1035

Asp Val  Asp Glu Cys Gln Asp  Pro Ala Ala Cys Arg  Pro Gly Arg
    1040                1045                1050

Cys Val  Asn Leu Pro Gly Ser  Tyr Arg Cys Glu Cys  Arg Pro Pro
    1055                1060                1065

Trp Val  Pro Gly Pro Ser Gly  Arg Asp Cys Gln Leu  Pro Glu Ser
    1070                1075                1080

Pro Ala  Glu Arg Ala Pro Glu  Arg Arg Asp Val Cys  Trp Ser Gln
    1085                1090                1095

Arg Gly  Glu Asp Gly Met Cys  Ala Gly Pro Leu Ala  Gly Pro Ala
    1100                1105                1110

Leu Thr  Phe Asp Asp Cys Cys  Cys Arg Gln Gly Arg  Gly Trp Gly
    1115                1120                1125

Ala Gln  Cys Arg Pro Cys Pro  Pro Arg Gly Ala Gly  Ser His Cys
    1130                1135                1140

Pro Thr  Ser Gln Ser Glu Ser  Asn Ser Phe Trp Asp  Thr Ser Pro
    1145                1150                1155

Leu Leu  Leu Gly Lys Pro Pro  Arg Asp Glu Asp Ser  Ser Glu Glu
```

```
                 1160                1165                1170

Asp Ser  Asp Glu Cys Arg  Cys Val Ser Gly  Arg Cys Val Pro Arg
     1175                1180                1185

Pro Gly  Gly Ala Val Cys  Glu Cys Pro Gly  Gly Phe Gln Leu Asp
     1190                1195                1200

Ala Ser  Arg Ala Arg Cys  Val Asp Ile Asp  Glu Cys Arg Glu Leu
     1205                1210                1215

Asn Gln  Arg Gly Leu Leu  Cys Lys Ser Glu  Arg Cys Val Asn Thr
     1220                1225                1230

Ser Gly  Ser Phe Arg Cys  Val Cys Lys Ala  Gly Phe Ala Arg Ser
     1235                1240                1245

Arg Pro  His Gly Ala Cys  Val Pro Gln Arg  Arg Arg
     1250                1255                1260

<210> SEQ ID NO 52
<211> LENGTH: 645
<212> TYPE: PRT
<213> ORGANISM: Artificial Sequence
<220> FEATURE:
<223> OTHER INFORMATION: Synthetic: GARP

<400> SEQUENCE: 52

Ala Gln His Gln Asp Lys Val Pro Cys Lys Met Val Asp Lys Lys Val
1               5                   10                  15

Ser Cys Gln Val Leu Gly Leu Leu Gln Val Pro Ser Val Leu Pro Pro
            20                  25                  30

Asp Thr Glu Thr Leu Asp Leu Ser Gly Asn Gln Leu Arg Ser Ile Leu
        35                  40                  45

Ala Ser Pro Leu Gly Phe Tyr Thr Ala Leu Arg His Leu Asp Leu Ser
    50                  55                  60

Thr Asn Glu Ile Ser Phe Leu Gln Pro Gly Ala Phe Gln Ala Leu Thr
65                  70                  75                  80

His Leu Glu His Leu Ser Leu Ala His Asn Arg Leu Ala Met Ala Thr
                85                  90                  95

Ala Leu Ser Ala Gly Gly Leu Gly Pro Leu Pro Arg Val Thr Ser Leu
            100                 105                 110

Asp Leu Ser Gly Asn Ser Leu Tyr Ser Gly Leu Leu Glu Arg Leu Leu
        115                 120                 125

Gly Glu Ala Pro Ser Leu His Thr Leu Ser Leu Ala Glu Asn Ser Leu
130                 135                 140

Thr Arg Leu Thr Arg His Thr Phe Arg Asp Met Pro Ala Leu Glu Gln
145                 150                 155                 160

Leu Asp Leu His Ser Asn Val Leu Met Asp Ile Glu Asp Gly Ala Phe
                165                 170                 175

Glu Gly Leu Pro Arg Leu Thr His Leu Asn Leu Ser Arg Asn Ser Leu
            180                 185                 190

Thr Cys Ile Ser Asp Phe Ser Leu Gln Gln Leu Arg Val Leu Asp Leu
        195                 200                 205

Ser Cys Asn Ser Ile Glu Ala Phe Gln Thr Ala Ser Gln Pro Gln Ala
    210                 215                 220

Glu Phe Gln Leu Thr Trp Leu Asp Leu Arg Glu Asn Lys Leu Leu His
225                 230                 235                 240

Phe Pro Asp Leu Ala Ala Leu Pro Arg Leu Ile Tyr Leu Asn Leu Ser
                245                 250                 255

Asn Asn Leu Ile Arg Leu Pro Thr Gly Pro Pro Gln Asp Ser Lys Gly
```

```
                260                 265                 270
Ile His Ala Pro Ser Glu Gly Trp Ser Ala Leu Pro Leu Ser Ala Pro
            275                 280                 285

Ser Gly Asn Ala Ser Gly Arg Pro Leu Ser Gln Leu Leu Asn Leu Asp
290                 295                 300

Leu Ser Tyr Asn Glu Ile Glu Leu Ile Pro Asp Ser Phe Leu Glu His
305                 310                 315                 320

Leu Thr Ser Leu Cys Phe Leu Asn Leu Ser Arg Asn Cys Leu Arg Thr
                325                 330                 335

Phe Glu Ala Arg Arg Leu Gly Ser Leu Pro Cys Leu Met Leu Leu Asp
            340                 345                 350

Leu Ser His Asn Ala Leu Glu Thr Leu Glu Leu Gly Ala Arg Ala Leu
            355                 360                 365

Gly Ser Leu Arg Thr Leu Leu Leu Gln Gly Asn Ala Leu Arg Asp Leu
        370                 375                 380

Pro Pro Tyr Thr Phe Ala Asn Leu Ala Ser Leu Gln Arg Leu Asn Leu
385                 390                 395                 400

Gln Gly Asn Arg Val Ser Pro Cys Gly Gly Pro Asp Glu Pro Gly Pro
                405                 410                 415

Ser Gly Cys Val Ala Phe Ser Gly Ile Thr Ser Leu Arg Ser Leu Ser
            420                 425                 430

Leu Val Asp Asn Glu Ile Glu Leu Leu Arg Ala Gly Ala Phe Leu His
        435                 440                 445

Thr Pro Leu Thr Glu Leu Asp Leu Ser Ser Asn Pro Gly Leu Glu Val
    450                 455                 460

Ala Thr Gly Ala Leu Gly Gly Leu Glu Ala Ser Leu Glu Val Leu Ala
465                 470                 475                 480

Leu Gln Gly Asn Gly Leu Met Val Leu Gln Val Asp Leu Pro Cys Phe
                485                 490                 495

Ile Cys Leu Lys Arg Leu Asn Leu Ala Glu Asn Arg Leu Ser His Leu
            500                 505                 510

Pro Ala Trp Thr Gln Ala Val Ser Leu Glu Val Leu Asp Leu Arg Asn
            515                 520                 525

Asn Ser Phe Ser Leu Leu Pro Gly Ser Ala Met Gly Gly Leu Glu Thr
        530                 535                 540

Ser Leu Arg Arg Leu Tyr Leu Gln Gly Asn Pro Leu Ser Cys Cys Gly
545                 550                 555                 560

Asn Gly Trp Leu Ala Ala Gln Leu His Gln Gly Arg Val Asp Val Asp
                565                 570                 575

Ala Thr Gln Asp Leu Ile Cys Arg Phe Ser Ser Gln Glu Glu Val Ser
            580                 585                 590

Leu Ser His Val Arg Pro Glu Asp Cys Glu Lys Gly Gly Leu Lys Asn
            595                 600                 605

Ile Asn Leu Ile Ile Ile Leu Thr Phe Ile Leu Val Ser Ala Ile Leu
        610                 615                 620

Leu Thr Thr Leu Ala Ala Cys Cys Cys Val Arg Arg Gln Lys Phe Asn
625                 630                 635                 640

Gln Gln Tyr Lys Ala
                645

<210> SEQ ID NO 53
<211> LENGTH: 610
<212> TYPE: PRT
<213> ORGANISM: Artificial Sequence
```

<220> FEATURE:
<223> OTHER INFORMATION: Synthetic: sGARP

<400> SEQUENCE: 53

```
Ala Gln His Gln Asp Lys Val Pro Cys Lys Met Val Asp Lys Lys Val
1               5                   10                  15
Ser Cys Gln Val Leu Gly Leu Leu Gln Val Pro Ser Val Leu Pro Pro
            20                  25                  30
Asp Thr Glu Thr Leu Asp Leu Ser Gly Asn Gln Leu Arg Ser Ile Leu
        35                  40                  45
Ala Ser Pro Leu Gly Phe Tyr Thr Ala Leu Arg His Leu Asp Leu Ser
    50                  55                  60
Thr Asn Glu Ile Ser Phe Leu Gln Pro Gly Ala Phe Gln Ala Leu Thr
65                  70                  75                  80
His Leu Glu His Leu Ser Leu Ala His Asn Arg Leu Ala Met Ala Thr
                85                  90                  95
Ala Leu Ser Ala Gly Gly Leu Gly Pro Leu Pro Arg Val Thr Ser Leu
            100                 105                 110
Asp Leu Ser Gly Asn Ser Leu Tyr Ser Gly Leu Leu Glu Arg Leu Leu
        115                 120                 125
Gly Glu Ala Pro Ser Leu His Thr Leu Ser Leu Ala Glu Asn Ser Leu
    130                 135                 140
Thr Arg Leu Thr Arg His Thr Phe Arg Asp Met Pro Ala Leu Glu Gln
145                 150                 155                 160
Leu Asp Leu His Ser Asn Val Leu Met Asp Ile Glu Asp Gly Ala Phe
                165                 170                 175
Glu Gly Leu Pro Arg Leu Thr His Leu Asn Leu Ser Arg Asn Ser Leu
            180                 185                 190
Thr Cys Ile Ser Asp Phe Ser Leu Gln Gln Leu Arg Val Leu Asp Leu
        195                 200                 205
Ser Cys Asn Ser Ile Glu Ala Phe Gln Thr Ala Ser Gln Pro Gln Ala
    210                 215                 220
Glu Phe Gln Leu Thr Trp Leu Asp Leu Arg Glu Asn Lys Leu Leu His
225                 230                 235                 240
Phe Pro Asp Leu Ala Ala Leu Pro Arg Leu Ile Tyr Leu Asn Leu Ser
                245                 250                 255
Asn Asn Leu Ile Arg Leu Pro Thr Gly Pro Pro Gln Asp Ser Lys Gly
            260                 265                 270
Ile His Ala Pro Ser Glu Gly Trp Ser Ala Leu Pro Leu Ser Ala Pro
        275                 280                 285
Ser Gly Asn Ala Ser Gly Arg Pro Leu Ser Gln Leu Leu Asn Leu Asp
    290                 295                 300
Leu Ser Tyr Asn Glu Ile Glu Leu Ile Pro Asp Ser Phe Leu Glu His
305                 310                 315                 320
Leu Thr Ser Leu Cys Phe Leu Asn Leu Ser Arg Asn Cys Leu Arg Thr
                325                 330                 335
Phe Glu Ala Arg Arg Leu Gly Ser Leu Pro Cys Leu Met Leu Leu Asp
            340                 345                 350
Leu Ser His Asn Ala Leu Glu Thr Leu Glu Leu Gly Ala Arg Ala Leu
        355                 360                 365
Gly Ser Leu Arg Thr Leu Leu Leu Gln Gly Asn Ala Leu Arg Asp Leu
    370                 375                 380
Pro Pro Tyr Thr Phe Ala Asn Leu Ala Ser Leu Gln Arg Leu Asn Leu
385                 390                 395                 400
```

```
Gln Gly Asn Arg Val Ser Pro Cys Gly Pro Asp Glu Pro Gly Pro
                405                 410                 415
Ser Gly Cys Val Ala Phe Ser Gly Ile Thr Ser Leu Arg Ser Leu Ser
            420                 425                 430
Leu Val Asp Asn Glu Ile Glu Leu Leu Arg Ala Gly Ala Phe Leu His
        435                 440                 445
Thr Pro Leu Thr Glu Leu Asp Leu Ser Ser Asn Pro Gly Leu Glu Val
    450                 455                 460
Ala Thr Gly Ala Leu Gly Gly Leu Glu Ala Ser Leu Glu Val Leu Ala
465                 470                 475                 480
Leu Gln Gly Asn Gly Leu Met Val Leu Gln Val Asp Leu Pro Cys Phe
                485                 490                 495
Ile Cys Leu Lys Arg Leu Asn Leu Ala Glu Asn Arg Leu Ser His Leu
            500                 505                 510
Pro Ala Trp Thr Gln Ala Val Ser Leu Glu Val Leu Asp Leu Arg Asn
        515                 520                 525
Asn Ser Phe Ser Leu Leu Pro Gly Ser Ala Met Gly Gly Leu Glu Thr
    530                 535                 540
Ser Leu Arg Arg Leu Tyr Leu Gln Gly Asn Pro Leu Ser Cys Cys Gly
545                 550                 555                 560
Asn Gly Trp Leu Ala Ala Gln Leu His Gln Gly Arg Val Asp Val Asp
                565                 570                 575
Ala Thr Gln Asp Leu Ile Cys Arg Phe Ser Ser Gln Glu Glu Val Ser
            580                 585                 590
Leu Ser His Val Arg Pro Glu Asp Cys Glu Lys Gly Gly Leu Lys Asn
        595                 600                 605
Ile Asn
    610

<210> SEQ ID NO 54
<211> LENGTH: 5
<212> TYPE: PRT
<213> ORGANISM: Artificial Sequence
<220> FEATURE:
<223> OTHER INFORMATION: Synthetic: Hinge sequence

<400> SEQUENCE: 54

Cys Pro Pro Cys Pro
1               5

<210> SEQ ID NO 55
<211> LENGTH: 13
<212> TYPE: PRT
<213> ORGANISM: Artificial Sequence
<220> FEATURE:
<223> OTHER INFORMATION: Synthetic

<400> SEQUENCE: 55

Ala Ser Thr Lys Gly Pro Ser Val Phe Pro Leu Ala Pro
1               5                   10

<210> SEQ ID NO 56
<211> LENGTH: 6
<212> TYPE: PRT
<213> ORGANISM: Artificial Sequence
<220> FEATURE:
<223> OTHER INFORMATION: Synthetic

<400> SEQUENCE: 56
```

```
Ala Ser Thr Lys Gly Pro
1               5

<210> SEQ ID NO 57
<211> LENGTH: 12
<212> TYPE: PRT
<213> ORGANISM: Artificial Sequence
<220> FEATURE:
<223> OTHER INFORMATION: Synthetic

<400> SEQUENCE: 57

Thr Val Ala Ala Pro Ser Val Phe Ile Phe Pro Pro
1               5                   10

<210> SEQ ID NO 58
<211> LENGTH: 5
<212> TYPE: PRT
<213> ORGANISM: Artificial Sequence
<220> FEATURE:
<223> OTHER INFORMATION: Synthetic

<400> SEQUENCE: 58

Thr Val Ala Ala Pro
1               5

<210> SEQ ID NO 59
<211> LENGTH: 16
<212> TYPE: PRT
<213> ORGANISM: Artificial Sequence
<220> FEATURE:
<223> OTHER INFORMATION: Synthetic

<400> SEQUENCE: 59

Ala Lys Thr Thr Pro Lys Leu Glu Glu Gly Glu Phe Ser Glu Ala Arg
1               5                   10                  15

<210> SEQ ID NO 60
<211> LENGTH: 17
<212> TYPE: PRT
<213> ORGANISM: Artificial Sequence
<220> FEATURE:
<223> OTHER INFORMATION: Synthetic

<400> SEQUENCE: 60

Ala Lys Thr Thr Pro Lys Leu Glu Glu Gly Glu Phe Ser Glu Ala Arg
1               5                   10                  15

Val

<210> SEQ ID NO 61
<211> LENGTH: 9
<212> TYPE: PRT
<213> ORGANISM: Artificial Sequence
<220> FEATURE:
<223> OTHER INFORMATION: Synthetic

<400> SEQUENCE: 61

Ala Lys Thr Thr Pro Lys Leu Gly Gly
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic

<400> SEQUENCE: 62
```

```
Ser Ala Lys Thr Thr Pro Lys Leu Gly Gly
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Synthetic

<400> SEQUENCE: 63

Ser Ala Lys Thr Thr Pro
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic

<400> SEQUENCE: 64

Arg Ala Asp Ala Ala Pro
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Arg Ala Asp Ala Ala Pro Thr Val Ser
1               5

<210> SEQ ID NO 66
<211> LENGTH: 12
<212> TYPE: PRT
<213> ORGANISM: Artificial Sequence
<220> FEATURE:
<223> OTHER INFORMATION: Synthetic

<400> SEQUENCE: 66

Arg Ala Asp Ala Ala Ala Ala Gly Gly Pro Gly Ser
1               5                   10

<210> SEQ ID NO 67
<211> LENGTH: 27
<212> TYPE: PRT
<213> ORGANISM: Artificial Sequence
<220> FEATURE:
<223> OTHER INFORMATION: Synthetic

<400> SEQUENCE: 67

Arg Ala Asp Ala Ala Ala Ala Gly Gly Gly Gly Ser Gly Gly Gly
1               5                   10                  15

Ser Gly Gly Gly Gly Ser Gly Gly Gly Gly Ser
            20                  25

<210> SEQ ID NO 68
<211> LENGTH: 18
<212> TYPE: PRT
<213> ORGANISM: Artificial Sequence
<220> FEATURE:
<223> OTHER INFORMATION: Synthetic
```

<400> SEQUENCE: 68

Ser Ala Lys Thr Thr Pro Lys Leu Glu Glu Gly Glu Phe Ser Glu Ala
1               5                   10                  15

Arg Val

<210> SEQ ID NO 69
<211> LENGTH: 5
<212> TYPE: PRT
<213> ORGANISM: Artificial Sequence
<220> FEATURE:
<223> OTHER INFORMATION: Synthetic

<400> SEQUENCE: 69

Ala Asp Ala Ala Pro
1               5

<210> SEQ ID NO 70
<211> LENGTH: 12
<212> TYPE: PRT
<213> ORGANISM: Artificial Sequence
<220> FEATURE:
<223> OTHER INFORMATION: Synthetic

<400> SEQUENCE: 70

Ala Asp Ala Ala Pro Thr Val Ser Ile Phe Pro Pro
1               5                   10

<210> SEQ ID NO 71
<211> LENGTH: 6
<212> TYPE: PRT
<213> ORGANISM: Artificial Sequence
<220> FEATURE:
<223> OTHER INFORMATION: Synthetic

<400> SEQUENCE: 71

Gln Pro Lys Ala Ala Pro
1               5

<210> SEQ ID NO 72
<211> LENGTH: 13
<212> TYPE: PRT
<213> ORGANISM: Artificial Sequence
<220> FEATURE:
<223> OTHER INFORMATION: Synthetic

<400> SEQUENCE: 72

Gln Pro Lys Ala Ala Pro Ser Val Thr Leu Phe Pro Pro
1               5                   10

<210> SEQ ID NO 73
<211> LENGTH: 6
<212> TYPE: PRT
<213> ORGANISM: Artificial Sequence
<220> FEATURE:
<223> OTHER INFORMATION: Synthetic

<400> SEQUENCE: 73

Ala Lys Thr Thr Pro Pro
1               5

<210> SEQ ID NO 74
<211> LENGTH: 13
<212> TYPE: PRT
<213> ORGANISM: Artificial Sequence
<220> FEATURE:

```
<223> OTHER INFORMATION: Synthetic

<400> SEQUENCE: 74

Ala Lys Thr Thr Pro Pro Ser Val Thr Pro Leu Ala Pro
1               5                   10

<210> SEQ ID NO 75
<211> LENGTH: 6
<212> TYPE: PRT
<213> ORGANISM: Artificial Sequence
<220> FEATURE:
<223> OTHER INFORMATION: Synthetic

<400> SEQUENCE: 75

Ala Lys Thr Thr Ala Pro
1               5

<210> SEQ ID NO 76
<211> LENGTH: 13
<212> TYPE: PRT
<213> ORGANISM: Artificial Sequence
<220> FEATURE:
<223> OTHER INFORMATION: Synthetic

<400> SEQUENCE: 76

Ala Lys Thr Thr Ala Pro Ser Val Tyr Pro Leu Ala Pro
1               5                   10

<210> SEQ ID NO 77
<211> LENGTH: 15
<212> TYPE: PRT
<213> ORGANISM: Artificial Sequence
<220> FEATURE:
<223> OTHER INFORMATION: Synthetic

<400> SEQUENCE: 77

Gly Gly Gly Gly Ser Gly Gly Gly Ser Gly Gly Gly Gly Ser
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic

<400> SEQUENCE: 78

Gly Glu Asn Lys Val Glu Tyr Ala Pro Ala Leu Met Ala Leu Ser
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic

<400> SEQUENCE: 79

Gly Pro Ala Lys Glu Leu Thr Pro Leu Lys Glu Ala Lys Val Ser
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic
```

<400> SEQUENCE: 80

Gly His Glu Ala Ala Val Met Gln Val Gln Tyr Pro Ala Ser
1               5                   10                  15

<210> SEQ ID NO 81
<211> LENGTH: 24
<212> TYPE: PRT
<213> ORGANISM: Artificial Sequence
<220> FEATURE:
<223> OTHER INFORMATION: Synthetic

<400> SEQUENCE: 81

Thr Val Ala Ala Pro Ser Val Phe Ile Phe Pro Pro Thr Val Ala Ala
1               5                   10                  15

Pro Ser Val Phe Ile Phe Pro Pro
            20

<210> SEQ ID NO 82
<211> LENGTH: 26
<212> TYPE: PRT
<213> ORGANISM: Artificial Sequence
<220> FEATURE:
<223> OTHER INFORMATION: Synthetic

<400> SEQUENCE: 82

Ala Ser Thr Lys Gly Pro Ser Val Phe Pro Leu Ala Pro Ala Ser Thr
1               5                   10                  15

Lys Gly Pro Ser Val Phe Pro Leu Ala Pro
            20                  25

<210> SEQ ID NO 83
<211> LENGTH: 692
<212> TYPE: PRT
<213> ORGANISM: Artificial Sequence
<220> FEATURE:
<223> OTHER INFORMATION: Synthetic: LRRC33 (also known as NRROS; Uniprot
      Accession No. Q86YC3)

<400> SEQUENCE: 83

Met Glu Leu Leu Pro Leu Trp Leu Cys Leu Gly Phe His Phe Leu Thr
1               5                   10                  15

Val Gly Trp Arg Asn Arg Ser Gly Thr Ala Thr Ala Ala Ser Gln Gly
                20                  25                  30

Val Cys Lys Leu Val Gly Gly Ala Ala Asp Cys Arg Gly Gln Ser Leu
            35                  40                  45

Ala Ser Val Pro Ser Ser Leu Pro Pro His Ala Arg Met Leu Thr Leu
        50                  55                  60

Asp Ala Asn Pro Leu Lys Thr Leu Trp Asn His Ser Leu Gln Pro Tyr
65                  70                  75                  80

Pro Leu Leu Glu Ser Leu Ser Leu His Ser Cys His Leu Glu Arg Ile
                85                  90                  95

Ser Arg Gly Ala Phe Gln Glu Gln Gly His Leu Arg Ser Leu Val Leu
            100                 105                 110

Gly Asp Asn Cys Leu Ser Glu Asn Tyr Glu Glu Thr Ala Ala Ala Leu
        115                 120                 125

His Ala Leu Pro Gly Leu Arg Arg Leu Asp Leu Ser Gly Asn Ala Leu
    130                 135                 140

Thr Glu Asp Met Ala Ala Leu Met Leu Gln Asn Leu Ser Ser Leu Arg
145                 150                 155                 160

```
Ser Val Ser Leu Ala Gly Asn Thr Ile Met Arg Leu Asp Asp Ser Val
            165                 170                 175

Phe Glu Gly Leu Glu Arg Leu Arg Glu Leu Asp Leu Gln Arg Asn Tyr
        180                 185                 190

Ile Phe Glu Ile Glu Gly Gly Ala Phe Asp Gly Leu Ala Glu Leu Arg
        195                 200                 205

His Leu Asn Leu Ala Phe Asn Asn Leu Pro Cys Ile Val Asp Phe Gly
    210                 215                 220

Leu Thr Arg Leu Arg Val Leu Asn Val Ser Tyr Asn Val Leu Glu Trp
225                 230                 235                 240

Phe Leu Ala Thr Gly Gly Glu Ala Ala Phe Glu Leu Glu Thr Leu Asp
            245                 250                 255

Leu Ser His Asn Gln Leu Leu Phe Phe Pro Leu Leu Pro Gln Tyr Ser
            260                 265                 270

Lys Leu Arg Thr Leu Leu Arg Asp Asn Asn Met Gly Phe Tyr Arg
            275                 280                 285

Asp Leu Tyr Asn Thr Ser Pro Arg Glu Met Val Ala Gln Phe Leu
    290                 295                 300

Leu Val Asp Gly Asn Val Thr Asn Ile Thr Thr Val Ser Leu Trp Glu
305                 310                 315                 320

Glu Phe Ser Ser Asp Leu Ala Asp Leu Arg Phe Leu Asp Met Ser
            325                 330                 335

Gln Asn Gln Phe Gln Tyr Leu Pro Asp Gly Phe Leu Arg Lys Met Pro
            340                 345                 350

Ser Leu Ser His Leu Asn Leu His Gln Asn Cys Leu Met Thr Leu His
            355                 360                 365

Ile Arg Glu His Glu Pro Pro Gly Ala Leu Thr Glu Leu Asp Leu Ser
    370                 375                 380

His Asn Gln Leu Ser Glu Leu His Leu Ala Pro Gly Leu Ala Ser Cys
385                 390                 395                 400

Leu Gly Ser Leu Arg Leu Phe Asn Leu Ser Ser Asn Gln Leu Leu Gly
            405                 410                 415

Val Pro Pro Gly Leu Phe Ala Asn Ala Arg Asn Ile Thr Thr Leu Asp
            420                 425                 430

Met Ser His Asn Gln Ile Ser Leu Cys Pro Leu Pro Ala Ala Ser Asp
            435                 440                 445

Arg Val Gly Pro Pro Ser Cys Val Asp Phe Arg Asn Met Ala Ser Leu
            450                 455                 460

Arg Ser Leu Ser Leu Glu Gly Cys Gly Leu Gly Ala Leu Pro Asp Cys
465                 470                 475                 480

Pro Phe Gln Gly Thr Ser Leu Thr Tyr Leu Asp Leu Ser Ser Asn Trp
            485                 490                 495

Gly Val Leu Asn Gly Ser Leu Ala Pro Leu Gln Asp Val Ala Pro Met
            500                 505                 510

Leu Gln Val Leu Ser Leu Arg Asn Met Gly Leu His Ser Ser Phe Met
            515                 520                 525

Ala Leu Asp Phe Ser Gly Phe Gly Asn Leu Arg Asp Leu Asp Leu Ser
            530                 535                 540

Gly Asn Cys Leu Thr Thr Phe Pro Arg Phe Gly Ser Leu Ala Leu
545                 550                 555                 560

Glu Thr Leu Asp Leu Arg Arg Asn Ser Leu Thr Ala Leu Pro Gln Lys
            565                 570                 575

Ala Val Ser Glu Gln Leu Ser Arg Gly Leu Arg Thr Ile Tyr Leu Ser
```

-continued

```
                580             585             590
Gln Asn Pro Tyr Asp Cys Cys Gly Val Asp Gly Trp Gly Ala Leu Gln
            595                 600             605

His Gly Gln Thr Val Ala Asp Trp Ala Met Val Thr Cys Asn Leu Ser
            610                 615             620

Ser Lys Ile Ile Arg Val Thr Glu Leu Pro Gly Val Pro Arg Asp
625                 630                 635                 640

Cys Lys Trp Glu Arg Leu Asp Leu Gly Leu Leu Tyr Leu Val Leu Ile
                645                 650                 655

Leu Pro Ser Cys Leu Thr Leu Leu Val Ala Cys Thr Val Ile Val Leu
                660                 665                 670

Thr Phe Lys Lys Pro Leu Leu Gln Val Ile Lys Ser Arg Cys His Trp
            675                 680                 685

Ser Ser Val Tyr
            690

<210> SEQ ID NO 84
<211> LENGTH: 660
<212> TYPE: PRT
<213> ORGANISM: Artificial Sequence
<220> FEATURE:
<223> OTHER INFORMATION: Synthetic: soluble LRRC33 (sLRRC33)

<400> SEQUENCE: 84

Met Asp Met Arg Val Pro Ala Gln Leu Leu Gly Leu Leu Leu Leu Trp
1               5                   10                  15

Phe Ser Gly Val Leu Gly Trp Arg Asn Arg Ser Gly Thr Ala Thr Ala
            20                  25                  30

Ala Ser Gln Gly Val Cys Lys Leu Val Gly Gly Ala Ala Asp Cys Arg
        35                  40                  45

Gly Gln Ser Leu Ala Ser Val Pro Ser Ser Leu Pro Pro His Ala Arg
    50                  55                  60

Met Leu Thr Leu Asp Ala Asn Pro Leu Lys Thr Leu Trp Asn His Ser
65                  70                  75                  80

Leu Gln Pro Tyr Pro Leu Leu Glu Ser Leu Ser Leu His Ser Cys His
                85                  90                  95

Leu Glu Arg Ile Ser Arg Gly Ala Phe Gln Glu Gln Gly His Leu Arg
            100                 105                 110

Ser Leu Val Leu Gly Asp Asn Cys Leu Ser Glu Asn Tyr Glu Glu Thr
        115                 120                 125

Ala Ala Ala Leu His Ala Leu Pro Gly Leu Arg Arg Leu Asp Leu Ser
    130                 135                 140

Gly Asn Ala Leu Thr Glu Asp Met Ala Ala Leu Met Leu Gln Asn Leu
145                 150                 155                 160

Ser Ser Leu Arg Ser Val Ser Leu Ala Gly Asn Thr Ile Met Arg Leu
                165                 170                 175

Asp Asp Ser Val Phe Glu Gly Leu Glu Arg Leu Arg Glu Leu Asp Leu
            180                 185                 190

Gln Arg Asn Tyr Ile Phe Glu Ile Glu Gly Gly Ala Phe Asp Gly Leu
        195                 200                 205

Ala Glu Leu Arg His Leu Asn Leu Ala Phe Asn Asn Leu Pro Cys Ile
    210                 215                 220

Val Asp Phe Gly Leu Thr Arg Leu Arg Val Leu Asn Val Ser Tyr Asn
225                 230                 235                 240

Val Leu Glu Trp Phe Leu Ala Thr Gly Gly Glu Ala Ala Phe Glu Leu
```

-continued

```
                245                 250                 255
Glu Thr Leu Asp Leu Ser His Asn Gln Leu Leu Phe Pro Leu Leu
            260                 265                 270

Pro Gln Tyr Ser Lys Leu Arg Thr Leu Leu Arg Asp Asn Asn Met
            275                 280                 285

Gly Phe Tyr Arg Asp Leu Tyr Asn Thr Ser Ser Pro Arg Glu Met Val
            290                 295                 300

Ala Gln Phe Leu Leu Val Asp Gly Asn Val Thr Asn Ile Thr Thr Val
305                 310                 315                 320

Ser Leu Trp Glu Glu Phe Ser Ser Asp Leu Ala Asp Leu Arg Phe
            325                 330                 335

Leu Asp Met Ser Gln Asn Gln Phe Gln Tyr Leu Pro Asp Gly Phe Leu
            340                 345                 350

Arg Lys Met Pro Ser Leu Ser His Leu Asn Leu His Gln Asn Cys Leu
            355                 360                 365

Met Thr Leu His Ile Arg Glu His Glu Pro Pro Gly Ala Leu Thr Glu
            370                 375                 380

Leu Asp Leu Ser His Asn Gln Leu Ser Glu Leu His Leu Ala Pro Gly
385                 390                 395                 400

Leu Ala Ser Cys Leu Gly Ser Leu Arg Leu Phe Asn Leu Ser Ser Asn
                405                 410                 415

Gln Leu Leu Gly Val Pro Pro Gly Leu Phe Ala Asn Ala Arg Asn Ile
            420                 425                 430

Thr Thr Leu Asp Met Ser His Asn Gln Ile Ser Leu Cys Pro Leu Pro
            435                 440                 445

Ala Ala Ser Asp Arg Val Gly Pro Pro Ser Cys Val Asp Phe Arg Asn
450                 455                 460

Met Ala Ser Leu Arg Ser Leu Ser Leu Glu Gly Cys Gly Leu Gly Ala
465                 470                 475                 480

Leu Pro Asp Cys Pro Phe Gln Gly Thr Ser Leu Thr Tyr Leu Asp Leu
                485                 490                 495

Ser Ser Asn Trp Gly Val Leu Asn Gly Ser Leu Ala Pro Leu Gln Asp
            500                 505                 510

Val Ala Pro Met Leu Gln Val Leu Ser Leu Arg Asn Met Gly Leu His
            515                 520                 525

Ser Ser Phe Met Ala Leu Asp Phe Ser Gly Phe Gly Asn Leu Arg Asp
            530                 535                 540

Leu Asp Leu Ser Gly Asn Cys Leu Thr Thr Phe Pro Arg Phe Gly Gly
545                 550                 555                 560

Ser Leu Ala Leu Glu Thr Leu Asp Leu Arg Arg Asn Ser Leu Thr Ala
                565                 570                 575

Leu Pro Gln Lys Ala Val Ser Glu Gln Leu Ser Arg Gly Leu Arg Thr
            580                 585                 590

Ile Tyr Leu Ser Gln Asn Pro Tyr Asp Cys Cys Gly Val Asp Gly Trp
            595                 600                 605

Gly Ala Leu Gln His Gly Gln Thr Val Ala Asp Trp Ala Met Val Thr
            610                 615                 620

Cys Asn Leu Ser Ser Lys Ile Ile Arg Val Thr Glu Leu Pro Gly Gly
625                 630                 635                 640

Val Pro Arg Asp Cys Lys Trp Glu Arg Leu Asp Leu Gly Leu His His
                645                 650                 655

His His His His
            660
```

<210> SEQ ID NO 85
<211> LENGTH: 689
<212> TYPE: PRT
<213> ORGANISM: Artificial Sequence
<220> FEATURE:
<223> OTHER INFORMATION: Synthetic: Human LRRC33-GARP chimera

<400> SEQUENCE: 85

```
Met Asp Met Arg Val Pro Ala Gln Leu Gly Leu Leu Leu Leu Trp
1               5                   10                  15

Phe Ser Gly Val Leu Gly Trp Arg Asn Arg Ser Gly Thr Ala Thr Ala
                20                  25                  30

Ala Ser Gln Gly Val Cys Lys Leu Val Gly Gly Ala Ala Asp Cys Arg
            35                  40                  45

Gly Gln Ser Leu Ala Ser Val Pro Ser Ser Leu Pro Pro His Ala Arg
        50                  55                  60

Met Leu Thr Leu Asp Ala Asn Pro Leu Lys Thr Leu Trp Asn His Ser
65                  70                  75                  80

Leu Gln Pro Tyr Pro Leu Leu Glu Ser Leu Ser Leu His Ser Cys His
                85                  90                  95

Leu Glu Arg Ile Ser Arg Gly Ala Phe Gln Glu Gln Gly His Leu Arg
            100                 105                 110

Ser Leu Val Leu Gly Asp Asn Cys Leu Ser Glu Asn Tyr Glu Glu Thr
        115                 120                 125

Ala Ala Ala Leu His Ala Leu Pro Gly Leu Arg Arg Leu Asp Leu Ser
    130                 135                 140

Gly Asn Ala Leu Thr Glu Asp Met Ala Ala Leu Met Leu Gln Asn Leu
145                 150                 155                 160

Ser Ser Leu Arg Ser Val Ser Leu Ala Gly Asn Thr Ile Met Arg Leu
                165                 170                 175

Asp Asp Ser Val Phe Glu Gly Leu Glu Arg Leu Arg Glu Leu Asp Leu
            180                 185                 190

Gln Arg Asn Tyr Ile Phe Glu Ile Glu Gly Gly Ala Phe Asp Gly Leu
        195                 200                 205

Ala Glu Leu Arg His Leu Asn Leu Ala Phe Asn Asn Leu Pro Cys Ile
    210                 215                 220

Val Asp Phe Gly Leu Thr Arg Leu Arg Val Leu Asn Val Ser Tyr Asn
225                 230                 235                 240

Val Leu Glu Trp Phe Leu Ala Thr Gly Gly Glu Ala Ala Phe Glu Leu
                245                 250                 255

Glu Thr Leu Asp Leu Ser His Asn Gln Leu Leu Phe Phe Pro Leu Leu
            260                 265                 270

Pro Gln Tyr Ser Lys Leu Arg Thr Leu Leu Leu Arg Asp Asn Asn Met
        275                 280                 285

Gly Phe Tyr Arg Asp Leu Tyr Asn Thr Ser Ser Pro Arg Glu Met Val
    290                 295                 300

Ala Gln Phe Leu Leu Val Asp Gly Asn Val Thr Asn Ile Thr Thr Val
305                 310                 315                 320

Ser Leu Trp Glu Glu Phe Ser Ser Asp Leu Ala Asp Leu Arg Phe
                325                 330                 335

Leu Asp Met Ser Gln Asn Gln Phe Gln Tyr Leu Pro Asp Gly Phe Leu
            340                 345                 350

Arg Lys Met Pro Ser Leu Ser His Leu Asn Leu His Gln Asn Cys Leu
        355                 360                 365
```

Met Thr Leu His Ile Arg Glu His Glu Pro Pro Gly Ala Leu Thr Glu
370                     375                 380

Leu Asp Leu Ser His Asn Gln Leu Ser Glu Leu His Leu Ala Pro Gly
385                 390                 395                 400

Leu Ala Ser Cys Leu Gly Ser Leu Arg Leu Phe Asn Leu Ser Ser Asn
                405                 410                 415

Gln Leu Leu Gly Val Pro Pro Gly Leu Phe Ala Asn Ala Arg Asn Ile
            420                 425                 430

Thr Thr Leu Asp Met Ser His Asn Gln Ile Ser Leu Cys Pro Leu Pro
        435                 440                 445

Ala Ala Ser Asp Arg Val Gly Pro Pro Ser Cys Val Asp Phe Arg Asn
450                 455                 460

Met Ala Ser Leu Arg Ser Leu Ser Leu Glu Gly Cys Gly Leu Gly Ala
465                 470                 475                 480

Leu Pro Asp Cys Pro Phe Gln Gly Thr Ser Leu Thr Tyr Leu Asp Leu
                485                 490                 495

Ser Ser Asn Trp Gly Val Leu Asn Gly Ser Leu Ala Pro Leu Gln Asp
            500                 505                 510

Val Ala Pro Met Leu Gln Val Leu Ser Leu Arg Asn Met Gly Leu His
        515                 520                 525

Ser Ser Phe Met Ala Leu Asp Phe Ser Gly Phe Gly Asn Leu Arg Asp
530                 535                 540

Leu Asp Leu Ser Gly Asn Cys Leu Thr Thr Phe Pro Arg Phe Gly Gly
545                 550                 555                 560

Ser Leu Ala Leu Glu Thr Leu Asp Leu Arg Arg Asn Ser Leu Thr Ala
                565                 570                 575

Leu Pro Gln Lys Ala Val Ser Glu Gln Leu Ser Arg Gly Leu Arg Thr
            580                 585                 590

Ile Tyr Leu Ser Gln Asn Pro Tyr Asp Cys Cys Gly Val Asp Gly Trp
        595                 600                 605

Gly Ala Leu Gln His Gly Gln Thr Val Ala Asp Trp Ala Met Val Thr
        610                 615                 620

Cys Asn Leu Ser Ser Lys Ile Ile Arg Val Thr Glu Leu Pro Gly Gly
625                 630                 635                 640

Val Pro Arg Asp Cys Lys Trp Glu Arg Leu Asp Leu Gly Leu Leu Ile
                645                 650                 655

Ile Ile Leu Thr Phe Ile Leu Val Ser Ala Ile Leu Leu Thr Thr Leu
            660                 665                 670

Ala Ala Cys Cys Cys Val Arg Arg Gln Lys Phe Asn Gln Gln Tyr Lys
        675                 680                 685

Ala

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89
<400> SEQUENCE: 89

000

<210> SEQ ID NO 90
<400> SEQUENCE: 90

000

<210> SEQ ID NO 91
<211> LENGTH: 369
<212> TYPE: DNA
<213> ORGANISM: Artificial Sequence
<220> FEATURE:
<223> OTHER INFORMATION: Synthetic: Ab1 Heavy chain variable region
      nucleic acid sequence

<400> SEQUENCE: 91

```
gaggtgcaac tcgtggagtc aggcggtgga cttgttcagc ctgggcgaag tctgagactc     60
tcatgtgcag caagtggatt cactttctcc agttacggca tgcactgggt gagacaggcg    120
cctggaaagg gtttggaatg ggtcgctgtg atctcttacg acgggtcaaa caaatattac    180
gcggattcag tgaaagggcg gttcactatt tcacgggata actccaagaa caccctgtat    240
ctgcagatga atagcctgag gcagaggac accgctgtgt actattgtgc ccgggacata    300
aggccttacg gcgattacag cgccgcattt gatatttggg gacaaggcac ccttgtgaca    360
gtatcttct                                                            369
```

<210> SEQ ID NO 92
<211> LENGTH: 338
<212> TYPE: DNA
<213> ORGANISM: Artificial Sequence
<220> FEATURE:
<223> OTHER INFORMATION: Synthetic: Ab1 Light chain variable region
      nucleic acid sequence

<400> SEQUENCE: 92

```
aattttatgc ttacccaacc acatagtgtg agtgagtctc ccggcaagac tgtaacaatt     60
tcatgtaccg gcagcagtgg ctccatcgct agcaattatg tgcaatggta ccaacagcgc    120
cccgggagcg caccttcaat agtgatattc gaggataacc aacggcctag tggggctccc    180
gatagattta gtgggagtat agatagctcc tccaactctg cctctctcac cattagcggg    240
ctgaaaacag aggatgaagc cgactattac tgccaaagct atgattctag caaccacggc    300
ggagtgtttg gcggaggaac acagctgaca gtcctagg                             338
```

<210> SEQ ID NO 93
<211> LENGTH: 372
<212> TYPE: DNA
<213> ORGANISM: Artificial Sequence
<220> FEATURE:
<223> OTHER INFORMATION: Synthetic: Ab2 Heavy chain variable region
      nucleic acid sequence

<400> SEQUENCE: 93

```
gaggtgcaac tggtgcaatc cggagccgag atgaaaaagc caggggagag cctgaagatc     60
```

```
tcttgtaagg gctctggcta taacttcgct agtgattgga tcggatgggt gaggcaaacc    120
cccggaaagg gcctcgagtg gatgggcgtg atctaccccg gcgactccga cacacgctat    180
agcgcctcat tccagggcca ggtcaccata agtgctgata aatcaataaa tacagcctac    240
ttgcaatggt caagtctgaa agcctcagat actgccatgt actattgtgc ctctgccgcc    300
ggcattgccg cggccggtca cgtcaccgcc ttcgacattt ggggtcaggg cactatggtc    360
actgtaagct cc                                                        372

<210> SEQ ID NO 94
<211> LENGTH: 339
<212> TYPE: DNA
<213> ORGANISM: Artificial Sequence
<220> FEATURE:
<223> OTHER INFORMATION: Synthetic: Ab2 Light chain variable region
      nucleic acid sequence

<400> SEQUENCE: 94
gacatagtca tgacccagtc acctgactct ttggccgtgt ctctggggga gagagccaca     60
ataaattgca agtcatcaca gagcgtcctg tactcctcca ataataaaaa ttacctggcc    120
tggtaccagc aaaagcccgg gcaacccccc aaattgttga tttactgggc tagtacaagg    180
gaatctggag tgccagaccg gttttctggt tctggatctg gtactgactt caccctgaca    240
atcagctccc tgcaggccga agacgtggct gtgtactatt gtcagcagta ctatagtaca    300
ccagttactt tcggccaagg cactaaactc gaaatcaag                           339
```

TGFβ1-BINDING IMMUNOGLOBULINS AND USE THEREOF

RELATED APPLICATIONS

This application is a 35 U.S.C. § 371 national stage filing of International Application No. PCT/US2017/021972, filed on Mar. 10, 2017, which in turn claims priority to U.S. Provisional Application No. 62/307,353, filed on Mar. 11, 2016; U.S. Provisional Application No. 62/443,615, filed on Jan. 6, 2017; and U.S. Provisional Application No. 62/452, 866, filed on Jan. 31, 2017; the entire contents of each of which are expressly incorporated herein by reference in their entireties.

SEQUENCE LISTING

The instant application contains a Sequence Listing which has been submitted electronically in ASCII format and is hereby incorporated by reference in its entirety. Said ASCII copy, created on May 26, 2017, is named 127036-00420 SL.txt and is 211,181 bytes in size.

BACKGROUND

Transforming growth factor β (TGFβ) superfamily of growth factors are involved in a number of signaling cascades that regulate diverse biological processes including, but not limited to: inhibition of cell growth, tissue homeostasis, extracellular matrix (ECM) remodeling, endothelial to mesenchymal transition (EMT), cell migration and invasion, and immune modulation/suppression, as well as mesenchymal to epithelial transition. In relation to ECM remodeling, TGFβ signaling may increase fibroblast populations and ECM deposition (e.g., collagen). In the immune system, TGFβ ligand modulates T regulatory cell function and maintenance of immune precursor cell growth and homeostasis. In normal epithelial cells, TGFβ is a potent growth inhibitor and promoter of cellular differentiation. However, as tumors develop and progress, they frequently lose their negative growth response to TGFβ. In this setting, TGFβ may become a promoter of tumor development due to its ability to stimulate angiogenesis, alter the stromal environment, and induce local and systemic immunosuppression. For these and other reasons, TGFβ has been a therapeutic target for a number of clinical indications. Despite much effort made to date by a number of groups, clinical development of a TGFβ therapeutic has been challenging.

Observations from preclinical studies, including in rats and dogs, have revealed certain toxicities associated with inhibition of TGFβ in vivo. Moreover, although several TGFβ inhibitors have been developed to date, most clinical programs targeting TGFβ have been discontinued due to side effects.

For example, Anderton et al. (Toxicology Pathology, 39: 916-24, 2011) reported that small molecule inhibitors of TGFβ type I (ALK5) receptor induced heart valve lesions characterized by hemorrhage, inflammation, degeneration and proliferation of valvular interstitial cells in a preclinical animal model. The toxicity was observed in all heart valves at all doses tested. Frazier et al. (Toxicology Pathology, 35: 284-295, 2007) reported that administration of the small molecule inhibitor of TGFβ type I (ALK5) receptor GW788388 induced physeal dysplasia in rats.

Stauber et al. (J. Clin. Practice 4:3, 2014) reported that a chronic (≥3 months) administration of the inhibitor of TGFβ receptor I kinase, LY2157299, which is being investigated for certain cancer treatments, caused multiple organ toxicities involving the cardiovascular, gastrointestinal, immune, bone/cartilage, reproductive, and renal systems, in rats and dogs.

Fresolimumab (GC1008), a "pan" TGFβ antibody capable of neutralizing all human isoforms of TGFβ, has been reported to induce an epithelial hyperplasia of the gingiva, bladder, and of the nasal turbinate epithelium after multiple adminstrations in studies with cynomolgus macaques (Lonning et al., Current Pharmaceutical Biotechnology 12: 2176-89, 2011). Similarly, a variety of skin rashes/lesions, gingival bleeding and fatigue have been reported in clinical trials after administration of multiple doses of the drug. The most notable adverse reaction to fresolimumab includes the induction of cutaneous keratoacanthomas and/or squamous cell carcinomas in human cancer patients (see, for example: Lacouture et al., 2015, Cancer Immunol Immunother, 64: 437-46; Stevenson et al., 2013, Oncolmmunology, 2:8, e26218; and Lonning et al., 2011). Additional evidence from a clinical trial suggests that in some cases this antibody may accelerate tumor progression (Stevenson et al., 2013, Oncolmmunology, 2:8, e26218).

Thus, new methods and compositions for modulating TGFβ signaling are necessary that can be used to effectively and safely treat diseases and disorders involving TGFβ, including, for example, cancer, fibrosis and inflammation.

SUMMARY OF THE INVENTION

The present disclosure relates to selective modulation of a subset of TGFβ effects. The invention is based at least in part on the notion that lack of isoform-specificity of known TGFβ antagonists to date may underlie the source of toxicities associated with TGFβ inhibition. Indeed, the inventors of the present disclosure have found that most TGFβ inhibitors described to date antagonize multiple or all of the TGFβ isoforms. Moreover, the general trend described in the art has been that inhibitors (such as anti-TGFβ antibodies) that antagonize multiple isoforms of TGFβ are favored, on the account that neutralization of multiple isoforms of TGFβ would be necessary or advantageous to achieve "maximum therapeutic efficacy" (see, for example, Bedinger et al. (2016) MABS 8(2): 389-404).

Contrary to this general teaching, the inventors of the present invention instead sought to develop agents that enable isoform-specific inhibition of TGFβ1, as opposed to inhibition that also affects TGFβ2 and/or TGFβ3, with the aim of eliminating or markedly reducing toxicities (e.g., adverse events, side effects) observed with known TGFβ antagonists in vivo. This novel approach is based, at least in part, on the notion that the clinical utility of a TGFβ inhibitor may rest not only on its efficacy, but also on its safety. It was reasoned that the ability to fine-tune the target with an unprecedented degree of specificity may achieve both efficacy and safety/tolerability in a clinical setting.

Accordingly, the invention encompasses the recognition that pharmaceutical agents that inhibit TGFβ signaling in an isoform-specific manner may provide improved safety profiles over agents that affect multiple TGFβ isoforms. By contrast, a number of known TGFβ antagonists in the art produce unacceptable levels of toxicity at a dose that is shown to be efficacious in vivo. In such instances, lower dosing may be employed to avoid the toxicity but it may no longer produce sufficient in vivo efficacy at the reduced dose. Without wishing to be bound by particular theory, it is contemplated that such toxicity at least in part stems from lack of isoform specificity/selectivity of the agent.

Thus, in one aspect, the invention provides methods for reducing toxicities (e.g., adverse events, unwanted side effects) associated with TGFβ inhibition in a subject. According to the invention, TGFβ1-specific inhibitors, such as those described herein, have a superior safety-efficacy profile, as compared to agents that elicit activities towards broader target (e.g., more than one isoforms of TGFβ). Such TGFβ1-specific inhibitors can therefore be administered to subjects in need thereof at a therapeutically effective dose without causing adverse effects. Such approach would therefore broaden the dosage range in which both efficacy and safety/tolerability can be achieved in patients. Thus, the invention provides methods for treating a disease associated with TGFβ1 signaling, by administering to a subject an effective amount of a TGFβ inhibitor that is specific or highly selective for the TGFβ1 isoform. In some embodiments, such TGFβ1 isoform-selective or TGFβ1 isoform-specific inhibitors may be small molecule agents or biologics (e.g., antibodies). Use of any such inhibitors for reducing toxicities (e.g., adverse events or side effects) associated with TGFβ inhibition in a subject is encompassed by the present invention. According to the invention, the effective amount is within a dosage range that enables both: i) efficacy (e.g., therapeutically beneficial effects); and, ii) safety (e.g., within acceptable levels of adverse effects or side effects). In some embodiments, adverse effects may include cardiovascular toxicities, gastrointestinal toxicities, immune toxicities, bone/cartilage toxicities, reproductive toxicities, and renal toxicities. In some embodiments, cardiovascular toxicities include, but are not limited to: heart valve lesions, e.g., hemorrhage, inflammation, degeneration and proliferation of valvular interstitial cells. In some embodiments, adverse effects may include bleeding. In some embodiments, adverse effects may include skin lesions or tumors. In some embodiments, adverse effects may include tumor progression.

Accordingly, in some embodiments, the invention provides isoform-specific TGFβ1 inhibitor antibodies or antigen-binding fragments thereof, characterized in that they selectively inhibit the step of TGFβ1 activation in vivo but do not inhibit the step of TGFβ2 and/or TGFβ3 activation. Such antibodies or fragments thereof can be administered to subjects who benefit from TGFβ1 inhibition, in an amount effective to achieve clinical efficacy without causing unacceptable or intolerable levels of adverse effects. Thus, the present invention teaches that TGFβ1 isoform-specific inhibitors be specifically selected to meet both the efficacy and safety criteria for the treatment of a disease or condition associated with TGFβ signaling in human patients.

In a related aspect, the invention provides production methods for isoform-specific TGFβ modulators with an improved safety profile (e.g., reduced in vivo toxicity). Such methods require that candidate agents be tested and selected for isoform specificity. In some embodiments, candidate agents are selected for specific activities against TGFβ1 signaling, and not TGFβ2 and/or TGFβ3 signaling. In some embodiments, such agents are TGFβ1 isoform-specific inhibitors. In some embodiments, such agents are antibodies or antigen-binding fragments thereof that specifically bind and block activation of TGFβ1, but not TGFβ2 and/or TGFβ3. In some embodiments, such antibodies or antigen-binding fragments thereof do not bind free mature TGFβ1 growth factor that is not associated with a pro/latent complex.

In another aspect, the present invention provides compositions and related methods for achieving further fine tuning of TGFβ signaling by modulating TGFβ activation in a context-dependent manner.

TGFβ is involved in conferring a number of cellular/tissue effects, and each such effect is mediated in part by its interaction with so-called "presenting molecules." Because expression of various presenting molecules is cell type- or tissue-specific it is contemplated that TGFβ confers a cellular effect, depending on its interaction with a particular presenting molecule (i.e., "context"). Thus, among other things, the present disclosure provides monoclonal antibodies that selectively bind TGFβ present in a particular context (i.e., a complex comprising TGFβ and a presenting molecule). In some embodiments, such monoclonal antibodies specifically bind at least one, at least two, or, at least three of the following complexes: i) TGFβ1-GARP; ii) TGFβ1-LRRC33; iii) TGFβ1-LTBP1; and, iv) TGFβ1-LTBP3. In some embodiments, such monoclonal antibodies specifically bind one of the following complexes: i) TGFβ1-GARP; ii) TGFβ1-LRRC33; iii) TGFβ1-LTBP1; and, iv) TGFβ1-LTBP3. In some embodiments, such monoclonal antibodies specifically bind two of the following complexes: i) TGFβ1-GARP; ii) TGFβ1-LRRC33; iii) TGFβ1-LTBP1; and, iv) TGFβ1-LTBP3. In some embodiments, such monoclonal antibodies specifically bind three of the following complexes: i) TGFβ1-GARP; ii) TGFβ1-LRRC33; iii) TGFβ1-LTBP1; and, iv) TGFβ1-LTBP3. In some embodiments, such monoclonal antibodies specifically bind all of the following complexes: i) TGFβ1-GARP; ii) TGFβ1-LRRC33; iii) TGFβ1-LTBP1; and, iv) TGFβ1-LTBP3. In some embodiments, such monoclonal antibodies do not bind mature TGFβ1 that is free TGFβ1 (e.g., not complexed with a presenting molecule).

The present disclosure includes monoclonal antibodies that bind to the small latent complex (e.g., "C4S") of TGFβ1.

The disclosure further provides monoclonal antibodies that selectively target and modulate TGFβ in a particular context. In some embodiments, such monoclonal antibodies either inhibit or activate TGFβ in a particular context.

Accordingly, the invention provides compositions and methods for modulating (activating or inhibiting) a subset of TGFβ activities. Thus, the invention includes monoclonal antibodies which can selectively modulate a subset of TGFβ-mediated signaling pathways without affecting the other TGFβ-mediated signaling pathways. In some embodiments, the subset of TGFβ-mediated signaling pathways includes at least one, at least two, or, at least three of: i) GARP-mediated TGFβ effects, ii) LRRC33-mediated TGFβ effects, iii) LTBP1-mediated TGFβ effects, and iv) LTBP3-mediated TGFβ effects. In some embodiments, such monoclonal antibodies specifically modulate one of the following TGFβ-mediated signaling pathways, without modulating the other three pathways: i) GARP-mediated TGFβ effects, ii) LRRC33-mediated TGFβ effects, iii) LTBP1-mediated TGFβ effects, and iv) LTBP3-mediated TGFβ effects. In some embodiments, such monoclonal antibodies specifically modulate two of the following TGFβ-mediated signaling pathways, without modulating the other two pathways: i) GARP-mediated TGFβ effects, ii) LRRC33-mediated TGFβ effects, iii) LTBP1-mediated TGFβ effects, and iv) LTBP3-mediated TGFβ effects. In some embodiments, such monoclonal antibodies specifically modulate three of the following TGFβ-mediated signaling pathways, without modulating the other one pathway: i) GARP-mediated TGFβ effects, ii) LRRC33-mediated TGFβ effects, iii) LTBP1-mediated TGFβ effects, and iv) LTBP3-mediated TGFβ effects. In some embodiments, such monoclonal antibodies specifically modulate all of the following TGFβ-mediated signaling pathways: i) GARP-mediated TGFβ effects, ii) LRRC33-mediated TGFβ effects, iii) LTBP1-mediated TGFβ effects, and iv) LTBP3-mediated TGFβ effects. In some embodiments, such monoclonal antibodies specifically modulate GARP-mediated TGFβ effects. In some embodiments, such monoclonal antibodies specifically modulate LRRC33-mediated TGFβ effects. In some embodiments, such monoclonal antibodies specifically modulate LTBP1-mediated TGFβ effects. In some embodiments, such monoclonal antibodies specifically modulate LTBP3-mediated TGFβ effects. Thus, the present invention provides methods for selectively targeting TGFβ activities in a context-dependent manner.

Aspects of the present invention include pharmaceutical compositions and methods for treating a disease or disorder in a human subject. In some embodiments, such disease or disorder includes conditions associated with immune regulation/dysregulation, conditions associated with T cell regulation/dysregulation; conditions associated with a fibrotic feature (fibrosis); and/or conditions associated with tumor.

Because the antibodies or fragments thereof that specifically target the pro/latent complex of TGFβ described herein modulate the activation step (i.e., release of a free, mature TGFβ growth factor from the inactive, latent preform complex), as opposed to targeting already released, free, mature growth factor, the mode of action of these modulatory agents depends on the source of the TGFβ growth factor in the tissue. It is therefore contemplated that identification of the source of TGFβ involved in a disease context may help select an agent that can effectively modulate TGFβ in the correct context. For example, to treat a disease phenotype that involves GARP-mediated TGFβ1 effects, it is desirable to select antibodies or fragments thereof that specifically target a GARP-proTGFβ1 complex. To treat a disease phenotype that involves LRRC33-mediated TGFβ1 effects, it is desirable to select antibodies or fragments thereof that specifically target a LRRC33-proTGFβ1 complex. To treat a disease phenotype that involves LTBP1-mediated TGFβ1 effects, it is desirable to select antibodies or fragments thereof that specifically target a LTBP1-proTGFβ1 complex. To treat a disease phenotype that involves LTBP2-mediated TGFβ1 effects, it is desirable to select antibodies or fragments thereof that specifically target a LTBP2-proTGFβ1 complex. To treat a disease phenotype that involves LTBP3-mediated TGFβ1 effects, it is desirable to select antibodies or fragments thereof that specifically target a LTBP3-proTGFβ1 complex. To treat a disease phenotype that involves LTBP4-mediated TGFβ1 effects, it is desirable to select antibodies or fragments thereof that specifically target a LTBP4-proTGFβ1 complex. To treat a disease phenotype that involves TGFβ1 effects mediated by multiple (e.g., two or more) contexts, it is desirable to select antibodies or fragments thereof that can target the corresponding multiple contexts of TGFβ1 presentation.

Certain diseases are associated with multiple biological roles of TGFβ signaling that are not limited to a single context of TGFβ function. In such situations, it may be beneficial to modulate TGFβ effects across multiple contexts. Thus, in some embodiments, the invention provides methods for targeting and modulating TGFβ1 in an isoform-specific manner, rather than in a context-specific manner. Such agents may be referred to as "isoform-specific, context-permissive" TGFβ1 modulators. In some embodiments, context-permissive TGFβ1 modulators target multiple contexts (e.g., multiple types of pro/latent-TGFβ1 complexes).

In some embodiments, context-permissive TGFβ1 modulators target all types of pro/latent TGFβ1 complexes (e.g., GARP-associated, LRRC33-associated, LTBP-associated, etc.) so as to encompass all contexts.

Whilst context-permissive TGFβ1 modulators are capable of targeting more than one types of pro/latent-TGFβ1 complexes (i.e., with different presenting molecules), in some embodiments, such modulators may favor one or more context over the other. Thus, in some embodiments, a context-permissive antibody that inhibits the activation of TGFβ1 may preferentially inhibit TGFβ1 activation mediated by one presenting molecule over another presenting molecule, even if such antibody is capable of binding to both types of pro/latent complexes. In some embodiments, such antibody is a monoclonal antibody that binds and inhibits activation of LTBP-associated TGFβ1, GARP-associated TGFβ1, and LRRC33-associated TGFβ1, but with preferential inhibitory activities toward LTBP-associated TGFβ1. In some embodiments, such antibody is a monoclonal antibody that binds and inhibits activation of LTBP1-associated TGFβ1, LTBP3-associated TGFβ1, GARP-associated TGFβ1, and LRRC33-associated TGFβ1, but with preferential inhibitory activities toward LTBP1- and LTBP-3-associated TGFβ1. In some embodiments, such antibody is a monoclonal antibody that binds and inhibits activation of LTBP1-associated TGFβ1, LTBP3-associated TGFβ1, GARP-associated TGFβ1, and LRRC33-associated TGFβ1, but with preferential inhibitory activities toward GARP-associated TGFβ1 and LRRC33-associated TGFβ1. In some embodiments, such antibody is a monoclonal antibody that binds and inhibits activation of GARP-associated TGFβ1 and LRRC33-associated TGFβ1, but with preferential inhibitory activities toward GARP-associated TGFβ1. In some embodiments, such antibody is a monoclonal antibody that binds and inhibits activation of GARP-associated TGFβ1 and LRRC33-associated TGFβ1, but with preferential inhibitory activities toward LRRC33-associated TGFβ1.

Thus, according to the invention, varying degrees of selectivity may be generated in order to target subset of TGFβ effects. Isoform-specific modulators of TGFβ (which target a single isoform of TGFβ) provide greater selectivity than pan-TGFβ modulators (which target multiple or all isoforms of TGFβ). Isoform-specific, context-permissive modulators of TGFβ (which target multiple contexts of a single isoform of TGFβ) provide greater selectivity than isoform-specific modulators. Isoform-specific, context specific modulators of TGFβ (which target single context of a single isoform of TGFβ) provide even greater selectivity than isoform-specific, context-permissive modulators.

Thus, in some embodiments, the invention includes methods for treating a disease associated with TGFβ signaling which comprise first identifying or confirming the source and/or context of disease-associated TGFβ, then selecting an agent that specifically targets the particular sub-pool of TGFβ in the tissue. In this way, it is contemplated that such approach may preserve normal function of TGFβ while preferentially modulating disease-associated function of TGFβ. In some embodiments, to identify the source/context of disease-associated TGFβ, expression of TGFβ presenting molecule(s) present in the diseased tissue may be assessed. To give but one example, within a disease tissue, there may be both LTBP-associated TGFβ1 latent complex, and GARP-associated TGFβ1 complex, and only the latter of the two may be expressed as a disease phenotype. In that scenario, it is desirable to inhibit GARP-mediated TGFβ1 signaling, while maintaining LTBP-mediated TGFβ1 signaling intact. Determination of the source/context of disease-associated TGFβ1 may be carried out with the use of antibodies that specifically bind TGFβ1 latent complex that includes a particular presenting molecule (e.g., GARP, LRRC33, LTBPs, etc.). For the treatment of conditions associated with T cell regulation/dysregulation, some embodiments of the invention comprise administration of a composition comprising an effective amount of a monoclonal antibody that modulates GARP-mediated TGFβ effects in the subject.

For the treatment of conditions associated with immune regulation/dysregulation, some embodiments of the invention comprise administration of a composition comprising an effective amount of a monoclonal antibody that modulates GARP-mediated TGFβ effects and/or LRRC33-mediated TGFβ effects in the subject.

For the treatment of conditions associated with fibrosis, some embodiments of the invention comprise administration of a composition comprising an effective amount of a monoclonal antibody that modulates LTBP1-mediated TGFβ effects and/or LTBP3-mediated TGFβ effects in the subject.

For the treatment of conditions associated with certain types of cancer, some embodiments of the invention comprise administration of a composition comprising an effective amount of a monoclonal antibody that modulates GARP-mediated TGFβ effects, LTBP1-mediated TGFβ effects and/or LTBP3-mediated TGFβ effects in the subject.

Aspects of the present disclosure relate to immunoglobulins, such as antibodies, or antigen binding portions thereof, that specifically bind to a GARP-TGFβ1 complex, a LTBP1-TGFβ1 complex, a LTBP3-TGFβ1 complex and/or a LRRC33-TGFβ1 complex. The antibodies, or antigen binding portions thereof, described herein, specifically bind to an epitope of TGFβ1 that is available for binding by the antibodies, or antigen binding portions thereof, when the TGFβ1 is present in a GARP-TGFβ1 complex, a LTBP1-TGFβ1 complex, a LTBP3-TGFβ1 complex and/or a LRRC33-TGFβ1.

In one aspect, provided herein is an isolated antibody, or antigen binding portion thereof, that specifically binds to an epitope of TGFβ1, wherein the epitope is available for binding by the antibody when the TGFβ1 is present in two or more of the following protein complexes: a GARP-TGFβ1 complex, a LTBP1-TGFβ1 complex, a LTBP3-TGFβ1 complex, and a LRRC33-TGFβ1 complex; and wherein the antibody does not bind free mature TGFβ1.

In some embodiments, the TGFβ1 is latent TGFβ1. In some embodiments, the TGFβ1 is proTGFβ1.

In some embodiments, the antibody, or antigen binding portion thereof, does not bind to TGFβ2. In some embodiments, the antibody, or antigen binding portion thereof, does not bind to TGFβ3. In some embodiments, the antibody, or antigen binding portion thereof, does not prevent the ability of TGFβ1 to bind to integrin.

In some embodiments, the antibody, or antigen binding portion thereof, comprises a heavy chain variable region comprising a complementarity determining region 3 (CDR3) having the amino acid sequence of SEQ ID NO: 5 and a light chain variable region comprising a CDR3 having the amino acid sequence of SEQ ID NO: 11. In some embodiments, the antibody, or antigen binding portion thereof, comprises a heavy chain variable region comprising a complementarity determining region 2 (CDR2) having the amino acid sequence of SEQ ID NO: 3 and a light chain variable region comprising a CDR2 having the amino acid sequence of SEQ ID NO: 9. In some embodiments, the antibody, or antigen binding portion thereof, comprises a heavy chain variable region comprising a complementarity determining region 1 (CDR1) having the amino acid sequence of SEQ ID NO: 1 and a light chain variable region comprising a CDR1 having the amino acid sequence of SEQ ID NO: 7.

In some embodiments, the antibody, or antigen binding portion thereof, comprises a heavy chain variable domain comprising an amino acid sequence having at least 70%, 75%, 80%, 85%, 90%, 95%, 96%, 97%, 98%, or 99% identity to the amino acid sequence set forth in SEQ ID NO: 13 and a light chain variable domain comprising an amino acid sequence having at least 70%, 75%, 80%, 85%, 90%, 95%, 96%, 97%, 98%, or 99% identity to the amino acid sequence set forth in SEQ ID NO: 14.

In some embodiments, the antibody, or antigen binding portion thereof, comprises a heavy chain variable domain comprising an amino acid sequence set forth in SEQ ID NO: 13 and a light chain variable domain comprising an amino acid sequence set forth in SEQ ID NO: 14.

In some embodiments, the antibody, or antigen binding portion thereof, comprises a heavy chain variable region comprising a CDR3 having the amino acid sequence of SEQ ID NO: 6 and a light chain variable region comprising a CDR3 having the amino acid sequence of SEQ ID NO: 12. In some embodiments, the antibody, or antigen binding portion thereof, comprises a heavy chain variable region comprising a CDR2 having the amino acid sequence of SEQ ID NO: 4 and a light chain variable region comprising a CDR2 having the amino acid sequence of SEQ ID NO: 10. In some embodiments, the antibody, or antigen binding portion thereof, comprises a heavy chain variable region comprising a CDR1 having the amino acid sequence of SEQ ID NO: 2 and a light chain variable region comprising a CDR1 having the amino acid sequence of SEQ ID NO: 8.

In some embodiments, the antibody, or antigen binding portion thereof, comprises a heavy chain variable domain comprising an amino acid sequence having at least 70%, 75%, 80%, 85%, 90%, 95%, 96%, 97%, 98%, or 99% identity to the amino acid sequence set forth in SEQ ID NO: 15 and a light chain variable domain comprising an amino acid sequence having at least 70%, 75%, 80%, 85%, 90%, 95%, 96%, 97%, 98%, or 99% identity to the amino acid sequence set forth in SEQ ID NO: 16.

In some embodiments, the antibody, or antigen binding portion thereof, comprises a heavy chain variable domain comprising an amino acid sequence set forth in SEQ ID NO: 15 and a light chain variable domain comprising an amino acid sequence set forth in SEQ ID NO: 16.

In some embodiments, the antibody, or antigen binding portion thereof, inhibits TGFβ1 activation.

In some embodiments, the antibody, or antigen binding portion thereof, inhibits the release of mature TGFβ1 from the GARP-TGFβ1 complex, the LTBP1-TGFβ1 complex, the LTBP3-TGFβ1 complex, or the LRRC33-TGFβ1 complex.

In some embodiments, the antibody, or antigen binding portion thereof, has a dissociation constant ($K_D$) to the epitope of TGFβ1 selected from the group consisting of: at least about $10^{-8}$ M; at least about $10^{-9}$ M; at least about $10^{-10}$ M; at least about $10^{-11}$ M; at least about $10^{-12}$ M; and at least about $10^{-13}$ M.

In some embodiments, the antibody, or antigen binding portion thereof, comprises a heavy chain immunoglobulin constant domain of a human IgM constant domain, a human IgG constant domain, a human $IgG_1$ constant domain, a human $IgG_2$ constant domain, a human $IgG_2A$ constant domain, a human $IgG_2B$ constant domain, a human $IgG_2$ constant domain, a human IgG$_3$ constant domain, a human IgG$_3$ constant domain, a human IgG$_4$ constant domain, a human IgA constant domain, a human IgA$_1$ constant domain, a human IgA$_2$ constant domain, a human IgD constant domain, or a human IgE constant domain. In some embodiments, the antibody, or antigen binding portion thereof, comprises a heavy chain immunoglobulin constant domain of a human IgG$_1$ constant domain or a human IgG$_4$ constant domain. In some embodiments, the antibody, or antigen binding portion thereof, comprises a heavy chain immunoglobulin constant domain of a human IgG$_4$ constant domain. In some embodiments, the antibody, or antigen binding portion thereof, comprises a heavy chain immunoglobulin constant domain of a human IgG$_4$ constant domain having a backbone substitution of Ser to Pro that produces an IgG$_1$-like hinge and permits formation of inter-chain disulfide bonds.

In some embodiments, the antibody or antigen binding portion thereof, further comprises a light chain immunoglobulin constant domain comprising a human Ig lambda constant domain or a human Ig kappa constant domain.

In some embodiments, the antibody is an IgG having four polypeptide chains which are two heavy chains and two light chains.

In some embodiments, wherein the antibody is a humanized antibody, a diabody, or a chimeric antibody. In some embodiments, the antibody is a humanized antibody. In some embodiments, the antibody is a human antibody. In some embodiments, the antibody comprises a framework having a human germline amino acid sequence.

In some embodiments, the antigen binding portion is a Fab fragment, a F(ab')2 fragment, a scFab fragment, or an scFv fragment.

In one aspect, provided herein is an anti-TGFβ1 antibody, or antigen binding portion thereof, that competes for binding with an antibody, or an antigen binding portion thereof, as described herein.

In another aspect, provided herein is an anti-TGFβ1 antibody, or antigen binding portion thereof, that binds to the same epitope as an antibody, or antigen binding portion thereof, as described herein.

In some embodiments, the antibody, or antigen binding portion thereof, is conjugated to a drug or a detectable moiety. In some embodiments, the antibody, or antigen binding portion thereof, is conjugated to the drug or to the detectable moiety via a linker. In some embodiments, the linker is a cleavable linker. In some embodiments, the detectable moiety is selected from the group consisting of a fluorescent agent, a luminescent agent, an enzymatic agent, and a radioactive agent.

In one aspect, provided herein is a pharmaceutical composition comprising an antibody, or antigen binding portion thereof, as described herein, and a pharmaceutically acceptable carrier.

In another aspect, provided herein is a method for inhibiting TGFβ1 activation, the method comprising exposing a GARP-TGFβ1 complex, a LTBP1-TGFβ1 complex, a LTBP3-TGFβ1 complex, or a LRRC33-TGFβ1 complex to an antibody, an antigen binding portion thereof, or a pharmaceutical composition described herein.

In some embodiments, the antibody, or antigen binding portion thereof, inhibits the release of mature TGFβ1 from the GARP-TGFβ1 complex, the LTBP1-TGFβ1 complex, a LTBP3-TGFβ1 complex, or the LRRC33-TGFβ1 complex.

In some embodiments, the method is performed in vitro. In some embodiments, the method is performed in vivo.

In some embodiments, the GARP-TGFβ1 complex or the LRRC33-TGFβ1 complex is present at the outer surface of a cell.

In some embodiments, the cell is a T-cell, a fibroblast, a macrophage, a monocyte, a dendritic cell, an antigen presenting cell, or a microglia.

In some embodiments, the LTBP1-TGFβ1 complex or the LTBP3-TGFβ1 complex is bound to an extracellular matrix. In some embodiments, the extracellular matrix comprises fibrillin. In some embodiments, the extracellular matrix comprises a protein comprising an RGD motif.

In another aspect, provided herein is a method for reducing TGFβ1 activation in a subject, the method comprising administering to the subject an effective amount of an antibody, an antigen binding portion thereof, or a pharmaceutical composition, as described herein, thereby reducing TGFβ1 activation in the subject.

In some embodiments, the subject has or is at risk of having fibrosis. In some embodiments, the subject has a muscular dystrophy. In some embodiments, the subject has Duchenne muscular dystrophy (DMD). In some embodiments, the subject has or is at risk of having liver fibrosis, kidney fibrosis, or lung fibrosis (e.g., idiopathic pulmonary fibrosis). In some embodiments, the subject has or is at risk of having cancer. In some embodiments, the subject has or is at risk of having dementia. In some embodiments, the subject has or is at risk of developing myelofibrosis.

In some embodiments, the subject further receives an additional therapy. In some embodiments, the additional therapy is selected from the group consisting of a myostatin inhibitor, a VEGF agonist, an IGF1 agonist, an FXR agonist, a CCR2 inhibitor, a CCR5 inhibitor, a dual CCR2/CCR5 inhibitor, a lysyl oxidase-like-2 inhibitor, an ASK1 inhibitor, an Acetyl-CoA Carboxylase (ACC) inhibitor, a p38 kinase inhibitor, Pirfenidone, Nintedanib, a GDF11 inhibitor, or any combination thereof.

In some embodiments, the antibody, or the antigen binding portion thereof, reduces the suppressive activity of regulatory T cells.

In some embodiments, the antibody, or the antigen binding portion thereof, does not induce organ toxicity in the subject. In some embodiments, the organ toxicity comprises cardiovascular toxicity, gastrointestinal toxicity, immunotoxicity, bone toxicity, cartilage toxicity, reproductive system toxicity, or renal toxicity.

In one aspect, provided herein is a method for treating cancer in a subject in need thereof, the method comprising administering to the subject an effective amount of an antibody, an antigen binding portion thereof, or a pharmaceutical composition, as described herein, thereby treating cancer in the subject.

In another aspect, provided herein is a method of reducing tumor growth in a subject in need thereof, the method comprising administering to the subject an effective amount of an antibody, an antigen binding portion thereof, or a pharmaceutical composition, as described herein, thereby reducing tumor growth in the subject.

In some embodiments, the antibody, or antigen binding portion thereof, is administered in combination with an additional agent or an additional therapy. In some embodiments, the additional agent is a checkpoint inhibitor. In some embodiments, the additional agent is selected from the group consisting of a PD-1 antagonist, a PDL1 antagonist, a PD-L1 or PDL2 fusion protein, a CTLA4 antagonist, a GITR agonist, an anti-ICOS antibody, an anti-ICOSL antibody, an anti-B7H3 antibody, an anti-B7H4 antibody, an anti-TIM3 antibody, an anti-LAG3 antibody, an anti-OX40 antibody, an anti-CD27 antibody, an anti-CD70 antibody, an anti-CD47 antibody, an anti-41BB antibody, an anti-PD-1 antibody, an oncolytic virus, and a PARP inhibitor. In some embodiments, the additional therapy is radiation, a chemotherapeutic, or a combination thereof. In some embodiments, the additional therapy is radiation. In some embodiments, the additional agent is a chemotherapeutic agent. In some embodiments, the chemotherapeutic agent is Taxol. In some embodiments, the additional agent is an anti-inflammatory agent. In some embodiments, the additional agent inhibits the process of monocyte/macrophage recruitment and/or tissue infiltration. In some embodiments, the additional agent is an inhibitor of hepatic stellate cell activation. In some embodiments, the additional agent is a chemokine receptor antagonist, e.g., CCR2 antagonists and CCR5 antagonists. In some embodiments, such chemokine receptor antagonist is a dual specific antagonist, such as a CCR2/CCR5 antagonist. In some embodiments, the additional agent to be administered as combination therapy is or comprises a member of the TGFβ superfamily of growth factors or regulators thereof. In some embodiments, such agent is selected from modulators (e.g., inhibitors and activators) of GDF8/myostatin and GDF11. In some embodiments, such agent is an inhibitor of GDF8/myostatin signaling. In some embodiments, such agent is a monoclonal antibody that specifically binds a pro/latent myostatin complex and blocks activation of myostatin. In some embodiments, the monoclonal antibody that specifically binds a pro/latent myostatin complex and blocks activation of myostatin does not bind free, mature myostatin.

In yet another aspect, provided herein is a method of treating a renal disorder in a subject in need thereof, the method comprising administering to the subject an effective amount of an antibody, an antigen binding portion thereof, or a pharmaceutical composition, as described herein, thereby treating the renal disorder in the subject.

In one aspect, provided herein is a nucleic acid encoding an antibody, or an antigen binding portion thereof, as described herein. Vectors comprising the nucleic acid are also provided.

In another aspect, provided herein is a cell comprising a nucleic acid encoding an antibody, or an antigen binding portion thereof, as described herein. Also provided is a cell comprising a vector comprising a nucleic acid encoding an antibody, or an antigen binding portion thereof, as described herein.

In yet another aspect, provided herein is a kit comprising an antibody, an antigen binding portion thereof, or a pharmaceutical composition, as described herein, and instructions for use thereof.

In another aspect, provided herein is a method for treating a myofiber damage, the method comprising a step of: administering to a subject having a myofiber damage an agent that selectively inhibits TGFβ1 over TGFβ2/3 in an amount effective to i) promote myofiber repair; ii) protect from contraction-induced injury; iii) reduce inflammation in muscle; and/or, iv) reduce fibrosis in muscle. In some embodiments, the amount does not cause unacceptable level of adverse effects in the subject.

In some embodiments, the myofiber damage is i) associated with a muscular dystrophy; or, ii) associated with an acute muscle injury. In some embodiments, the agent blocks activation of TGFβ1 but not TGFβ2 or TGFβ3. In some embodiments, the agent is a monoclonal antibody. In some embodiments, the monoclonal antibody binds a GARP-proTGFβ1 latent complex, an LRRC33-proTGFβ1 latent complex, an LTBP1-proTGFβ1 latent complex, an LTBP2-proTGFβ1 latent complex, an LTBP3-proTGFβ1 latent complex, and/or an LTBP4-proTGFβ1 latent complex. In some embodiments, the subject further receives a myostatin inhibitor.

In some embodiments, the method further comprises a step of: identifying a source or context of disease-associated TGFβ1.

In yet another aspect, provided herein is a method for producing a pharmaceutical composition that modulates TGFβ signaling, the method comprising steps of: providing one or more agents that modulate signaling of at least one isoform of TGFβ; measuring activities of the one or more agents towards all isoforms of TGFβ; selecting an agent that is specific to a single isoform of TGFβ; formulating into a pharmaceutical composition comprising an isoform-specific TGFβ modulator and a pharmaceutically acceptable excipient. Also provided is a pharmaceutical composition produced by this method.

In some embodiments, the isoform-specific TGFβ modulator is a TGFβ1-specific modulator. In some embodiments, the TGFβ1-specific modulator is an inhibitor of TGFβ1. In some embodiments, the isoform-specific TGFβ modulator is an antibody or a fragment thereof. In some embodiments, the antibody or fragment thereof specifically binds a pro/latent complex of TGFβ1. In some embodiments, the antibody or fragment thereof does not bind free mature TGFβ1 which is not in the pro/latent complex. In some embodiments, the pro/latent complex comprises GARP, LRRC33, LTBP1, LTBP2, LTBP3 or LTBP4.

In another aspect, provided herein is a method for treating a disease associated with TGFβ signaling, the method comprising a step of: administering to a subject in need thereof a pharmaceutical composition provided herein, in an amount effective to treat the disease, wherein the amount achieves statistically significant clinical efficacy and safety when administered to a patient population having the disease.

In yet another aspect, provided herein is a TGFβ inhibitor for use in reducing adverse effects in a subject, wherein the TGFβ inhibitor is isoform-selective. In some embodiments, the TGFβ inhibitor is an antibody that specifically inhibits TGFβ1.

BRIEF DESCRIPTION OF THE DRAWINGS

FIG. 2A shows latent-transforming growth factor beta-binding proteins (LTBPs) presenting TGFβ in a fibrotic disease niche and a wound healing niche. FIG. 2B illustrates that glycoprotein-A repetitions predominant protein (GARP) modulates TGFβ activation in the inflammatory niche.

FIG. 4A is a chromatogram of the sample and FIG. 4B shows a blot of the products and a schematic illustrating the complex.

FIGS. 5A and 5B show the purification of the sGARP-TGFβ1 LAP complex. FIG. 5A is a chromatogram of the sample and FIG. 5B shows a blot of the products and a schematic illustrating the complex.

FIG. 6A is a chromatogram of the sample and FIG. 6B shows a blot of the products and a schematic illustrating the complex. NR stands for non-reducing and R stands for reducing.

FIGS. 11A-11C show inhibition of integrin-mediated TGFβ1 release from fibroblasts. FIGS. 11A and 11B are graphs depicting the inhibition of endogenous TGFβ1 in either normal human dermal fibroblasts (circles), normal human lung fibroblasts (squares), murine C57BL/6J lung fibroblasts (inverted triangles), or murine DBA2/J muscle fibroblasts (circles) using increasing concentrations of either Ab1 (FIG. 11A) or Ab2 (FIG. 11B). FIG. 11C provides a schematic of the co-culture assay system.

FIGS. 15A-15H are bar graphs depicting the relative mRNA levels of either plasminogen activator inhibitor-1 (PAI-1; FIG. 15A), connective tissue growth factor (CTGF; FIG. 15B), TGFβ1 (FIG. 15C), fibronectin-1 (FIG. 15D), α-smooth muscle actin (α-SMA; FIG. 15E), monocyte chemotactic protein 1 (MCP-1; FIG. 15F), collagen type I alpha 1 (Col1a1; FIG. 15G), or collagen type III alpha 1 chain (Col3a1; FIG. 15H) in kidney tissue from mice that underwent permanent right unilateral UUO surgery and were administered either PBS (control), 30 mg/kg of murine IgG1 control antibody, 3 mg/kg of Ab2, or 30 mg/kg of Ab2 intraperitoneally (i.p.) the day prior to surgical intervention, and then 1 and 3 days after the surgery (second to fifth bars of each graph); or mice that were administered PBS and underwent a laparotomy (sham control; first bar of each graph). This data is representative of multiple experiments.

FIG. 18A depicts that Ab1 and Ab2 specifically bind proTGFβ1 as measured by ELISA, but not proTGFβ2, proTGFβ3, or mature TGFβ1. FIG. 18B depicts an example of purified LTBP-proTGFβ1 expressed and purified for use as antigens to determine antibody binding specificity. FIG. 18C depicts an example of an antibody which binds (as measured by ELISA) specifically to the LTBP1-proTGFβ1 complex.

DETAILED DESCRIPTION

Figure 1:
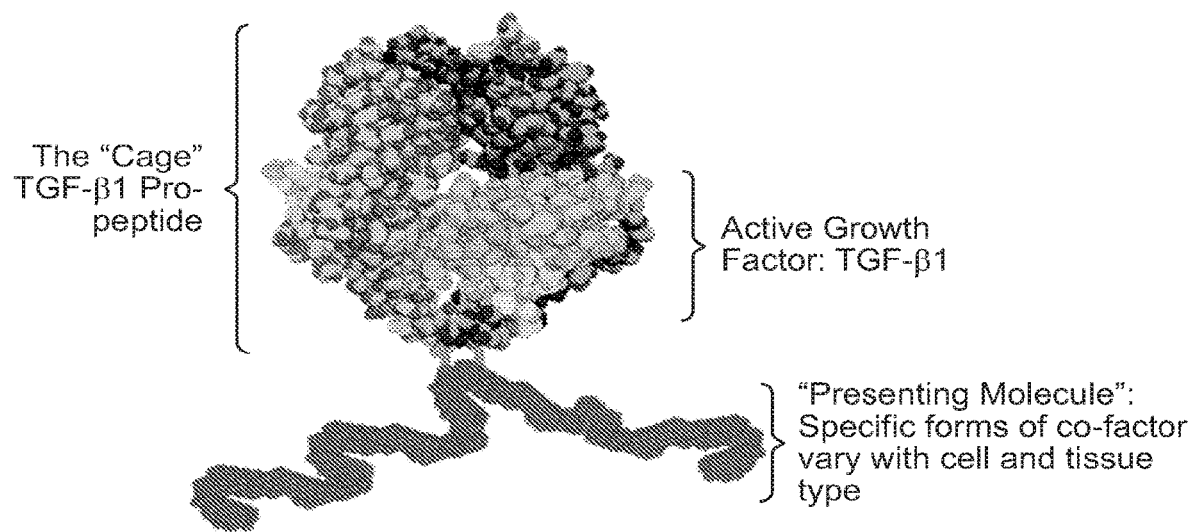
FIG. 1 is a schematic depicting TGFβ bound in a latent complex in the tissue microenvironment.

In mammals, the transforming growth factor-beta (TGFβ) superfamily is comprised of at least 33 gene products. These include the bone morphogenic proteins (BMPs), activins, growth and differentiation factors (GDFs), and the three isoforms of the TGFβ family: TGFβ1, TGFβ2, and TGFβ3. The TGFβs are thought to play key roles in diverse processes, such as inhibition of cell proliferation, extracellular matrix (ECM) remodeling, and immune homeostasis. The importance of TGFβ1 for T cell homeostasis is demonstrated by the observation that TGFβ1−/− mice survive only 3-4 weeks, succumbing to multiorgan failure due to massive immune activation (Kulkarni, A. B., et al., Proc Natl Acad Sci USA, 1993. 90(2): p. 770-4; Shull, M. M., et al., Nature, 1992. 359(6397): p. 693-9). The roles of TGFβ2 and TGFβ3 are less clear. Whilst the three TGFβ isoforms have distinct temporal and spatial expression patterns, they signal through the same receptors, TGFβRI and TGFβRII, although in some cases, for example for TGFβ2 signaling, type III receptors such as betaglycan are also required (Feng, X. H. and R. Derynck, Annu Rev Cell Dev Biol, 2005. 21: p. 659-93; Massague, J., Annu Rev Biochem, 1998. 67: p. 753-91). Ligand-induced oligomerization of TGFβRI/II triggers the phosphorylation of SMAD transcription factors, resulting in the transcription of target genes, such as Col1a1, Col3a1, ACTA2, and SERPINE1 (Massague, J., J. Seoane, and D. Wotton, Genes Dev, 2005. 19(23): p. 2783-810). SMAD-independent TGFβ signaling pathways have also been described, for example in cancer or in the aortic lesions of Marfan mice (Derynck, R. and Y. E. Zhang, Nature, 2003. 425(6958): p. 577-84; Holm, T. M., et al., Science, 2011. 332(6027): p. 358-61).

The biological importance of the TGFβ pathway in humans has been validated by genetic diseases. Camurati-Engelman disease results in bone dysplasia due to an autosomal dominant mutation in the TGFβ1 gene, leading to constitutive activation of TGFβ1 signaling (Janssens, K., et al., J Med Genet, 2006. 43(1): p. 1-11). Patients with Loeys/Dietz syndrome carry autosomal dominant mutations in components of the TGFβ signaling pathway, which cause aortic aneurism, hypertelorism, and bifid uvula (Van Laer, L., H. Dietz, and B. Loeys, Adv Exp Med Biol, 2014. 802: p. 95-105). As TGFβ pathway dysregulation has been implicated in multiple diseases, several drugs that target the TGFβ pathway have been developed and tested in patients, but with limited success.

The inventors of the present disclosure reasoned that, while all three isoforms of TGFβ are capable of signaling through the same receptors and transducing the downstream effectors in cells expressing the receptors, each TGFβ isoform may generate distinct biological effects in vivo. Moreover, the inventors contemplate that, at least in some circumstances, the mode by which the growth factor-receptor interaction is triggered may further provide signaling specificity in vivo. In light of this recognition, it is noted that TGFβ inhibitors described in the literature to date lack specificity as briefly summarized below.

Fresolimumab, a humanized monoclonal antibody that binds and inhibits all three isoforms of TGFβ has been tested clinically in patients with focal segmental glomerulosclerosis, malignant melanoma, renal cell carcinoma, and systemic sclerosis (Rice, L. M., et al., J Clin Invest, 2015. 125(7): p. 2795-807; Trachtman, H., et al., Kidney Int, 2011. 79(11): p. 1236-43; Morris, J. C., et al., PLoS One, 2014. 9(3): p. e90353). Additional companies have developed monoclonal antibodies against the TGFβ growth factors with varying degrees of selectivity for TGFβ isoforms. Such agents likely elicit toxicities in vivo through residual activity against other TGFβ family members besides TGFβ1. To the best of the knowledge of the inventors of the present disclosure, complete specificity for a single isoform has not been achieved by targeting the mature growth factor, due to the high degree of sequence identity between isoforms.

Other approaches to target the TGFβ pathway include ACE-1332, a soluble TGFβRII-Fc ligand trap from Acceleron (Yung, L. M., et al., A Am J Respir Crit Care Med, 2016. 194(9): p. 1140-1151), or small molecule inhibitors of the ALK5 kinase, such as Lilly's galunisertib. While ACE-1332 binds TGFβ1 and TGFβ3 with equally high affinity (Yung, L. M., et al., Am J Respir Crit Care Med, 2016. 194(9): p. 1140-1151). ALK5 inhibitors block the activity of all growth factors that signal through TGFR1. Substantial toxicities have been found in preclinical studies using ALK5 inhibitors (Anderton, M. J., et al., Toxicol Pathol, 2011. 39(6): p. 916-24; Stauber, A., et al., Clinical Toxicology, 2014. 4(3): p. 1-10), and sophisticated clinical dosing schemes are required to maintain efficacy while reducing adverse events (Herbertz, S., et al., Drug Des Devel Ther, 2015. 9: p. 4479-99). In fact, the question of TGFβ signaling specificity and its possible effect on toxicity observed with the known TGFβ inhibitors has not been raised in most, if not all, of the candidate drugs that attempted to block TGFβ. For example, how much of the toxicities are due to inhibition of TGFβ1 versus TGFβ2 and/or TGFβ3 has not been addressed. Similarly, modes of TGFβ activation have not been taken into account in designing or developing ways to antagonize TGFβ signaling.

Figure 2A:
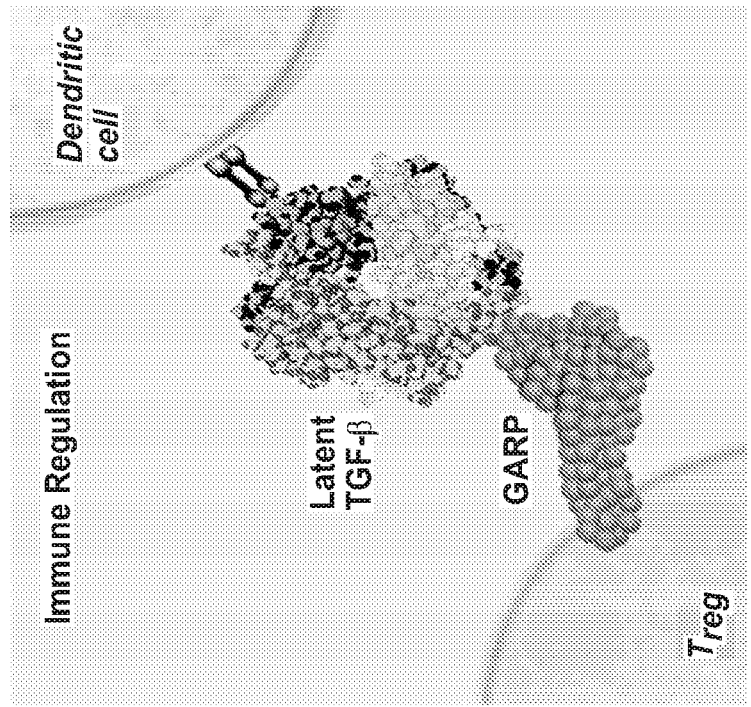
FIGS. 2A and 2B are schematics depicting niche modulation in the microenvironment.
Figure 2B:
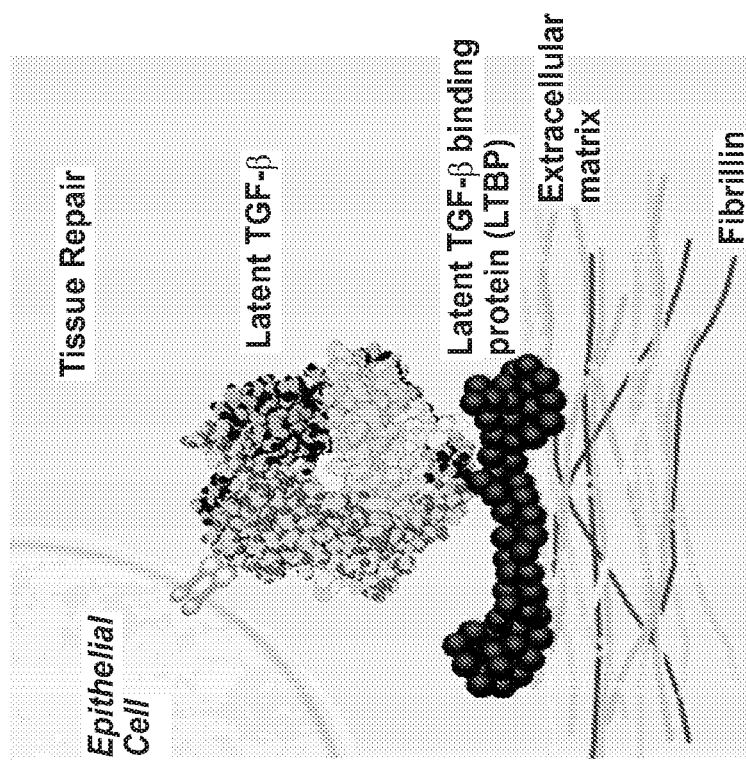

Recent structural insights into the activation mechanism of TGFβ1 have enabled the present inventors to take novel, more specific, approaches to TGFβ inhibition (Shi, M., et al., Nature, 2011. 474(7351): p. 343-9). Unlike other cytokines, TGFβ superfamily members are not secreted as active growth factors, but as dimeric pro-proteins which consist of an N-terminal prodomain and a C-terminal growth factor domain. Cleavage of proTGFβ1 by furin proteases separates the homodimeric growth factor domain from its prodomain, also referred to as latency associated peptide (LAP). However, the growth factor and LAP remain noncovalently associated, forming a latent complex which is unable to bind its receptors and induce signaling (FIG. 1). During translation latent TGFβ1, also called the small latent complex (SLC), becomes linked to "presenting molecules" via disulfide bridges, forming the large latent complex (LLC). These molecules allow proTGFβ1 to be presented in specific cellular or tissue contexts. Two cysteines near the N-terminus of the latent TGFβ1 link to appropriately positioned cysteines on the presenting molecule. The identity of the presenting molecule depends on the environment and cell type producing latent TGFβ1. For example, fibroblasts secrete latent TGFβ1 tethered to latent TGFβ-binding proteins (LTBPs), which then associates with proteins in the extracellular matrix (ECM) (i.e., fibronectin, fibrillin-1) to link latent TGFβ to the ECM (Robertson et al. Matrix Biol 47: 44-53 (2015) (FIG. 2A). On the surface of activated regulatory T cells latent TGFβ1 is covalently linked to the transmembrane protein GARP (FIG. 2B), and recently a protein closely related to GARP, LRRC33, was identified as a presenting molecule for TGFβ1 on the surface of monocytes, macrophages and microglia (Wang, R., et al., Mol Biol Cell, 2012. 23(6): p. 1129-39 and T. A. Springer, Int. BMP Conference 2016).

In mammals there are four known LTBPs, LTBP1-4, each with multiple splice variants (Robertson, I. B., et al., Matrix Biol, 2015. 47: p. 44-53). LTBP2 is the only LTBP that does not associate with latent TGFβ (Saharinen, J. and J. Keski-Oja, Mol Biol Cell, 2000. 11(8): p. 2691-704). While the association between LTBP1 or LTBP3 and latent TGFβ1 has been well validated, the role of LTBP4 in TGFβ presentation is less clear. The complex with LTBP4 and latent TGFβ1 appears to form much less efficiently, potentially due to the absence of several negatively charged residues in the TGFβ-binding domain of LTBP4 (Saharinen, J. and J. Keski-Oja, Mol Biol Cell, 2000. 11(8): p. 2691-704; Chen, Y., et al., J Mol Biol, 2005. 345(1): p. 175-86). Both LTBP4S−/− mice and Urban-Rifkin-Davis syndrome patients, who have null mutations in LTBP4, suffer from disrupted elastic fiber assembly (Urban, Z., et al., Am J Hum Genet, 2009. 85(5): p. 593-605; Dabovic, B., et al., J Cell Physiol, 2015. 230(1): p. 226-36). Additionally, while LTBP4S−/− mice have a lung septation and an elastogenesis defect, transgenic mice with an LTBP4 that cannot form a complex with latent TGFβ1 have no obvious phenotype (Dabovic, B., et al., J Cell Physiol, 2015. 230(1): p. 226-36). Whether LTBP4 is directly involved in regulation of latent TGFβ1 by functioning as a presenting molecule is unclear; LTBP4 may instead be required for proper formation of elastic fibrils in the ECM and its loss indirectly affect latent TGFβ1 activation through defects in the ECM.

A number of studies have shed light on the mechanisms of TGFβ1 activation. Three integrins, αVβ6, αVβ8, and αVβ1 have been demonstrated to be key activators of latent TGFβ1 (Reed, N. I., et al., Sci Transl Med, 2015. 7(288): p. 288ra79; Travis, M. A. and D. Sheppard, Annu Rev Immunol, 2014. 32: p. 51-82; Munger, J. S., et al., Cell, 1999. 96(3): p. 319-28). aV integrins bind the RGD sequence present in TGFβ1 and TGFβ1 LAPs with high affinity (Dong, X., et al., Nat Struct Mol Biol, 2014. 21(12): p. 1091-6). Transgenic mice with a mutation in the TGFβ1 RGD site that prevents integrin binding, but not secretion, phenocopy the TGFβ1−/− mouse (Yang, Z., et al., J Cell Biol, 2007. 176(6): p. 787-93). Mice that lack both β6 and β8 integrins recapitulate all essential phenotypes of TGFβ1 and TGFβ3 knockout mice, including multiorgan inflammation and cleft palate, confirming the essential role of these two integrins for TGFβ1 activation in development and homeostasis (Aluwihare, P., et al., J Cell Sci, 2009. 122(Pt 2): p. 227-32). Key for integrin-dependent activation of latent TGFβ1 is the covalent tether to presenting molecules; disruption of the disulfide bonds between GARP and TGFβ1 LAP by mutagenesis does not impair complex formation, but completely abolishes TGFβ1 activation by αVβ6 (Wang, R., et al., Mol Biol Cell, 2012. 23(6): p. 1129-39). The recent structure of latent TGFβ1 illuminates how integrins enable release of active TGFβ1 from the latent complex: the covalent link of latent TGFβ1 to its presenting molecule anchors latent TGFβ1, either to the ECM through LTBPs, or to the cytoskeleton through GARP or LRRC33. Integrin binding to the RGD sequence results in a force-dependent change in the structure of LAP, allowing active TGFβ1 to be released and bind nearby receptors (Shi, M., et al., Nature, 2011. 474(7351): p. 343-9). The importance of integrin-dependent TGFβ1 activation in disease has also been well validated. A small molecular inhibitor of αVβ1 protects against bleomycin-induced lung fibrosis and carbon tetrachloride-induced liver fibrosis (Reed, N. I., et al., Sci Transl Med, 2015. 7(288): p. 288ra79), and αVβ6 blockade with an antibody or loss of integrin β6 expression suppresses bleomycin-induced lung fibrosis and radiation-induced fibrosis (Munger, J. S., et al., Cell, 1999. 96(3): p. 319-28); Horan, G. S., et al., Am J Respir Crit Care Med, 2008. 177(1): p. 56-65). In addition to integrins, other mechanisms of TGFβ1 activation have been implicated, including thrombospondin-1 and activation by proteases such as matrix metalloproteinases (MMPs), cathepsin D or kallikrein. However, the majority of these studies were performed in vitro using purified proteins; there is less evidence for the role of these molecules from in vivo studies. Knockout of thrombospondin-1 recapitulates some aspects of the TGFβ1−/− phenotype in some tissues, but is not protective in bleomycin-induced lung fibrosis, known to be TGFβ-dependent (Ezzie, M. E., et al., Am J Respir Cell Mol Biol, 2011. 44(4): p. 556-61). Additionally, knockout of candidate proteases did not result in a TGFβ1 phenotype (Worthington, J. J., J. E. Klementowicz, and M. A. Travis, Trends Biochem Sci, 2011. 36(1): p. 47-54). This could be explained by redundancies or by these mechanisms being critical in specific diseases rather than development and homeostasis.

TGFβ has been implicated in a number of biological processes, including fibrosis, immune-modulation and cancer progression. TGFβ1 was the first identified member of the TGFβ superfamily of proteins. Like other members of the TGFβ superfamily, TGFβ1 and the isoforms TGFβ2 and TGFβ3, are initially expressed as inactive precursor pro-protein forms (termed proTGFβ). TGFβ proteins (e.g., TGFβ1, TGFβ2 and TGFβ3) are proteolytically cleaved by proprotein convertases (e.g., furin) to yield the latent form (termed latent TGFβ). In some embodiments, a pro-protein form or latent form of a TGFβ protein (e.g., TGFβ1, TGFβ2 and TGFβ3) may be referred to as "pro/latent TGFβ protein". TGFβ1 may be presented to other molecules in complex with multiple molecules including, for example, GARP (to form a GARP-TGFβ1 complex), LRRC33 (to form a LRRC33-TGFβ1 complex), LTBP1 (to form a LTBP1-TGFβ1 complex), and/or LTBP3 (to form a LTBP3-TGFβ1 complex). The TGFβ1 present in these complexes may be in either latent form (latent TGFβ1) or in precursor form (proTGFβ1).

The present invention is directed to immunoglobulins, e.g., antibodies, or antigen binding portions thereof, that specifically bind to (1) a TGFβ protein (e.g., pro/latent TGFβ1, pro/latent TGFβ2, and pro/latent TGFβ3) in complex with a GARP protein, (2) a TGFβ protein in complex with a LTBP protein (e.g., LTBP1 or LTBP3), and/or (3) a TGFβ protein in complex with a LRRC33 protein. In some embodiments, the antibodies, or antigen binding portions thereof, disclosed herein bind to an epitope of TGFβ1 that is available for binding by the antibody, or antigen binding portions thereof, when the TGFβ1 is present in a GARP-TGFβ1 complex, a LTBP1-TGFβ1 complex, a LTBP3-TGFβ1 complex, and/or a LRRC33-TGFβ1 complex. Without wishing to be bound by any particular theory, the ability of the antibodies, and antigen binding portions thereof, disclosed herein to bind to TGFβ protein (e.g., TGFβ1) that is in complex with either a GARP protein, a LTBP protein, and/or a LRRC33 protein allows for the targeting of TGFβ protein in a context-independent manner, and may be particularly suitable for therapeutic applications.

Definitions

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, the term "specific binding" or "specifically binds" means that the interaction of the antibody, or antigen binding portion thereof, with an antigen is dependent upon the presence of a particular structure (e.g., an antigenic determinant or epitope). For example, the antibody, or antigen binding portion thereof, binds to a specific protein rather than to proteins generally. In some embodiments, an antibody, or antigen binding portion thereof, specifically binds to a target, e.g., TGFβ1, if the antibody has a $K_D$ for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, the term "specific binding to an epitope of TGFβ1", "specifically binds to an epitope of TGFβ1", "specific binding to TGFβ1", or "specifically binds to TGFβ1" as used herein, refers to an antibody, or antigen binding portion thereof, that binds to TGFβ1 and has a dissociation constant ($K_D$) of $1.0 \times 10^{-7}$ M or less, as determined by surface plasmon resonance. In one embodiment, an antibody, or antigen binding portion thereof, can specifically bind to both human and a non-human (e.g., mouse) orthologues of TGFβ1.

In some embodiments, the binding affinity of an antibody, or antigen binding portion thereof, to a GARP-TGFβ1 complex, a LTBP1-TGFβ1 complex, a LTBP3-TGFβ1 complex, and/or a LRRC33-TGFβ1 complex is determined using an Octet assay. In some embodiments, an Octet assay is an assay that determines one or more kinetic parameters indicative of binding between an antibody and antigen. In some embodiments, an Octet® system (ForteBio, Menlo Park, Calif.) is used to determine the binding affinity of an antibody, or antigen binding portion thereof, to a GARP-TGFβ1 complex, a LTBP1-TGFβ1 complex, a LTBP3-TGFβ1 complex, and/or a LRRC33-TGFβ1 complex. For example, binding affinities of antibodies may be determined using the forteBio Octet $QK^e$ dip and read label free assay system utilizing bio-layer interferometry. In some embodiments, antigens are immobilized to biosensors (e.g., streptavidin-coated biosensors) and the antibodies and complexes (e.g., biotinylated GARP-TGFβ1 complexes and biotinylated LTBP-TGFβ1 complexes) are presented in solution at high concentration (50 μg/mL) to measure binding interactions. In some embodiments, the binding affinity of an antibody, or antigen binding portion thereof, to a GARP-TGFβ1 complex, a LTBP1-TGFβ1 complex, a LTBP3-TGFβ1 complex, and/or a LRRC33-TGFβ1 complex is determined using the protocol outlined in Table 6.

Figure 3:
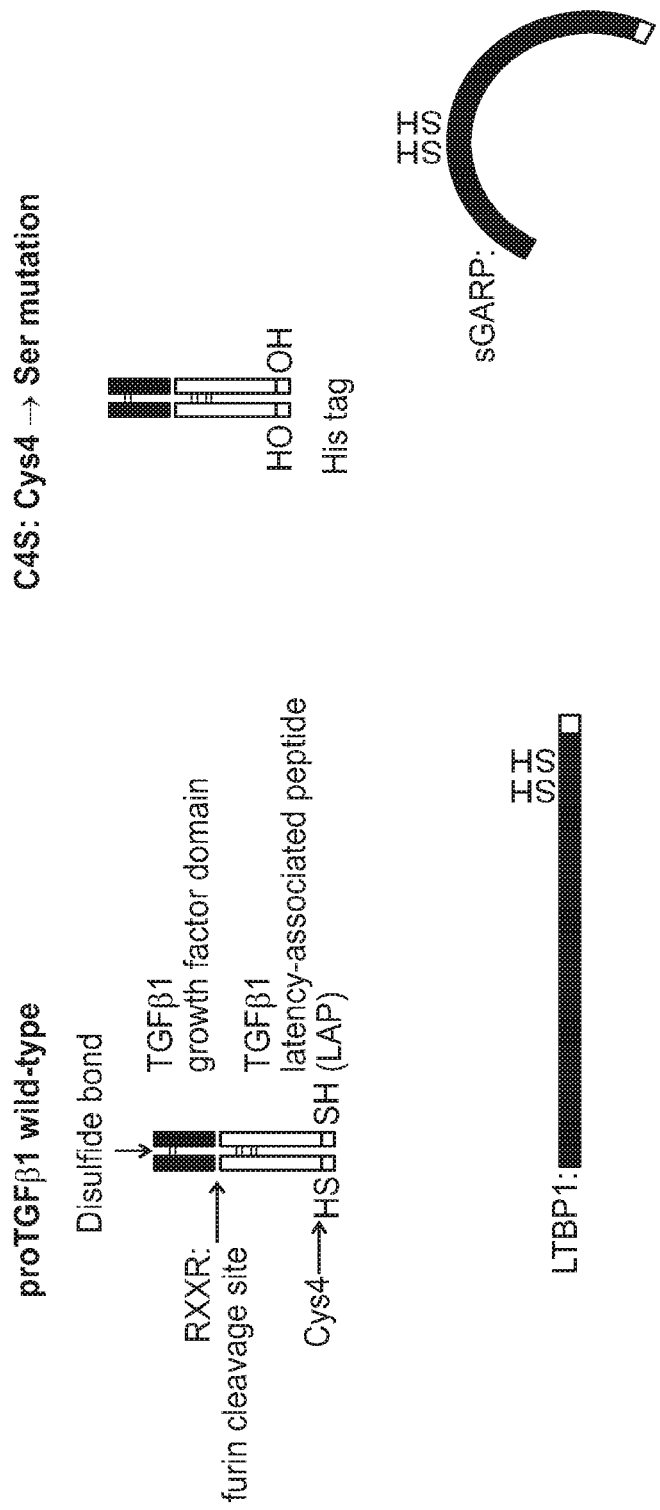
FIG. 3 illustrates a protein expression platform for making a GARP-TGFβ1 complex and a LTBP-TGFβ1 complex. The HEK293-based expression system uses NiNTA affinity purification and gel filtration to obtain multimilligram quantities of purified protein. Schematics of wild-type proTGFβ1, LTPB1, sGARP, and proTGFβ1 C4S are shown.

As used herein, the term "GARP-TGFβ1 complex" refers to a protein complex comprising a pro-protein form or latent form of a transforming growth factor-01 (TGFβ1) protein and a glycoprotein-A repetitions predominant protein (GARP). In some embodiments, a pro-protein form or latent form of TGFβ1 protein may be referred to as "pro/latent TGFβ1 protein". In some embodiments, a GARP-TGFβ1 complex comprises GARP covalently linked with pro/latent TGFβ1 via one or more disulfide bonds. In other embodiments, a GARP-TGFβ1 complex comprises GARP non-covalently linked with pro/latent TGFβ1. In some embodiments, a GARP-TGFβ1 complex is a naturally-occurring complex, for example a GARP-TGFβ1 complex in a cell. An exemplary GARP-TGFβ1 complex is shown in FIG. 3.

As used herein, the term "LTBP1-TGFβ1 complex" refers to a protein complex comprising a pro-protein form or latent form of transforming growth factor-01 (TGFβ1) protein and a latent TGF-beta binding protein 1 (LTBP1). In some embodiments, a LTBP1-TGFβ1 complex comprises LTBP1 covalently linked with pro/latent TGFβ1 via one or more disulfide bonds. In other embodiments, a LTBP1-TGFβ1 complex comprises LTBP1 non-covalently linked with pro/latent TGFβ1. In some embodiments, a LTBP1-TGFβ1 complex is a naturally-occurring complex, for example a LTBP1-TGFβ1 complex in a cell. An exemplary LTBP1-TGFβ1 complex is shown in FIG. 3.

As used herein, the term "LTBP3-TGFβ1 complex" refers to a protein complex comprising a pro-protein form or latent form of transforming growth factor-01 (TGFβ1) protein and a latent TGF-beta binding protein 1 (LTBP3). In some embodiments, a LTBP3-TGFβ1 complex comprises LTBP3 covalently linked with pro/latent TGFβ1 via one or more disulfide bonds. In other embodiments, a LTBP3-TGFβ1 complex comprises LTBP1 non-covalently linked with pro/latent TGFβ1. In some embodiments, a LTBP3-TGFβ1 complex is a naturally-occurring complex, for example a LTBP3-TGFβ1 complex in a cell. An exemplary LTBP3-TGFβ1 complex is shown in FIG. 3.

As used herein, the term "LRRC33-TGFβ1 complex" refers to a complex between a pro-protein form or latent form of transforming growth factor-01 (TGFβ1) protein and a Leucine-Rich Repeat-Containing Protein 33 (LRRC33; also known as Negative Regulator Of Reactive Oxygen Species or NRROS). In some embodiments, a LRRC33-TGFβ1 complex comprises LRRC33 covalently linked with pro/latent TGFβ1 via one or more disulfide bonds. In other embodiments, a LRRC33-TGFβ1 complex comprises LRRC33 non-covalently linked with pro/latent TGFβ1. In some embodiments, a LRRC33-TGFβ1 complex is a naturally-occurring complex, for example a LRRC33-TGFβ1 complex in a cell.

The term "antibody" refers to an immunoglobulin molecule that specifically binds to a target antigen, and includes, for instance, chimeric, humanized, fully human, and bispecific antibodies. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. Antibodies, or antigen binding portions thereof, can be produced in hybridomas, by recombinant DNA techniques, or by enzymatic or chemical cleavage of intact antibodies. The term antibodies, as used herein, includes monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), respectively. In some embodiments, the term also encompasses peptibodies.

Naturally-occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human antibody light chains are typically classified as kappa and lambda light chains. Heavy chains are typically classified as mu, delta, gamma, alpha, or epsilon, and define the isotype of the antibody. An antibody can be of any type (e.g., IgM, IgD, IgG, IgA, IgY, and IgE) and class (e.g., IgG1, IgG2, IgG3, IgG4, IgM1, IgM2, IgA1, and IgA2). Within full-length light and heavy chains, typically, the variable and constant regions are joined by a "J" region of about 12 or more amino acids, with the heavy chain also including a "D" region of about 10 more amino acids (see, e.g., Fundamental Immunology, Ch. 7 (Paul, W., ed., 2nd ed. Raven Press, N.Y. (1989)) (incorporated by reference in its entirety)). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk (1987) J. Mol. Biol. 196: 901-917; Chothia et al. (1989) Nature 342: 878-883. The CDRs of a light chain can also be referred to as CDR-L1, CDR-L2, and CDR-L3, and the CDRs of a heavy chain can also be referred to as CDR-H1, CDR-H2, and CDR-H3. In some embodiments, an antibody can comprise a small number of amino acid deletions from the carboxy end of the heavy chain(s). In some embodiments, an antibody comprises a heavy chain having 1-5 amino acid deletions in the carboxy end of the heavy chain. In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In some embodiments, various methods of analysis can be employed to identify or approximate the CDR regions. Examples of such methods include, but are not limited to, the Kabat definition, the Chothia definition, the AbM definition, and the contact definition.

A "functional antigen binding site" of a binding protein is one that that can bind to a target, antigen, or ligand. The antigen binding affinity of the antigen binding site is not necessarily as strong as the parent binding protein from which the antigen binding site is derived, but the ability to bind antigen must be measurable using any one of a variety of methods known for evaluating binding protein binding to an antigen. Moreover, the antigen binding affinity of each of the antigen binding sites of a multispecific binding protein herein need not be quantitatively the same.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

An immunoglobulin constant domain refers to a heavy or light chain constant domain. Human IgG heavy chain and light chain constant domain amino acid sequences are known in the art.

The term "compete" when used in the context of antigen binding proteins (e.g., an antibody or antigen binding portion thereof) that compete for the same epitope means competition between antigen binding proteins as determined by an assay in which the antigen binding protein being tested prevents or inhibits (e.g., reduces) specific binding of a reference antigen binding protein to a common antigen (e.g., TGFβ1 or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay; solid phase direct biotin-avidin EIA; solid phase direct labeled assay, and solid phase direct labeled sandwich assay. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "antigen" refers to a molecular structure that provides an epitope, e.g., a molecule or a portion of a molecule, or a complex of molecules or portions of molecules, capable of being bound by a selective binding agent, such as an antigen binding protein (including, e.g., an antibody). Thus, a selective binding agent may specifically bind to an antigen that is formed by two or more components in a complex. In some embodiments, the antigen is capable of being used in an animal to produce antibodies capable of binding to that antigen. An antigen can possess one or more epitopes that are capable of interacting with different antigen binding proteins, e.g., antibodies.

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region that can bind the antigen. The exact boundaries of these CDRs have been defined differently according to different systems. The system described by Kabat (Kabat et al. (1987; 1991) Sequences of Proteins of Immunological Interest (National Institutes of Health, Bethesda, Md.) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk (1987) J. Mol. Biol. 196: 901-917; and Chothia et al. (1989) Nature 342: 877-883) found that certain sub-portions within Kabat CDRs adopt nearly identical peptide backbone conformations, despite having great diversity at the level of amino acid sequence. These sub-portions were designated as L1, L2 and L3 or H1, H2 and H3, where the "L" and the "H" designate the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9: 133-139 and MacCallum (1996) J. Mol. Biol. 262(5): 732-45. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

The terms "crystal" and "crystallized" as used herein, refer to a binding protein (e.g., an antibody), or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 201-16, Oxford University Press, New York, N.Y., (1999).

The term "epitope" includes any molecular determinant (e.g., polypeptide determinant) that can specifically bind to a binding agent, immunoglobulin or T-cell receptor. In certain embodiments, epitope determinants include chemically active surface groupings of molecules, such as amino acids, sugar side chains, phosphoryl, or sulfonyl, and, in certain embodiments, may have specific three-dimensional structural characteristics, and/or specific charge characteristics. An epitope is a region of an antigen that is bound by a binding protein. An epitope thus consists of the amino acid residues of a region of an antigen (or fragment thereof) known to bind to the complementary site on the specific binding partner. An antigenic fragment can contain more than one epitope. In certain embodiments, an antibody is the to specifically bind an antigen when it recognizes its target antigen in a complex mixture of proteins and/or macromolecules. For example, antibodies are said to "bind to the same epitope" if the antibodies cross-compete (one prevents the binding or modulating effect of the other). In addition, structural definitions of epitopes (overlapping, similar, identical) are informative, but functional definitions are often more relevant as they encompass structural (binding) and functional (modulation, competition) parameters.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The terms "antigen binding portion" or "antigen binding fragment" of an antibody, as used herein, refers to one or more fragments of an antibody that retain the ability to specifically bind to an antigen (e.g., TGFβ1). Antigen binding portions include, but are not limited to, any naturally occurring, enzymatically obtainable, synthetic, or genetically engineered polypeptide or glycoprotein that specifically binds an antigen to form a complex. In some embodiments, an antigen-binding portion of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments, a monovalent fragment consisting of the VL, VH, CL and CH1 domains; (ii) F(ab')2 fragments, a bivalent fragment comprising two Fab fragments linked by a disulfide bridge at the hinge region; (iii) Fd fragments consisting of the VH and CH1 domains; (iv) Fv fragments consisting of the VL and VH domains of a single arm of an antibody; (v) single-chain Fv (scFv) molecules (see, e.g., Bird et al. (1988) SCIENCE 242:423-426; and Huston et al. (1988) PROC. NAT'L. ACAD. SCI. USA 85:5879-5883); (vi) dAb fragments (see, e.g., Ward et al. (1989) NATURE 341: 544-546); and (vii) minimal recognition units consisting of the amino acid residues that mimic the hypervariable region of an antibody (e.g., an isolated complementarity determining region (CDR)). Other forms of single chain antibodies, such as diabodies are also encompassed. The term antigen binding portion of an antibody includes a "single chain Fab fragment" otherwise known as an "scFab," comprising an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH—CH1, c) VH-CL-linker-VL-CH1 or d) VL-CH1-linker-VH-CL; and wherein said linker is a polypeptide of at least 30 amino acids, preferably between 32 and 50 amino acids.

An "isolated antibody", as used herein, refers to an antibody that is substantially free of other antibodies having different antigenic specificities. In some embodiments, an isolated antibody is substantially free of other cellular material and/or chemicals.

An "affinity matured" antibody is an antibody with one or more alterations in one or more CDRs thereof, which result an improvement in the affinity of the antibody for antigen compared to a parent antibody, which does not possess those alteration(s). Exemplary affinity matured antibodies will have nanomolar or even picomolar affinities for the target antigen. Affinity matured antibodies are produced by procedures known in the art. Marks et al. (1992) Bio/Technology 10: 779-783 describes affinity maturation by VH and VL domain shuffling. Random mutagenesis of CDR and/or framework residues is described by Barbas, et al. (1994) Proc Nat. Acad. Sci. USA 91: 3809-3813; Schier et al. (1995) Gene 169: 147-155; Yelton et al., (1995) J. Immunol. 155: 1994-2004; Jackson et al. (1995) J. Immunol. 154(7): 3310-9; and Hawkins et al. (1992) J. Mol. Biol. 226: 889-896; and selective mutation at selective mutagenesis positions, contact or hypermutation positions with an activity enhancing amino acid residue is described in U.S. Pat. No. 6,914,128.

The term "CDR-grafted antibody" refers to antibodies, which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "chimeric antibody" refers to antibodies, which comprise heavy and light chain variable region sequences from one species and constant region sequences from another species, such as antibodies having murine heavy and light chain variable regions linked to human constant regions.

The term "human antibody," as used herein, is intended to include antibodies having variable and constant regions derived from human germline immunoglobulin sequences. The human antibodies of the present disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "humanized antibody" refers to antibodies, which comprise heavy and light chain variable region sequences from a non-human species (e.g., a mouse) but in which at least a portion of the VH and/or VL sequence has been altered to be more "human-like," i.e., more similar to human germline variable sequences. One type of humanized antibody is a CDR-grafted antibody, in which human CDR sequences are introduced into non-human VH and VL sequences to replace the corresponding nonhuman CDR sequences. Also "humanized antibody" is an antibody, or a variant, derivative, analog or fragment thereof, which immuno specifically binds to an antigen of interest and which comprises an FR region having substantially the amino acid sequence of a human antibody and a CDR region having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the FR regions are those of a human immunoglobulin consensus sequence. In an embodiment a humanized antibody also comprises at least a portion of an immunoglobulin Fc region, typically that of a human immunoglobulin. In some embodiments a humanized antibody contains the light chain as well as at least the variable domain of a heavy chain. The antibody also may include the CH1, hinge, CH2, CH3, and CH4 regions of the heavy chain. In some embodiments a humanized antibody only contains a humanized light chain. In some embodiments a humanized antibody only contains a humanized heavy chain. In specific embodiments a humanized antibody only contains a humanized variable domain of a light chain and/or humanized heavy chain.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, —H2, and —H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin (see, e.g., Shapiro et al. (2002) Crit. Rev. Immunol. 22(3): 183-200; Marchalonis et al. (2001) Adv. Exp. Med. Biol. 484: 13-30). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "neutralizing" refers to counteracting the biological activity of an antigen when a binding protein specifically binds to the antigen. In an embodiment, the neutralizing binding protein binds to the antigen/target, e.g., cytokine, kinase, growth factor, cell surface protein, soluble protein, phosphatase, or receptor ligand, and reduces its biologically activity by at least about 20%, 40%, 60%, 80%, 85%, 90%, 95%. 96%, 97%. 98%, 99% or more.

The term "binding protein" as used herein includes any polypeptide that specifically binds to an antigen (e.g., TGFβ1), including, but not limited to, an antibody, or antigen binding portions thereof, a DVD-IgTM, a TVD-Ig, a RAb-Ig, a bispecific antibody and a dual specific antibody.

The term "monoclonal antibody" or "mAb" when used in a context of a composition comprising the same may refer to an antibody preparation obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "recombinant human antibody," as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom, H. R. (1997) TIB Tech. 15: 62-70; Azzazy, H. and Highsmith, W. E. (2002) Clin. Biochem. 35: 425-445; Gavilondo, J. V. and Larrick, J. W. (2002) BioTechniques 29: 128-145; Hoogenboom, H. and Chames, P. (2000) Immunol. Today 21: 371-378, incorporated herein by reference), antibodies isolated from an animal (e.g., a mouse) that is transgenic for human immunoglobulin genes (see, Taylor, L. D. et al. (1992) Nucl. Acids Res. 20: 6287-6295; Kellermann, S-A. and Green, L. L. (2002) Cur. Opin. in Biotechnol. 13:

593-597; Little, M. et al. (2000) Immunol. Today 21: 364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "Dual Variable Domain Immunoglobulin" or "DVD-Ig™" and the like include binding proteins comprising a paired heavy chain DVD polypeptide and a light chain DVD polypeptide with each paired heavy and light chain providing two antigen binding sites. Each binding site includes a total of 6 CDRs involved in antigen binding per antigen binding site. A DVD-IgTM is typically has two arms bound to each other at least in part by dimerization of the CH3 domains, with each arm of the DVD being bispecific, providing an immunoglobulin with four binding sites. DVD-IgTM are provided in US Patent Publication Nos. 2010/0260668 and 2009/0304693, each of which are incorporated herein by reference including sequence listings.

As used herein, "Triple Variable Domain Immunoglobulin" or "TVD-Ig" and the like are binding proteins comprising a paired heavy chain TVD binding protein polypeptide and a light chain TVD binding protein polypeptide with each paired heavy and light chain providing three antigen binding sites. Each binding site includes a total of 6 CDRs involved in antigen binding per antigen binding site. A TVD binding protein may have two arms bound to each other at least in part by dimerization of the CH3 domains, with each arm of the TVD binding protein being trispecific, providing a binding protein with six binding sites.

As used herein, "Receptor-Antibody Immunoglobulin" or "RAb-Ig" and the like are binding proteins comprising a heavy chain RAb polypeptide, and a light chain RAb polypeptide, which together form three antigen binding sites in total. One antigen binding site is formed by the pairing of the heavy and light antibody variable domains present in each of the heavy chain RAb polypeptide and the light chain RAb polypeptide to form a single binding site with a total of 6 CDRs providing a first antigen binding site. Each the heavy chain RAb polypeptide and the light chain RAb polypeptide include a receptor sequence that independently binds a ligand providing the second and third "antigen" binding sites. A RAb-Ig is typically has two arms bound to each other at least in part by dimerization of the CH3 domains, with each arm of the RAb-Ig being trispecific, providing an immunoglobulin with six binding sites. RAb-Igs are described in US Patent Application Publication No. 2002/0127231, the entire contents of which including sequence listings are incorporated herein by reference).

The term "bispecific antibody," as used herein, and as differentiated from a "bispecific half-Ig binding protein" or "bispecific (half-Ig) binding protein", refers to full-length antibodies that are generated by quadroma technology (see Milstein, C. and Cuello, A. C. (1983) Nature 305(5934): p. 537-540), by chemical conjugation of two different monoclonal antibodies (see Staerz, U. D. et al. (1985) Nature 314(6012): 628-631), or by knob-into-hole or similar approaches, which introduce mutations in the Fc region that do not inhibit CH3-CH3 dimerization (see Holliger, P. et al. (1993) Proc. Natl. Acad. Sci USA 90(14): 6444-6448), resulting in multiple different immunoglobulin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen binding arms (in both specificity and CDR sequences), and is monovalent for each antigen it binds to.

The term "dual-specific antibody," as used herein, and as differentiated from a bispecific half-Ig binding protein or bispecific binding protein, refers to full-length antibodies that can bind two different antigens (or epitopes) in each of its two binding arms (a pair of HC/LC) (see PCT Publication No. WO 02/02773). Accordingly, a dual-specific binding protein has two identical antigen binding arms, with identical specificity and identical CDR sequences, and is bivalent for each antigen to which it binds.

The term "pan-TGFβ antibody" refers to any antibody that is capable of binding to more than one isoform of TGFβ, for example, at least two of TGFβ1, TGFβ2, and TGFβ3. In some embodiments, a pan-TGFβ antibody binds all three isoforms, i.e., TGFβ1, TGFβ2, and TGFβ3. In some embodiments, a pan-TGFβ antibody binds and neutralizes all three isoforms, i.e., TGFβ1, TGFβ2, and TGFβ3.

The term "$K_{on}$," as used herein, is intended to refer to the on rate constant for association of a binding protein (e.g., an antibody) to the antigen to form the, e.g., antibody/antigen complex as is known in the art. The "$K_{on}$" also is known by the terms "association rate constant," or "$k_a$," as used interchangeably herein. This value indicating the binding rate of an antibody to its target antigen or the rate of complex formation between an antibody and antigen also is shown by the equation: Antibody ("Ab")+Antigen ("Ag")→Ab-Ag.

The term "$K_{off}$," as used herein, is intended to refer to the off rate constant for dissociation of a binding protein (e.g., an antibody) from the, e.g., antibody/antigen complex as is known in the art. The "$K_{off}$" also is known by the terms "dissociation rate constant" or "$k_d$" as used interchangeably herein. This value indicates the dissociation rate of an antibody from its target antigen or separation of Ab-Ag complex over time into free antibody and antigen as shown by the equation: Ab+Ag←Ab−Ag.

The terms "equilibrium dissociation constant" or "$K_r$)," as used interchangeably herein, refer to the value obtained in a titration measurement at equilibrium, or by dividing the dissociation rate constant ($k_{off}$) by the association rate constant ($k_{on}$). The association rate constant, the dissociation rate constant, and the equilibrium dissociation constant are used to represent the binding affinity of a binding protein, e.g., antibody, to an antigen. Methods for determining association and dissociation rate constants are well known in the art. Using fluorescencebased techniques offers high sensitivity and the ability to examine samples in physiological buffers at equilibrium. Other experimental approaches and instruments, such as a BIAcore® (biomolecular interaction analysis) assay, can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.), can also be used.

The term "linker" is used to denote polypeptides comprising two or more amino acid residues joined by peptide bonds and are used to link one or more antigen binding portions. Such linker polypeptides are well known in the art (see, e.g., Holliger, P. et al. (1993) Proc. Natl. Acad. Sci. USA 90: 6444-6448; Poljak, R. J. et al. (1994) Structure 2:1121-1123). Exemplary linkers include, but are not limited to, ASTKGPSVFPLAP (SEQ ID NO: 55), ASTKGP (SEQ ID NO: 56); TVAAPSVFIFPP (SEQ ID NO: 57); TVAAP (SEQ ID NO: 58); AKTTPKLEEGEFSEAR (SEQ ID NO: 59); AKTTPKLEEGEFSEARV (SEQ ID NO: 60); AKTTPKLGG (SEQ ID NO: 61); SAKTTPKLGG (SEQ ID NO: 62); SAKTTP (SEQ ID NO: 63); RADAAP (SEQ ID NO: 64); RADAAPTVS (SEQ ID NO: 65); RADAAAAGGPGS (SEQ ID NO: 66); RADAAAA(G4S)$_4$ (SEQ ID NO: 67); SAKTTPKLEEGEFSEARV (SEQ ID NO: 68); ADAAP (SEQ ID NO: 69); ADAAPTVSIFPP (SEQ ID NO: 70); QPKAAP (SEQ ID NO: 71); QPKAAPSVTLFPP (SEQ ID NO: 72); AKTTPP (SEQ ID NO: 73); AKTTPPSVTPLAP (SEQ ID NO: 74); AKTTAP (SEQ ID NO: 75); AKTTAPSVYPLAP (SEQ ID NO: 76); GGGGSGGGGSGGGGS (SEQ ID NO: 77); GENKVEYAPALMALS (SEQ ID NO: 78); GPAKELTPLKEAKVS (SEQ ID NO: 79); GHEAAAVMQVQYPAS (SEQ ID NO: 80); TVAAPSVFIFPPTVAAPSVFIFPP (SEQ ID NO: 81); and ASTKGPSVFPLAPASTKGPSVFPLAP (SEQ ID NO: 82).

The term "cancer" as used herein refers to the physiological condition in multicellular eukaryotes that is typically characterized by unregulated cell proliferation.

"Label" and "detectable label" or "detectable moiety" mean a moiety attached to a specific binding partner, such as an antibody or an analyte, e.g., to render the reaction between members of a specific binding pair, such as an antibody and an analyte, detectable, and the specific binding partner, e.g., antibody or analyte, so labeled is referred to as "detectably labeled." Thus, the term "labeled binding protein" as used herein, refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm); chromogens; fluorescent labels (e.g., FITC, rhodamine, and lanthanide phosphors); enzymatic labels (e.g., horseradish peroxidase, luciferase, and alkaline phosphatase); chemiluminescent markers; biotinyl groups; predetermined polypeptide epitopes recognized by a secondary reporter (e.g., leucine zipper pair sequences, binding sites for secondary antibodies, metal binding domains, and epitope tags); and magnetic agents, such as gadolinium chelates. Representative examples of labels commonly employed for immunoassays include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of "detectably labeled" is intended to encompass the latter type of detectable labeling.

The term "surface plasmon resonance," as used herein, refers to an optical phenomenon that allows for the analysis of real-time bispecific interactions by detection of alterations in protein concentrations within a biosensor matrix, for example, using the BIAcore® system (BIAcore International AB, a GE Healthcare company, Uppsala, Sweden and Piscataway, N.J.). For further descriptions, see Jonsson, U. et al. (1993) Ann. Biol. Clin. 51: 19-26; Jonsson, U. et al. (1991) Biotechniques 11: 620-627; Johnsson, B. et al. (1995) J. Mol. Recognit. 8: 125-131; and Johnnson, B. et al. (1991) Anal. Biochem. 198: 268-277.

A "plasmid" or "vector" includes a nucleic acid construct designed for delivery to a host cell or transfer between different host cell. An "expression plasmid" or "expression vector" can be a plasmid that has the ability to incorporate and express heterologous nucleic acid fragments in a cell. An expression plasmid may comprise additional elements, for example, the expression vector may have two replication systems, thus allowing it to be maintained in two organisms. The nucleic acid incorporated into the plasmid can be operatively linked to an expression control sequence when the expression control sequence controls and regulates the transcription and translation of that polynucleotide sequence.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

Other than in the operating examples, or where otherwise indicated, all numbers expressing quantities of ingredients or reaction conditions used herein should be understood as modified in all instances by the term "about." The term "about" when used in connection with percentages can mean±1%.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, e.g., 10-20, 1-10, 30-40, etc.

Antibodies, and Antigen-Binding Portions Thereof that Specifically Bind to a GARP-TGFβ1 Complex, a LTBP1-TGFβ1 Complex, a LTBP3-TGFβ1 Complex, and/or a LRRC33-TGFβ1 Complex The present invention is based, at least in part, on the discovery of antibodies, and antigen binding portions thereof, that bind TGFβ1 that is present in a GARP-TGFβ1 complex, a LTBP1-TGFβ1 complex, a LTBP3-TGFβ1 complex, and/or a LRRC33-TGFβ1 complex. Accordingly, some aspects of the invention relate to antibodies, or antigen binding portions thereof, that specifically bind to an epitope of TGFβ1, wherein the epitope is available for binding by the antibody, or antigen binding portions thereof, when the TGFβ1 is present in a GARP-TGFβ1 complex, a LTBP1-TGFβ1 complex, a LTBP3-TGFβ1 complex, and/or a LRRC33-TGFβ1 complex. In some embodiments, the epitope is available due to a conformational change in TGFβ1 when in complex with GARP, LTBP1, LTBP3, and/or LRRC33. In some embodiments, the epitope in TGFβ1 to which the antibodies, or antigen binding portions thereof, bind is not available when TGFβ1 is not in complex with GARP, LTBP1, LTBP3, and/or LRRC33. In some embodiments, the antibodies, or antigen binding portions thereof, do not specifically bind to TGFβ2. In some embodiments, the antibodies, or antigen binding portions thereof, do not specifically bind to TGFβ3. In some embodiments, the antibodies, or antigen binding portions thereof, do not prevent TGFβ1 from binding to integrin. For example, in some embodiments, the antibodies, or antigen binding portions thereof, do not mask the integrin-binding site of TGFβ1. In some embodiments, the antibodies, or antigen binding portions thereof, inhibit the activation of TGFβ1. In some embodiments, the antibodies, or antigen binding portions thereof, inhibit the release of mature TGFβ1 from a GARP-TGFβ1 complex, a LTBP1-TGFβ1 complex, a LTBP3-TGFβ1 complex, and/or a LRRC33-TGFβ1 complex.

Antibodies, or antigen binding portions thereof, provided herein specifically bind to an epitope of TGFβ1, wherein the epitope is available for binding by the antibody, or antigen binding portions thereof, when the TGFβ1 is present in a GARP-TGFβ1, a LTBP1-TGFβ1 complex, a LTBP2-TGFβ1 complex, and/or a LRRC33-TGFβ1 complex. In some embodiments, the TGFβ1 comprises a naturally occurring mammalian amino acid sequence. In some embodiment, the TGFβ1 comprises a naturally occurring human amino acid sequence. In some embodiments, the TGFβ1 comprises a human, a monkey, a rat or a mouse amino acid sequence. In some embodiments, an antibody, or antigen binding portion thereof, described herein does not specifically bind to TGFβ2. In some embodiments, an antibody, or antigen binding portion thereof, described herein does not specifically bind to TGFβ3. In some embodiments, an antibody, or antigen binding portion thereof, described herein does not specifically bind to TGFβ2 or TGFβ3. In some embodiments, an antibody, or antigen binding portion thereof, described herein specifically binds to a TGFβ1 comprising the amino acid sequence set forth in SEQ ID NO: 21. The amino acid sequences of TGFβ2, and TGFβ3 amino acid sequence are set forth in SEQ ID NOs: 22 and 23, respectively. In some embodiments, an antibody, or antigen binding portion thereof, described herein specifically binds to a TGFβ1 comprising a non-naturally-occurring amino acid sequence (otherwise referred to herein as a non-naturally-occurring TGFβ1). For example, a non-naturally-occurring TGFβ1 may comprise one or more recombinantly generated mutations relative to a naturally-occurring TGFβ1 amino acid sequence. In some embodiments, a TGFβ1, TGFβ2, or TGFβ3 amino acid sequence comprises the amino acid sequence as set forth in SEQ ID NOs: 24-35, as shown in Table 1. In some embodiments, a TGFβ1, TGFβ2, or TGFβ3 amino acid sequence comprises the amino acid sequence as set forth in SEQ ID NOs: 36-43, as shown in Table 2.

TGFβ1

(SEQ ID NO: 21)
LSTCKTIDMELVKRKRIEAIRGQILSKLRLASPPSQGEVPPGPLPEAVLAL
YNSTRDRVAGESAEPEPEPEADYYAKEVTRVLMVETHNEIYDKFKQSTHSI
YMFFNTSELREAVPEPVLLSRAELRLLRLKLKVEQHVELYQKYSNNSWRYL
SNRLLAPSDSPEWLSFDVTGVVRQWLSRGGEIEGFRLSAHCSCDSRDNTLQ
VDINGFTTGRRGDLATIHGMNRPFLLLMATPLERAQHLQSSRHRRALDTNY
CFSSTEKNCCVRQLYIDFRKDLGWKWIHEPKGYHANFCLGPCPYIWSLDTQ
YSKVLALYNQHNPGASAAPCCVPQALEPLPIVYYVGRKPKVEQLSNMIVRS
CKCS

TGFβ2

(SEQ ID NO: 22)
SLSTCSTLDMDQFMRKRIEAIRGQILSKLKLTSPPEDYPEPEEVPPEVISI
YNSTRDLLQEKASRRAAACERERSDEEYYAKEVYKIDMPPFFPSENAIPPT
FYRPYFRIVRFDVSAMEKNASNLVKAEFRVFRLQNPKARVPEQRIELYQIL
KSKDLTSPTQRYIDSKVVKTRAEGEWLSFDVTDAVHEWLHHKDRNLGFKIS

LHCPCCTFVPSNNYIIPNKSEELEARFAGIDGTSTYTSGDQKTIKSTRKKN
SGKTPHLLLMLLPSYRLESQQTNRRKKRALDAAYCFRNVQDNCCLRPLYID
FKRDLGWKWIHEPKGYNANFCAGACPYLWSSDTQHSRVLSLYNTINPEASA
SPCCVSQDLEPLTILYYIGKTPKIEQLSNMIVKSCKCS

TGFβ3

(SEQ ID NO: 23)
SLSLSTCTTLDFGHIKKKRVEAIRGQILSKLRLTSPPEPTVMTHVPYQVLA
LYNSTRELLEEMHGEREEGCTQENTESEYYAKEIHKFDMIQGLAEHNELAV
CPKGITSKVFRFNVSSVEKNRTNLFRAEFRVLRVPNPSSKRNEQRIELFQI
LRPDEHIAKQRYIGGKNLPTRGTAEWLSFDVTDTVREWLLRRESNLGLEIS
IHCPCHTFQPNGDILENIHEVMEIKFKGVDNEDDHGRGDLGRLKKQKDHHN
PHLILMMIPPHRLDNPGQGGQRKKRALDTNYCFRNLEENCCVRPLYIDFRQ
DLGWKWVHEPKGYYANFCSGPCPYLRSADTTHSTVLGLYNTLNPEASASPC
CVPQDLEPLTILYYVGRTPKVEQLSNMVVKSCKCS

TABLE 1

Exemplary TGFβ1, TGFβ2, and TGFβ3 amino acid sequences

| Protein | Sequence | SEQ ID NO |
|---|---|---|
| proTGFβ1 | LSTCKTIDMELVKRKRIEAIRGQILSKLRLASPPSQGEV<br>PPGPLPEAVLALYNSTRDRVAGESAEPEPEPEADYYA<br>KEVTRVLMVETHNEIYDKFKQSTHSIYMFFNTSELRE<br>AVPEPVLLSRAELRLLRLKLKVEQHVELYQKYSNNS<br>WRYLSNRLLAPSDSPEWLSFDVTGVVRQWLSRGGEIE<br>GFRLSAHCSCDSRDNTLQVDINGFTTGRRGDLATIHG<br>MNRPFLLLMATPLERAQHLQSSRHRRALDTNYCFSST<br>EKNCCVRQLYIDFRKDLGWKWIHEPKGYHANFCLGP<br>CPYIWSLDTQYSKVLALYNQHNPGASAAPCCVPQALE<br>PLPIVYYVGRKPKVEQLSNMIVRSCKCS | 24 |
| proTGFβ1 C4S | LSTSKTIDMELVKRKRIEAIRGQILSKLRLASPPSQGEV<br>PPGPLPEAVLALYNSTRDRVAGESAEPEPEPEADYYA<br>KEVTRVLMVETHNEIYDKFKQSTHSIYMFFNTSELRE<br>AVPEPVLLSRAELRLLRLKLKVEQHVELYQKYSNNS<br>WRYLSNRLLAPSDSPEWLSFDVTGVVRQWLSRGGEIE<br>GFRLSAHCSCDSRDNTLQVDINGFTTGRRGDLATIHG<br>MNRPFLLLMATPLERAQHLQSSRHRRALDTNYCFSST<br>EKNCCVRQLYIDFRKDLGWKWIHEPKGYHANFCLGP<br>CPYIWSLDTQYSKVLALYNQHNPGASAAPCCVPQALE<br>PLPIVYYVGRKPKVEQLSNMIVRSCKCS | 25 |
| proTGFβ1 D2G | LSTCKTIDMELVKRKRIEAIRGQILSKLRLASPPSQGEV<br>PPGPLPEAVLALYNSTRDRVAGESAEPEPEPEADYYA<br>KEVTRVLMVETHNEIYDKFKQSTHSIYMFFNTSELRE<br>AVPEPVLLSRAELRLLRLKLKVEQHVELYQKYSNNS<br>WRYLSNRLLAPSDSPEWLSFDVTGVVRQWLSRGGEIE<br>GFRLSAHCSCDSRDNTLQVDINGFTTGRRGDLATIHG<br>MNRPFLLLMATPLERAQHLQSSRHGALDTNYCFSSTE<br>KNCCVRQLYIDFRKDLGWKWIHEPKGYHANFCLGPC<br>PYIWSLDTQYSKVLALYNQHNPGASAAPCCVPQALEP<br>LPIVYYVGRKPKVEQLSNMIVRSCKCS | 26 |
| proTGFβ1 C4S D2G | LSTSKTIDMELVKRKRIEAIRGQILSKLRLASPPSQGEV<br>PPGPLPEAVLALYNSTRDRVAGESAEPEPEPEADYYA<br>KEVTRVLMVETHNEIYDKFKQSTHSIYMFFNTSELRE<br>AVPEPVLLSRAELRLLRLKLKVEQHVELYQKYSNNS<br>WRYLSNRLLAPSDSPEWLSFDVTGVVRQWLSRGGEIE<br>GFRLSAHCSCDSRDNTLQVDINGFTTGRRGDLATIHG<br>MNRPFLLLMATPLERAQHLQSSRHGALDTNYCFSSTE<br>KNCCVRQLYIDFRKDLGWKWIHEPKGYHANFCLGPC<br>PYIWSLDTQYSKVLALYNQHNPGASAAPCCVPQALEP<br>LPIVYYVGRKPKVEQLSNMIVRSCKCS | 27 |

TABLE 1-continued

Exemplary TGFβ1, TGFβ2, and TGFβ3 amino acid sequences

| Protein | Sequence | SEQ ID NO |
|---|---|---|
| proTGFβ2 | SLSTCSTLDMDQFMRKRIEAIRGQILSKLKLTSPPEDYP EPEEVPPEVISIYNSTRDLLQEKASRRAAACERERSDEE YYAKEVYKIDMPPFFPSENAIPPTFYRPYFRIVRFDVSA MEKNASNLVKAEFRVFRLQNPKARVPEQRIELYQILK SKDLTSPTQRYIDSKVVKTRAEGEWLSFDVTDAVHE WLHHKDRNLGFKISLHCPCCTFVPSNNYIIPNKSEELE ARFAGIDGTSTYTSGDQKTIKSTRKKNSGKTPHLLLM LLPSYRLESQQTNRRKKRALDAAYCFRNVQDNCCLR PLYIDFKRDLGWKWIHEPKGYNANFCAGACPYLWSS DTQHSRVLSLYNTINPEASASPCCVSQDLEPLTILYYIG KTPKIEQLSNMIVKSCKCS | 28 |
| proTGFβ2 C5S | SLSTSSTLDMDQFMRKRIEAIRGQILSKLKLTSPPEDYP EPEEVPPEVISIYNSTRDLLQEKASRRAAACERERSDEE YYAKEVYKIDMPPFFPSENAIPPTFYRPYFRIVRFDVSA MEKNASNLVKAEFRVFRLQNPKARVPEQRIELYQILK SKDLTSPTQRYIDSKVVKTRAEGEWLSFDVTDAVHE WLHHKDRNLGFKISLHCPCCTFVPSNNYIIPNKSEELE ARFAGIDGTSTYTSGDQKTIKSTRKKNSGKTPHLLLM LLPSYRLESQQTNRRKKRALDAAYCFRNVQDNCCLR PLYIDFKRDLGWKWIHEPKGYNANFCAGACPYLWSS DTQHSRVLSLYNTINPEASASPCCVSQDLEPLTILYYIG KTPKIEQLSNMIVKSCKCS | 29 |
| proTGFβ2 C5S D2G | SLSTSSTLDMDQFMRKRIEAIRGQILSKLKLTSPPEDYP EPEEVPPEVISIYNSTRDLLQEKASRRAAACERERSDEE YYAKEVYKIDMPPFFPSENAIPPTFYRPYFRIVRFDVSA MEKNASNLVKAEFRVFRLQNPKARVPEQRIELYQILK SKDLTSPTQRYIDSKVVKTRAEGEWLSFDVTDAVHE WLHHKDRNLGFKISLHCPCCTFVPSNNYIIPNKSEELE ARFAGIDGTSTYTSGDQKTIKSTRKKNSGKTPHLLLM LLPSYRLESQQTNRRKGALDAAYCFRNVQDNCCLRPL YIDFKRDLGWKWIHEPKGYNANFCAGACPYLWSSDT QHSRVLSLYNTINPEASASPCCVSQDLEPLTILYYIGKT PKIEQLSNMIVKSCKCS | 30 |
| proTGFβ2 D2G | SLSTCSTLDMDQFMRKRIEAIRGQILSKLKLTSPPEDYP EPEEVPPEVISIYNSTRDLLQEKASRRAAACERERSDEE YYAKEVYKIDMPPFFPSENAIPPTFYRPYFRIVRFDVSA MEKNASNLVKAEFRVFRLQNPKARVPEQRIELYQILK SKDLTSPTQRYIDSKVVKTRAEGEWLSFDVTDAVHE WLHHKDRNLGFKISLHCPCCTFVPSNNYIIPNKSEELE ARFAGIDGTSTYTSGDQKTIKSTRKKNSGKTPHLLLM LLPSYRLESQQTNRRKGALDAAYCFRNVQDNCCLRPL YIDFKRDLGWKWIHEPKGYNANFCAGACPYLWSSDT QHSRVLSLYNTINPEASASPCCVSQDLEPLTILYYIGKT PKIEQLSNMIVKSCKCS | 31 |
| proTGFβ3 | SLSLSTCTTLDFGHIKKKRVEAIRGQILSKLRLTSPPEPT VMTHVPYQVLALYNSTRELLEEMHGEREEGCTQENT ESEYYAKEIHKFDMIQGLAEHNELAVCPKGITSKVFRF NVSSVEKNRTNLFRAEFRVLRVPNPSSKRNEQRIELFQ ILRPDEHIAKQRYIGGKNLPTRGTAEWLSFDVTDTVRE WLLRRESNLGLEISIHCPCHTFQPNGDILENIHEVMEIK FKGVDNEDDHGRGDLGRLKKQKDHHNPHLILMMIPP HRLDNPGQGGQRKKRALDTNYCFRNLEENCCVRPLY IDFRQDLGWKWVHEPKGYYANFCSGPCYLRSADTT HSTVLGLYNTLNPEASASPCCVPQDLEPLTILYYVGRT PKVEQLSNMVVKSCKCS | 32 |
| proTGFβ3 C7S | SLSLSTSTTLDFGHIKKKRVEAIRGQILSKLRLTSPPEPT VMTHVPYQVLALYNSTRELLEEMHGEREEGCTQENT ESEYYAKEIHKFDMIQGLAEHNELAVCPKGITSKVFRF NVSSVEKNRTNLFRAEFRVLRVPNPSSKRNEQRIELFQ ILRPDEHIAKQRYIGGKNLPTRGTAEWLSFDVTDTVRE WLLRRESNLGLEISIHCPCHTFQPNGDILENIHEVMEIK FKGVDNEDDHGRGDLGRLKKQKDHHNPHLILMMIPP HRLDNPGQGGQRKKRALDTNYCFRNLEENCCVRPLY IDFRQDLGWKWVHEPKGYYANFCSGPCYLRSADTT HSTVLGLYNTLNPEASASPCCVPQDLEPLTILYYVGRT PKVEQLSNMVVKSCKCS | 33 |

TABLE 1-continued

Exemplary TGFβ1, TGFβ2, and TGFβ3 amino acid sequences

| Protein | Sequence | SEQ ID NO |
|---|---|---|
| proTGFβ3 C7S D2G | SLSLSTSTTLDFGHIKKKRVEAIRGQILSKLRLTSPPEPT VMTHVPYQVLALYNSTRELLEEMHGEREEGCTQENT ESEYYAKEIHKFDMIQGLAEHNELAVCPKGITSKVFRF NVSSVEKNRTNLFRAEFRVLRVPNPSSKRNEQRIELFQ ILRPDEHIAKQRYIGGKNLPTRGTAEWLSFDVTDTVRE WLLRRESNLGLEISIHCPCHTFQPNGDILENIHEVMEIK FKGVDNEDDHGRGDLGRLKKQKDHHNPHLILMMIPP HRLDNPGQGGQRKGALDTNYCFRNLEENCCVRPLYI DFRQDLGWKWVHEPKGYYANFCSGPCPYLRSADTTH STVLGLYNTLNPEASASPCCVPQDLEPLTILYYVGRTP KVEQLSNMVVKSCKCS | 34 |
| proTGFβ3 D2G | SLSLSTCTTLDFGHIKKKRVEAIRGQILSKLRLTSPPEPT VMTHVPYQVLALYNSTRELLEEMHGEREEGCTQENT ESEYYAKEIHKFDMIQGLAEHNELAVCPKGITSKVFRF NVSSVEKNRTNLFRAEFRVLRVPNPSSKRNEQRIELFQ ILRPDEHIAKQRYIGGKNLPTRGTAEWLSFDVTDTVRE WLLRRESNLGLEISIHCPCHTFQPNGDILENIHEVMEIK FKGVDNEDDHGRGDLGRLKKQKDHHNPHLILMMIPP HRLDNPGQGGQRKGALDTNYCFRNLEENCCVRPLYI DFRQDLGWKWVHEPKGYYANFCSGPCPYLRSADTTH STVLGLYNTLNPEASASPCCVPQDLEPLTILYYVGRTP KVEQLSNMVVKSCKCS | 35 |

TABLE 2

Exemplary non-human amino acid sequences

| Protein | Species | Sequence | SEQ ID NO |
|---|---|---|---|
| proTGFβ1 | Mouse | LSTCKTIDMELVKRKRIEAIRGQILSKLRLASPPSQG EVPPGPLPEAVLALYNSTRDRVAGESADPEPEPEAD YYAKEVTRVLMVDRNNAIYEKTKDISHSIYMFFNT SDIREAVPEPPLLSRAELRLQRLKSSVEQHVELYQK YSNNSWRYLGNRLLTPTDTPEWLSFDVTGVVRQW LNQGDGIQGFRFSAHCSCDSKDNKLHVEINGISPKR RGDLGTIHDMNRPFLLLMATPLERAQHLSSRHRR ALDTNYCFSSTEKNCCVRQLYIDFRKDLGWKWIHE PKGYHANFCLGPCPYIWSLDTQYSKVLALYNQHNP GASASPCCVPQALEPLPIVYYVGRKPKVEQLSNMIV RSCKCS | 36 |
| proTGFβ1 | Cyno | LSTCKTIDMELVKRKRIEAIRGQILSKLRLASPPSQG EVPPGPLPEAVLALYNSTRDRVAGESAEPEPEPEAD YYAKEVTRVLMVETHNEIYDKFKQSTHSIYMFFNT SELREAVPEPVLLSRAELRLLRLKLKVEQHVELYQK YSNNSWRYLSNRLLAPSDSPEWLSFDVTGVVRQW LSRGGEIEGFRLSAHCSCDSKDNTLQVDINGFTTGR RGDLATIHGMNRPFLLLMATPLERAQHLQSSRHRR ALDTNYCFSSTEKNCCVRQLYIDFRKDLGWKWIHE PKGYHANFCLGPCPYIWSLDTQYSKVLALYNQHNP GASAAPCCVPQALEPLPIVYYVGRKPKVEQLSNMI VRSCKCS | 37 |
| TGFβ1 LAP C4S | Mouse | LSTSKTIDMELVKRKRIEAIRGQILSKLRLASPPSQG EVPPGPLPEAVLALYNSTRDRVAGESADPEPEPEAD YYAKEVTRVLMVDRNNAIYEKTKDISHSIYMFFNT SDIREAVPEPPLLSRAELRLQRLKSSVEQHVELYQK YSNNSWRYLGNRLLTPTDTPEWLSFDVTGVVRQW LNQGDGIQGFRFSAHCSCDSKDNKLHVEINGISPKR RGDLGTIHDMNRPFLLLMATPLERAQHLSSRHRR | 38 |
| TGFβ1 LAP C4S | Cyno | LSTSKTIDMELVKRKRIEAIRGQILSKLRLASPPSQG EVPPGPLPEAVLALYNSTRDRVAGESAEPEPEPEAD YYAKEVTRVLMVETHNEIYDKFKQSTHSIYMFFNT SELREAVPEPVLLSRAELRLLRLKLKVEQHVELYQK YSNNSWRYLSNRLLAPSDSPEWLSFDVTGVVRQW LSRGGEIEGFRLSAHCSCDSKDNTLQVDINGFTTGR RGDLATIHGMNRPFLLLMATPLERAQHLQSSRHRR | 39 |

TABLE 2-continued

Exemplary non-human amino acid sequences

| Protein | Species | Sequence | SEQ ID NO |
|---|---|---|---|
| proTGFβ1 C4S D2G | Mouse | LSTSKTIDMELVKRKRIEAIRGQILSKLRLASPPSQG EVPPGPLPEAVLALYNSTRDRVAGESADPEPEPEAD YYAKEVTRVLMVDRNNAIYEKTKDISHSIYMFFNT SDIREAVPEPPLLSRAELRLQRLKSSVEQHVELYQK YSNNSWRYLGNRLLTPTDTPEWLSFDVTGVVRQW LNQGDGIQGFRFSAHCSCDSKDNKLHVEINGISPKR RGDLGTIHDMNRPFLLLMATPLERAQHLSSRHGA LDTNYCFSSTEKNCCVRQLYIDFRKDLGWKWIHEP KGYHANFCLGPCPYIWSLDTQYSKVLALYNQHNPG ASASPCCVPQALEPLPIVYYVGRKPKVEQLSNMIVR SCKCS | 40 |
| proTGFβ1 C4S | Mouse | STSKTIDMELVKRKRIEAIRGQILSKLRLASPPSQG EVPPGPLPEAVLALYNSTRDRVAGESADPEPEPEAD YYAKEVTRVLMVDRNNAIYEKTKDISHSIYMFFNT SDIREAVPEPPLLSRAELRLQRLKSSVEQHVELYQK YSNNSWRYLGNRLLTPTDTPEWLSFDVTGVVRQW LNQGDGIQGFRFSAHCSCDSKDNKLHVEINGISPKR RGDLGTIHDMNRPFLLLMATPLERAQHLSSRHRR ALDTNYCFSSTEKNCCVRQLYIDFRKDLGWKWIHE PKGYHANFCLGPCPYIWSLDTQYSKVLALYNQHNP GASASPCCVPQALEPLPIVYYVGRKPKVEQLSNMIV RSCKCS | 41 |
| proTGFβ1 C4S | Cyno | LSTSKTIDMELVKRKRIEAIRGQILSKLRLASPPSQG EVPPGPLPEAVLALYNSTRDRVAGESAEPEPEPEAD YYAKEVTRVLMVETHNEIYDKFKQSTHSIYMFFNT SELREAVPEPVLLSRAELRLLRLKLKVEQHVELYQK YSNNSWRYLSNRLLAPSDSPEWLSFDVTGVVRQW LSRGGEIEGFRLSAHCSCDSKDNTLQVDINGFTTGR RGDLATIHGMNRPFLLLMATPLERAQHLQSSRHRR ALDTNYCFSSTEKNCCVRQLYIDFRKDLGWKWIHE PKGYHANFCLGPCPYIWSLDTQYSKVLALYNQHNP GASAAPCCVPQALEPLPIVYYVGRKPKVEQLSNMI VRSCKCS | 42 |
| proTGFβ1 C4S D2G | Cyno | LSTSKTIDMELVKRKRIEAIRGQILSKLRLASPPSQG EVPPGPLPEAVLALYNSTRDRVAGESAEPEPEPEAD YYAKEVTRVLMVETHNEIYDKFKQSTHSIYMFFNT SELREAVPEPVLLSRAELRLLRLKLKVEQHVELYQK YSNNSWRYLSNRLLAPSDSPEWLSFDVTGVVRQW LSRGGEIEGFRLSAHCSCDSKDNTLQVDINGFTTGR RGDLATIHGMNRPFLLLMATPLERAQHLQSSRHGA LDTNYCFSSTEKNCCVRQLYIDFRKDLGWKWIHEP KGYHANFCLGPCPYIWSLDTQYSKVLALYNQHNPG ASAAPCCVPQALEPLPIVYYVGRKPKVEQLSNMIVR SCKCS | 43 |
| LTBP3 | CYNO | GPAGERGAGGGGALARERFKVVFAPVICKRTCLKG QCRDSCQQGSNMTLIGENGHSTDTLTGSGFRVVVC PLPCMNGGQCSSRNQCLCPPDFTGRFCQVPAGGAG GGTGGSGPGLSRAGALSTGALPPLAPEGDSVASKH AIYAVQVIADPPGPGEGPPAQHAAFLVPLGPGQISA EVQAPPPVVNVRVHHPPEASVQVHRIESSNAEGAA PSQHLLPHPKPSHPRPPTQKPLGRCFQDTLPKQPCG SNPLPGLTKQEDCCGSIGTAWGQSKCHKCPQLYT GVQKPGPVRGEVGADCPQGYKRLNSTHCQDINEC AMPGVCRHGDCLNNPGSYRCVCPPGHSLGPSRTQC IADKPEEKSLCFRLVSPEHQCQHPLTTRLTRQLCCC SVGKAWGARCQRCPADGTAAFKEICPAGKGYHILT SHQTLTIQGESDFSLFLHPDGPPKPQQLPESPSQAPP PEDTEEERGVTTDSPVSEERSVQQSHPTATTSPARP YPELISRPSPPTMRWFLPDLPPSRSAVEIAPTQVTET DECRLNQNICGHGECVPGPPDYSCHCNPGYRSHPQ HRYCVDVNECEAEPCGPGRGICMNTGGSYNCHCN RGYRLHVGAGGRSCVDLNECAKPHLCGDGGFCINF PGHYKCNCYPGYRLKASRPPVCEDIDECRDPSSCPD GKCENKPGSFKCIACQPGYRSQGGGACRDVNECAE GSPCSPGWCENLPGSFRCTCAQGYAPAPDGRSCVD VDECEAGDVCDNGICTNTPGSFQCCLSGYHLSRD RSHCEDIDECDFPAACIGGDCINTNGSYRCLCPQGH RLVGGRKCQDIDECTQDPGLCLPHGACKNLQGSYV CVCDEGFTPTQDQHGCEEVEQPHHKKECYLNFDDT | 44 |

TABLE 2-continued

Exemplary non-human amino acid sequences

| Protein | Species | Sequence | SEQ ID NO |
|---|---|---|---|
| | | VFCDSVLATNVTQQECCCSLGAGWGDHCEIYPCPV YSSAEFHSLCPDGKYTQDNNIVNYGIPAHRDIDEC MLFGAEICKEGKCVNTQPGYECYCKQGFYYDGNL LECVDVDECLDESNCRNGVCENTRGGYRCACTPPA EYSPAQRQCLSPEEMDVDECQDPAACRPGRCVNLP GSYRCECRPPWVPGPSGRDCQLPESPAERAPERRD VCWSQRGEDGMCAGPQAGPALTFDDCCCRQGRG WGAQCRPCPPRGAGSQCPTSQSESNSFWDTSPLLL GKPRRDEDSSEEDSDECRCVSGRCVPRPGGAVCEC PGGFQLDASRARCVDIDECRELNQRGLLCKSERCV NTSGSFRCVCKAGFARSRPHGACVPQRRR | |
| LTBP3 | Mouse | GPAGERGTGGGGALARERFKVVFAPVICKRTCLKG QCRDSCQQGSNMTLIGENGHSTDTLTGSAFRVVVC PLPCMNGGQCSSRNQCLCPPDFTGRFCQVPAAGTG AGTGSSGPGLARTGAMSTGPLPPLAPEGESVASKH AIYAVQVIADPPGPGEGPPAQHAAFLVPLGPGQISA EVQAPPPVVNVRVHHPPEASVQVHRIEGPNAEGPA SSQHLLPHPKPPHPRPPTQKPLGRCFQDTLPKQPCG SNPLPGLTKQEDCCGSIGTAWGQSKCHKCPQLQYT GVQKPVPVRGEVGADCPQGYKRLNSTHCQDINEC AMPGNVCHGDCLNNPGSYRCVCPPGHSLGPLAAQ CIADKPEEKSLCFRLVSTEHQCQHPLTTRLTRQLCC CSVGKAWGARCQRCPADGTAAFKEICPGKGYHILT SHQTLTIQGESDFSLFLHPDGPPKPQQLPESPSRAPP LEDTEEERGVTMDPPVSEERSVQQSHPTTTTSPPRP YPELISRPSPPTFHRFLPDLPPSRSAVEIAPTQVTETD ECRLNQNICGHGQCVPGPSDYSCHCNAGYRSHPQH RYCVDVNECEAEPCGPGKGICMNTGGSYNCHCNR GYRLHVGAGGRSCVDLNECAKPHLCGDGGFCINFP GHYKCNCYPGYRLKASRPPICEDIDECRDPSTCPDG KCENKPGSFKCIACQPGYRSQGGGACRDVNECSEG TPCSPGWCENLPGSYRCTCAQYEPAQDGLSCIDVD ECEAGKVCQDGICTNTPGSFQCQCLSGYHLSRDRS RCEDIDECDFPAACIGGDCINTNGSYRCLCPLGHRL VGGRKCKKDIDECSQDPGLCLPHACENLQGSYVCV CDEGFTLTQDQHGCEEVEQPHHKKECYLNFDDTVF CDSVLATNVTQQECCCSLGAGWGDHCEIYPCPVYS SAEFHSLVPDGKRLHSGQQHCELCIPAHRDIDECILF GAEICKEGKCVNTQPGYECYCKQGFYYDGNLLEC VDVDECLDESNCRNGVCENTRGGYRCACTPPAEYS PAQAQCLIPERWSTPQRDVKCAGASEERTACVWGP WAGPALTFDDCCCRQPRLGTQCRPCPPRGTGSQCP TSQSESNSFWDTSPLLLGKSPRDEDSSEEDSDECRC VSGRCVPRPGGAVCECPGGFQLDASRARCVDIDEC RELNQRGLLCKSERCVNTSGSFRCVCKAGFTRSRP HGPACLSAAADDAAIAHTSVIDHRGYFH | 45 |
| LTBP1S | Cyno | NHTGRIKVVFTPSICKVTCTKGSCQNSCEKGNTTTLI SENGHAADTLTATNFRVVLCHLPCMNGGQCSSRD KCQCPPNFTGKLCQIPVHGASVPKLYQHSQQPGKA LGTHVIHSTHTLPLTVTSQQGVKVKFPPNIVNIHVK HPPEASVQIHQVSRIDGPTGQKTKEAQPGQSQVSYQ GLPVQKTQTIHSTYSHQQVIPHVYPVAAKTQLGRCF QETIGSQCGKALPGLSKQEDCCGTVGTSWGFNKCQ KCPKKPSYHGYNQMMECLPGYKRVNNTFCQDINE CQLQGVCPNGECLNTMGSYRCTCKIGFGPDPTFSSC VPDPPVISEEKGPCYRLVSSGRQCMHPLSVHLTKQL CCCSVGKAWGPHCEKCPLPGTAAFKEICPGGMYT VSGVHRRRPIHHHVGKGPVFVKPKNTQPVAKSTHP PPLPAKEEPVEALTFSREHGPGVAEPEVATAPPEKEI PSLDQEKTKLEPGQPQLSPGISTIHLHPQFPPVVIEKTS PPVPVEVAPEASTSSASQVIAPTQVTEINECTVNPDI CGAGHCINLPVRYTCICYEGYKFSEQQRKCVDIDEC TQVQHLCSQGRCENTEGSFLCICPAGFMASEEGTNC IDVDECLRPDVCGEGHCVNTVGAFRCEYCDSGYR MTQRGRCEDIDECLNPSTCPDEQCVNSPGSYQCVP CTEGFRGWNGQCLDVDECLEPNVCTGNDCSNLEG SYMCSCHKGYTRTPDHKHCKDIDECQQGNLCVNG QCKNTEGSFRCTCGQGYQLSAAKDQCEDIDECQHH HLCAHGQCRNTEGSFQCVCDQGYRASGLGDHCEDI NECLEDKSVCQRGDCINTAGSYDCTCPDGFQLDDN KTCQDINECEHPGLCGPQGECLNTEGSFHCVCQQG FSISADGRTCEDIDECVNNTVCDSHGFCDNTAGSFR | 46 |

TABLE 2-continued

Exemplary non-human amino acid sequences

| Protein | Species | Sequence | SEQ ID NO |
|---------|---------|----------|-----------|
| | | CLCYQGFQAPQDGQGCVDVNECELLSGVCGEAFC ENVEGSFLCVCADENQEYSPMTGQCRSRTSTDLDV EQPKEEKKECYYNLNDASLCDNVLAPNVTKQECC CTSGAGWGDNCEIFPCPVLGTAEFTEMCPKGKGFV PAGESSSEAGGENYKDADECLLFGQEICKNGFCLNT RPGYECYCKQGTYYDPVKLQCFDMDECQDPSSCID GQCVNTEGSYNCFCTHPMVLDASEKRCIRPAESNE QIEETDVYQDLCWEHLSDEYVCSRPLVGKQTTYTE CCCLYGEAWGMQCALCPMKDSDDYAQLCNIPVTG RRQPYGRDALVDFSEQYAPEADPYFIQDRFLNSFEE LQAEEECGILNGCENGRCVRVQEGYTCDCFDGYHLD TAKMTCVDVNECDELNNRMSLCKNAKCINTEGSY KCLCLPGYVPSDKPNYCTPLNTALNLEKDSDLE | |
| LTBP1S | mouse | NHTGRIKVVFTPSICKVTCTKGNCQNSCQKGNTTTL ISENGHAADTLTATNFRVVICHLPCMNGGQCSSRD KCQCPPNFTGKLCQIPVLGASMPKLYQHAQQQGKA LGSHVIHSTHTLPLTMTSQQGVKVKFPPNIVNIHVK HPPEASVQIHQVSRIDSPGGQKVKEAQPGQSQVSYQ GLPVQKTQTVHSTYSHQQLIPHVYPVAAKTQLGRC FQETIGSQCGKALPGLSKQEDCCGTVGTSWGFNKC QKCPKKQSYHGYTQMMECLQGYKRVNNTFCQDIN ECQLQGVCPNGECLNTMGSYRCSCKMGFGPDPTFS SCVPDPPVISEEKGPCYRLVSPGRHCMHPLSVHLTK QICCCSVGKAWGPHCEKCPLPGTAAFKEICPGGMG YTVSGVHRRRPIHQHIGKEAVYVKPKNTQPVAKST HPPPLPAKEEPVEALTSSWEHGPRGAEPEVVTAPPE KEIPSLDQEKTRLEPGQPQLSPGVSTIHLHPQFPVVV EKTSPPVPVEVAPEASTSSASQVIAPTQVTEINECTV NPDICGAGHCINLPVRYTCICYEGYKFSEQLRKCVD IDECAQVRHLCSQGRCENTEGSFLCVCPAGFMASE EGTNCIDVDECLRPDMCRDGRCINTAGAFRCEYCD SGYRMSRRGYCEDIDECLKPSTCPEEQCVNTPGSYQ CVPCTEGFRGWNGQCLDVDECLQPKVCTNGSCTN LEGSYMCSCHRGYSPTPDHRHCQDIDECQQGNLCM NGQCRNTDGSFRCTCGQGYQLSAAKDQCEDIDECE HHHLCSHGQCRNTEGSFQCVCNQGYRASVLGDHC EDINECLEDSSVCQGGDCINTAGSYDCTCPDGFQLN DNKGCQDINECAQPGLCGSHGECLNTQGSFHCVCE QGFSISADGRTCEDIDECVNNTVCDSHGFCDNTAGS FRCLCYQGFQAPQDGQGCVDVNECELLSGVCGEAF CENVEGSFLCVCADENQEYSPMTGQCRSRVTEDSG VDRQPREEKKECYYNLNDASLCDNVLAPNVTKQE CCCTSGAGWGDNCEIFPCPVQGTAEFTEMCPRGKG LVPAGESSYDTGGENYKDADECLLFGEEICKNGYC LNTQPGYECYCKQGTYYDPVKLQCFDMDECQDPN SCIDGQCVNTEGSYNCFCTHPMVLDASEKRCVQPT ESNEQIEETDVYQDLCWEHLSEEYVCSRPLVGKQT TYTECCCLYGEAWGMQCALCPMKDSDDYAQLCNI PVTGRRRPYGRDALVDFSEQYGPETDPYFIQDRFLN SFEELQAEEECGILNGCENGRCVRVQEGYTCDCFDG YHLDMAKMTCVDVNECSELNNRMSLCKNAKCINT EGSYKCLCLPGYIPSDKPNYCTPLNSALNLDKESDL E | 47 |
| GARP | mouse | ISQRREQVPCRTVNKEALCHGLGLLQVPSVLSLDIQ ALYLSGNQLQSILVSPLGFYTALRHLDLSDNQISFLQ AGVFQALPYLEHLNLAHNRLATGMALNSGGLGRL PLLVSLDLSGNSLHGNLVERLLGETPRLRTLSLAEN SLTRLARHTFWGMPAVEQLDLHSNVLMDIEDGAFE ALPHLTHLNLSRNSLTCISDFSLQQLQVLDLSCNSIE AFQTAPEPQAQFQLAWLDLRENKLLHFPDLAVFPR LIYLNVSNNLIQLPAGLPRGSEDLHAPSEGWSASPLS NPSRNASTHPLSQLLNLDLSYNEIELVPASFLEHLTS LRFLNLSRNCLRSFEARQVDSLPCLVLLDLSHNVLE ALELGTKVLGSLQTLLLQDNALQELPPYTFASLASL QRLNLQGNQVSPCGGPAEPGPPGCVDFSGIPTLHVL NMAGNSMGMLRAGSFLHTPLTELDLSTNPGLDVA TGALVGLEASLEVLELQGNGLTVLRVDLPCFLRLK RLNLAENQLSHLPAWTRAVSLEVLDLRNNSFSLLP GNAMGGLETSLRRLYLQGNPLSCCGNGWLAAQLH QGRVDVDATQDLICRFGSQEELSLSLVRPEDCEKG GLKNVNLILLLSFTLVSAIVLTTLATICFLRRQKLSQ QYKA | 48 |

TABLE 2-continued

Exemplary non-human amino acid sequences

| Protein | Species | Sequence | SEQ ID NO |
|---|---|---|---|
| sGARP | mouse | ISQRREQVPCRTVNKEALCHGLGLLQVPSVLSLDIQ ALYLSGNQLQSILVSPLGFYTALRHLDLSDNQISFLQ AGVFQALPYLEHLNLAHNRLATGMALNSGGLGRL PLLVSLDLSGNSLHGNLVERLLGETPRLRTLSLAEN SLTRLARHTFWGMPAVEQLDLHSNVLMDIEDGAFE ALPHLTHLNLSRNSLTCISDFSLQQLQVLDLSCNSIE AFQTAPEPQAQFQLAWLDLRENKLLHFPDLAVFPR LIYLNVSNNLIQLPAGLPRGSEDLHAPSEGWSASPLS NPSRNASTHPLSQLLNLDLSYNEIELVPASFLEHLTS LRFLNLSRNCLRSFEARQVDSLPCLVLLDLSHNVLE ALELGTKVLGSLQTLLLQDNALQELPPYTFASLASL QRLNLQGNQVSPCGGPAEPGPPGCVDFSGIPTLHVL NMAGNSMGMLRAGSFLHTPLTELDLSTNPGLDVA TGALVGLEASLEVLELQGNGLTVLRVDLPCFLRLK RLNLAENQLSHLPAWTRAVSLEVLDLRNNSFSLLP GNAMGGLETSLRRLYLQGNPLSCCGNGWLAAQLH QGRVDVDATQDLICRFGSQEELSLSLVRPEDCEKG GLKNVN | 49 |

In some embodiments, an antibody, or antigen binding portion thereof, as described herein, is capable of binding to a LTBP1-TGFβ1 complex. In some embodiments, antigenic protein complexes (e.g., a LTBP-TGFβ1 complex) may comprise one or more LTBP proteins (e.g., LTBP1, LTBP2, LTBP3, and LTBP4). In some embodiments, the LTBP1 protein is a naturally-occurring protein. In some embodiments, the LTBP1 protein is a non-naturally occurring protein. In some embodiments, the LTBP1 protein is a recombinant protein. Such recombinant LTBP1 protein may comprise LTBP1, alternatively spliced variants thereof and/ or fragments thereof. Recombinant LTBP1 proteins may also be modified to comprise one or more detectable labels. In some embodiments, the LTBP1 protein comprises a leader sequence (e.g., a native or non-native leader sequence). In some embodiments, the LTBP1 protein does not comprise a leader sequence (i.e., the leader sequence has been processed or cleaved). Such detectable labels may include, but are not limited to biotin labels, polyhistidine tags, myc tags, HA tags and/or fluorescent tags. In some embodiments, the LTBP1 protein is a mammalian LTBP1 protein. In some embodiments, the LTBP1 protein is a human, a monkey, a mouse, or a rat LTBP1 protein. In some embodiments, the LTBP1 protein comprises an amino acid sequence as set forth in SEQ ID NOs: 46 and 47 in Table 2. In some embodiments, the LTBP1 protein comprises an amino acid sequence as set forth in SEQ ID NO: 50 in Table 3.

In some embodiments, an antibody, or antigen binding portion thereof, as described herein, is capable of binding to a LTBP3-TGFβ1 complex. In some embodiments, the LTBP3 protein is a naturally-occurring protein. In some embodiments, the LTBP3 protein is a non-naturally occurring protein. In some embodiments, the LTBP3 protein is a recombinant protein. Such recombinant LTBP3 protein may comprise LTBP3, alternatively spliced variants thereof and/ or fragments thereof. In some embodiments, the LTBP3 protein comprises a leader sequence (e.g., a native or non-native leader sequence). In some embodiments, the LTBP3 protein does not comprise a leader sequence (i.e., the leader sequence has been processed or cleaved). Recombinant LTBP3 proteins may also be modified to comprise one or more detectable labels. Such detectable labels may include, but are not limited to biotin labels, polyhistidine tags, myc tags, HA tags and/or fluorescent tags. In some embodiments, the LTBP3 protein is a mammalian LTBP3 protein. In some embodiments, the LTBP3 protein is a human, a monkey, a mouse, or a rat LTBP3 protein. In some embodiments, the LTBP3 protein comprises an amino acid sequence as set forth in SEQ ID NOs: 44 and 45 in Table 2. In some embodiments, the LTBP1 protein comprises an amino acid sequence as set forth in SEQ ID NO: 51 in Table 3.

In some embodiments, an antibody, or antigen binding portion thereof, as described herein, is capable of binding to a GARP-TGFβ1 complex. In some embodiments, the GARP protein is a naturally-occurring protein. In some embodiments, the GARP protein is a non-naturally occurring protein. In some embodiments, the GARP protein is a recombinant protein. Such a GARP may be recombinant, referred to herein as recombinant GARP. Some recombinant GARPs may comprise one or more modifications, truncations and/or mutations as compared to wild type GARP. Recombinant GARPs may be modified to be soluble. In some embodiments, the GARP protein comprises a leader sequence (e.g., a native or non-native leader sequence). In some embodiments, the GARP protein does not comprise a leader sequence (i.e., the leader sequence has been processed or cleaved). In other embodiments, recombinant GARPs are modified to comprise one or more detectable labels. In further embodiments, such detectable labels may include, but are not limited to biotin labels, polyhistidine tags, flag tags, myc tags, HA tags and/or fluorescent tags. In some embodiments, the GARP protein is a mammalian GARP protein. In some embodiments, the GARP protein is a human, a monkey, a mouse, or a rat GARP protein. In some embodiments, the GARP protein comprises an amino acid sequence as set forth in SEQ ID NOs: 48-49 in Table 2. In some embodiments, the GARP protein comprises an amino acid sequence as set forth in SEQ ID NOs: 52 and 53 in Table 4. In some embodiments, the antibodies, or antigen binding portions thereof, described herein do not bind to TGFβ1 in a context-dependent manner, for example binding to TGFβ1 would only occur when the TGFβ1 molecule was complexed with a specific presenting molecule, such as GARP. Instead, the antibodies, and antigen-binding portions thereof, bind to TGFβ1 in a context-independent manner. In other words, the antibodies, or antigen-binding portions thereof, bind to TGFβ1 when bound to any presenting molecule: GARP, LTBP1, LTBP3, and/or LRCC33.

In some embodiments, an antibody, or antigen binding portion thereof, as described herein, is capable of binding to a LRRC33-TGFβ1 complex. In some embodiments, the LRRC33 protein is a naturally-occurring protein. In some embodiments, the LRRC33 protein is a non-naturally occurring protein. In some embodiments, the LRRC33 protein is a recombinant protein. Such a LRRC33 may be recombinant, referred to herein as recombinant LRRC33. Some recombinant LRRC33 proteins may comprise one or more modifications, truncations and/or mutations as compared to wild type LRRC33. Recombinant LRRC33 proteins may be modified to be soluble. For example, in some embodiments, the ectodomain of LRRC33 may be expressed with a C-terminal His-tag in order to express soluble LRRC33 protein (sLRRC33; see, e.g., SEQ ID NO: 84). In some embodiments, the LRRC33 protein comprises a leader sequence (e.g., a native or non-native leader sequence). In some embodiments, the LRRC33 protein does not comprise a leader sequence (i.e., the leader sequence has been processed or cleaved). In other embodiments, recombinant LRRC33 proteins are modified to comprise one or more detectable labels. In further embodiments, such detectable labels may include, but are not limited to biotin labels, polyhistidine tags, flag tags, myc tags, HA tags and/or fluorescent tags. In some embodiments, the LRRC33 protein is a mammalian LRRC33 protein. In some embodiments, the LRRC33 protein is a human, a monkey, a mouse, or a rat LRRC33 protein. In some embodiments, the LRRC33 protein comprises an amino acid sequence as set forth in SEQ ID NOs: 83, 84, and 85 in Table 4.

TABLE 3

Exemplary LTBP amino acid sequences.

| Protein | Sequence | SEQ ID NO |
|---|---|---|
| LTBP1S | NHTGRIKVVFTPSICKVTCTKGSCQNSCEKGNTTTLI SENGHAADTLTATNFRVVICHLPCMNGGQCSSRDK CQCPPNFTGKLCQIPVHGASVPKLYQHSQQPGKALG THVIHSTHTLPLTVTSQQGVKVKFPPNIVNIHVKHPP EASVQIHQVSRIDGPTGQKTKEAQPGQSQVSYQGLP VQKTQTIHSTYSHQQVIPHVYPVAAKTQLGRCFQETI GSQCGKALPGLSKQEDCCGTVGTSWGFNKCQKCPK KPSYHGYNQMMECLPGYKRVNNTFCQDINECQLQG VCPNGECLNTMGSYRCTCKIGFGPDPTFSSCVPDDPPV ISEEKGPCYRLVSSGRQCMHPLSVHLTKQLCCCSVG KAWGPHCEKCPLPGTAAFKEICPGGMGYTVSGVHR RRPIHHHVGKGPVFVKPKNTQPVAKSTHPPPLPAKE EPVEALTFSREHGPGVAEPEVATAPPEKEIPSLDQEK TKLEPGQPQLSPGISTIHLHPQFPVVIEKTSPPVPVEV APEASTSSASQVIAPTQVTEINECTVNPDICGAGHCIN LPVRYTCICYEGYRFSEQQRKCVDIDECTQVQHLCS QGRCENTEGSFLCICPAGFMASEEGTNCIDVDECLRP DVCGEGHCVNTVGAFRCEYCDSGYRMTQRGRCEDI DECLNPSTCPDEQCVNSPGSYQCVPCTEGFRGWNG QCLDVDECLEPNVCANGDCSNLEGSYMCSCHKGYT RTPDHKHCRDIDECQQGNLCVNGQCKNTEGSFRCT CGQGYQLSAAKDQCEDIDECQHRHLCAHGQCRNTE GSFQCVCDQGYRASGLGDHCEDINECLEDKSVCQR GDCINTAGSYDCTCPDGFQLDDNKTCQDINECEHPG LCGPQGECLNTEGSFHCVCQQGFSISADGRTCEDIDE CVNNTVCDSHGFCDNTAGSFRCLCYQGFQAPQDGQ GCVDVNECELLSGVCGEAFCENVEGSFLCVCADEN QEYSPMTGQCRSRTSTDLDVDVDQPKEEKKECYYN LNDASLCDNVLAPNVTKQECCCTSGVGWGDNCEIF PCPVLGTAEFTEMCPKGKGFVPAGESSSEAGGENYK DADECLLFGQEICKNGFCLNTRPGYECYCKQGTYY DPVKLQCFDMDECQDPSSCIDGQCVNTEGSYNCFCT HPMVLDASEKRCIRPAESNEQIEETDVYQDLCWEHL SDEYVCSRPLVGKQTTYTECCCLYGEAWGMQCALC PLKDSDDYAQLCNIPVTGRRQPYGRDALVDFSEQYT PEADPYFIQDRFLNSFEELQAEECGILNGCENGRCVR VQEGYTCDCFDGYHLDTAKMTCVDVNECDELNNR MSLCKNAKCINTDGSYKCLCLPGYVPSDKPNYCTPL NTALNLEKDSDLE | 50 |
| LTBP3 | GPAGERGAGGGGALARERFKVVFAPVICKRTCLKG QCRDSCQQGSNMTLIGENGHSTDTLTGSGFRVVVCP LPCMNGGQCSSRNQCLCPPDFTGRFCQVPAGGAGG GTGGSGPGLSRTGALSTGALPPLAPEGDSVASKHAI YAVQVIADPPGPGEGPPAQHAAFLVPLGPGQISAEV QAPPPVVNVRVHHPPEASVQVHRIESSNAESAAPSQ HLLPHPKPSHPRPPTQKPLGRCFQDTLPKQPCGSNPL PGLTKQEDCCGSIGTAWGQSKCHKCPQLQYTGVQK PGPVRGEVGADCPQGYKRLNSTHCQDINECAMPGV CRHGDCLNNPGSYRCVCPPGHSLGPSRTQCIADKPE EKSLCFRLVSPEHQCQHPLTTRLTRQLCCCSVGKAW GARCQRCPTDGTAAFKEICPAGKGYHILTLSHQTLTIQ | 51 |

TABLE 3-continued

Exemplary LTBP amino acid sequences.

| Protein | Sequence | SEQ ID NO |
|---------|----------|-----------|
| | GESDFSLFLHPDGPPKPQQLPESPSQAPPPEDTEEERG VTTDSPVSEERSVQQSHPTATTTPARPYPELISRPSPP TMRWFLPDLPPSRSAVEIAPTQVTETDECRLNQNICG HGECVPGPPDYSCHCNPGYRSHPQHRYCVDVNECE AEPCGPGRGICMNTGGSYNCHCNRGYRLHVGAGGR SCVDLNECAKPHLCGDGGFCINFPGHYKCNCYPGY RLKASRPPVCEDIDECRDPSSCPDGKCCENKPGSFKCI ACQPGYRSQGGGACRDVNECAEGSPCSPGWCENLP GSFRCTCAQGYAPAPDGRSCLDVDECEAGDVCDNG ICSNTPGSFQCQCLSGYHLSRDRSHCEDIDECDFPAA CIGGDCINTNGSYRCLCPQGHRLVGGRKCQDIDECS QDPSLCLPHGACKNLQGSYVCVCDEGFTPTQDQHG CEEVEQPHHKKECYLNFDDTVFCDSVLATNVTQQE CCCSLGAGWGDHCEIYPCPVYSSAEFHSLCPDGKGY TQDNNIVNYGIPAHRDIDECMLFGSEICKEGKCVNT QPGYECYCKQGFYYDGNLLECVDVDECLDESNCRN GVCENTRGGYRCACTPPAEYSPAQRQCLSPEEMDV DECQDPAACRPGRCVNLPGSYRCECRPPWVPGPSGR DCQLPESPAERAPERRDVCWSQRGEDGMCAGPLAG PALTFDDCCCRQGRGWGAQCRPCPPRGAGSHCPTS QSESNSFWDTSPLLLGKPPRDEDSSEEDSDECRCVSG RCVPRPGGAVCECPGGFQLDASRARCVDIDECRELN QRGLLCKSERCVNTSGSFRCVCKAGFARSRPHGACV PQRRR | |

TABLE 4

Exemplary GARP and LRRC33 amino acid sequences.

| Protein | Sequence | SEQ ID NO |
|---------|----------|-----------|
| GARP | AQHQDKVPCKMVDKKVSCQVLGLLQVPSVLPPDTET LDLSGNQLRSILASPLGFYTALRHLDLSTNEISFLQPGA FQALTHLEHLSLAHNRLAMATALSAGGLGPLPRVTSL DLSGNSLYSGLLERLLGEAPSLHTLSLAENSLTRLTRH TFRDMPALEQLDLHSNVLMDIEDGAFEGLPRLTHLNL SRNSLTCISDFSLQQLRVLDLSCNSIEAFQTASQPQAEF QLTWLDLRENKLLHFPDLAALPRLIYLNLSNNLIRLPT GPPQDSKGIHAPSEGWSALPLSAPSGNASGRPLSQLLN LDLSYNEIELIPDSFLEHLTSLCFLNLSRNCLRTFEARR LGSLPCLMLLDLSHNALETLELGARALGSLRTLLLQG NALRDLPPYTFANLASLQRLNLQGNRVSPCGGPDEPG PSGCVAFSGITSLRSLSLVDNEIELLRAGAFLHTPLTEL DLSSNPGLEVATGALGGLEASLEVLALQGNGLMVLQ VDLPCFICLKRLNLAENRLSHLPAWTQAVSLEVLDLR NNSFSLLPGSAMGGLETSLRRLYLQGNPLSCCGNGWL AAQLHQGRVDVDATQDLICRFSSQEEVSLSHVRPEDC EKGGLKNINLIIILTFILVSAILLTTLAACCCVRRQKFNQ QYKA | 52 |
| sGARP | AQHQDKVPCKMVDKKVSCQVLGLLQVPSVLPPDTET LDLSGNQLRSILASPLGFYTALRHLDLSTNEISFLQPGA FQALTHLEHLSLAHNRLAMATALSAGGLGPLPRVTSL DLSGNSLYSGLLERLLGEAPSLHTLSLAENSLTRLTRH TFRDMPALEQLDLHSNVLMDIEDGAFEGLPRLTHLNL SRNSLTCISDFSLQQLRVLDLSCNSIEAFQTASQPQAEF QLTWLDLRENKLLHFPDLAALPRLIYLNLSNNLIRLPT GPPQDSKGIHAPSEGWSALPLSAPSGNASGRPLSQLLN LDLSYNEIELIPDSFLEHLTSLCFLNLSRNCLRTFEARR LGSLPCLMLLDLSHNALETLELGARALGSLRTLLLQG NALRDLPPYTFANLASLQRLNLQGNRVSPCGGPDEPG PSGCVAFSGITSLRSLSLVDNEIELLRAGAFLHTPLTEL DLSSNPGLEVATGALGGLEASLEVLALQGNGLMVLQ VDLPCFICLKRLNLAENRLSHLPAWTQAVSLEVLDLR NNSFSLLPGSAMGGLETSLRRLYLQGNPLSCCGNGWL AAQLHQGRVDVDATQDLICRFSSQEEVSLSHVRPEDC EKGGLKNIN | 53 |

TABLE 4-continued

Exemplary GARP and LRRC33 amino acid sequences.

| Protein | Sequence | SEQ ID NO |
|---|---|---|
| LRRC33 (also known as NRROS; Uniprot Accession No. Q86YC3) | MELLPLWLCLGFHFLTVGWRNRSGTATAASQGVC KLVGGAADCRGQSLASVPSSLPPHARMLTLDANPLKT LWNHSLQPYPLLESLSLHSCHLERISRGAFQEQGHLRS LVLGDNCLSENYEETAAALHALPGLRRLDLSGNALTE DMAALMLQNLSSLRSVSLAGNTIMRLDDSVFEGLERL RELDLQRNYIFEIEGGAFDGLAELRHLNLAFNNLPCIV DFGLTRLRVLNVSYNVLEWFLATGGEAAFELETLDLS HNQLLFFPLLPQYSKLRTLLLRDNNMGFYRDLYNTSS PREMVAQFLLVDGNVTNITTVSLWEEFSSSDLADLRF LDMSQNFQYLPDGFLRKMPSLSHLNLHQNCLMTLHI REHEPPGALTELDLSHNQLSELHLAPGLASCLGSLRLF NLSSNQLLGVPPGLFANARNITTLDMSHNQISLCPLPA ASDRVGPPSCVDFRNMASLRSLSLEGCGLGALPDCPF QGTSLTYLDLSSNWGVLNGSLAPLQDVAPMLQVLSL RNMGLHSSFMALDFSGFGNLRDLDLSGNCLTTFPRFG GSLALETLDLRRNSLTALPQKAVSEQLSRGLRTIYLSQ NPYDCCGVDGWGALQHGQTVADWAMVTCNLSSKII RVTELPGGVPRDCKWERLDLGLLYLVLILPSCLTLLV ACTVIVLTFKKPLLQVIKSRCHWSSVY<br>* Native signal peptide is depicted in bold font. | 83 |
| soluble LRRC33 (sLRRC33) | MDMRVPAQLLGLLLLWFSGVLGWRNRSGTATAAS QGVCKLVGGAADCRGQSLASVPSSLPPHARMLTLDA NPLKTLWNHSLQPYPLLESLSLHSCHLERISRGAFQEQ GHLRSLVLGDNCLSENYEETAAALHALPGLRRLDLSG NALTEDMAALMLQNLSSLRSVSLAGNTIMRLDDSVFE GLERLRELDLQRNYIFEIEGGAFDGLAELRHLNLAFNN LPCIVDFGLTRLRVLNVSYNVLEWFLATGGEAAFELE TLDLSHNQLLFFPLLPQYSKLRTLLLRDNNMGFYRDL YNTSSPREMVAQFLLVDGNVTNITTVSLWEEFSSSDL ADLRFLDMSQNQFQYLPDGFLRKMPSLSHLNLHQNC LMTLHIREHEPPGALTELDLSHNQLSELHLAPGLASCL GSLRLFNLSSNQLLGVPPGLFANARNITTLDMSHNQIS LCPLPAASDRVGPPSCVDFRNMASLRSLSLEGCGLGA LPDCPFQGTSLTYLDLSSNWGVLNGSLAPLQDVAPML QVLSLRNMGLHSSFMALDFSGFGNLRDLDLSGNCLTT FPRFGGSLALETLDLRRNSLTALPQKAVSEQLSRGLRT IYLSQNPYDCCGVDGWGALQHGQTVADWAMVTCNL SSKIIRVTELPGGVPRDCKWERLDLGL<u>HHHHHH</u><br>* Modified human kappa light chain signal peptide is depicted in bold font.<br>** Histidine tag is underlined. | 84 |
| Human LRRC33-GARP chimera | MDMRVPAQLLGLLLLWFSGVLG<u>WRNRSGTATAAS QGVCKLVGGAADCRGQSLASVPSSLPPHARMLTLDA NPLKTLWNHSLQPYPLLESLSLHSCHLERISRGAFQEQ GHLRSLVLGDNCLSENYEETAAALHALPGLRRLDLSG NALTEDMAALMLQNLSSLRSVSLAGNTIMRLDDSVFE GLERLRELDLQRNYIFEIEGGAFDGLAELRHLNLAFNN LPCIVDFGLTRLRVLNVSYNVLEWFLATGGEAAFELE TLDLSHNQLLFFPLLPQYSKLRTLLLRDNNMGFYRDL YNTSSPREMVAQFLLVDGNVTNITTVSLWEEFSSSDL ADLRFLDMSQNQFQYLPDGFLRKMPSLSHLNLHQNC LMTLHIREHEPPGALTELDLSHNQLSELHLAPGLASCL GSLRLFNLSSNQLLGVPPGLFANARNITTLDMSHNQIS LCPLPAASDRVGPPSCVDFRNMASLRSLSLEGCGLGA LPDCPFQGTSLTYLDLSSNWGVLNGSLAPLQDVAPML QVLSLRNMGLHSSFMALDFSGFGNLRDLDLSGNCLTT FPRFGGSLALETLDLRRNSLTALPQKAVSEQLSRGLRT IYLSQNPYDCCGVDGWGALQHGQTVADWAMVTCNL SSKIIRVTELPGGVPRDCKWERLDLGL</u>*LIIILTFILVSAIL LTTLAACCC*<u>VRRQKFNQQYKA</u><br>* Modified human kappa light chain signal peptide is depicted in bold font.<br>** LRRC33 ectodomain is underlined.<br># GARP transmembrane domain is italicized.<br>## GARP intracellular tail is double underlined. | 85 |

In some embodiments, the antibodies, or antigen binding portions thereof, of the present invention that specifically bind to an epitope of TGFβ1 that is available for binding by the antibody when the TGFβ1 is present in a GARP-TGFβ1 complex, a LTBP1-TGFβ1 complex, a LTBP3-TGFβ1 complex, and/or a LRRC33-TGFβ1 complex and the nucleic acid molecules of the present disclosure that encode the antibodies include one or more of the CDR amino acid sequences shown in Table 5.

TABLE 5

Complementary determining regions of the heavy chain (CDRHs) and the light chain (CDRLs) as determined using the Kabat numbering scheme are shown for antibodies Ab1 and Ab2.

| Antibody | Ab1 | Ab2 |
| --- | --- | --- |
| CDRH1 (SEQ ID NOs: 1-2) | SYGMH (SEQ ID NO: 1) | SDWIG (SEQ ID NO: 2) |
| CDRH2 (SEQ ID NOs: 3-4) | VISYDGSNKYYADSVKG (SEQ ID NO: 3) | VIYPGDSDTRYSASFQG (SEQ ID NO: 4) |
| CDRH3 (SEQ ID NOs: 5-6) | DIRPYGDYSAAFDI (SEQ ID NO: 5) | AAGIAAAGHVTAFDI (SEQ ID NO: 6) |
| CDRL1 (SEQ ID NOs: 7-8) | TGSSGSIASNYVQ (SEQ ID NO: 7) | KSSQSVLYSSNNKNYLA (SEQ ID NO: 8) |
| CDRL2 (SEQ ID NOs: 9-10) | EDNQRPS (SEQ ID NO: 9) | WASTRES (SEQ ID NO: 10) |
| CDRL3 (SEQ ID NOs: 11-12) | QSYDSSNHGGV (SEQ ID NO: 11) | QQYYSTPVT (SEQ ID NO: 12) |

In some embodiments, antibodies of the present invention that specifically bind to GARP-TGFβ1 complex, a LTBP1-TGFβ1 complex, a LTBP3-TGFβ1 complex, and/or a LRRC33-TGFβ1 complex include any antibody, or antigen binding portion thereof, comprising a CDRH1, CDRH2, CDRH3, CDRL1, CDRL2, or CDRL3, or combinations thereof, as provided for any one of the antibodies shown in Table 5. In some embodiments, antibodies that specifically bind to GARP-TGFβ1 complex, a LTBP1-TGFβ1 complex, a LTBP3-TGFβ1 complex, and/or a LRRC33-TGFβ1 complex include the CDRH1, CDRH2, CDRH3, CDRL1, CDRL2, and CDRL3 of any one of the antibodies shown in Table 5. The present invention also provides any nucleic acid sequence that encodes a molecule comprising a CDRH1, CDRH2, CDRH3, CDRL1, CDRL2, or CDRL3 as provided for any one of the antibodies shown in Table 5. Antibody heavy and light chain CDR3 domains may play a particularly important role in the binding specificity/affinity of an antibody for an antigen. Accordingly, the antibodies that specifically bind to GARP-TGFβ1 complex, a LTBP1-TGFβ1 complex, a LTBP3-TGFβ1 complex, and/or a LRRC33-TGFβ1 complex of the disclosure, or the nucleic acid molecules encoding these antibodies, or antigen binding portions thereof, may include at least the heavy and/or light chain CDR3s of the antibodies as shown in Table 5.

Aspects of the invention relate to a monoclonal antibody, or antigen binding portion thereof, that binds specifically to a GARP-TGFβ1 complex, a LTBP1-TGFβ1 complex, a LTBP3-TGFβ1 complex, and/or a LRRC33-TGFβ1 complex, and that comprises six complementarity determining regions (CDRs): CDRH1, CDRH2, CDRH3, CDRL1, CDRL2, and CDRL3.

In some embodiments, CDRH1 comprises a sequence as set forth in any one of SEQ ID NOs: 1 and 2. In some embodiments, CDRH2 comprises a sequence as set forth in any one of SEQ ID NOs: 3 and 4. In some embodiments, CDRH3 comprises a sequence as set forth in any one of SEQ ID NOs: 5 and 6. CDRL1 comprises a sequence as set forth in any one of SEQ ID NOs: 7 and 8. In some embodiments, CDRL2 comprises a sequence as set forth in any one of SEQ ID NOs: 9 and 10. In some embodiments, CDRL3 comprises a sequence as set forth in any one of SEQ ID NOs: 11 and 12.

In some embodiments (e.g., as for antibody Ab1, shown in Table 5), the antibody or antigen binding portion thereof, that specifically binds to a GARP-TGFβ1 complex, a LTBP1-TGFβ1 complex, a LTBP3-TGFβ1 complex, and/or a LRRC33-TGFβ1 complex comprises: a CDRH1 comprising an amino acid sequence as set forth in SEQ ID NO: 1, a CDRH2 comprising an amino acid sequence as set forth in SEQ ID NO: 3, a CDRH3 comprising an amino acid sequence as set forth in SEQ ID NO: 5, a CDRL1 comprising an amino acid sequence as set forth in SEQ ID NO: 7, a CDRL2 comprising an amino acid sequence as set forth in SEQ ID NO: 9, and a CDRL3 comprising an amino acid sequence as set forth in SEQ ID NO: 11.

In some embodiments, the antibody, or antigen binding portion thereof, comprises a heavy chain variable region comprising a complementarity determining region 3 (CDR3) having the amino acid sequence of SEQ ID NO: 5 and a light chain variable region comprising a CDR3 having the amino acid sequence of SEQ ID NO: 11. In some embodiments, the antibody, or antigen binding portion thereof, comprises a heavy chain variable region comprising a complementarity determining region 2 (CDR2) having the amino acid sequence of SEQ ID NO: 3 and a light chain variable region comprising a CDR2 having the amino acid sequence of SEQ ID NO: 9. In some embodiments, the antibody, or antigen binding portion thereof, comprises a heavy chain variable region comprising a complementarity determining region 1 (CDR1) having the amino acid sequence of SEQ ID NO: 1 and a light chain variable region comprising a CDR1 having the amino acid sequence of SEQ ID NO: 7.

In some embodiments, the antibody, or antigen binding portion thereof, comprises a heavy chain variable domain comprising an amino acid sequence having at least 70%, 75%, 80%, 85%, 90%, 95%, 96%, 97%, 98%, or 99% identity to the amino acid sequence set forth in SEQ ID NO: 13 and a light chain variable domain comprising an amino acid sequence having at least 70%, 75%, 80%, 85%, 90%, 95%, 96%, 97%, 98%, or 99% identity to the amino acid sequence set forth in SEQ ID NO: 14. In some embodiments, the antibody, or antigen binding portion thereof, comprises a heavy chain variable domain comprising an amino acid sequence set forth in SEQ ID NO: 13 and a light chain variable domain comprising an amino acid sequence set forth in SEQ ID NO: 14.

In some embodiments, the antibody or antigen binding portion thereof, that specifically binds to a GARP-TGFβ1 complex, a LTBP1-TGFβ1 complex, a LTBP3-TGFβ1 complex, and/or a LRRC33-TGFβ1 complex comprises a heavy chain variable domain amino acid sequence encoded by a nucleic acid sequence having at least 70%, 75%, 80%, 85%, 90%, 95%, 96%, 97%, 98%, or 99% identity to the nucleic acid sequence set forth in SEQ ID NO: 91, and a light chain variable domain amino acid sequence encoded by a nucleic acid sequence having at least 70%, 75%, 80%, 85%, 90%, 95%, 96%, 97%, 98%, or 99% identity to the nucleic acid sequence set forth in SEQ ID NO: 92. In some embodiments, the antibody or antigen binding portion thereof, comprises a heavy chain variable domain amino acid sequence encoded by the nucleic acid sequence set forth in SEQ ID NO: 91, and a light chain variable domain amino acid sequence encoded by the nucleic acid sequence set forth in SEQ ID NO: 92.

In some embodiments (e.g., as for antibody Ab2, shown in Table 5), the antibody or antigen binding portion thereof, that specifically binds to a GARP-TGFβ1 complex, a LTBP1-TGFβ1 complex, a LTBP3-TGFβ1 complex, and/or a LRRC33-TGFβ1 complex comprises a CDRH1 comprising an amino acid sequence as set forth in SEQ ID NO: 2, a CDRH2 comprising an amino acid sequence as set forth in SEQ ID NO: 3, a CDRH3 comprising an amino acid sequence as set forth in SEQ ID NO: 6, a CDRL1 comprising an amino acid sequence as set forth in SEQ ID NO: 8, a CDRL2 comprising an amino acid sequence as set forth in SEQ ID NO: 10, and a CDRL3 comprising an amino acid sequence as set forth in SEQ ID NO: 12.

In some embodiments, the antibody, or antigen binding portion thereof, comprises a heavy chain variable region comprising a CDR3 having the amino acid sequence of SEQ ID NO: 6 and a light chain variable region comprising a CDR3 having the amino acid sequence of SEQ ID NO: 12. In some embodiments, the antibody, or antigen binding portion thereof, comprises a heavy chain variable region comprising a CDR2 having the amino acid sequence of SEQ ID NO: 4 and a light chain variable region comprising a CDR2 having the amino acid sequence of SEQ ID NO: 10. In some embodiments, the antibody, or antigen binding portion thereof, comprises a heavy chain variable region comprising a CDR1 having the amino acid sequence of SEQ ID NO: 2 and a light chain variable region comprising a CDR1 having the amino acid sequence of SEQ ID NO: 8.

In some embodiments, the antibody, or antigen binding portion thereof, comprises a heavy chain variable domain comprising an amino acid sequence having at least 70%, 75%, 80%, 85%, 90%, 95%, 96%, 97%, 98%, or 99% identity to the amino acid sequence set forth in SEQ ID NO: 15 and a light chain variable domain comprising an amino acid sequence having at least 70%, 75%, 80%, 85%, 90%, 95%, 96%, 97%, 98%, or 99% identity to the amino acid sequence set forth in SEQ ID NO: 16. In some embodiments, the antibody, or antigen binding portion thereof, comprises a heavy chain variable domain comprising an amino acid sequence set forth in SEQ ID NO: 15 and a light chain variable domain comprising an amino acid sequence set forth in SEQ ID NO: 16.

In some embodiments, the antibody or antigen binding portion thereof, that specifically binds to a GARP-TGFβ1 complex, a LTBP1-TGFβ1 complex, a LTBP3-TGFβ1 complex, and/or a LRRC33-TGFβ1 complex comprises a heavy chain variable domain amino acid sequence encoded by a nucleic acid sequence having at least 70%, 75%, 80%, 85%, 90%, 95%, 96%, 97%, 98%, or 99% identity to the nucleic acid sequence set forth in SEQ ID NO: 93, and a light chain variable domain amino acid sequence encoded by a nucleic acid sequence having at least 70%, 75%, 80%, 85%, 90%, 95%, 96%, 97%, 98%, or 99% identity to the nucleic acid sequence set forth in SEQ ID NO: 94. In some embodiments, the antibody or antigen binding portion thereof, comprises a heavy chain variable domain amino acid sequence encoded by the nucleic acid sequence set forth in SEQ ID NO: 93, and a light chain variable domain amino acid sequence encoded by the nucleic acid sequence set forth in SEQ ID NO: 94.

In some examples, any of the antibodies of the disclosure that specifically bind to a GARP-TGFβ1 complex, a LTBP1-TGFβ1 complex, a LTBP3-TGFβ1 complex, and/or a LRRC33-TGFβ1 complex include any antibody (including antigen binding portions thereof) having one or more CDR (e.g., CDRH or CDRL) sequences substantially similar to CDRH1, CDRH2, CDRH3, CDRL1, CDRL2, and/or CDRL3. For example, the antibodies may include one or more CDR sequences as shown in Table 5 (SEQ ID NOs: 1-12) containing up to 5, 4, 3, 2, or 1 amino acid residue variations as compared to the corresponding CDR region in any one of SEQ ID NOs: 1-12. The complete amino acid sequences for the heavy chain variable region and light chain variable region of the antibodies listed in Table 5 (e.g., Ab1 and Ab2), as well as nucleic acid sequences encoding the heavy chain variable region and light chain variable region of the antibodies are provided below.

Ab1-Heavy chain variable region amino acid sequence
(SEQ ID NO: 13)
EVQLVESGGGLVQPGRSLRLSCAASGFTFSSYGMHWVRQAPGKGLEWVAV

ISYDGSNKYYADSVKGRFTISRDNSKNTLYLQMNSLRAEDTAVYYCARDI

RPYGDYSAAFDIWGQGTLVTVSS

Ab1-Heavy chain variable region nucleic acid sequence
(SEQ ID NO: 91)
GAGGTGCAACTCGTGGAGTCAGGCGGTGGACTTGTTCAGCCTGGGCGAAG

TCTGAGACTCTCATGTGCAGCAAGTGGATTCACTTTCTCCAGTTACGGCA

TGCACTGGGTGAGACAGGCGCCTGGAAAGGGTTTGGAATGGGTCGCTGTG

ATCTCTTACGACGGGTCAAACAAATATTACGCGGATTCAGTGAAAGGGCG

GTTCACTATTTCACGGGATAACTCCAAGAACACCCTGTATCTGCAGATGA

ATAGCCTGAGGGCAGAGGACACCGCTGTGTACTATTGTGCCCGGGACATA

AGGCCTTACGGCGATTACAGCGCCGCATTTGATATTTGGGGACAAGGCAC

CCTTGTGACAGTATCTTCT

Ab1-Light chain variable region amino acid
sequence
(SEQ ID NO: 14)
NFMLTQPHSVSESPGKTVTISCTGSSGSIASNYVQWYQQRPGSAPSIVIF

EDNQRPSGAPDRFSGSIDSSSNSASLTISGLKTEDEADYYCQSYDSSNHG

GVFGGGTQLTVL

Ab1-Light chain variable region nucleic acid
sequence
(SEQ ID NO: 92)
AATTTTATGCTTACCCAACCACATAGTGTGAGTGAGTCTCCCGGCAAGAC

TGTAACAATTTCATGTACCGGCAGCAGTGGCTCCATCGCTAGCAATTATG

TGCAATGGTACCAACAGCGCCCCGGGAGCGCACCTTCAATAGTGATATTC

GAGGATAACCAACGGCCTAGTGGGGCTCCCGATAGATTTAGTGGGAGTAT

AGATAGCTCCTCCAACTCTGCCTCTCTCACCATTAGCGGGCTGAAAACAG

AGGATGAAGCCGACTATTACTGCCAAAGCTATGATTCTAGCAACCACGGC

GGAGTGTTTGGCGGAGGAACACAGCTGACAGTCCTAGG

Ab1-Heavy chain amino acid sequence
(SEQ ID NO: 15)
EVQLVESGGGLVQPGRSLRLSCAASGFTFSSYGMHWVRQAPGKGLEWVAV

ISYDGSNKYYADSVKGRFTISRDNSKNTLYLQMNSLRAEDTAVYYCARDI

RPYGDYSAAFDIWGQGTLVTVSSASTKGPSVFPLAPCSRSTSESTAALGC

LVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKP

KDTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLG

Ab1-Light chain amino acid sequence
(SEQ ID NO: 16)
NFMLTQPHSVSESPGKTVTISCTGSSGSIASNYVQWYQQRPGSAPSIVIF

EDNQRPSGAPDRFSGSIDSSSNSASLTISGLKTEDEADYYCQSYDSSNHG

GVFGGGTQLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS

Ab2-Heavy chain variable region amino acid
sequence
(SEQ ID NO: 17)
EVQLVQSGAEMKKPGESLKISCKGSGYNFASDWIGWVRQTPGKGLEWMGV

IYPGDSDTRYSASFQGQVTISADKSINTAYLQWSSLKASDTAMYYCASAA

GIAAAGHVTAFDIWGQGTMVTVSS

Ab2-Heavy chain variable region nucleic acid
sequence
(SEQ ID NO: 93)
GAGGTGCAACTGGTGCAATCCGGAGCCGAGATGAAAAAGCCAGGGGAGAG

CCTGAAGATCTCTTGTAAGGGCTCTGGCTATAACTTCGCTAGTGATTGGA

TCGGATGGGTGAGGCAAACCCCCGGAAAGGGCCTCGAGTGGATGGGCGTG

ATCTACCCCGGCGACTCCGACACACGCTATAGCGCCTCATTCCAGGGCCA

GGTCACCATAAGTGCTGATAAATCAATAAATACAGCCTACTTGCAATGGT

CAAGTCTGAAAGCCTCAGATACTGCCATGTACTATTGTGCCTCTGCCGCC

GGCATTGCCGCGGCCGGTCACGTCACCGCCTTCGACATTTGGGGTCAGGG

CACTATGGTCACTGTAAGCTCC

Ab2-Light chain variable region amino acid
sequence
(SEQ ID NO: 18)
DIVMTQSPDSLAVSLGERATINCKSSQSVLYSSNNKNYLAWYQQKPGQPP

KLLIYWASTRESGVPDRFSGSGSGTDFTLTISSLQAEDVAVYYCQQYYST

PVTFGQGTKLEIK

Ab2-Light chain variable region nucleic acid
sequence
(SEQ ID NO: 94)
GACATAGTCATGACCCAGTCACCTGACTCTTTGGCCGTGTCTCTGGGGGA

GAGAGCCACAATAAATTGCAAGTCATCACAGAGCGTCCTGTACTCCTCCA

ATAATAAAAATTACCTGGCCTGGTACCAGCAAAAGCCCGGGCAACCCCCC

AAATTGTTGATTTACTGGGCTAGTACAAGGGAATCTGGAGTGCCAGACCG

GTTTTCTGGTTCTGGATCTGGTACTGACTTCACCCTGACAATCAGCTCCC

TGCAGGCCGAAGACGTGGCTGTGTACTATTGTCAGCAGTACTATAGTACA

CCAGTTACTTTCGGCCAAGGCACTAAACTCGAAATCAAG

Ab2-Heavy chain amino acid sequence
(SEQ ID NO: 19)
EVQLVQSGAEMKKPGESLKISCKGSGYNFASDWIGWVRQTPGKGLEWMGV

IYPGDSDTRYSASFQGQVTISADKSINTAYLQWSSLKASDTAMYYCASAA

GIAAAGHVTAFDIWGQGTMVTVSSASTKGPSVFPLAPCSRSTSESTAALG

CLVKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFPPK

PKDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLS

LG

Ab2-Light chain amino acid sequence
(SEQ ID NO: 20)
DIVMTQSPDSLAVSLGERATINCKSSQSVLYSSNNKNYLAWYQQKPGQP

PKLLIYWASTRESGVPDRFSGSGSGTDFTLTISSLQAEDVAVYYCQQYY

STPVTFGQGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC

In some embodiments, antibodies of the disclosure that specifically bind to a GARP-TGFβ1 complex, a LTBP1-TGFβ1 complex, a LTBP3-TGFβ1 complex, and a LRRC33-TGFβ1 complex include any antibody that includes a heavy chain variable domain of SEQ ID NO: 13 or 17, or a light chain variable domain of SEQ ID NO: 14 or 18. In some embodiments, antibodies of the disclosure that specifically bind to a GARP-TGFβ1 complex, a LTBP1-TGFβ1 complex, a LTBP3-TGFβ1 complex, and a LRRC33-TGFβ1 complex include any antibody that includes the heavy chain variable and light chain variable pairs of SEQ ID NOs: 13 and 14; and 17 and 18.

Aspects of the disclosure provide antibodies that specifically bind to a GARP-TGFβ1 complex, a LTBP1-TGFβ1 complex, a LTBP3-TGFβ1 complex, and a LRRC33-TGFβ1 complex having a heavy chain variable and/or a light chain variable amino acid sequence homologous to any of those described herein. In some embodiments, the antibody that that specifically binds to a GARP-TGFβ1 complex, a LTBP1-TGFβ1 complex, a LTBP3-TGFβ1 complex, and a LRRC33-TGFβ1 complex comprises a heavy chain variable sequence or a light chain variable sequence that is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to the heavy chain variable amino acid sequence of SEQ ID NO: 13 or 17, or a light chain variable sequence of SEQ ID NO: 14 or 18. In some embodiments, the homologous heavy chain variable and/or a light chain variable amino acid sequences do not vary within any of the CDR sequences provided herein. For example, in some embodiments, the degree of sequence variation (e.g., 80%, 81%, 82%, 83%, 84%, 85%, 86%, 87%, 88%, 89%, 90%, 91%, 92%, 93%, 94%, 95%, 96%, 97%, 98%, or 99%) may occur within a heavy chain variable and/or a light chain variable amino acid sequence excluding any of the CDR sequences provided herein.

In some embodiments, antibodies of the disclosure that specifically bind to a GARP-TGFβ1 complex, a LTBP1-TGFβ1 complex, a LTBP3-TGFβ1 complex, and/or a LRRC33-TGFβ1 complex include any antibody, or antigen binding portion thereof, that includes a heavy chain of SEQ ID NO: 15 or 19, or a light chain of SEQ ID NO: 16 or 20. In some embodiments, antibodies of the disclosure that specifically bind to a GARP-TGFβ1 complex, a LTBP1-TGFβ1 complex, a LTBP3-TGFβ1 complex, and/or a LRRC33-TGFβ1 complex include any antibody that includes the heavy chain and light chain pairs of SEQ ID NOs: 15 and 16; or 19 and 20.

Aspects of the disclosure provide antibodies that specifically bind to a GARP-TGFβ1 complex, a LTBP1-TGFβ1 complex, a LTBP3-TGFβ1 complex, and/or a LRRC33-TGFβ1 complex having a heavy chain and/or a light chain amino acid sequence homologous to any of those described herein. In some embodiments, the antibody that specifically binds to a GARP-TGFβ1 complex, a LTBP1-TGFβ1 complex, a LTBP3-TGFβ1 complex, and/or a LRRC33-TGFβ1 complex comprises a heavy chain sequence or a light chain sequence that is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to the heavy chain sequence of SEQ ID NO: 15, or 19, or a light chain amino acid sequence of SEQ ID NO: 16, or 20. In some embodiments, the homologous heavy chain and/or a light chain amino acid sequences do not vary within any of the CDR sequences provided herein. For example, in some embodiments, the degree of sequence variation (e.g., 80%, 81%, 82%, 83%, 84%, 85%, 86%, 87%, 88%, 89%, 90%, 91%, 92%, 93%, 94%, 95%, 96%, 97%, 98%, or 99%) may occur within a heavy chain and/or a light chain amino acid sequence excluding any of the CDR sequences provided herein.

Aspects of the disclosure provide antibodies that specifically bind to a GARP-TGFβ1 complex, a LTBP1-TGFβ1 complex, a LTBP3-TGFβ1 complex, and/or a LRRC33-TGFβ1 complex having a heavy chain and/or a light chain amino acid sequence homologous to any of those described herein. In some embodiments, the antibody that that specifically binds to a GARP-TGFβ1 complex, a LTBP1-TGFβ1 complex, a LTBP3-TGFβ1 complex, and/or a LRRC33-TGFβ1 complex comprises a heavy chain sequence or a light chain sequence that is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to the heavy chain sequence of SEQ ID NO: 15 or 19, or a light chain amino acid sequence of SEQ ID NO: 16 or 20. In some embodiments, the homologous heavy chain and/or a light chain amino acid sequences do not vary within any of the CDR sequences provided herein. For example, in some embodiments, the degree of sequence variation (e.g., 80%, 81%, 82%, 83%, 84%, 85%, 86%, 87%, 88%, 89%, 90%, 91%, 92%, 93%, 94%, 95%, 96%, 97%, 98%, or 99%) may occur within a heavy chain and/or a light chain amino acid sequence excluding any of the CDR sequences provided herein.

In some embodiments, the "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In any of the antibodies or antigen-binding fragments described herein, one or more conservative mutations can be introduced into the CDRs or framework sequences at positions where the residues are not likely to be involved in an antibody-antigen interaction. In some embodiments, such conservative mutation(s) can be introduced into the CDRs or framework sequences at position(s) where the residues are not likely to be involved in interacting with a GARP-TGFβ1 complex, a LTBP1-TGFβ1 complex, a LTBP3-TGFβ1 complex, and a LRRC33-TGFβ1 complex as determined based on the crystal structure. In some embodiments, likely interface (e.g., residues involved in an antigen-antibody interaction) may be deduced from known structural information on another antigen sharing structural similarities.

As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like (CPPCP (SEQ ID NO: 54)) hinge sequence. Accordingly, any of the antibodies may include a stabilizing 'Adair' mutation or the amino acid sequence CPPCP (SEQ ID NO: 54).

Antibodies of this disclosure that specifically bind to a GARP-TGFβ1 complex, a LTBP1-TGFβ1 complex, a LTBP3-TGFβ1 complex, and/or a LRRC33-TGFβ1 complex may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include $V_H$ and $V_L$ domains, or an antigen binding portion thereof, combined with any suitable constant regions.

In some embodiments, antibodies that specifically bind to a GARP-TGFβ1 complex, a LTBP1-TGFβ1 complex, a LTBP3-TGFβ1 complex, and/or a LRRC33-TGFβ1 complex may or may not include the framework region of the antibodies of SEQ ID NOs: 13-20. In some embodiments, antibodies that specifically bind to a GARP-TGFβ1 complex, a LTBP1-TGFβ1 complex, a LTBP3-TGFβ1 complex, and/or a LRRC33-TGFβ1 complex are murine antibodies and include murine framework region sequences.

In some embodiments, antibodies that specifically bind to a GARP-TGFβ1 complex, a LTBP1-TGFβ1 complex, a LTBP3-TGFβ1 complex, and/or a LRRC33-TGFβ1 complex of the disclosure can bind to a GARP-TGFβ1 complex, a LTBP1-TGFβ1 complex, a LTBP3-TGFβ1 complex, and/or a LRRC33-TGFβ1 complex with relatively high affinity, e.g., with a $K_D$ less than $10^{-6}$ M, $10^{-7}$ M, $10^{-8}$ M, 10 M, $10^{-10}$ M, $10^{-11}$ M or lower. For example, antibodies that specifically bind to a GARP-TGFβ1 complex, a LTBP1-TGFβ1 complex, a LTBP3-TGFβ1 complex, and/or a LRRC33-TGFβ1 complex can bind a GARP-TGFβ1 complex, a LTBP1-TGFβ1 complex, a LTBP3-TGFβ1 complex, and/or a LRRC33-TGFβ1 complex with an affinity between 5 pM and 500 nM, e.g., between 50 pM and 100 nM, e.g., between 500 pM and 50 nM. The disclosure also includes antibodies or antigen binding fragments that compete with any of the antibodies described herein for binding to a GARP-TGFβ1 complex, a LTBP1-TGFβ1 complex, a LTBP3-TGFβ1 complex, and/or a LRRC33-TGFβ1 complex and that have an affinity of 50 nM or lower (e.g., 20 nM or lower, 10 nM or lower, 500 pM or lower, 50 pM or lower, or 5 pM or lower). The affinity and binding kinetics of the antibodies that specifically bind to a GARP-TGFβ1 complex, a LTBP1-TGFβ1 complex, a LTBP3-TGFβ1 complex, and/or a LRRC33-TGFβ1 complex can be tested using any suitable method including but not limited to biosensor technology (e.g., OCTET or BIACORE).

Antibodies that Inhibit TGFβ

The present invention in one aspect provides functional antibodies. As used herein, "a functional antibody" confers one or more biological activities by virtue of its ability to bind an antigen. Functional antibodies may include inhibiting antibodies (or inhibitory antibodies) and activating antibodies. Thus, the present disclosure includes TGFβ antibodies which can modulate (e.g., inhibit or activate) a biological process mediated by TGFβ signaling.

As used herein, the term "inhibiting antibody" refers to an antibody that inhibits mature growth factor release or reduces growth factor activity. Inhibiting antibodies include antibodies targeting any epitope that reduces growth factor release or activity when associated with such antibodies. Such epitopes may lie on prodomains of TGFβ proteins (e.g. TGFβ1), growth factors or other epitopes that lead to reduced growth factor activity when bound by antibody. Inhibiting antibodies of the present invention include, but are not limited to, TGFβ1-inhibiting antibodies.

Embodiments of the present disclosure include methods of using inhibiting antibodies in solution, in cell culture and/or in subjects to modify growth factor signaling.

Polypeptides

Some aspects of the disclosure relate to a polypeptide having a sequence selected from the group consisting of SEQ ID NO: 13, SEQ ID NO: 17, SEQ ID NO: 15, and SEQ ID NO: 19. In some embodiments, the polypeptide is a variable heavy chain domain or a heavy chain domain. In some embodiments, the polypeptide is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to any one of the amino acid sequences set forth in SEQ ID NO: 13, SEQ ID NO: 17, SEQ ID NO: 15, and SEQ ID NO: 19.

Some aspects of the disclosure relate to a polypeptide having a sequence selected from the group consisting of SEQ ID NO: 14, SEQ ID NO: 18, SEQ ID NO: 16, and SEQ ID NO: 20. In some embodiments, the polypeptide is a variable light chain domain or a light chain domain. In some embodiments, the polypeptide is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to any one of the amino acid sequences set forth in SEQ ID NO: 14, SEQ ID NO: 18, SEQ ID NO: 16, and SEQ ID NO: 20.

Antibodies Competing with Antibodies that Specifically Bind to a GARP-TGFβ1 Complex, a LTBP1-TGFβ1 Complex, a LTBP3-TGFβ1 Complex, and/or a LRRC33-TGFβ1 Complex Aspects of the disclosure relate to antibodies that compete or cross-compete with any of the antibodies provided herein. The term "compete", as used herein with regard to an antibody, means that a first antibody binds to an epitope (e.g., an epitope of a GARP-TGFβ1 complex, a LTBP1-TGFβ1 complex, a LTBP3-TGFβ1 complex, and/or a LRRC33-TGFβ1 complex) in a manner sufficiently similar to the binding of a second antibody, such that the result of binding of the first antibody with its epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its epitope or ligand, whether to the same, greater, or lesser extent, the antibodies are said to "cross-compete" with each other for binding of their respective epitope(s). Both competing and cross-competing antibodies are within the scope of this disclosure. Regardless of the mechanism by which such competition or cross-competition occurs (e.g., steric hindrance, conformational change, or binding to a common epitope, or portion thereof), the skilled artisan would appreciate that such competing and/or cross-competing antibodies are encompassed and can be useful for the methods and/or compositions provided herein.

Aspects of the disclosure relate to antibodies that compete or cross-compete with any of the specific antibodies, or antigen binding portions thereof, as provided herein. In some embodiments, an antibody, or antigen binding portion thereof, binds at or near the same epitope as any of the antibodies provided herein. In some embodiments, an antibody, or antigen binding portion thereof, binds near an epitope if it binds within 15 or fewer amino acid residues of the epitope. In some embodiments, any of the antibody, or antigen binding portion thereof, as provided herein, binds within 1, 2, 3, 4, 5, 6, 7, 8, 9, 10, 11, 12, 13, 14 or 15 amino acid residues of an epitope that is bound by any of the antibodies provided herein. In another embodiment, provided herein is an antibody, or antigen binding portion thereof, competes or cross-competes for binding to any of the antigens provided herein (e.g., a GARP-TGFβ1 complex, a LTBP1-TGFβ1 complex, a LTBP3-TGFβ1 complex, and/or a LRRC33-TGFβ1 complex) with an equilibrium dissociation constant, $K_D$, between the antibody and the protein of less than $10^{-6}$ M. In other embodiments, an antibody competes or cross-competes for binding to any of the antigens provided herein with a $K_D$ in a range from $10^{-11}$ M to $10^{-6}$ M. In some embodiments, provided herein is an anti-TGFβ1 antibody, or antigen binding portion thereof, that competes for binding with an antibody, or antigen binding portion thereof, described herein. In some embodiments, provided herein is an anti-TGFβ1 antibody, or antigen binding portion thereof, that binds to the same epitope as an antibody, or antigen binding portion thereof, described herein.

Any of the antibodies provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). In some embodiments, the epitope is a TGFβ1 epitope that is only available for binding by the antibody, or antigen binding portion thereof, described herein, when the TGFβ1 is in a GARP-TGFβ1 complex, a LTBP1-TGFβ1 complex, a LTBP3-TGFβ1 complex, and/or a LRRC33-TGFβ1 complex. Peptides of varying lengths (e.g., at least 4-6 amino acids long) can be isolated or synthesized (e.g., recombinantly) and used for binding assays with an antibody. In another example, the epitope to which the antibody binds can be determined in a systematic screen by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the GARP-TGFβ1 complex, a LTBP1-TGFβ1 complex, a LTBP3-TGFβ1 complex, and/or a LRRC33-TGFβ1 complex have been replaced (swapped) with sequences from a closely related, but antigenically distinct protein, such as another member of the TGFβ protein family (e.g., GDF11). By assessing binding of the antibody to the mutant of the a GARP-TGFβ1 complex, a LTBP1-TGFβ1 complex, a LTBP3-TGFβ1 complex, and/or a LRRC33-TGFβ1 complex, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Further, the interaction of the any of the antibodies provided herein with one or more residues in aa GARP-TGFβ1 complex, a LTBP1-TGFβ1 complex, a LTBP3-TGFβ1 complex, and/or a LRRC33-TGFβ1 complex can be determined by routine technology. For example, a crystal structure can be determined, and the distances between the residues in a GARP-TGFβ1 complex, a LTBP1-TGFβ1 complex, a LTBP3-TGFβ1 complex, and/or a LRRC33-TGFβ1 complex and one or more residues in the antibody can be determined accordingly. Based on such distance, whether a specific residue in a GARP-TGFβ1 complex, a LTBP1-TGFβ1 complex, a LTBP3-TGFβ1 complex, and/or a LRRC33-TGFβ1 complex interacts with one or more residues in the antibody can be determined. Further, suitable methods, such as competition assays and target mutagenesis assays can be applied to determine the preferential binding of a candidate antibody.

Production of Antibodies that Bind a GARP-TGFβ1 Complex, a LTBP1-TGFβ1 Complex, a LTBP3-TGFβ1 Complex, and/or a LRRC33-TGFβ1 Complex Numerous methods may be used for obtaining antibodies, or antigen binding fragments thereof, of the disclosure. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597; WO 92/18619; WO 91/17271; WO 92/20791; WO 92/15679; WO 93/01288; WO 92/01047; WO 92/09690; and WO 90/02809.

In addition to the use of display libraries, the specified antigen (e.g., a GARP-TGFβ1 complex, a LTBP1-TGFβ1 complex, a LTBP3-TGFβ1 complex, and/or a LRRC33-TGFβ1 complex) can be used to immunize a non-human animal, e.g., a rodent, e.g., a mouse, hamster, or rat. In one embodiment, the non-human animal is a mouse.

In another embodiment, a monoclonal antibody is obtained from the non-human animal, and then modified, e.g., chimeric, using suitable recombinant DNA techniques. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen binding fragments. Furthermore, transgenic animals, preferably mammals, comprising the aforementioned host cells may be used for the large scale production of the antibody or antibody fragments.

The transformed host cells can be grown in fermenters and cultured using any suitable techniques to achieve optimal cell growth. Once expressed, the whole antibodies, their dimers, individual light and heavy chains, other immunoglobulin forms, or antigen binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen binding fragments can then be isolated from the growth medium, cellular lysates, or cellular membrane fractions. The isolation and purification of the, e.g., microbially expressed antibodies or antigen binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen binding fragment may be undertaken by culturing a modified recombinant host under culture conditions appropriate for the growth of the host cells and the expression of the coding sequences. The antibodies or antigen binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in *E. coli*, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, polynucleotides may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain(s) of the immunoglobulin chains encoding sequences and expression control sequences) can be transferred into the host cell by suitable methods, which vary depending on the type of cellular host.

Modifications

Antibodies, or antigen binding portions thereof, of the disclosure may be modified with a detectable label or detectable moiety, including, but not limited to, an enzyme, prosthetic group, fluorescent material, luminescent material, bioluminescent material, radioactive material, positron emitting metal, nonradioactive paramagnetic metal ion, and affinity label for detection and isolation of a GARP-TGFβ1 complex, a LTBP1-TGFβ1 complex, a LTBP3-TGFβ1 complex, and/or a LRRC33-TGFβ1 complex. The detectable substance or moiety may be coupled or conjugated either directly to the polypeptides of the disclosure or indirectly, through an intermediate (such as, for example, a linker (e.g., a cleavable linker)) using suitable techniques. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115}$mIn, $^{113}$mIn, $^{112}$In, $^{111}$In), and technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$Ho, $^{90}$Y, $^{47}$Sc, $^{86}$R, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{113}$Sn, $^{117}$Sn). The detectable substance may be coupled or conjugated either directly to the antibodies of the disclosure that bind specifically to a GARP-TGFβ 1 complex, a LTBP1-TGFβ 1 complex, a LTBP3-TGFβ 1 complex, and/or a LRRC33-TGFβ 1 complex, or indirectly, through an intermediate (such as, for example, a linker) using suitable techniques. Any of the antibodies provided herein that are conjugated to a detectable substance may be used for any suitable diagnostic assays, such as those described herein.

In addition, antibodies, or antigen binding portions thereof, of the disclosure may also be modified with a drug. The drug may be coupled or conjugated either directly to the polypeptides of the disclosure, or indirectly, through an intermediate (such as, for example, a linker (e.g., a cleavable linker)) using suitable techniques.

Targeting Agents

In some embodiments methods of the present disclosure comprise the use of one or more targeting agents to target an antibody, or antigen binding portion thereof, as disclosed herein, to a particular site in a subject for purposes of modulating mature TGFβ release from a GARP-TGFβ 1 complex, a LTBP1-TGFβ 1 complex, a LTBP3-TGFβ 1 complex, and/or a LRRC33-TGFβ 1 complex. For example, LTBP1-TGFβ 1 and LTBP3-TGFβ 1 complexes are typically localized to extracellular matrix. Thus, in some embodiments, antibodies disclosed herein can be conjugated to extracellular matrix targeting agents for purposes of localizing the antibodies to sites where LTBP1-TGFβ 1 and LTBP3-TGFβ 1 complexes reside. In such embodiments, selective targeting of antibodies leads to selective modulation of LTBP1-TGFβ1 and/or LTBP3-TGFβ 1 complexes. In some embodiments, selective targeting of antibodies leads to selective inhibition of LTBP1-TGFβ1 and/or LTBP3-TGFβ1 complexes (e.g., for purposes of treating fibrosis). In some embodiments, extracellular matrix targeting agents include heparin binding agents, matrix metalloproteinase binding agents, lysyl oxidase binding domains, fibrillin-binding agents, hyaluronic acid binding agents, and others.

Similarly, GARP-TGFβ 1 complexes are typically localized to the surface of cells, e.g., activated $FOXP3^+$ regulatory T cells (Tregs). Thus, in some embodiments, antibodies disclosed herein can be conjugated to immune cell (e.g., Treg cell) binding agents for purposes of localizing antibodies to sites where GARP-TGFβ1 complexes reside. In such embodiments, selective targeting of antibodies leads to selective modulation of GARP-TGFβ1 complexes. In some embodiments, selective targeting of antibodies leads to selective inhibition of GARP-TGFβ1 complexes (e.g., selective inhibition of the release of mature TGFβ1 for purposes of immune modulation, e.g., in the treatment of cancer). In such embodiments, Treg cell targeting agents may include, for example, CCL22 and CXCL12 proteins or fragments thereof.

In some embodiments, bispecific antibodies may be used having a first portion that selectively binds GARP-TGFβ1 complex and a LTBP-TGFβ1 complex and a second portion that selectively binds a component of a target site, e.g., a component of the ECM (e.g., fibrillin) or a component of a Treg cell (e.g., CTLA-4).

Pharmaceutical Compositions

The invention further provides pharmaceutical compositions used as a medicament suitable for administration in human and non-human subjects. One or more antibodies that specifically binds a GARP-TGFβ1 complex, a LTBP1-TGFβ1 complex, a LTBP3-TGFβ1 complex, and/or a LRRC33-TGFβ1 complex can be formulated or admixed with a pharmaceutically acceptable carrier (excipient), including, for example, a buffer, to form a pharmaceutical composition. Such formulations may be used for the treatment of a disease or disorder that involves TGFβ signaling. In some embodiments, such disease or disorder associated with TGFβ signaling involves one or more contexts, i.e., the TGFβ is associated with a particular type or types of presenting molecules. In some embodiments, such context occurs in a cell type-specific and/or tissue-specific manner. In some embodiments, for example, such context-dependent action of TGFβ signaling is mediated in part via GARP, LRRC33, LTBP1 and/or LTBP3.

In some embodiments, the antibody of the present invention binds specifically to two or more contexts of TGFβ, such that the antibody binds TGFβ in a complex with presenting molecules selected from two or more of: GARP, LRRC33, LTBP1 and LTBP3. Thus, such pharmaceutical compositions may be administered to patients for alleviating a TGFβ-related indication (e.g., fibrosis, immune disorders, and/or cancer). "Acceptable" means that the carrier is compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. In one example, a pharmaceutical composition described herein contains more than one antibody that specifically binds a GARP-TGFβ1 complex, a LTBP1-TGFβ1 complex, a LTBP3-TGFβ1 complex, and/or a LRRC33-TGFβ1 complex where the antibodies recognize different epitopes/residues of the a GARP-TGFβ1 complex, a LTBP1-TGFβ1 complex, a LTBP3-TGFβ1 complex, and/or a LRRC33-TGFβ1 complex.

The pharmaceutical compositions to be used in the present methods can comprise pharmaceutically acceptable carriers, excipients, or stabilizers in the form of lyophilized formulations or aqueous solutions (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing an antibody that specifically binds a GARP-TGFβ1 complex, a LTBP1-TGFβ1 complex, a LTBP3-TGFβ1 complex, and/or a LRRC33-TGFβ1 complex, which can be prepared by any suitable method, such as described in Epstein et al., *Proc. Natl. Acad. Sci. USA* 82:3688 (1985); Hwang et al. *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies that specifically bind a GARP-TGFβ1 complex, a LTBP1-TGFβ1 complex, a LTBP3-TGFβ1 complex, and/or a LRRC33-TGFβ1 complex may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 mg to about 500 mg of the active ingredient of the present disclosure. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an antibody that specifically binds a GARP-TGFβ1 complex, a LTBP1-TGFβ1 complex, a LTBP3-TGFβ1 complex, and/or a LRRC33-TGFβ1 complex with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Use of Antibodies, and Antigen-Binding Portions Thereof, that Specifically Bind a GARP-TGFβ1 Complex, a LTBP1-TGFβ1 Complex, a LTBP3-TGFβ1 Complex, and/or a LRRC33-TGFβ1 Complex In some embodiments, antibodies, antigen binding portions thereof, and compositions of the disclosure may be used to treat a wide variety of diseases, disorders and/or conditions. In some cases, such diseases, disorders and/or conditions may be TGFβ-related indications. As used herein, the term "TGFβ-related indication" refers to any disease, disorder and/or condition related to expression, activity and/or metabolism of a TGFβ family member protein or any disease, disorder and/or condition that may benefit from modulation of the activity and/or levels of one or more TGFβ family member protein. TGFβ-related indications may include, but are not limited to, fibrosis, cancer (including, but not limited to colon cancer, renal cancer, breast cancer, malignant melanoma and glioblastoma, facilitation of rapid hematopoiesis following chemotherapy, bone healing, wound healing, dementia, myelofibrosis, a renal disease, unilateral ureteral obstruction (UUO), tooth loss and/or degeneration, endothelial proliferation syndromes, asthma and allergy, gastrointestinal disorders, anemia of the aging, aortic aneurysm, orphan indications (such as Marfan's syndrome and Camurati-Engelmann disease,) obesity, diabetes, arthritis, multiple sclerosis, muscular dystrophy, amyotrophic lateral sclerosis (ALS) Parkinson's disease, osteoporosis, osteoarthritis, osteopenia, metabolic syndromes, nutritional disorders, organ atrophy, chronic obstructive pulmonary disease (COPD), and anorexia. Additional indications may include any of those disclosed in US Pub. No. 2013/0122007, U.S. Pat. No. 8,415,459 or International Pub. No. WO 2011/151432, the contents of each of which are herein incorporated by reference in their entirety.

Fibrosis

In some embodiments, antibodies and/or compositions of the present disclosure may be useful for altering fibrosis. In some embodiments, such antibodies and/or compositions are antagonists of TGFβ (e.g., TGFβ1). TGFβ1 is recognized as the central orchestrator of the fibrotic response. Antibodies targeting TGFβ1 decrease fibrosis in numerous preclinical models. Such antibodies and/or antibody-based compounds include LY2382770 (Eli Lilly, Indianapolis, Ind.). Also included are those described in U.S. Pat. Nos. 6,492,497, 7,151,169, 7,723,486 and U.S. Appl. Publ. No. 2011/0008364, the contents of each of which are herein incorporated by reference in their entirety.

Fibrotic indications for which antibodies and/or compositions of the present disclosure may be used therapeutically include, but are not limited to lung indications (e.g. idiopathic pulmonary fibrosis (IPF), chronic obstructive pulmonary disorder (COPD), allergic asthma, acute lung injury, eosinophilic esophagitis, pulmonary arterial hypertension and chemical gas-injury), kidney indications (e.g., diabetic glomerulosclerosis, focal segmental glomeruloclerosis (FSGS), chronic kidney disease, fibrosis associated with kidney transplantation and chronic rejection, IgA nephropathy, and hemolytic uremic syndrome), liver fibrosis (e.g., non-alcoholic steatohepatitis (NASH), chronic viral hepatitis, parasitemia, inborn errors of metabolism, toxin-mediated fibrosis, such as alcohol fibrosis, non-alcoholic steatohepatitis-hepatocellular carcinoma (NASH-HCC), primary biliary cirrhosis, and sclerosing cholangitis), cardiovascular fibrosis (e.g., cardiomyopathy, hypertrophic cardiomyopathy, atherosclerosis and restenosis,) systemic sclerosis, skin fibrosis (e.g. skin fibrosis in systemic sclerosis, diffuse cutaneous systemic sclerosis, scleroderma, pathological skin scarring, keloid, post-surgical scarring, scar revision surgery, radiation-induced scarring and chronic wounds) and cancers or secondary fibrosis (e.g. myelofibrosis, head and neck cancer, M7 acute megakaryoblastic leukemia and mucositis). Other diseases, disorders or conditions related to fibrosis that may be treated using compounds and/or compositions of the present disclosure, include, but are not limited to Marfan's syndrome, stiff skin syndrome, scleroderma, rheumatoid arthritis, bone marrow fibrosis, Crohn's disease, ulcerative colitis, systemic lupus erythematosus, muscular dystrophy, (such as DMD), Dupuytren's contracture, Camurati-Engelmann disease, neural scarring, dementia, proliferative vitreoretinopathy, corneal injury, complications after glaucoma drainage surgery, and multiple sclerosis. Many such fibrotic indications are also associated with inflammation of the affected tissue(s), indicating involvement of an immune component.

The antibodies described herein may be used to treat fibrosis. In some embodiments, TGFβ1 isoform-specific agents are administered to a subject in an amount effective to treat the fibrosis. The effective amount of such an antibody is an amount effective to achieve both therapeutic efficacy and clinical safety in the subject. In some embodiments, such an antibody is a context-specific antibody that can block activation of TGFβ1 that is mediated by an LTBP-containing, ECM-associated TGFβ1. In some embodiments, the LTBP is LTBP1 and/or LTBP3. In some embodiments, antibody is a context-permissive antibody that can block activation of an LTBP-mediated TGFβ1 localized in the ECM and GARP-mediated TGFβ1 localized in immune cells. In some embodiments, antibody is a context-permissive antibody that can block activation of an LTBP-mediated TGFβ1 localized in the ECM and LRRC33-mediated TGFβ1 localized in monocytes/macrophages. In some embodiments, the LTBP is LTBP1 and/or LTBP3. In some embodiments, targeting and inhibiting TGFβ1 presented by LRRC33 on profibrotic, M2-like macrophages in the fibrotic microenvironment may be beneficial.

Assays useful in determining the efficacy of the antibodies and/or compositions of the present disclosure for the alteration of fibrosis include, but are not limited to, histological assays for counting fibroblasts and basic immunohistochemical analyses known in the art.

Cancer

Various cancers may be treated with antibodies and/or compositions of the present disclosure. As used herein, the term "cancer" refers to any of various malignant neoplasms characterized by the proliferation of anaplastic cells that tend to invade surrounding tissue and metastasize to new body sites and also refers to the pathological condition characterized by such malignant neoplastic growths. Cancers may be tumors or hematological malignancies, and include but are not limited to, all types of lymphomas/leukemias, carcinomas and sarcomas, such as those cancers or tumors found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus.

In cancer, TGFβ (e.g., TGFβ1) may be either growth promoting or growth inhibitory. As an example, in pancreatic cancers, SMAD4 wild type tumors may experience inhibited growth in response to TGFβ, but as the disease progresses, constitutively activated type II receptor is typically present. Additionally, there are SMAD4-null pancreatic cancers. In some embodiments, antibodies, antigen binding portions thereof, and/or compositions of the present disclosure are designed to selectively target components of TGFβ signaling pathways that function uniquely in one or more forms of cancer. Leukemias, or cancers of the blood or bone marrow that are characterized by an abnormal proliferation of white blood cells, i.e., leukocytes, can be divided into four major classifications including acute lymphoblastic leukemia (ALL), chronic lymphocytic leukemia (CLL), acute myelogenous leukemia or acute myeloid leukemia (AML) (AML with translocations between chromosome 10 and 11 [410, 11)], chromosome 8 and 21 [t(8;21)], chromosome 15 and 17 [t(15;17)], and inversions in chromosome 16 [inv(16)]; AML with multilineage dysplasia, which includes patients who have had a prior myelodysplastic syndrome (MDS) or myeloproliferative disease that transforms into AML; AML and myelodysplastic syndrome (MDS), therapy-related, which category includes patients who have had prior chemotherapy and/or radiation and subsequently develop AML or MDS; d) AML not otherwise categorized, which includes subtypes of AML that do not fall into the above categories; and e) acute leukemias of ambiguous lineage, which occur when the leukemic cells cannot be classified as either myeloid or lymphoid cells, or where both types of cells are present); and chronic myelogenous leukemia (CML).

The types of carcinomas include, but are not limited to, papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma.

The types of sarcomas include, but are not limited to, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

In some embodiments, antibodies and methods of the disclosure may be used to treat one or more types of cancer or cancer-related conditions that may include, but are not limited to colon cancer, renal cancer, breast cancer, malignant melanoma and glioblastomas (Schlingensiepen et al., 2008; Ouhtit et al., 2013).

In some embodiments, the antibodies, or antigen binding portions thereof, that specifically bind a GARP-TGFβ1 complex, a LTBP1-TGFβ1 complex, a LTBP3-TGFβ1 complex, and/or a LRRC33-TGFβ1 complex, as described herein, may be used in methods for treating cancer in a subject in need thereof, said method comprising administering the antibody, or antigen binding portion thereof, to the subject such that the cancer is treated. In certain embodiments, the cancer is colon cancer.

In some embodiments, the antibodies, or antigen binding portions thereof, that specifically bind a GARP-TGFβ1 complex, a LTBP1-TGFβ1 complex, a LTBP3-TGFβ1 complex, and/or a LRRC33-TGFβ1 complex, as described herein, may be used in methods for treating solid tumors. In some embodiments, solid tumors may be desmoplastic tumors, which are typically dense and hard for therapeutic molecules to penetrate. By targeting the ECM component of such tumors, such antibodies may "loosen" the dense tumor tissue to disintegrate, facilitating therapeutic access to exert its anti-cancer effects. Thus, additional therapeutics, such as any known anti-tumor drugs, may be used in combination.

In some embodiments, the antibodies, or antigen binding portions thereof, that specifically bind a GARP-TGFβ1 complex, a LTBP1-TGFβ1 complex, a LTBP3-TGFβ1 complex, and/or a LRRC33-TGFβ1 complex, as described herein, may be used in methods for inhibiting or decreasing solid tumor growth in a subject having a solid tumor, said method comprising administering the antibody, or antigen binding portion thereof, to the subject such that the solid tumor growth is inhibited or decreased. In certain embodiments, the solid tumor is a colon carcinoma tumor. In some embodiments, the antibodies, or antigen binding portions thereof useful for treating a cancer is an isoform-specific, context-permissive inhibitor of TGFβ1 activation. In some embodiments, such antibodies target a GARP-TGFβ1 complex, a LTBP1-TGFβ1 complex, a LTBP3-TGFβ1 complex, and a LRRC33-TGFβ1 complex. In some embodiments, such antibodies target a GARP-TGFβ1 complex, a LTBP1-TGFβ1 complex, and a LTBP3-TGFβ1 complex. In some embodiments, such antibodies target a LTBP1-TGFβ1 complex, a LTBP3-TGFβ1 complex, and a LRRC33-TGFβ1 complex. In some embodiments, such antibodies target a GARP-TGFβ1 complex and a LRRC33-TGFβ1 complex.

In certain embodiments, the antibodies, or antigen binding portions thereof, that specifically bind a GARP-TGFβ1 complex, a LTBP1-TGFβ1 complex, a LTBP3-TGFβ1 complex, and/or a LRRC33-TGFβ1 complex, as described herein, are administered to a subject having cancer or a tumor, either alone or in combination with an additional agent, e.g., an anti-PD-1 antibody (e.g, an anti-PD-1 antagonist). Other combination therapies which are included in the invention are the administration of an antibody, or antigen binding portion thereof, described herein, with radiation, or a chemotherapeutic agent. Exemplary additional agents include, but are not limited to, a PD-1 antagonist, a PDL1 antagonist, a PD-L1 or PDL2 fusion protein, a CTLA4 antagonist, a GITR agonist, an anti-ICOS antibody, an anti-ICOSL antibody, an anti-B7H3 antibody, an anti-B7H4 antibody, an anti-TIM3 antibody, an anti-LAG3 antibody, an anti-OX40 antibody, an anti-CD27 antibody, an anti-CD70 antibody, an anti-CD47 antibody, an anti-41BB antibody, an anti-PD-1 antibody, an oncolytic virus, and a PARP inhibitor.

Role of TGFβ in Skeletal Muscle Conditions

In skeletal muscle TGFβ plays a variety of roles including inhibition of proliferation and differentiation, induction of atrophy, and development of fibrosis. TGFβ reduces satellite cell proliferation and prevents differentiation (via inhibition of MyoD and myogenin) (Allen, R. E. and L. K. J Cell Physiol, 1987. 133(3): p. 567-72; Brennan, T. J., et al., Proc Natl Acad Sci USA, 1991. 88(9): p. 3822-6; Massague, J., et al., Proc Natl Acad Sci USA, 1986. 83(21): p. 8206-10; Olson, E. N., et al., J Cell Biol, 1986. 103(5): p. 1799-805). The isoform of TGFβ (i.e., TGFβ1, 2, or 3) is not specified in these early papers, but is presumed to be TGFβ1. TGFβ also contributes to muscle fibrosis; direct injection of recombinant TGFβ1 results in skeletal muscle fibrosis, and pan-TGFβ inhibition decreases fibrosis in acute and chronically injured muscle (Li, Y., et al., Am J Pathol, 2004. 164(3): p. 1007-19; Mendias, C. L., et al., Muscle Nerve, 2012. 45(1): p. 55-9; Nelson, C. A., et al., Am J Pathol, 2011. 178(6): p. 2611-21). TGFβ1 is expressed by myofibers, macrophages, regulatory T cells, fibroblasts, and fibrocytes within the skeletal muscle (Li, Y., et al., Am J Pathol, 2004. 164(3): p. 1007-19; Lemos, D. R., et al., Nat Med, 2015. 21(7): p. 786-94; Villalta, S. A., et al., Sci Transl Med, 2014. 6(258): p. 258ra142; Wang, X., et al., J Immunol, 2016. 197(12): p. 4750-4761); and expression is increased upon injury and in disease (Li, Y., et al., Am J Pathol, 2004. 164(3): p. 1007-19; Nelson, C. A., et al., Am J Pathol, 2011. 178(6): p. 2611-21; Bernasconi, P., et al., J Clin Invest, 1995. 96(2): p. 1137-44; Ishitobi, M., et al., Neuroreport, 2000. 11(18): p. 4033-5). TGFβ2 and TGFβ3 are also upregulated (at the mRNA level) in mdx muscle, although to a lesser extent than TGFβ1 (Nelson, C. A., et al., Am J Pathol, 2011. 178(6): p. 2611-21; Zhou, L., et al., Neuromuscul Disord, 2006. 16(1): p. 32-8). Pessina, et al., recently used lineage tracing experiments to show that cells of multiple origins within dystrophic muscle adopt a fibrogenic fate via a TGFβ-dependent pathway (Pessina, P., et al., Stem Cell Reports, 2015. 4(6): p. 1046-60).

TGFβ1 has been implicated in human muscular dystrophies. Duchenne muscular dystrophy (DMD) is a severe, progressive, and ultimately fatal disease caused by the absence of dystrophin (Bushby, K., et al., Lancet Neurol, 2010. 9(1): p. 77-93). Lack of dystrophin results in increased susceptibility to contraction-induced injury, leading to continual muscle degeneration (Petrof, B. J., et al., Proc Natl Acad Sci USA, 1993. 90(8): p. 3710-4; Dellorusso, C., et al., J Muscle Res Cell Motil, 2001. 22(5): p. 467-75; Pratt, S. J., et al., Cell Mol Life Sci, 2015. 72(1): p. 153-64). Repeated rounds of repair contribute to chronic inflammation, fibrosis, exhaustion of the satellite cell pool, eventual loss of mobility and death (Bushby, K., et al., Lancet Neurol, 2010. 9(1): p. 77-93; McDonald, C. M., et al., Muscle Nerve, 2013. 48(3): p. 343-56). Expression of TGFβ1 is significantly increased in patients with DMD and correlates with the extent of fibrosis observed in these patients (Bernasconi, P., et al., J Clin Invest, 1995. 96(2): p. 1137-44; Chen, Y. W., et al., Neurology, 2005. 65(6): p. 826-34). Excessive ECM deposition has detrimental effects on the contractile properties of the muscle and can limit access to nutrition as the myofibers are isolated from their blood supply (Klingler, W., et al., Acta Myol, 2012. 31(3): p. 184-95). Recently, additional data has further implicated TGFβ1 in muscular dystrophies. Variants in LTBP4 have been found to modify disease severity in mouse and human. In mouse, a variant of LTBP4 is protective in mice lacking dystrophin or γ-sarcoglycan (Coley, W. D., et al., Hum Mol Genet, 2016. 25(1): p. 130-45; Heydemann, A., et al., J Clin Invest, 2009. 119(12): p. 3703-12). In humans, two groups independently identified a variant of LTBP4 as protective in DMD, delaying loss of ambulation by several years (Flanigan, K. M., et al., Ann Neurol, 2013. 73(4): p. 481-8; van den Bergen, J. C., et al., J Neurol Neurosurg Psychiatry, 2015. 86(10): p. 1060-5). Although the nature of the genetic variants in mouse and human differs, in both species the protective variant results in decreased TGFβ signaling (Heydemann, A., et al., J Clin Invest, 2009. 119(12): p. 3703-12); Ceco, E., et al., Sci Transl Med, 2014. 6(259): p. 259ra144). Many of the functions of TGFβ1 in skeletal muscle biology have been inferred from experiments in which purified active growth factor is injected into animals or added to cells in culture (Massague, J., et al., Proc Natl Acad Sci USA, 1986. 83(21): p. 8206-10; Li, Y., et al., Am J Pathol, 2004. 164(3): p. 1007-19; Mendias, C. L., et al., Muscle Nerve, 2012. 45(1): p. 55-9). Given the importance of cellular context for specific functions of TGFβ1 (see, for example, Hinck et al., Cold Spring Harb. Perspect. Biol, 2016. 8(12)) it is possible that some of the effects observed in these experiments do not reflect the endogenous role(s) of the cytokine in vivo. For example, treatment of human dermal fibroblasts with recombinant TGFβ1, myostatin, or GDF11 results in nearly identical changes in gene expression in these cells, although in vivo the roles of these proteins are quite different (Tanner, J. W., Khalil, A., Hill, J., Franti, M., MacDonnell, S. M., Growth Differentiation Factor 11 Potentiates Myofibroblast Activation, in Fibrosis: From Basic Mechanisms to Targeted therapies. 2016: Keystone, CO).

Multiple investigators have used inhibitors of TGFβ to clarify the role of the growth factor in vivo. Treatment of mdx mice with the pan-TGFβ neutralizing antibody 1D11 clearly results in reduced fibrosis (by histology and hydroxyproline content), reduced muscle damage (reduced serum creatine kinase and greater myofiber density), and improved muscle function (by plethysmography, force generation of isolated EDL muscles, and increased forelimb grip strength) (Nelson, C. A., et al., Am J Pathol, 2011. 178(6): p. 2611-21; Andreetta, F., et al., J Neuroimmunol, 2006. 175(1-2): p. 77-86; Gumucio, J. P., et al., J Appl Physiol (1985), 2013. 115(4): p. 539-45). In addition, myofiber-specific expression of a dominant negative TGFβ type II receptor protects against muscle damage after cardiotoxin injury and in 6-sarcoglycan-/- mice (Accornero, F., et al., Hum Mol Genet, 2014. 23(25): p. 6903-15). The proteoglycan decorin, which is abundant in skeletal muscle and inhibits TGFβ activity, decreases muscle fibrosis in mdx mice and following laceration injury (Li, Y., et al., Mol Ther, 2007. 15(9): p. 1616-22; Gosselin, L. E., et al., Muscle Nerve, 2004. 30(5): p. 645-53). Other molecules with TGFβ inhibitory activity, such as suramin (an anti-neoplastic agent) and losartan (an angiotensin receptor blocker) have been effective in improving muscle pathology and reducing fibrosis in mouse models of injury, Marfan's syndrome, and muscular dystrophy (Spurney, C. F., et al., J Cardiovasc Pharmacol Ther, 2011. 16(1): p. 87-95; Taniguti, A. P., et al., Muscle Nerve, 2011. 43(1): p. 82-7; Bedair, H. S., et al., Am J Sports Med, 2008. 36(8): p. 1548-54; Cohn, R. D., et al., Nat Med, 2007. 13(2): p. 204-10). While all of the therapeutic agents described above do inhibit TGFβ1 or its signaling, none of them is specific for the TGFβ1 isoform. For example, 1D11 binds to and inhibits the TGFβ1, 2, and 3 isoforms (Dasch, J. R., et al., J Immunol, 1989. 142(5): p. 1536-41). Suramin inhibits the ability of multiple growth factors to bind to their receptors, including PDGF, FGF, and EGF, in addition to TGFβ1 (Hosang, M., J Cell Biochem, 1985. 29(3): p. 265-73; Olivier, S., et al., Eur J Cancer, 1990. 26(8): p. 867-71; Scher, H. I. and W. D. Heston, Cancer Treat Res, 1992. 59: p. 131-51). Decorin also inhibits myostatin activity, both by direct binding and through upregulation of follistatin, a myostatin inhibitor (Miura, T., et al., Biochem Biophys Res Commun, 2006. 340(2): p. 675-80; Brandan, E., C. Cabello-Verrugio, and C. Vial, Matrix Biol, 2008. 27(8): p. 700-8; Zhu, J., et al., J Biol Chem, 2007. 282(35): p. 25852-63). Losartan affects additional signaling pathways through its effects on the renin-angiotensin-aldosterone system, including the IGF-1/AKT/mTOR pathway (Burks, T. N., et al., Sci Transl Med, 2011. 3(82): p. 82ra37; Sabharwal, R. and M. W. Chapleau, Exp Physiol, 2014. 99(4): p. 627-31; McIntyre, M., et al., Pharmacol Ther, 1997. 74(2): p. 181-94). Therefore, all of these therapies inhibit additional molecules which may contribute to their therapeutic effects, as well as toxicities.

Considering the postulated role of TGFβ in muscle homeostasis, repair, and regeneration, agents, such as monoclonal antibodies described herein, that selectively modulate TGFβ1 signaling may be effective for treating damaged muscle fibers, such as in chronic/genetic muscular dystrophies and acute muscle injuries, without the toxicities associated with more broadly-acting TGFβ inhibitors developed to date.

Accordingly, the present invention provides methods for treating damaged muscle fibers using an agent that preferentially modulates a subset, but not all, of TGFβ effects in vivo. Such agents can selectively modulate TGFβ1 signaling ("isoform-specific modulation"). In some embodiments, such agents can further selectively modulate TGFβ1 in a particular context ("context-specific modulation").

Muscle Fiber Repair in Chronic Muscular Diseases

The invention encompasses methods to improve muscle quality and function in DMD patients, by limiting fibrosis and contributing to a normalization of muscle morphology and function. As TGFβ1 also inhibits myogenesis, TGFβ1 blockade may promote regeneration in dystrophic muscle, adding further therapeutic benefit. TGFβ1 inhibitors may be used in combination with dystrophin upregulating therapies, such as Exondys 51 (Eteplirsen). Given the potential therapeutic benefits of TGFβ1 inhibition in muscular dystrophy, it is critical to (1) differentiate the role(s) of TGFβ1 from those of TGFβ2 and TGFβ3, and (2) clarify in which molecular context(s) TGFβ1 inhibition would be most beneficial. As mentioned above, pan-TGFβ inhibitors have been associated with significant toxicities, limiting the clinical use of these compounds (Anderton, M. J., et al., Toxicol Pathol, 2011. 39(6): p. 916-24; Stauber, A., et al., Clinical Toxicology, 2014. 4(3): p. 1-10). It is unclear which of the TGFβ isoform(s) causes these toxicities. Some of the described toxicities may be due to TGFβ1 inhibition in the immune system. For example, while 1D11 significantly reduced levels of fibrosis in the diaphragm, treatment also increased numbers of CD4+ and CD8+ T cells in the muscle, suggesting an increased inflammatory response upon pan-TGFβ inhibition which could be detrimental with long-term treatment (Andreetta, F., et al., J Neuroimmunol, 2006. 175(1-2): p. 77-86). Indeed, depletion of T cells from muscle improves the muscle pathology of mdx mice, suggesting T-cell mediated inflammatory responses are detrimental to dystrophic muscle (Spencer, M. J., et al., Clin Immunol, 2001. 98(2): p. 235-43). Increases in T cell numbers upon 1D11 administration are likely due to the effects of TGFβ1 on regulatory T (Treg) cells. Tregs present TGFβ1 on their cell surface via GARP, and release of TGFβ1 from this complex enhances Treg suppressive activity, thus limiting T cell mediated inflammation (Wang, R., et al., Mol Biol Cell, 2012. 23(6): p. 1129-39; Edwards, J. P., A. M. Thornton, and E. M. Shevach, J Immunol, 2014. 193(6): p. 2843-9; Nakamura, K., et al., J Immunol, 2004. 172(2): p. 834-42; Nakamura, K., A. Kitani, and W. Strober, J Exp Med, 2001. 194(5): p. 629-44). Indeed, depletion of Tregs using the PC61 antibody resulted in increased inflammation and muscle damage in the diaphragm of mdx mice, while augmentation of Treg numbers and activity reduced muscle damage (Villalta, S. A., et al., Sci Transl Med, 2014. 6(258): p. 258ra142). Interestingly, an additional population of immunosuppressive T cells, Tr1 cells, has recently been identified. These cells produce large amounts of TGFβ3, which is required for their suppressive activity (Gagliani, N., et al., Nat Med, 2013. 19(6): p. 739-46; Okamura, T., et al., Proc Natl Acad Sci USA, 2009. 106(33): p. 13974-9; Okamura, T., et al., Nat Commun, 2015. 6: p. 6329). While the role of Tr1 cells in skeletal muscle is unknown, the possibility exists that inhibition of both TGFβ1 and TGFβ3 by 1D11 could have additive pro-inflammatory effects by inhibiting both Tregs and Tr1 cells.

Figure 11C:
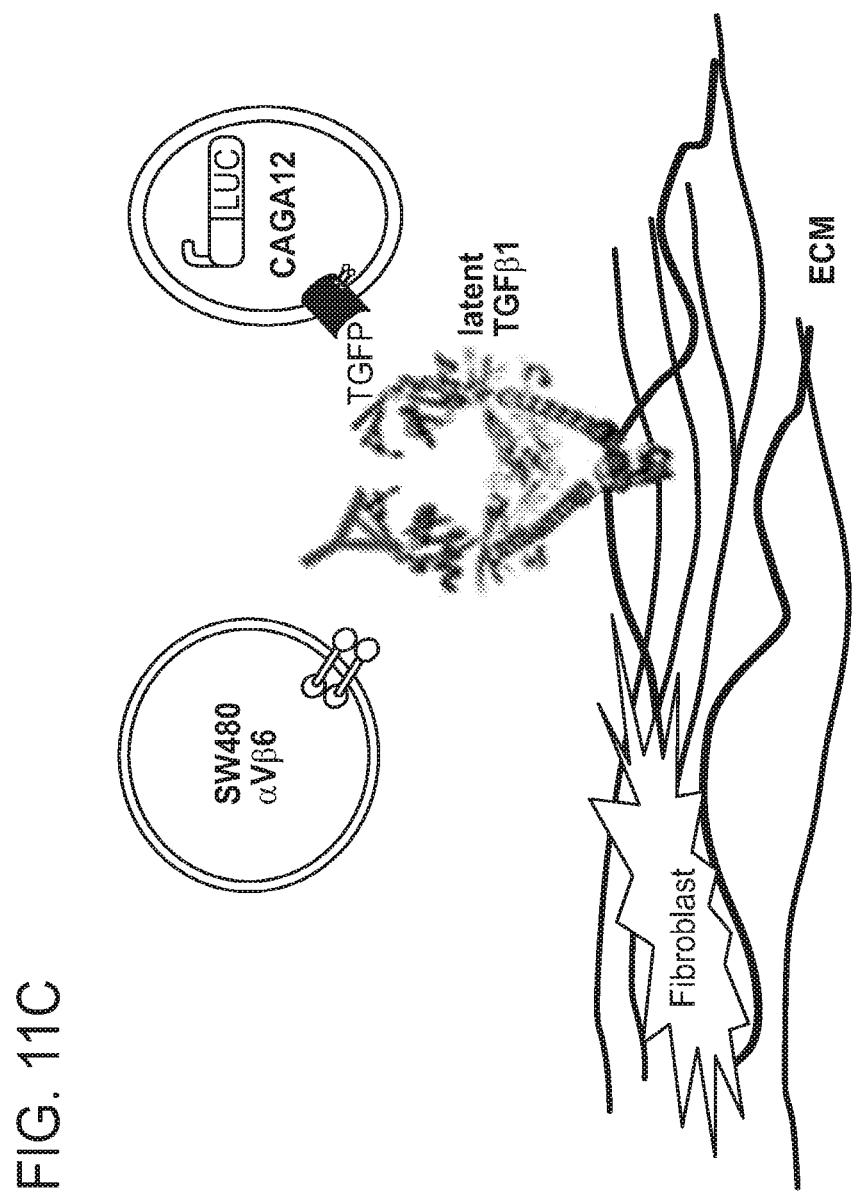
Figure 16:
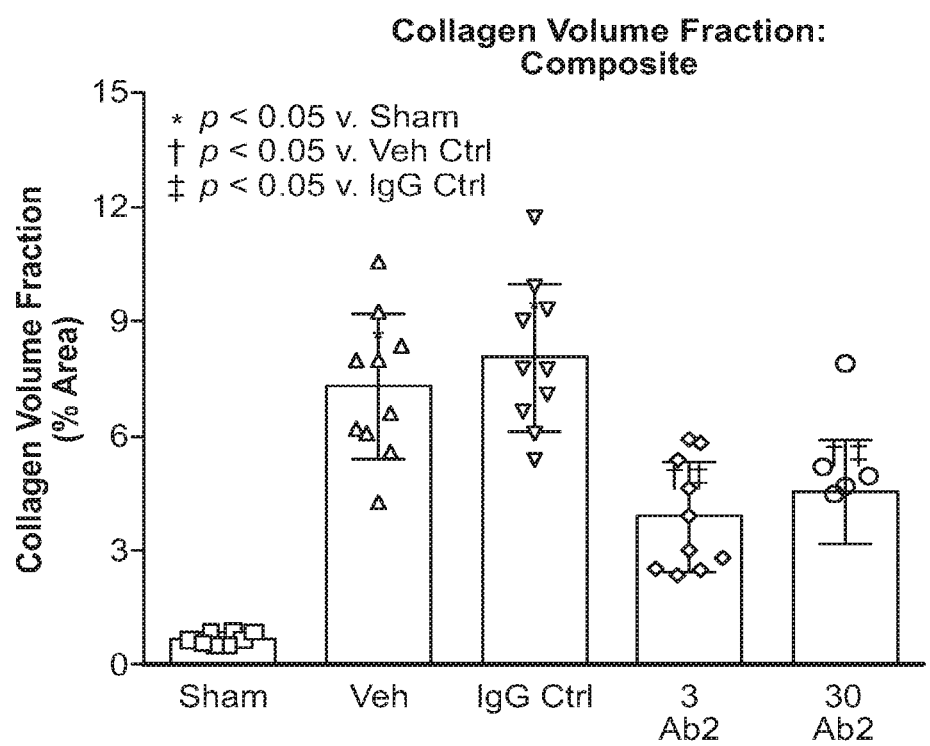
FIG. 16 depicts the composite cortical collagen volume fraction (CVF) from three serial sections of the harvested right kidney from mice that were stained with picrosirius red and subjected to quantitative histological analyses using color spectrum segmentation. CVF from mice that underwent permanent right unilateral UUO surgery and were administered either PBS ("Veh"), 30 mg/kg of murine IgG1 control antibody ("IgG Ctrl"), 3 mg/kg of Ab2 ("3 Ab2"), or 30 mg/kg of Ab2 ("30 Ab2") intraperitoneally (i.p.) prior to surgical intervention (second to fifth bars of each graph); or mice that were administered PBS and underwent a laparotomy ("Sham"; first bar of each graph).
Figure 18A:
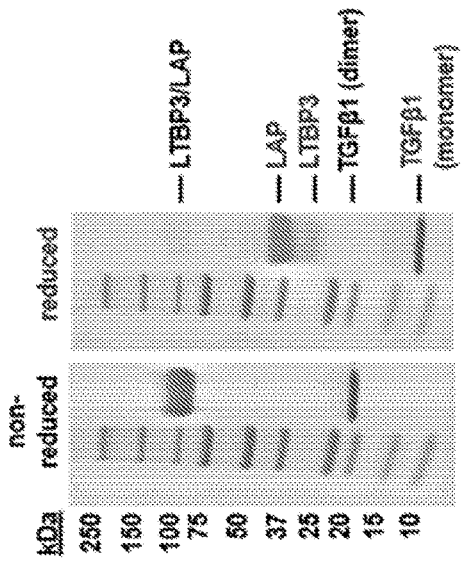
FIG. 18A-18C show binding specificity of exemplary monoclonal antibodies.

The structural insights described above regarding TGFβ1 latency and activation allow for novel approaches to drugs discovery that specifically target activation of TGFβ1 (Shi, M., et al., Nature, 2011. 474(7351): p. 343-9). The high degree of sequence identity shared between the three mature TGFβ growth factors is not shared by the latent complexes, allowing for the discovery of antibodies that are exquisitely specific to proTGFβ1. Using proprietary approaches to antibody discovery, the instant inventors have identified antibodies (Ab1 and Ab2) which specifically bind to proTGFβ1 (FIG. 18A). Using an in vitro co-culture system these antibodies were demonstrated to inhibit integrin-mediated release of TGFβ1. In this system, fibroblasts derived from human skin or mouse skeletal muscles are the source of latent TGFβ1, a cell line expressing aVf3.6 allows for release of active TGFβ1, which is then measured using a third cell line expressing a SMAD2/3 responsive luciferase reporter (FIGS. 11A-C). One of these antibodies, Ab1, has been tested in vivo and shown efficacy in the UUO (unilateral ureteral obstruction) mouse model of kidney fibrosis. In this model, treatment of mice (n=10) with 9 mg/kg/week Ab1 prevented upregulation of TGFβ1-responsive genes (FIG. 15) and reduced the extent of fibrosis following injury (by picrosirius red staining) (FIG. 16). TGFβ1 specific therapies may have improved efficacy and safety profiles compared to pan-TGFβ inhibitors, a critical aspect for a therapeutic which would be used long term as in the DMD population. TGFβ1 inhibitory antibodies can be used to determine if specific TGFβ1 inhibition has potential as a therapeutic for DMD or other muscle diseases, and to clarify the role of TGFβ1 in skeletal muscle regeneration.

Chronic Vs. Acute Myofiber Injuries and Selection of Optimal Therapeutics

In normal, but regenerating muscle following an acute injury (such as traumatic injury to otherwise healthy muscles or motor neurons), it is believed that the initial infiltration of inflammatory macrophages is required to clear out the damaged tissue and to secrete factors (e.g., cytokines) necessary for satellite cell activation. Subsequently, these cells switch to the M2 phenotype to drive wound resolution.

By contrast, in chronic conditions, such as diseases including DMD, the pro-inflammatory macrophages predominated at all time, and that switch to M2 does not happen (or at least not efficiently enough), and the pro-inflammatory macrophages continue to drive inflammation and muscle damage. In DMD, the NFkB pathway is perpetually active, resulting in constitutive inflammation. In some embodiments, therefore, an NFkB inhibitor may be administered to DMD patients in order to reduce the chronic inflammation.

Thus, in chronic conditions such as DMD, therapeutic focus may be on muscle repair as opposed to muscle regeneration. This is because DMD muscle fibers are defective but not destroyed they are damaged by tears in the membrane, dysregulation of calcium transients, and ROS damage from the macrophages. In comparison, in cases of injuries to healthy muscles, therapeutic focus may be on regeneration. For example, in cardiotoxin models, muscle fibers are killed and have to be regenerated. This simulates the process of recovery after a traumatic injury, such as crush injury.

Evidence suggests that LRRC33 is expressed in thioglycollate-induced peritoneal macrophages, which have an M2-like phenotype (characterized in that they express high levels of Arginase, no iNOS, and high levels of CD206).

In situations where LRRC33 is expressed primarily on the M2 cells and where its presentation of TGFβ1 ("context") is important for the pro-wound healing effects of these cells, it may be beneficial to activate LRRC33-mediated TGFβ1 to promote repair and/or myogenesis. On the other hand, in situations where LRRC33 is also expressed on the pro-inflammatory M1 cells, then it may be beneficial to inhibit LRRC33-mediated TGFβ1, given that inflammation drives the fibrosis, especially in the dystrophic setting, such as DMD. Thus, identifying the source/context of disease-associated TGFβ1 can be an important step in selecting the right modulator of the TGFβ signaling, which will inform what level of selectivity should be considered (e.g., isoform-specific, context-permissive TGFβ1 modulators, or, context-specific TGFβ1 modulators; TGFβ1 inhibitors or activators, etc.).

Apart from chronic inflammation, the hallmark of DMD is excessive, and progressive, fibrosis. In advanced disease the fibrosis is so severe that it can actually isolate individual muscle fibers from their blood supply. It also alters the contractile properties of the muscle. In human patients, there is a strong correlation between the extent of TGFβ1 upregulation and fibrosis, and a strong link between the extent of fibrosis and negative mobility outcomes. Therefore, in some embodiments, LTBP-proTGFβ1 inhibitors may be administered to dystrophic patients for the prevention and/or reduction of fibrosis to selectively target the ECM-associated TGFβ1 effects in the disease. In some embodiments, various isoform- and/or context-selective agents described herein can be employed to achieve inhibition of TGFβ1 signaling to prevent fibrosis and promote myogenesis, but without having unwanted effects on the immune system (e.g., through GARP or LRRC33).

Treatments

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, antibodies, or antigen binding portions thereof, that specifically bind a GARP-TGFβ1 complex, a LTBP1-TGFβ1 complex, a LTBP3-TGFβ1 complex, and/or a LRRC33-TGFβ1 complex can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a TGFβ-related indication, such as those noted above. A subject having a TGFβ-related indication can be identified by routine medical examination, e.g., laboratory tests, organ functional tests, CT scans, or ultrasounds. A subject suspected of having any of such indication might show one or more symptoms of the indication. A subject at risk for the indication can be a subject having one or more of the risk factors for that indication.

As used herein, the terms "effective amount" and "effective dose" refer to any amount or dose of a compound or composition that is sufficient to fulfill its intended purpose(s), i.e., a desired biological or medicinal response in a tissue or subject at an acceptable benefit/risk ratio. For example, in certain embodiments of the present invention, the intended purpose may be to inhibit TGFβ-1 activation in vivo, to achieve clinically meaningful outcome associated with the TGFβ-1 inhibition. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a TGFβ-related indication. Alternatively, sustained continuous release formulations of an antibody that specifically binds a GARP-TGFβ1 complex, a LTBP1-TGFβ1 complex, a LTBP3-TGFβ1 complex, and/or a LRRC33-TGFβ1 complex may be appropriate. Various formulations and devices for achieving sustained release would be apparent to the skilled artisan and are within the scope of this disclosure.

In one example, dosages for an antibody that specifically binds a GARP-TGFβ1 complex, a LTBP1-TGFβ1 complex, a LTBP3-TGFβ1 complex, and/or a LRRC33-TGFβ1 complex as described herein may be determined empirically in individuals who have been given one or more administration(s) of the antibody. Individuals are given incremental dosages of the antagonist. To assess efficacy, an indicator of the TGFβ-related indication can be followed. For example, methods for measuring for myofiber damage, myofiber repair, inflammation levels in muscle, and/or fibrosis levels in muscle are well known to one of ordinary skill in the art.

The present invention encompasses the recognition that agents capable of modulating the activation step of TGFβs in an isoform-specific manner may provide improved safety profiles when used as a medicament. Accordingly, the invention includes antibodies and antigen-binding fragments thereof that specifically bind and inhibit activation of TGFβ1, but not TGFβ2 or TGFβ3, thereby conferring specific inhibition of the TGFβ1 signaling in vivo while minimizing unwanted side effects from affecting TGFβ2 and/or TGFβ3 signaling.

In some embodiments, the antibodies, or antigen binding portions thereof, as described herein, are not toxic when administered to a subject. In some embodiments, the antibodies, or antigen binding portions thereof, as described herein, exhibit reduced toxicity when administered to a subject as compared to an antibody that specifically binds to both TGFβ1 and TGFβ2. In some embodiments, the antibodies, or antigen binding portions thereof, as described herein, exhibit reduced toxicity when administered to a subject as compared to an antibody that specifically binds to both TGFβ1 and TGFβ3. In some embodiments, the antibodies, or antigen binding portions thereof, as described herein, exhibit reduced toxicity when administered to a subject as compared to an antibody that specifically binds to TGFβ1, TGFβ2 and TGFβ3.

Generally, for administration of any of the antibodies described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a TGFβ-related indication, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. Pharmacokinetics experiments have shown that the serum concentration of an antibody disclosed herein (e.g., Ab2) remains stable for at least 7 days after administration to a preclinical animal model (e.g., a mouse model). Without wishing to be bound by any particular theory, this stability post-administration may be advantageous since the antibody may be administered less frequently while maintaining a clinically effective serum concentration in the subject to whom the antibody is administered (e.g., a human subject). In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. The particular dosage regimen, e.g., dose, timing and repetition, will depend on the particular individual and that individual's medical history, as well as the properties of the individual agents (such as the half-life of the agent, and other relevant considerations).

For the purpose of the present disclosure, the appropriate dosage of an antibody that specifically binds a GARP-TGFβ1 complex, a LTBP1-TGFβ1 complex, a LTBP3-TGFβ1 complex, and/or a LRRC33-TGFβ1 complex will depend on the specific antibody (or compositions thereof) employed, the type and severity of the indication, whether the antibody is administered for preventive or therapeutic purposes, previous therapy, the patient's clinical history and response to the antagonist, and the discretion of the attending physician. In some embodiments, a clinician will administer an antibody that specifically binds a GARP-TGFβ1 complex, a LTBP1-TGFβ1 complex, a LTBP3-TGFβ1 complex, and/or a LRRC33-TGFβ1 complex, until a dosage is reached that achieves the desired result. Administration of an antibody that specifically binds a GARP-TGFβ1 complex, a LTBP1-TGFβ1 complex, a LTBP3-TGFβ1 complex, and/or a LRRC33-TGFβ1 complex can be continuous or intermittent, depending, for example, upon the recipient's physiological condition, whether the purpose of the administration is therapeutic or prophylactic, and other factors known to skilled practitioners. The administration of antibody that specifically binds a GARP-TGFβ1 complex, a LTBP1-TGFβ1 complex, a LTBP3-TGFβ1 complex, and/or a LRRC33-TGFβ1 complex may be essentially continuous over a preselected period of time or may be in a series of spaced dose, e.g., either before, during, or after developing a TGFβ-related indication.

As used herein, the term "treating" refers to the application or administration of a composition including one or more active agents to a subject, who has a TGFβ-related indication, a symptom of the indication, or a predisposition toward the indication, with the purpose to cure, heal, alleviate, relieve, alter, remedy, ameliorate, improve, or affect the indication, the symptom of the indication, or the predisposition toward the indication.

Alleviating a TGFβ-related indication with an antibody that specifically binds a GARP-TGFβ1 complex, a LTBP1-TGFβ1 complex, a LTBP3-TGFβ1 complex, and/or a LRRC33-TGFβ1 complex includes delaying the development or progression of the indication, or reducing indication's severity. Alleviating the indication does not necessarily require curative results. As used therein, "delaying" the development of an indication associated with a TGFβ-related indication means to defer, hinder, slow, retard, stabilize, and/or postpone progression of the indication. This delay can be of varying lengths of time, depending on the history of the indication and/or individuals being treated. A method that "delays" or alleviates the development of an indication, or delays the onset of the indication, is a method that reduces probability of developing one or more symptoms of the indication in a given time frame and/or reduces extent of the symptoms in a given time frame, when compared to not using the method. Such comparisons are typically based on clinical studies, using a number of subjects sufficient to give a statistically significant result.

DBA2/J mice have a 40 bp deletion in the LTBP4 allele. Dysregulation of the ECM to which latent TGFb1 is associated may expose the epitope to which Ab1 binds. There may be diseases in which the epitope to which Ab1 binds gets exposed, and those diseases may be therapeutic opportunities for Ab1 if TGFb1 inhibition is indicated.

Combination Therapies

The disclosure further encompasses pharmaceutical compositions and related methods used as combination therapies for treating subjects who may benefit from TGFβ inhibition in vivo. In any of these embodiments, such subjects may receive combination therapies that include a first composition comprising at least one TGFβ inhibitor, e.g., antibody or antigen-binding portion thereof, described herein, in conjunction with a second composition comprising at least one additional therapeutic intended to treat the same or overlapping disease or clinical condition. The first and second compositions may both act on the same cellular target, or discrete cellular targets. In some embodiments, the first and second compositions may treat or alleviate the same or overlapping set of symptoms or aspects of a disease or clinical condition. In some embodiments, the first and second compositions may treat or alleviate a separate set of symptoms or aspects of a disease or clinical condition. To give but one example, the first composition may treat a disease or condition associated with TGFβ signaling, while the second composition may treat inflammation or fibrosis associated with the same disease, etc. Such combination therapies may be administered in conjunction with each other. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies.

In preferred embodiments, combination therapies produce synergistic effects in the treatment of a disease. The term "synergistic" refers to effects that are greater than additive effects (e.g., greater efficacy) of each monotherapy in aggregate.

In some embodiments, combination therapies comprising a pharmaceutical composition described herein produce efficacy that is overall equivalent to that produced by another therapy (such as monotherapy of a second agent) but are associated with fewer unwanted adverse effect or less severe toxicity associated with the second agent, as compared to the monotherapy of the second agent. In some embodiments, such combination therapies allow lower dosage of the second agent but maintain overall efficacy. Such combination therapies may be particularly suitable for patient populations where a long-term treatment is warranted and/or involving pediatric patients.

Accordingly, the invention provides pharmaceutical compositions and methods for use in combination therapies for the reduction of TGFβ1 protein activation and the treatment or prevention of diseases or conditions associated with TGFβ1 signaling, as described herein. Accordingly, the methods or the pharmaceutical compositions further comprise a second therapy. In some embodiments, the second therapy may be useful in treating or preventing diseases or conditions associated with TGFβ1 signaling. The second therapy may diminish or treat at least one symptom(s) associated with the targeted disease. The first and second therapies may exert their biological effects by similar or unrelated mechanisms of action; or either one or both of the first and second therapies may exert their biological effects by a multiplicity of mechanisms of action.

It should be understood that the pharmaceutical compositions described herein may have the first and second therapies in the same pharmaceutically acceptable carrier or in a different pharmaceutically acceptable carrier for each described embodiment. It further should be understood that the first and second therapies may be administered simultaneously or sequentially within described embodiments.

The one or more anti-TGFβ antibodies, or antigen binding portions thereof, of the invention may be used in combination with one or more of additional therapeutic agents. Examples of the additional therapeutic agents which can be used with an anti-TGFβ antibody of the invention include, but are not limited to, a myostatin inhibitor, a VEGF agonist, an IGF1 agonist, an FXR agonist, a CCR2 inhibitor, a CCR5 inhibitor, a dual CCR2/CCR5 inhibitor, a lysyl oxidase-like-2 inhibitor, an ASK1 inhibitor, an Acetyl-CoA Carboxylase (ACC) inhibitor, a p38 kinase inhibitor, Pirfenidone, Nintedanib, a GDF11 inhibitor, and the like.

In some embodiments, the additional agent is a checkpoint inhibitor. In some embodiments, the additional agent is selected from the group consisting of a PD-1 antagonist, a PDL1 antagonist, a PD-L1 or PDL2 fusion protein, a CTLA4 antagonist, a GITR agonist, an anti-ICOS antibody, an anti-ICOSL antibody, an anti-B7H3 antibody, an anti-B7H4 antibody, an anti-TIM3 antibody, an anti-LAG3 antibody, an anti-OX40 antibody, an anti-CD27 antibody, an anti-CD70 antibody, an anti-CD47 antibody, an anti-41BB antibody, an anti-PD-1 antibody, an oncolytic virus, and a PARP inhibitor. In some embodiments, the additional therapy is radiation. In some embodiments, the additional agent is a chemotherapeutic agent. In some embodiments, the chemotherapeutic agent is Taxol. In some embodiments, the additional agent is an anti-inflammatory agent. In some embodiments, the additional agent inhibits the process of monocyte/macrophage recruitment and/or tissue infiltration. In some embodiments, the additional agent is an inhibitor of hepatic stellate cell activation. In some embodiments, the additional agent is a chemokine receptor antagonist, e.g., CCR2 antagonists and CCR5 antagonists. In some embodiments, such chemokine receptor antagonist is a dual specific antagonist, such as a CCR2/CCR5 antagonist. In some embodiments, the additional agent to be administered as combination therapy is or comprises a member of the TGFβ superfamily of growth factors or regulators thereof. In some embodiments, such agent is selected from modulators (e.g., inhibitors and activators) of GDF8/myostatin and GDF11. In some embodiments, such agent is an inhibitor of GDF8/myostatin signaling. In some embodiments, such agent is a monoclonal antibody that specifically binds a pro/latent myostatin complex and blocks activation of myostatin. In some embodiments, the monoclonal antibody that specifically binds a pro/latent myostatin complex and blocks activation of myostatin does not bind free, mature myostatin.

Such combination therapies may advantageously utilize lower dosages of the administered therapeutic agents, thus avoiding possible toxicities or complications associated with the various monotherapies.

Modulating TGFβ Activity

Methods of the present disclosure include methods of modulating growth factor activity in one or more biological system. Such methods may include contacting one or more biological system with an antibody and/or composition of the disclosure. In some cases, these methods include modifying the level of free growth factor in a biological system (e.g. in a cell niche or subject). Antibodies and/or compositions according to such methods may include, but are not limited to biomolecules, including, but not limited to recombinant proteins, protein complexes and/or antibodies, or antigen portions thereof, described herein.

In some embodiments, methods of the present disclosure may be used to reduce or eliminate growth factor activity, termed "inhibiting methods" herein. Some such methods may comprise mature growth factor retention in a TGFβ complex (e.g., a TGFβ1 complexed with GARP, LTBP1, LTBP3 and/or LRRC33) and/or promotion of reassociation of growth factor into a TGFβ complex. In some cases, inhibiting methods may comprise the use of an antibody that specifically binds a GARP-TGFβ1 complex, a LTBP1-TGFβ1 complex, a LTBP3-TGFβ1 complex, and/or a LRRC33-TGFβ1 complex. According to some inhibiting methods, one or more inhibiting antibody is provided.

In some embodiments, antibodies, antigen binding portions thereof, and compositions of the disclosure may be used for inhibiting TGFβ1 activation. In some embodiments, provided herein is a method for inhibiting TGFβ1 activation comprising exposing a GARP-TGFβ1 complex, a LTBP1-TGFβ1 complex, a LTBP3-TGFβ1 complex, and/or a LRRC33-TGFβ1 complex to an antibody, an antigen binding portion thereof, or a pharmaceutical composition described herein. In some embodiments, the antibody, antigen binding portion thereof, or pharmaceutical composition, inhibits the release of mature TGFβ1 from the GARP-TGFβ1 complex, the LTBP1-TGFβ1 complex, a LTBP3-TGFβ1 complex, and/or the LRRC33-TGFβ1 complex. In some embodiments, the method is performed in vitro. In some embodiments, the method is performed in vivo. In some embodiments, the method is performed ex vivo.

In some embodiments, the GARP-TGFβ1 complex, the LTBP1-TGFβ1 complex, the LTBP3-TGFβ1 complex, or the LRRC33-TGFβ1 complex is present at the outer surface of a cell. In some embodiments, the cell is a T-cell, a fibroblast, a macrophage, a monocyte, or a microglia.

In some embodiments, the LRRC33-TGFβ1 complex is present at the outer surface of profibrotic (M2-like) macrophages. In some embodiments, the profibrotic (M2-like) macrophages are present in the fibrotic microenvironment. In some embodiments, targeting of the LRRC33-TGFβ1 complex at the outer surface of profibrotic (M2-like) macrophages provides a superior effect as compared to solely targeting LTBP1-TGFβ1 and/or LTBP1-TGFβ1 complexes.

In some embodiments, the GARP-TGFβ1 complex, the LTBP1-TGFβ1 complex, the LTBP3-TGFβ1 complex, and/or the LRRC33-TGFβ1 complex is bound to an extracellular matrix. In some embodiments, the extracellular matrix comprises fibrillin. In some embodiments, the extracellular matrix comprises a protein comprising an RGD motif.

In some embodiments, provided herein is a method for reducing TGFβ1 protein activation in a subject comprising administering an antibody, an antigen binding portion thereof, or a pharmaceutical composition described herein to the subject, thereby reducing TGFβ1 protein activation in the subject. In some embodiments, the subject has or is at risk of having fibrosis. In some embodiments, the subject has or is at risk of having cancer. In some embodiments, the subject has or is at risk of having dementia.

In some embodiments, the antibodies, or the antigen binding portions thereof, as described herein, reduce the suppressive activity of regulatory T cells (Tregs).

Kits for Use in Alleviating Diseases/Disorders Associated with a TGFβ-Related Indication The present disclosure also provides kits for use in alleviating diseases/disorders associated with a TGFβ-related indication. Such kits can include one or more containers comprising an antibody, or antigen binding portion thereof, that specifically binds to a GARP-TGFβ1 complex, a LTBP1-TGFβ1 complex, a LTBP3-TGFβ1 complex, and/or a LRRC33-TGFβ1 complex, e.g., any of those described herein.

In some embodiments, the kit can comprise instructions for use in accordance with any of the methods described herein. The included instructions can comprise a description of administration of the antibody, or antigen binding portion thereof, that specifically binds a GARP-TGFβ1 complex, a LTBP1-TGFβ1 complex, a LTBP3-TGFβ1 complex, and/or a LRRC33-TGFβ1 complex to treat, delay the onset, or alleviate a target disease as those described herein. The kit may further comprise a description of selecting an individual suitable for treatment based on identifying whether that individual has the target disease. In still other embodiments, the instructions comprise a description of administering an antibody, or antigen binding portion thereof, to an individual at risk of the target disease.

The instructions relating to the use of antibodies, or antigen binding portions thereof, that specifically binds a GARP-TGFβ1 complex, a LTBP1-TGFβ1 complex, a LTBP3-TGFβ1 complex, and/or a LRRC33-TGFβ1 complex generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable. The label or package insert indicates that the composition is used for treating, delaying the onset and/or alleviating a disease or disorder associated with a TGFβ-related indication. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an antibody, or antigen binding portion thereof, that specifically binds a GARP-TGFβ1 complex, a LTBP1-TGFβ1 complex, a LTBP3-TGFβ1 complex, and/or a LRRC33-TGFβ1 complex as those described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

Assays for Detecting a GARP-TGFβ1 Complex, a LTBP1-TGFβ1 Complex, a LTBP3-TGFβ1 Complex, and/or a LRRC33-TGFβ1 Complex In some embodiments, methods and compositions provided herein relate to a method for detecting a GARP-TGFβ1 complex, a LTBP1-TGFβ1 complex, a LTBP3-TGFβ1 complex, and/or a LRRC33-TGFβ1 complex in a sample obtained from a subject. As used herein, a "subject" refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, poultry, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is a patient or a healthy volunteer.

In some embodiments, a method for detecting a GARP-TGFβ1 complex, a LTBP1-TGFβ1 complex, a LTBP3-TGFβ1 complex, and/or a LRRC33-TGFβ1 complex in a sample obtained from a subject involves (a) contacting the sample with an antibody that specifically binds a GARP-TGFβ1 complex, a LTBP1-TGFβ1 complex, a LTBP3-TGFβ1 complex, and/or a LRRC33-TGFβ1 complex under conditions suitable for binding of the antibody to the antigen, if the antigen is present in the sample, thereby forming binding complexes; and (b) determining the level of the antibody bound to the antigen (e.g., determining the level of the binding complexes).

In one embodiment, a screening assay that utilizes biotinylated latent TGFβ1 complexes immobilized onto a surface, which allows for the activation of latent TGFβ by integrins by providing tether. Other, non-integrin activators could also be tested in that system. Readout can be through reporter cells or other TGFβ-dependent cellular responses.

Cell-Based Assays for Measuring TGFβ Activation

Figure 22A:
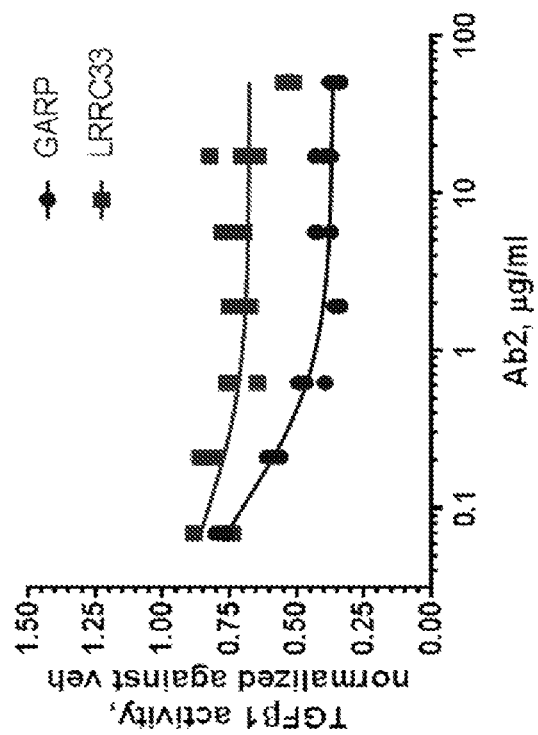
FIGS. 22A and 22B are graphs depicting the inhibition of GARP-proTGFβ1 complex or LRRC33-proTGFβ1 complex in SW480/(36 cells transiently transfectanted with plasmids to express proTGFβ1 and a presenting molecule (i.e., GARP or LRRC33) using increasing concentrations of either Ab1 (FIG. 22A) or Ab2 (FIG. 22B). The IC50 (m/mL) of Ab1 for the GARP-TGFβ1 complex was 0.445, and the IC50 (m/mL) of Ab1 for the LRRC33-TGFβ1 complex was 1.325.
Figure 22B:
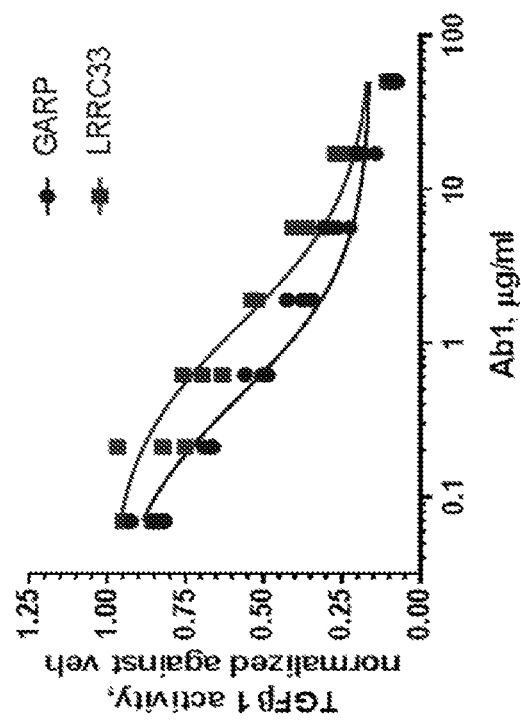

Activation of TGFβ (and inhibition thereof by a TGFβ test inhibitor, such as an antibody) may be measured by any suitable method known in the art. For example, integrin-mediated activation of TGFβ can be utilized in a cell-based assay, such as the "CAGA12" luciferase assay, described in more detail herein. An exemplary embodiment of such assay is depicted in FIG. 11C for illustrative purposes. As shown, such an assay system may comprise the following components: i) a source of TGFβ (recombinant, endogenous or transfected); ii) a source of integrin (recombinant, endogenous, or transfected); and iii) a reporter system that responds to TGFβ activation, such as cells expressing TGFβ receptors capable of responding to TGFβ and translating the signal into a readable output (e.g., luciferase activity in CAGA12 cells or other reporter cell lines). In some embodiments, the reporter cell line comprises a reporter gene (e.g., a luciferase gene) under the control of a TGFβ-responsive promoter (e.g., a PAI-1 promoter). In some embodiments, certain promoter elements that confer sensitivity may be incorporated into the reporter system. In some embodiments, such promoter element is the CAGA12 element. Reporter cell lines that may be used in the assay have been described, for example, in Abe et al. (1994) Anal Biochem. 216(2): 276-84, incorporated herein by reference. In some embodiments, each of the aforementioned assay components are provided from the same source (e.g., the same cell). In some embodiments, two of the aforementioned assay components are provided from the same source, and a third assay component is provided from a different source. In some embodiments, all three assay components are provided from different sources. For example, in some embodiments, the integrin and the latent TGFβ complex (proTGFβ and a presenting molecule) are provided for the assay from the same source (e.g., the same transfected cell line). In some embodiments, the integrin and the TGF are provided for the assay from separate sources (e.g., two different cell lines, a combination of purified integrin and a transfected cell). When cells are used as the source of one or more of the assay components, such components of the assay may be endogenous to the cell, stably expressed in the cell, transiently transfected, or any combination thereof. The results from a non-limiting exemplary embodiment of a cell-based assay for measuring TGFβ activation demonstrating the inhibition of either GARP-proTGFβ1 complex or LRRC33-proTGFβ1 complex using antibodies Ab1 and Ab2, disclosed herein, is shown at FIG. 22A and FIG. 22B, respectively. In this exemplary assay, the IC50 (µg/mL) of Ab1 for the GARP-TGFβ1 complex was 0.445, and the IC50 (µg/mL) of Ab1 for the LRRC33-TGFβ1 complex was 1.325.

A skilled artisan could readily adapt such assays to various suitable configurations. For instance, a variety of sources of TGFβ may be considered. In some embodiments, the source of TGFβ is a cell that expresses and deposits TGFβ (e.g., a primary cell, a propagated cell, an immortalized cell or cell line, etc.). In some embodiments, the source of TGFβ is purified and/or recombinant TGFβ immobilized in the assay system using suitable means. In some embodiments, TGFβ immobilized in the assay system is presented within an extracellular matrix (ECM) composition on the assay plate, with or without de-cellularization, which mimics fibroblast-originated TGFβ. In some embodiments, TGFβ is presented on the cell surface of a cell used in the assay. Additionally, a presenting molecule of choice may be included in the assay system to provide suitable latent-TGFβ complex. One of ordinary skill in the art can readily determine which presenting molecule(s) may be present or expressed in certain cells or cell types. Using such assay systems, relative changes in TGFβ activation in the presence or absence of a test agent (such as an antibody) may be readily measured to evaluate the effects of the test agent on TGFβ activation in vitro. Data from exemplary cell-based assays are provided in the Example section below.

Such cell-based assays may be modified or tailored in a number of ways depending on the TGFβ isoform being studied, the type of latent complex (e.g., presenting molecule), and the like. In some embodiments, a cell known to express integrin capable of activating TGFβ may be used as the source of integrin in the assay. Such cells include SW480/06 cells (e.g., clone 1E7). In some embodiments, integrin-expressing cells may be co-transfected with a plasmid encoding a presenting molecule of interest (such as GARP, LRRC33, LTBP (e.g., LTBP1 or LTBP3), etc.) and a plasmid encoding a pro-form of the TGFβ isoform of interest (such as proTGFβ1). After transfection, the cells are incubated for sufficient time to allow for the expression of the transfected genes (e.g., about 24 hours), cells are washed, and incubated with serial dilutions of a test agent (e.g., an antibody). Then, a reporter cell line (e.g., CAGA12 cells) is added to the assay system, followed by appropriate incubation time to allow TGFβ signaling. After an incubation period (e.g., about 18-20 hours) following the addition of the test agent, signal/read-out (e.g., luciferase activity) is detected using suitable means (e.g., for luciferase-expressing reporter cell lines, the Bright-Glo reagent (Promega) can be used). In some embodiments, Luciferase fluorescence may be detected using a BioTek (Synergy H1) plate reader, with autogain settings.

Nucleic Acids

In some embodiments, antibodies, antigen binding portions thereof, and/or compositions of the present disclosure may be encoded by nucleic acid molecules. Such nucleic acid molecules include, without limitation, DNA molecules, RNA molecules, polynucleotides, oligonucleotides, mRNA molecules, vectors, plasmids and the like. In some embodiments, the present disclosure may comprise cells programmed or generated to express nucleic acid molecules encoding compounds and/or compositions of the present disclosure. In some cases, nucleic acids of the disclosure include codon-optimized nucleic acids. Methods of generating codon-optimized nucleic acids are known in the art and may include, but are not limited to those described in U.S. Pat. Nos. 5,786,464 and 6,114,148, the contents of each of which are herein incorporated by reference in their entirety.

The present invention is further illustrated by the following examples, which are not intended to be limiting in any way. The entire contents of all references, patents and published patent applications cited throughout this application, as well as the Figures, are hereby incorporated herein by reference.

EXAMPLES

Example 1: Inhibition of TGFβ1

The TGFβ superfamily includes propeptides complexed with active growth factors (FIG. 1). Selection strategies to obtain antibodies that stabilize the complex, resulting in more selective and potent inhibition, were developed.

Figure 4A:
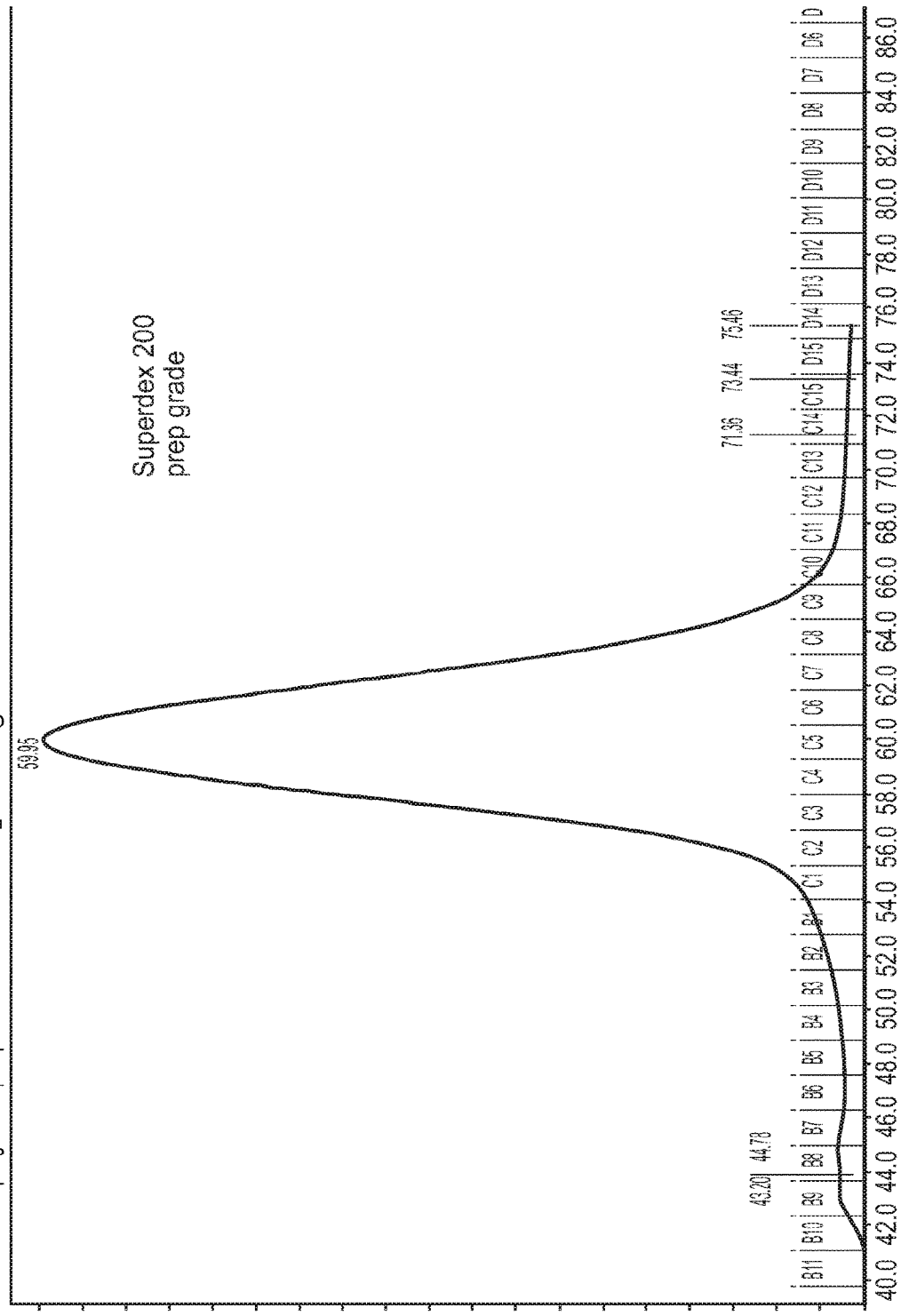
FIGS. 4A and 4B show the purification of the sGARP-proTGFβ1 complex.
Figure 4B:
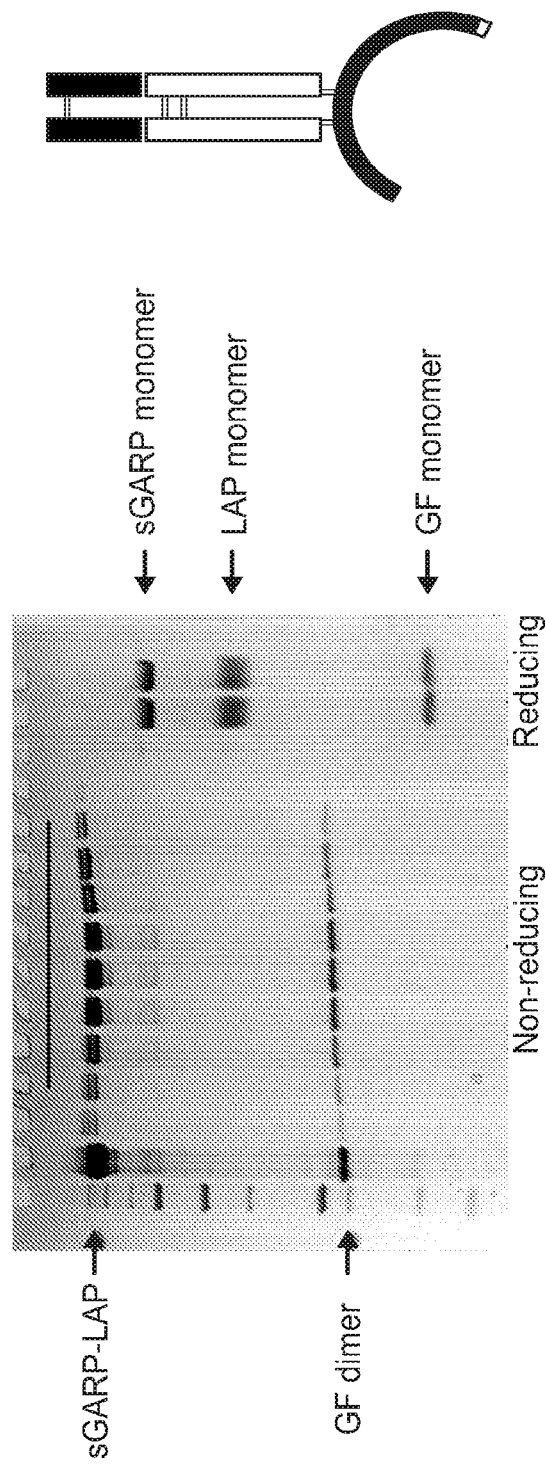
Figure 5B:
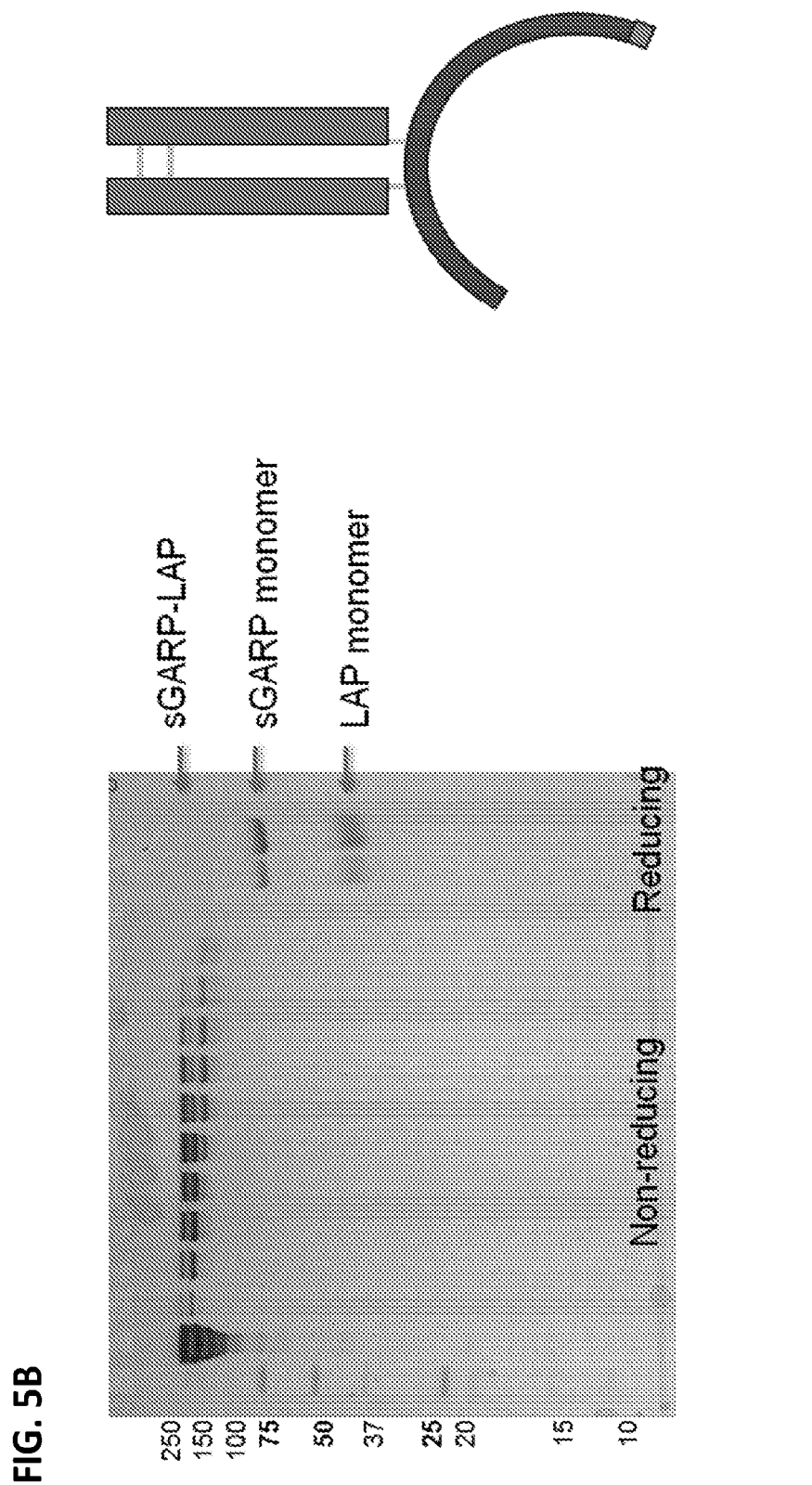
Figure 6A:
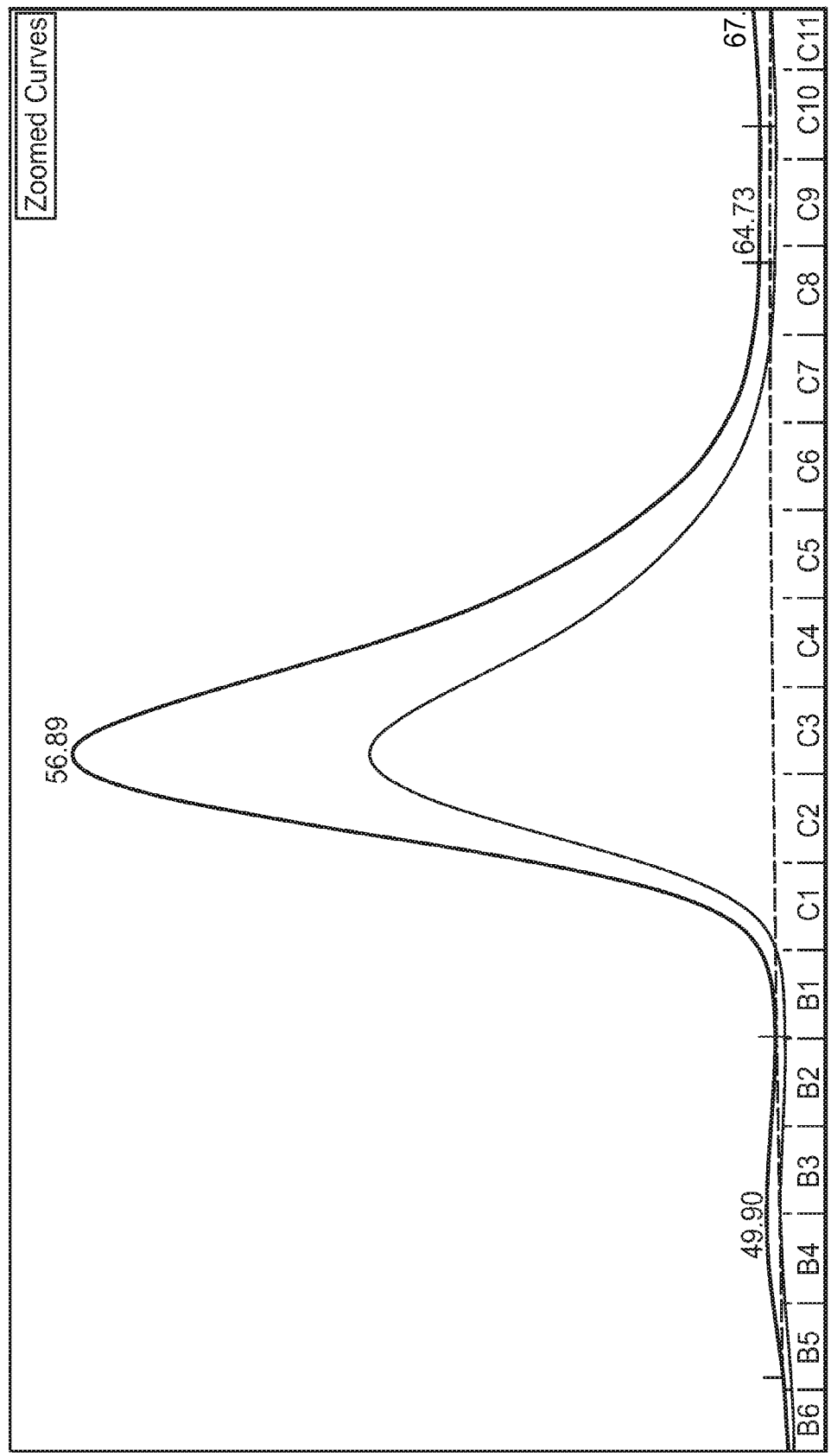
FIGS. 6A and 6B show the purification of the LTBP1 complexed with proTGFβ1.
Figure 6B:
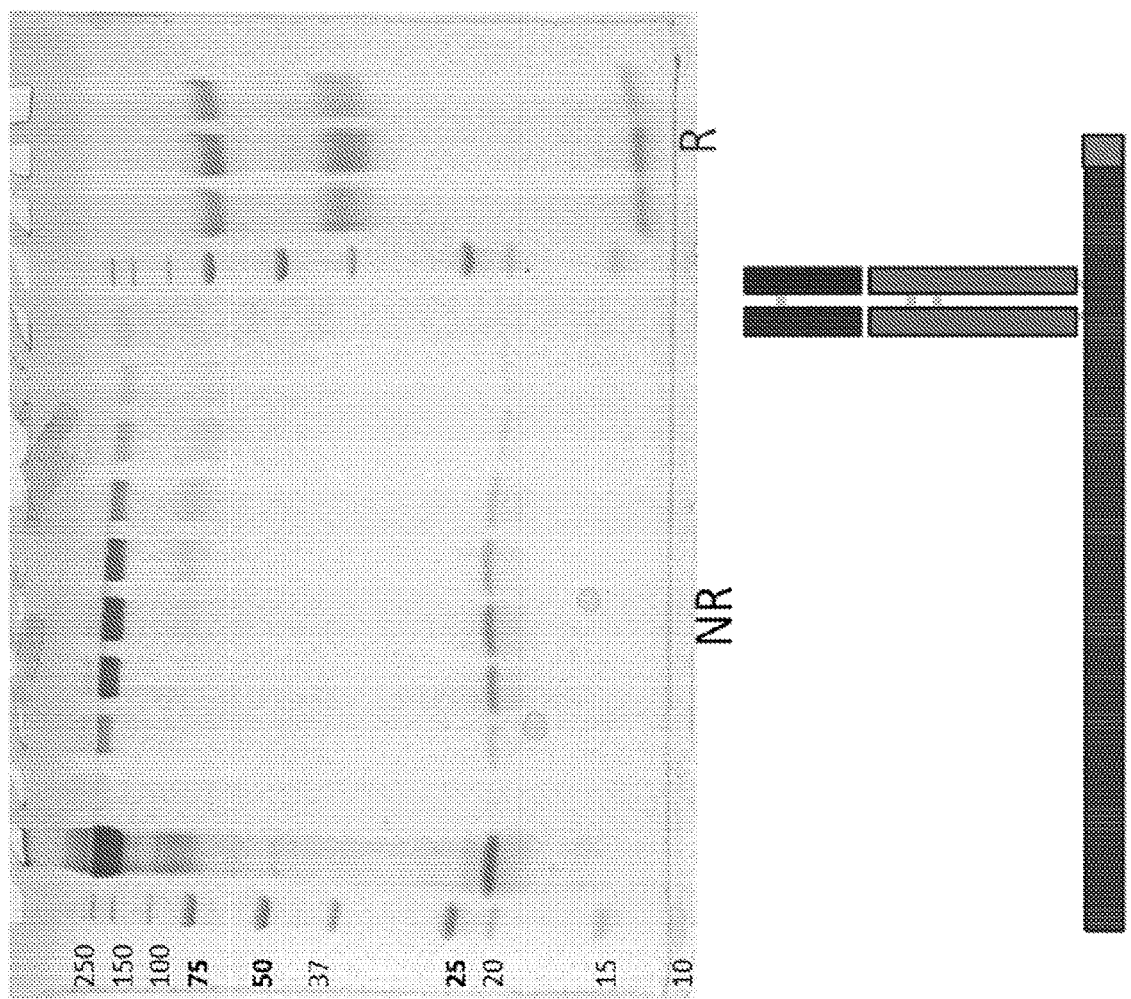

Using a HEK293-based expression system, NiNTA affinity and gel filtration were performed to obtain multimilligram quantities of purified protein, which were used to generate TGFβ1 complexed to LTBP (LTBP-TGFβ1 complex) and TGFβ1 complexed to GARP (GARP-TGFβ1 complex) (FIG. 3). The diversity of proteins manufactured enabled the testing of species cross-reactivity and epitope mapping. The purification of an sGARP-proTGFβ complex (FIGS. 4A and 4B), an sGARP-TGFβ LAP complex (FIG. 5), and a LTBP1-proTGFβ1 complex (FIG. 6) are shown.

Figure 7:
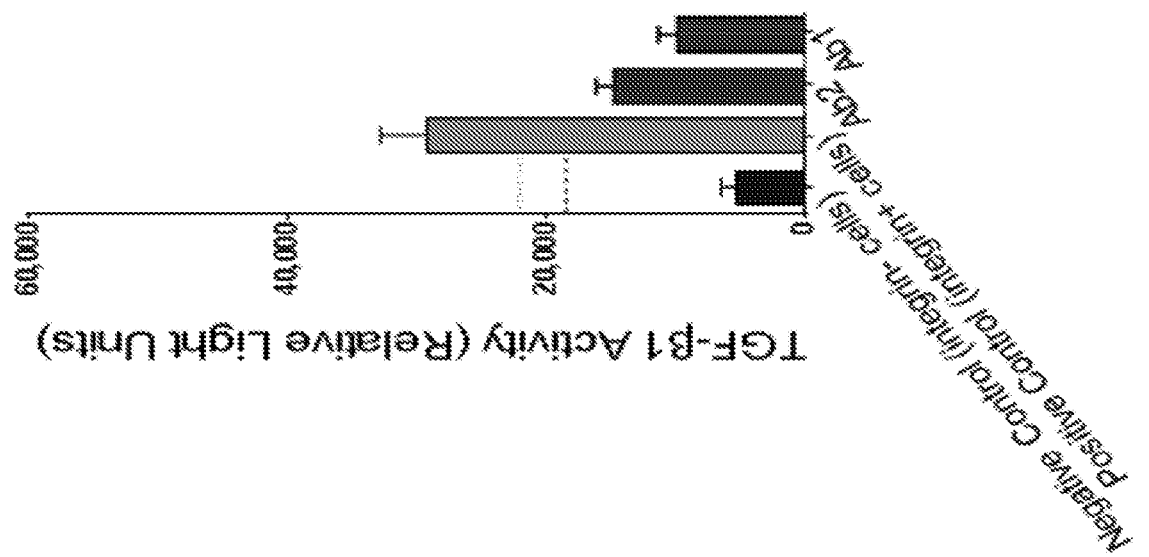
FIG. 7 is a graph showing that Ab1 and Ab2 block activation of TGFβ1 activity.
Figure 8:
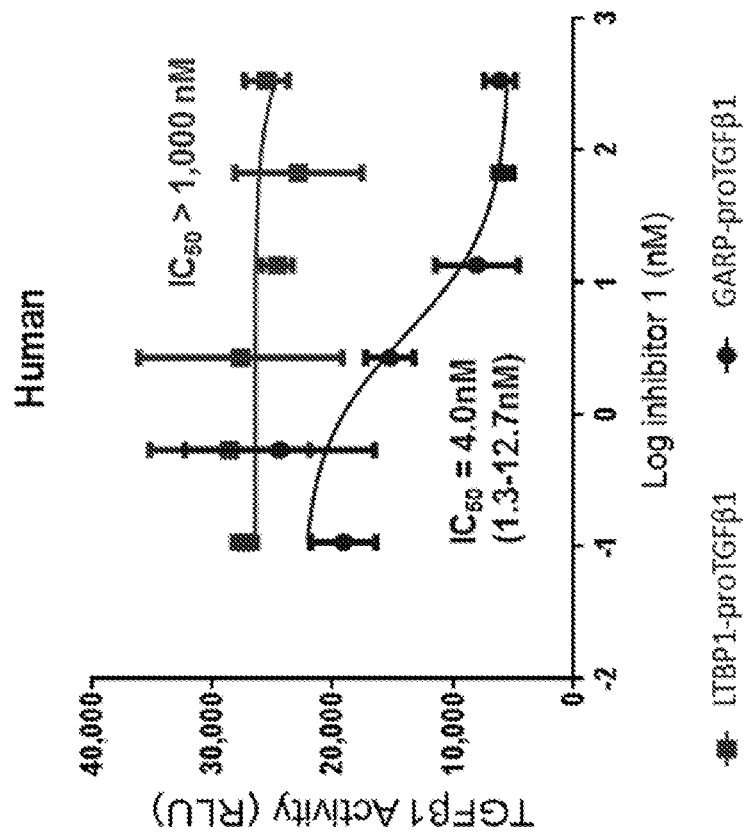
FIG. 8 shows an initial dose-response analysis of Ab1 in human cells.

The candidate antibodies were tested using an in vitro luminescence assays (FIG. 8). In the screen, antibodies that inhibited growth factor release turned reporter cells "off" when faced with a stimulus for normal activation. Ab1 and Ab2 were shown to be inhibitors of activation of latent TGFβ1 complexes (FIG. 7) and were cross-reactive to mouse.

Figure 9:
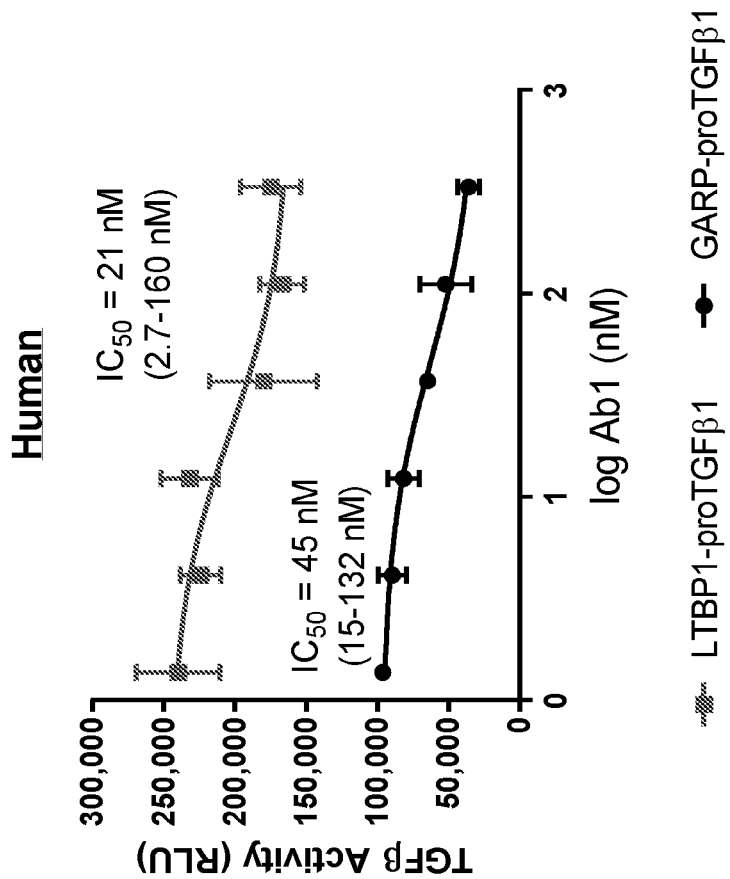
FIG. 9 shows CAGA12 reporter cell assays illustrating TGFβ1 inhibition by Ab1 in human cells.
Figure 10:
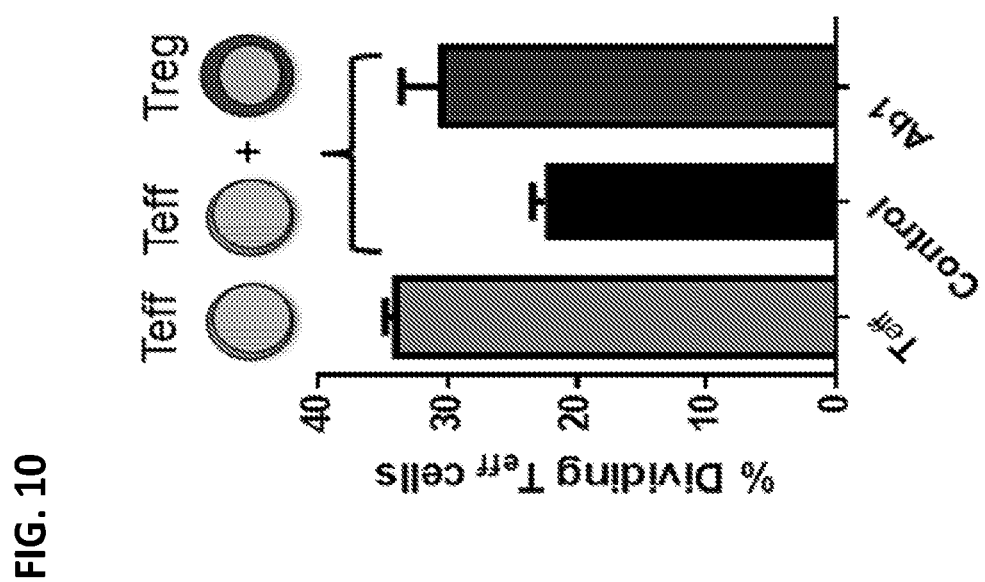
FIG. 10 is a graph showing that inhibition of the GARP complex blocks suppressive activity of T regulatory (Treg) cells in T cells isolated from healthy donor blood.

Initial dose-response analysis curves of Ab1 in cells expressing human TGFβ1 showed TGFβ1 activity inhibition (FIG. 8). Using a more sensitive CAGA12 reporter cell line, Ab1 showed similar inhibition of human proTGFβ1 activity (FIG. 9). Furthermore, the inhibition of a GARP complex was shown to block the suppressive activity of T regulatory cells (Tregs) as measured by the percent of dividing T effector cells (Teff) in T cells isolated from healthy donor blood (FIG. 10).

The affinity of GARP-proTGFβ1 inhibitors was measured by Octet assay on human GARP-proTGFβ1 cells, while activity was measured by CAGA12 reporter cells testing human GARP-proTGFβ1 inhibition. The protocol used to measure the affinity of antibodies Ab1 and Ab2 to the complexes provided herein is summarized in Table 6. The results are shown in Table 7.

TABLE 6

Protocol for performing Octet binding assay.

Materials:
96 well black polypropylene plates
Streptavidin-coated tips for Octet
10x kinetics buffer (diluted 1:10 in PBS)
1. Soak required amount of streptavidin tips in 1X kinetics buffer; place in machine to equilibrate
2. Load sample plate:
    200 μl of buffer or antibody dilution to each well
        a. Column 1 - baseline (buffer)
        b. Column 2 - biotinylated protein (e.g., sGARP-proTGFβ1 or LTBP1-proTGFβ1); diluted to 5 μg/mL
        c. Column 3 - baseline 2 (buffer)
        d. Column 4 - antibody association for Ab1
        e. Column 5 - antibody association for Ab2
        f. Column 6 - dissociation Ab 1 (buffer)
        g. Column 7 - dissociation Ab2 (buffer)
3. Make dilutions in the 96 well plate:
        a. Dilute both antibodies to 50 μg/mL in 300 μl of 1x buffer in row A.
        b. Add 200 μl of buffer to the rest of each column
        c. Transfer 100 μl down the column to make 3-fold dilutions
4. Place the sample plate in the machine next to the tips plate
5. Set up the software
        a. Indicate buffer, load, sample (one assay per antibody tested)
        b. Indicate steps of the protocol (baseline, load, association, dissociation) for set amounts of time:
            Baseline: 60 seconds
            Loading: 300 seconds
            Baseline 2: 60 seconds
            Association: 300 seconds
            Dissociation: 600 seconds
6. Analyze data
        a. Subtract baseline from reference well
        b. Set normalization to last five seconds of baseline
        c. Align to dissociation
        d. Analyze to association and dissociation (1:1 binding model, fit curves)
        e. Determine the best $R^2$ values; include concentrations with best $R^2$ values
        f. Select global fit
        g. Set colors of samples by sensor type
        h. Analyze
        i. Save table and export

TABLE 7

Affinity and Activity of GARP-proTGFβ1 Inhibitors

| Clone | Affinity for GARP-proTGFβ1 (nM ± SEM) | Inhibition (IC50) of GARP-proTGFβ1 (nM; 95% CI) | Max effect (% inhibition) |
| --- | --- | --- | --- |
| Ab1 | 0.046 ± 0.043 | 3.4 (2.1-5.4) | 75% |
| Ab2 | 0.561 ± 0.014 | 3.9 (1.5-10.3) | 50% |

The clones were further screened for binding selectivity (Table 8) and species cross-reactivity (Table 9). Ab1 and Ab2 did not bind to TGFβ1, TGFβ2, or TGFβ3, but did bind the proTGFβ1 complexes and showed species cross-reactivity.

TABLE 8

Selectivity of GARP-proTGFβ1 Inhibitors

| Clone | GARP-proTGFβ1 | LTBP1-proTGFβ1 | LTBP3-proTGFβ1 |
| --- | --- | --- | --- |
| Ab1 | +++ | +++ | +++ |
| Ab2 | +++ | +++ | +++ |

TABLE 9

Species Cross-Reactivity of GARP-proTGFβ1 Inhibitors

| Clone | huGARP-proTGFβ1 | muGARP-proTGFβ1 | cyGARP-proTGFβ1 |
| --- | --- | --- | --- |
| Ab1 | +++ | ++ | +++ |
| Ab2 | +++ | +++ | +++ |

+++ KD < 1 nM,
++ KD 1-10 nM
+ KD 10-100 nM
– No binding

Example 2: Ab1 and Ab2 Specifically Bind to proTGFβ1 Complexes from Multiple Species To determine if Ab1 and Ab2 are capable of specifically binding to proTGFβ1 complexes from multiple species, Octet binding assays were performed as described in Table 6. As shown in Table 10 (below), both antibodies (i.e., Ab1 and Ab2) specifically bound to human and murine LTBP1-proTGFβ1 complexes, human LTBP3-proTGFβ1 complexes, and human GARP-proTGFβ1 complexes. However, only Ab2 specifically bound to rat LTBP1-proTGFβ1 complexes.

TABLE 10

Affinity of Ab1 and Ab2 for proTGFβ1 Complexes from Multiple Species

| | Ab1 ($K_D$) | Ab2 ($K_D$) |
|---|---|---|
| human LTBP1-proTGFβ1 | 16 ± 1.3 | 5.8 ± 0.6 |
| human LTBP3-proTGFβ1 | 85 ± 5.0 | 122 ± 3.9 |
| mouse LTBP1-proTGFβ1 | 203 ± 13 | 61 ± 4.0 |
| rat LTBP1-proTGFβ1 | No binding detected | 38 ± 6.8 |
| human GARP-proTGFβ1 | 293 ± 22 | 58 ± 6.2 |

Example 3: Ab1 and Ab2 Inhibit Endogenous TGFβ1 in Human and Murine Fibroblasts To determine if Ab1 and Ab2 were capable of inhibiting endogenous TGF-β1 secreted by primary cultured fibroblasts of different origin, a quantitative in vitro assay was performed in which the activity of secreted TGF-β1 was determined by measuring luciferase levels produced by mink lung epithelial cells that were stably transfected with a nucleic acid comprising a luciferase reporter gene fused to a CAGA12 synthetic promoter, and co-cultured with fibroblasts treated with either Ab1 or Ab2. As shown in FIGS. 11A and 11B, both Ab1 and Ab2 were inhibited endogenous TGF-β1 secreted by normal human dermal fibroblasts, murine C57BL.6J lung fibroblasts, and DBA2/J muscle fibroblasts. Differences in the maximal inhibition observed with each antibody were cell line-specific.

Example 4: Ab2 Binds to LRRC33-proTGFβ1

Figure 12A:
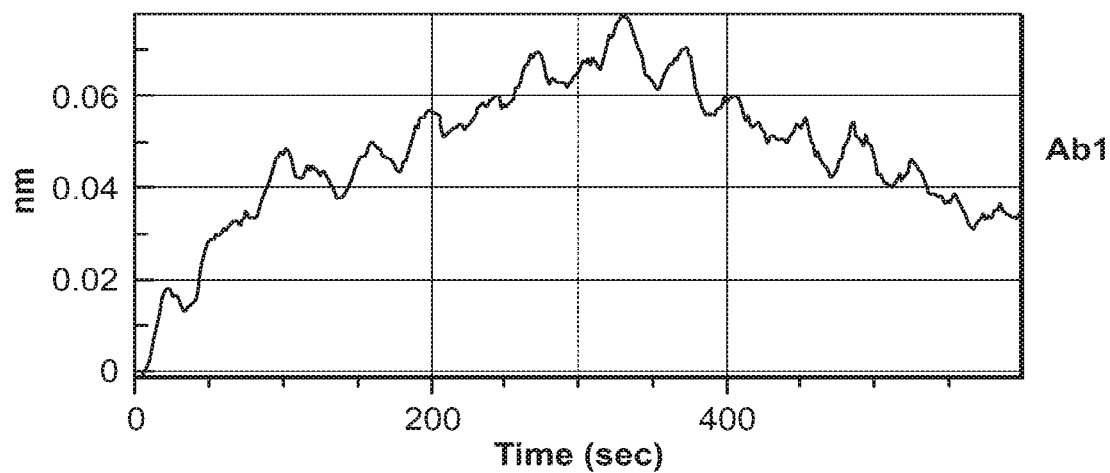
FIGS. 12A and 12B depict the binding of either Ab1 (FIG. 12A) or Ab2 (FIG. 12B) to the LRRC33-proTGFβ1 complex.
Figure 12B:
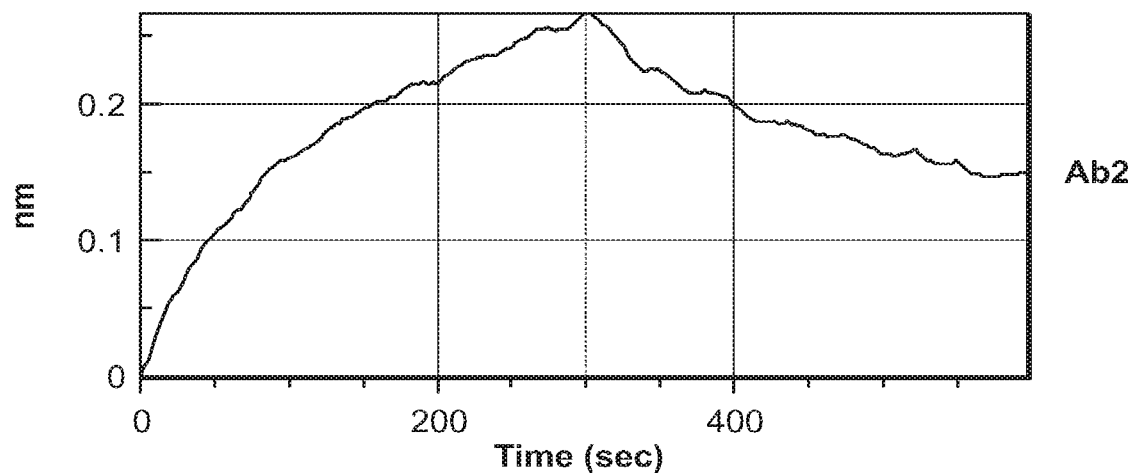

To determine whether Ab1 and Ab2 bind to proTGFβ1 that is complexed with LRRC33, Octet binding assays were performed. As shown in FIGS. 12A and 12B, both Ab1 and Ab2 are capable of binding to the LRRC33-proTGFβ1 protein complex. However, Ab1 shows a slow on-rate for binding the LRRC33-proTGFβ1 protein complex. Binding of Ab1 and Ab2 to the LRRC33-proTGFβ1 protein complex was further confirmed using ELISA.

Example 5: Ab1 and Ab2 Inhibit the Activity of Both GARP-proTGFβ1 and LRRC33-proTGFβ1

Figure 13A:
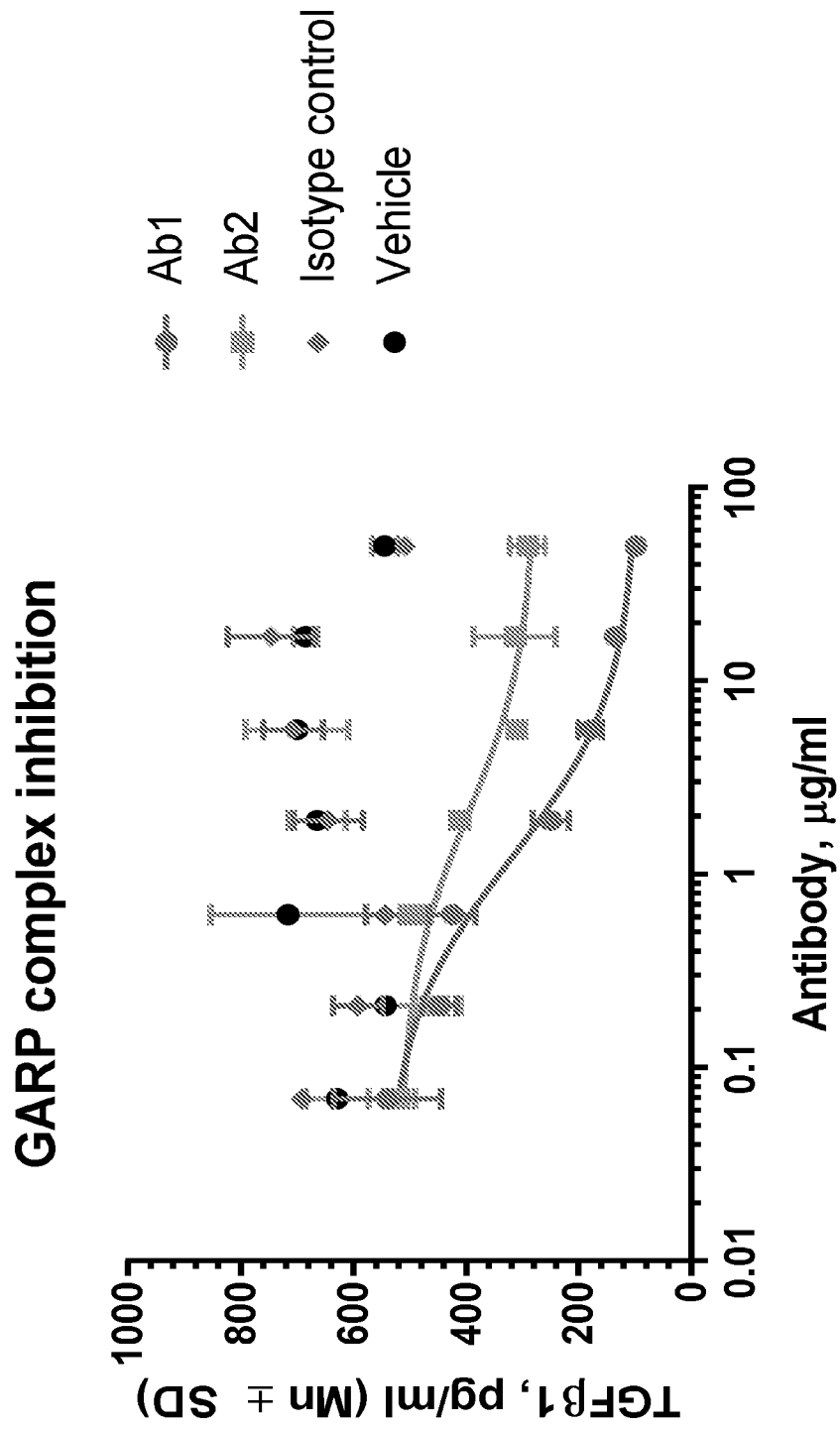
FIGS. 13A and 13B are graphs depicting the inhibition of GARP-TGFβ1 complex (FIG. 13A) or LRRC33-TGFβ1 complex (FIG. 13B) in SW480/06 cell transfectants using increasing concentrations of either Ab1 ("Ab1"), Ab2 ("Ab2"), isotype control IgG1 antibody ("Isotype control"), or vehicle control ("Vehicle").
Figure 13B:
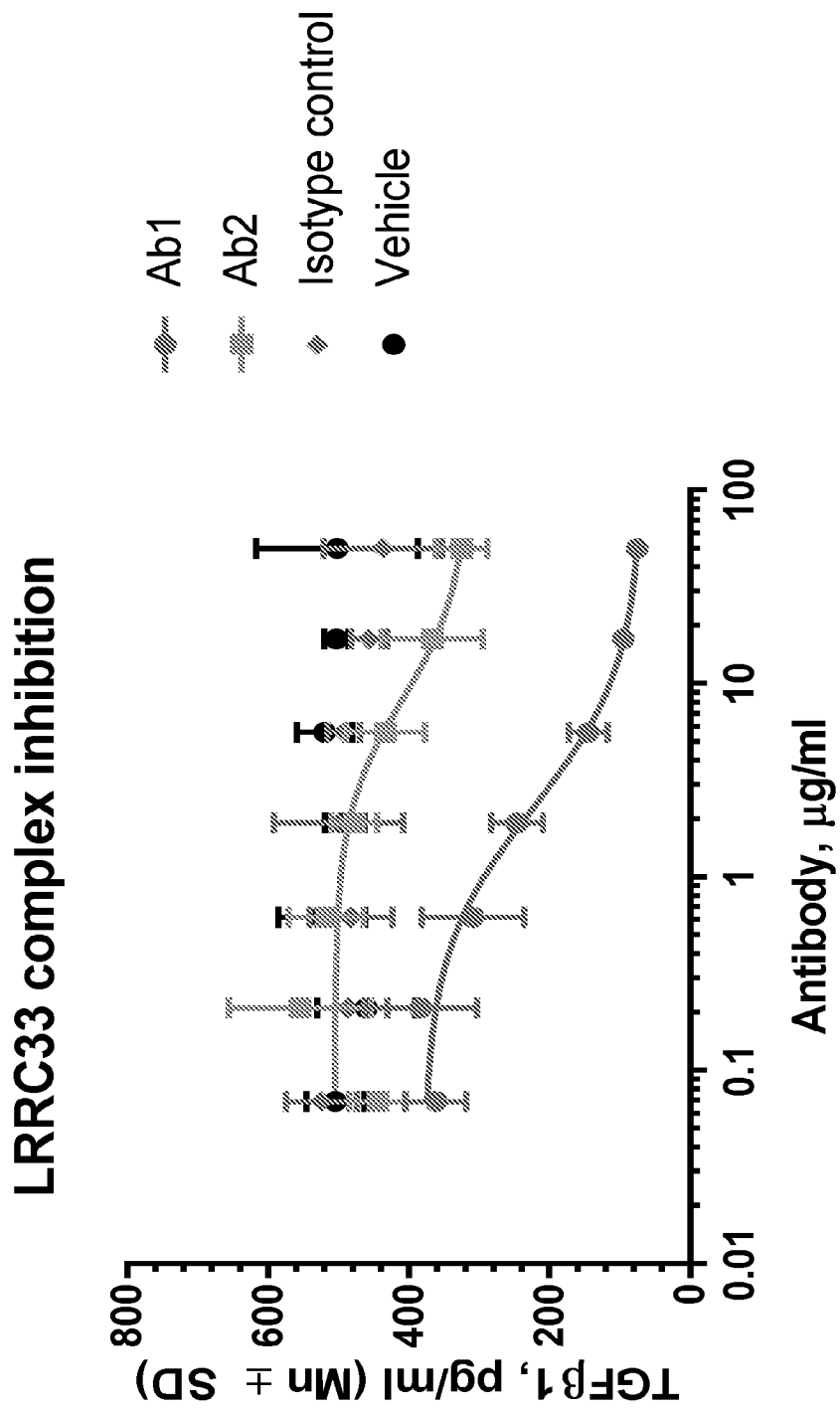

To determine whether Ab1 and Ab2 inhibit the activity of GARP-proTGF-β1 and/or LRRC33-proTGF-β1, an in vitro cell-based assay was performed. In this assay system, an engineered human colon cancer cell line (SW480/(36 cells) stably transfected with (36 integrin was co-transfected with a construct to express proTGF-β1 and a construct to express a presenting molecule (i.e., GARP or LRRC33). To express the presenting molecules, constructs encoding chimeric LRRC33-GARP (SEQ ID NO: 85) or GARP were employed. The transfected cells were incubated to allow for sufficient expression and deposition of the components (integrins and proTGFβ1 complexed with a respective presenting molecule). Activation of TGFβ1 in the presence or absence of Ab1 or Ab2 was assayed using reporter cells (CAGA12 cells) expressing TGFβ receptors coupled to its downstream signal transduction pathway, to measure the inhibitory activity of the antibody. As shown in FIGS. 13A and 13B, Ab1 and Ab2 inhibited both GARP-proTGF-β1 and LRRC33-proTGF-β1.

An additional cell-based assay was performed to detect inhibition of either GARP-proTGFβ1 complex or LRRC33-proTGFβ1 complex using antibodies Ab1 and Ab2. As shown in FIG. 22A and FIG. 22B, Ab1 and Ab2 inhibited both GARP-proTGF-β1 and LRRC33-proTGF-β1. In this assay, the IC50 (m/mL) of Ab1 for the GARP-TGFβ1 complex was 0.445, and the IC50 (m/mL) of Ab1 for the LRRC33-TGFβ1 complex was 1.325.

Example 6: Effects of Ab2 on Renal Biomarkers and Fibrosis in a Unilateral Ureteral Occluded (UUO) Mouse Model The unilateral ureteral occluded mouse model has been widely used to study interstitial fibrosis, a common pathological process which may lead to end-stage renal disease (see Isaka et al. (2008) Contrib. Nephrol. 159: 109-21, and Chevalier (1999) Pediatr. Nephrol. 13: 612-9). UUO mice are characterized by renal myofibroblast activation, tubular atrophy and interstitial fibrosis with minimal glomerular lesions (see Lian et al. (2011) Acta Pharmacol. Sin. 32: 1513-21). Increased expression of TGFβ1 is considered to play a role in the phenotype observed in UUO mice. To evaluate the effect of Ab2 on the presentation of interstitial fibrosis in the UUO mouse model, the following experiment was performed.

Figure 14:
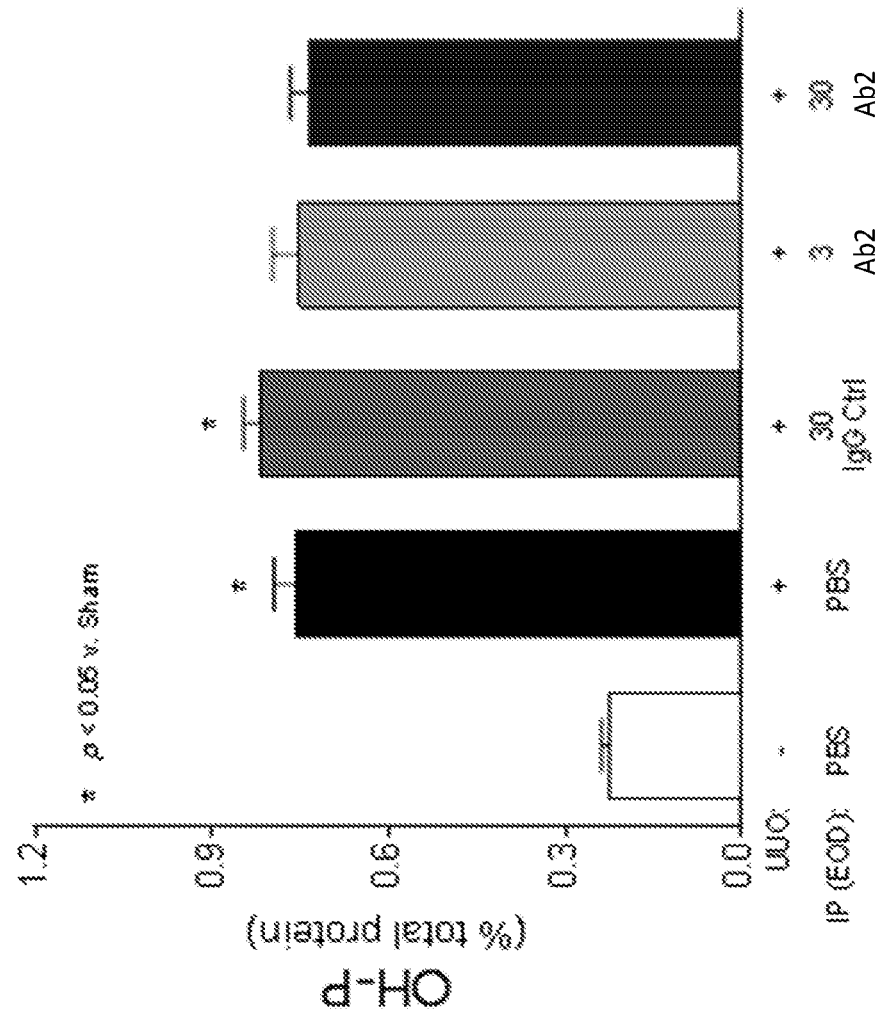
FIG. 14 is a bar graph depicting the levels of hydroxyproline in kidney tissue from mice that underwent permanent right unilateral UUO surgery and were administered either PBS (control), 30 mg/kg of murine IgG1 control antibody, 3 mg/kg of Ab2, or 30 mg/kg of Ab2 intraperitoneally (i.p.) prior to surgical intervention (second to fifth bars); or mice that were administered PBS and underwent a laparotomy (sham control; first bar).
Figure 15D:
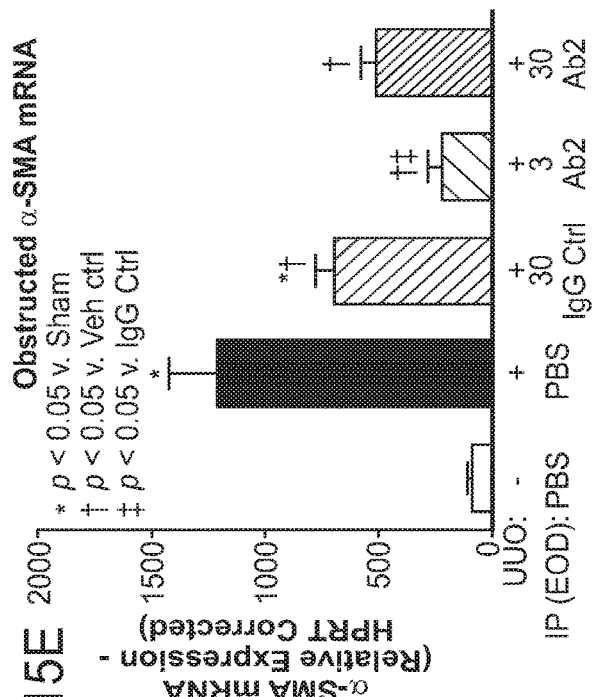
Figure 15E:
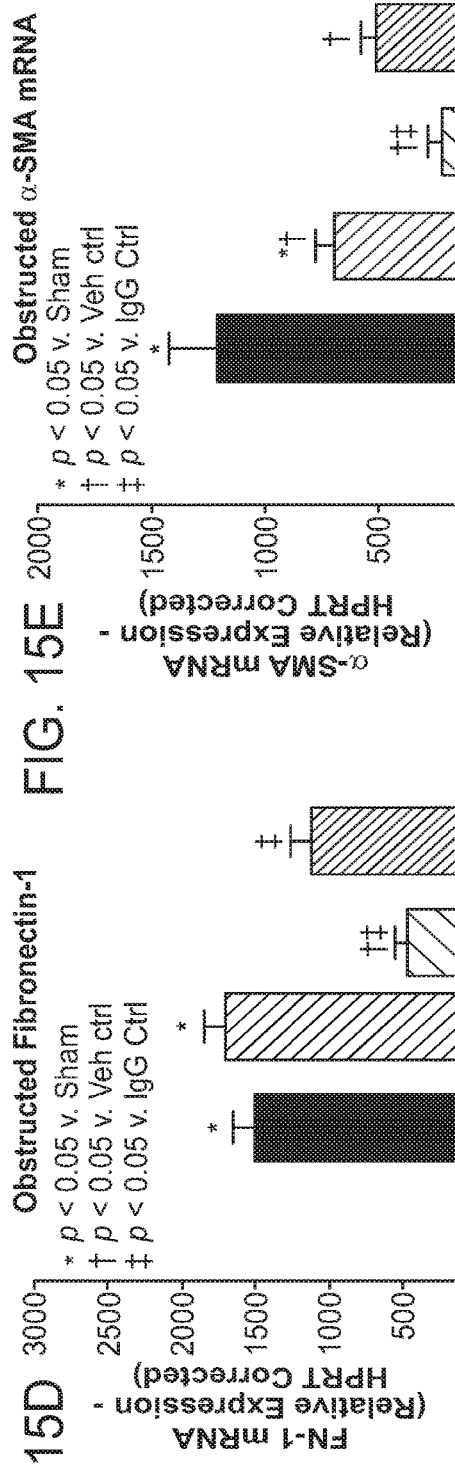
Figure 15F:
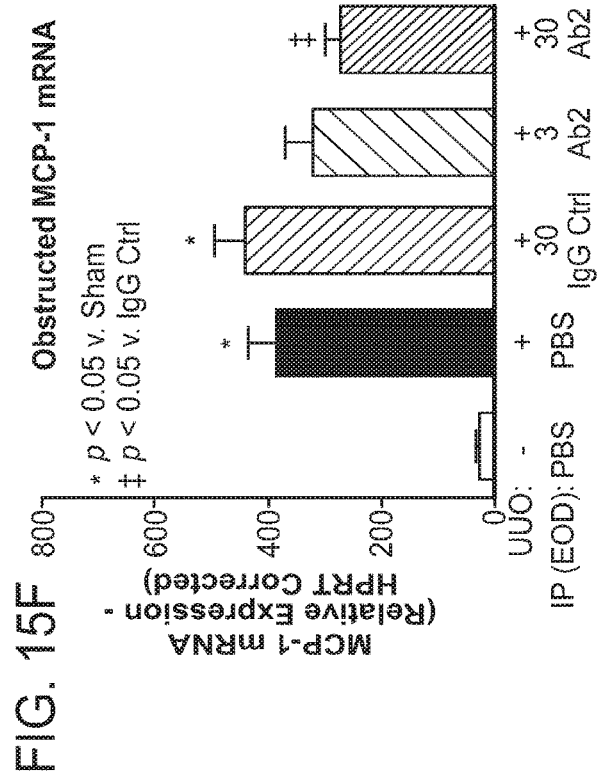
Figure 15H:
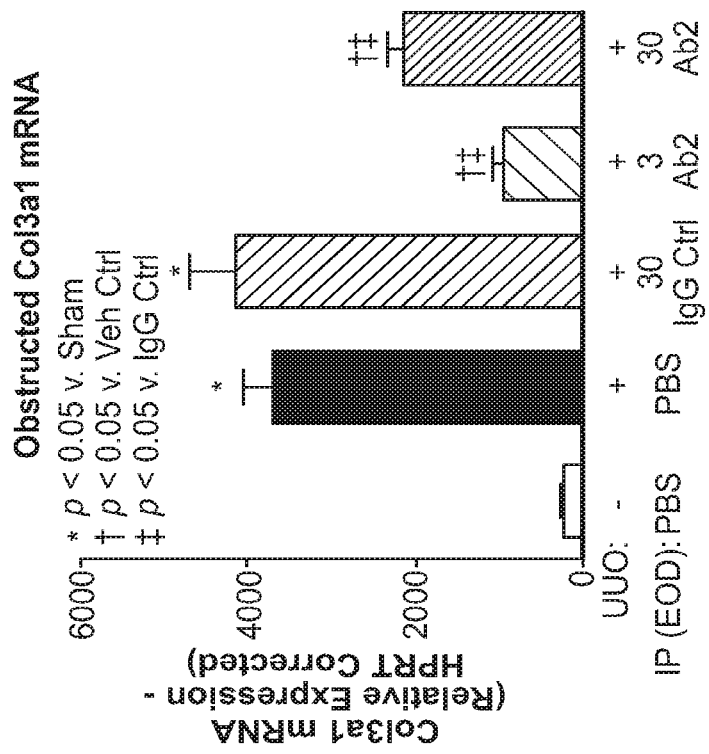
Figure 15G:
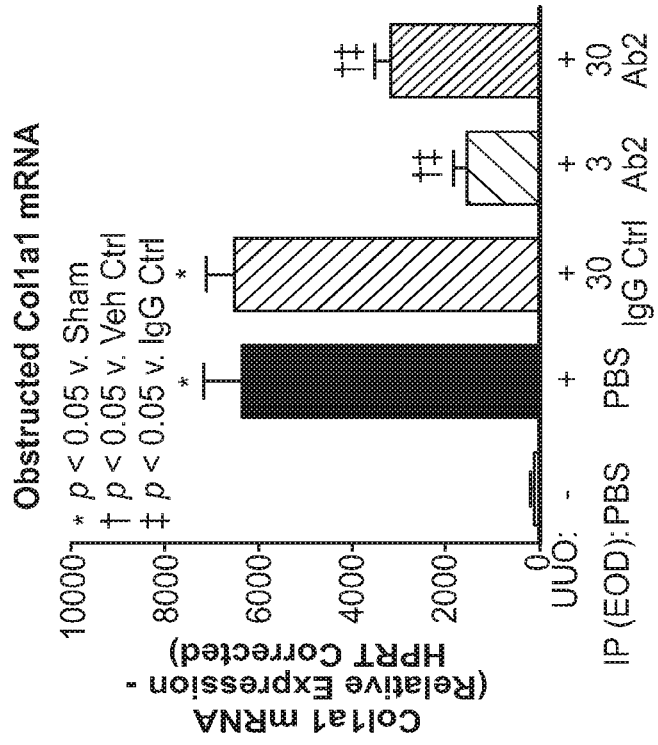

Briefly, 7-8 week old male CD-1 mice (Charles River Laboratories) were 4 groups of mice (n=10) were administered either Ab2 (3 mg/kg or 30 mg/kg; dosing volume of 10 mL/kg), murine IgG1 control antibody (30 mg/kg; dosing volume of 10 mL/kg), or PBS, as vehicle control intraperitoneally (i.p.) prior to surgical intervention. Treatments were administered one day prior to surgery (d–1), one day after surgery (d1), and 3 days after surgery (d3). On day 0 (d0), mice were anesthetized with isoflurane anesthesia on a nosecone, and a laparotomy performed followed by permanent right unilateral UUO surgery. An additional control group of mice (n=8) was administered PBS as described above, but solely underwent sham surgery (i.e., laparotomy with no occlusion of the ureter). Immediately following completion of the surgical procedure, all mice received one subcutaneous injection of 0.001 mg/kg buprenorphine. Mice were sacrificed five days after surgery and tissues were harvested for analysis. After harvest, both kidneys were placed in ice-cold 0.9% NaCl, de-encapsulated and weighed. Hydroxyproline levels to assess collagen content of the kidney tissue were assessed. As shown in FIG. 14, kidney hydroxyproline levels, a marker of tissue fibrosis and collagen deposition, were significantly increased in mice that received surgical intervention as compared to mice receiving sham surgery.

A mid traverse section of each right kidney was immersion fixed in 10% neutral buffered formalin for 48 hours, which was then transferred to 70% ethanol for histological processing and analysis. Fixed kidney sections were paraffin embedded, sectioned (three 5 μm serial sections acquired 200-250 μm apart per animal kidney to enable greater sampling and representation of kidney injury), stained with Picrosirius Red, and subjected to quantitative histological analyses using color spectrum segmentation to determine cortical collagen volume fraction (CVF). One composite CVF score was calculated for each animal by determining the average CVF score for each of the three serial sections. Statistical analyses were performed using the unpaired t-test.

As shown in FIG. 16, renal cortical fibrosis, as determined by CVF, was increased in UUO obstructed kidneys as compared to control sham-treated mice. Mice receiving either 3 mg/kg or 30 mg/kg of Ab2 showed an significant attenuation in UUO-induced increases in CVF, as compared to mice receiving either vehicle control (PBS) or IgG control.

Relative mRNA expression levels of plasminogen activator inhibitor-1 (PAI-1), connective tissue growth factor (CTGF), TGFβ1, fibronectin-1, α-smooth muscle actin (α-SMA), monocyte chemotactic protein 1 (MCP-1), collagen type I alpha 1 (Col1a1), and collagen type III alpha 1 chain (Col3a1), in the harvested kidney tissue was determined (FIG. 15A-15H). mRNA levels were normalized using the housekeeping gene hypoxanthine phosphoribosyltransferase 1 (HPRT1) mRNA levels. Moreover, in mice receiving either 3 mg/kg or 30 mg/kg of Ab2 prior to surgical intervention, mRNA levels of PAI-1, CTGF, TGFβ1, fibronectin 1, Col1a1, and Col3a1 were significantly decreased, as compared to mice receiving 30 mg/kg IgG1 control. Mice receiving 3 mg/kg of Ab2 prior to surgical intervention, mRNA levels of α-SMA was significantly decreased, as compared to mice receiving 30 mg/kg IgG1 control. Further, mice receiving 30 mg/kg of Ab2 prior to surgical intervention, mRNA levels of MCP-1 was significantly decreased, as compared to mice receiving 30 mg/kg IgG1 control.

In summary, significant effects were observed in mice treated with Ab2 in the UUO mouse model, with the exception of hydroxyproline levels. As shown in FIGS. 15A-15H and 16, Ab2 treatment significantly attenuated UUO-induced increases in CVF, and significantly decreased gene expression of known fibrosis markers, such as PAI-1, CTGF, TGFβ1, fibronectin 1, Col1a1, and Col3a1. These data demonstrate that TGFβ1 is the major form of TGFβ playing a role in renal disease and that, surprisingly, TGFβ2 and TGFβ3 are likely not involved in pathogenesis.

Example 7: Effects of Ab1 and Ab2 Alone or in Combination with Anti-PD-1 Antibody on Tumor Progression in the MC38 Murine Colon Carcinoma Syngeneic Mouse Model To evaluate the effects of Ab1 and Ab2, alone or in combination with an anti-PD-1 antibody to decrease colon carcinoma tumor progression, the MC38 murine colon carcinoma C57BL/6 mouse syngeneic model was used.

Tumor Cell Culture

MC38 murine colon carcinoma cells were grown in Dulbecco's Modified Eagle's Medium (DMEM) containing 10% fetal bovine serum, 100 units/mL penicillin G sodium, 100 µg/mL streptomycin sulfate, 25 µg/mL gentamicin, and 2 mM glutamine. Cell cultures were maintained in tissue culture flasks in a humidified incubator at 37° C., in an atmosphere of 5% CO2 and 95% air.

In Vivo Implantation and Tumor Growth

The MC38 cells used for implantation were harvested during log phase growth and resuspended in phosphate buffered saline (PBS). On the day of tumor implant, each test mouse was injected subcutaneously in the right flank with $5 \times 10^5$ cells (0.1 mL cell suspension), and tumor growth was monitored as the average size approached the target range of 80 to 120 mm$^3$. Eleven days later, designated as Day 1 of the study, mice were sorted according to calculated tumor size into groups each consisting of twelve animals with individual tumor volumes ranging from 63 to 196 mm$^3$ and group mean tumor volumes of 95 to 98 mm$^3$. Tumors were measured in two dimensions using calipers, and volume was calculated using the formula:

$$\text{Tumor Volume} (\text{mm}^3) = \frac{w^2 \times l}{2}$$

where w=width and l=length, in mm, of the tumor. Tumor weight may be estimated with the assumption that 1 mg is equivalent to 1 mm$^3$ of tumor volume.

Treatment

Briefly eight week old female C57BL/6 mice (n=12) bearing subcutaneous MC38 tumors (63-172 mm$^3$) on Day 1 were administered intraperitoneally (i.p.) twice a week for four weeks either Ab1, Ab2, murine IgG1 control antibody (each at 30 mg/kg in a dosing volume of 10 mL/kg). When tumors reached 150 mm$^3$ (Day 6) in the control groups, mice were administered either rat anti-mouse PD-1 antibody (RMP1-14) or rat IgG2A control antibody i.p. twice a week for two weeks (each antibody at 5 mg/kg in a dosing volume of 10 mL/kg).

Group 1 served as tumor growth controls, and received murine IgG1 isotype control antibody in combination with rat IgG2a control antibody. Group 2 received Ab1 in combination with rat IgG2a control antibody. Group 3 received Ab2 in combination with rat IgG2a control antibody. Group 3 received murine IgG1 control antibody in combination with anti-PD-1 antibody. Group 4 received Ab1 in combination with anti-PD-1 antibody. Group 5 received Ab2 in combination with anti-PD-1 antibody. Group 6 (n=16) was not treated and served as a sampling control group.

Endpoint and Tumor Growth Delay (TGD) Analysis

Tumors were measured using calipers twice per week, and each animal was euthanized when its tumor reached the endpoint volume of 1,000 mm$^3$ or at the end of the study (Day 60), whichever happened earlier. Mice that exited the study for tumor volume endpoint were documented as euthanized for tumor progression (TP), with the date of euthanasia. The time to endpoint (TTE) for analysis was calculated for each mouse using the following equation:

$$TTE = \frac{\log 10(\text{endpoint volume}) - b}{M}$$

where TTE is expressed in days, endpoint volume is expressed in mm$^3$, b is the intercept, and m is the slope of the line obtained by linear regression of a log-transformed tumor growth data set. The data set consisted of the first observation that exceeded the endpoint volume used in analysis and the three consecutive observations that immediately preceded the attainment of this endpoint volume. The calculated TTE is usually less than the TP date, the day on which the animal was euthanized for tumor size. Mice with tumors that did not reach the endpoint volume were assigned a TTE value equal to the last day of the study (Day 60). In instances in which the log-transformed calculated TTE preceded the day prior to reaching endpoint or exceeded the day of reaching tumor volume endpoint, a linear interpolation was performed to approximate the TTE. Mice classified as having died from non-treatment-related (NTR) causes were excluded from TTE calculations (and all further analyses). Animals classified as TR (treatment-related) deaths or NTRm (non-treatment-related death due to metastasis) were assigned a TTE value equal to the day of death.

Treatment outcome was evaluated from tumor growth delay (TGD), defined as the increase in the median time to endpoint (TTE) in a treatment group compared to the control group:

$$TGD = T - C,$$

expressed in days, or as a percentage of the median TTE of the control group:

$$\% \, TGD = \frac{T-C}{C} \times 100$$

where:
T=median TTE for a treatment group, and
C=median TTE for the designated control group.

MTV and Criteria for Regression Responses

Treatment efficacy may be determined from the tumor volumes of animals remaining in the study on the last day. The MTV (n) was defined as the median tumor volume on the last day of the study in the number of animals remaining (n) whose tumors had not attained the endpoint volume.

Treatment efficacy may also be determined from the incidence and magnitude of regression responses observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm$^3$ for one or more of these three measurements. In a CR response, the tumor volume was less than 13.5 mm$^3$ for three consecutive measurements during the course of the study. An animal with a CR response at the termination of a study was additionally classified as a tumor-free survivor (TFS). Animals were monitored for regression responses.

Tumor Growth Inhibition

Tumor growth inhibition (TGI) analysis evaluates the difference in median tumor volumes (MTVs) of treated and control mice. For this study, the endpoint for determining TGI was Day 29, which was the day control mice reached the mean tumor volume of 1500 mm$^3$. The MTV (n), the median tumor volume for the number of animals, n, on the day of TGI analysis, was determined for each group. Percent tumor growth inhibition (% TGI) was defined as the difference between the MTV of the designated control group and the MTV of the drug-treated group, expressed as a percentage of the MTV of the control group:

$$\% \, TGI = \left( \frac{MTV_{control} - MTV_{drug-treated}}{MTV_{control}} \right) \times$$
$$100 = [1 - (MTV_{drug-treated} / MTV_{control})] \times 100$$

The data set for TGI analysis included all mice in a group, except those that died due to treatment-related (TR) or non-treatment-related (NTR) causes prior to the day of TGI analysis.

Figure 17:
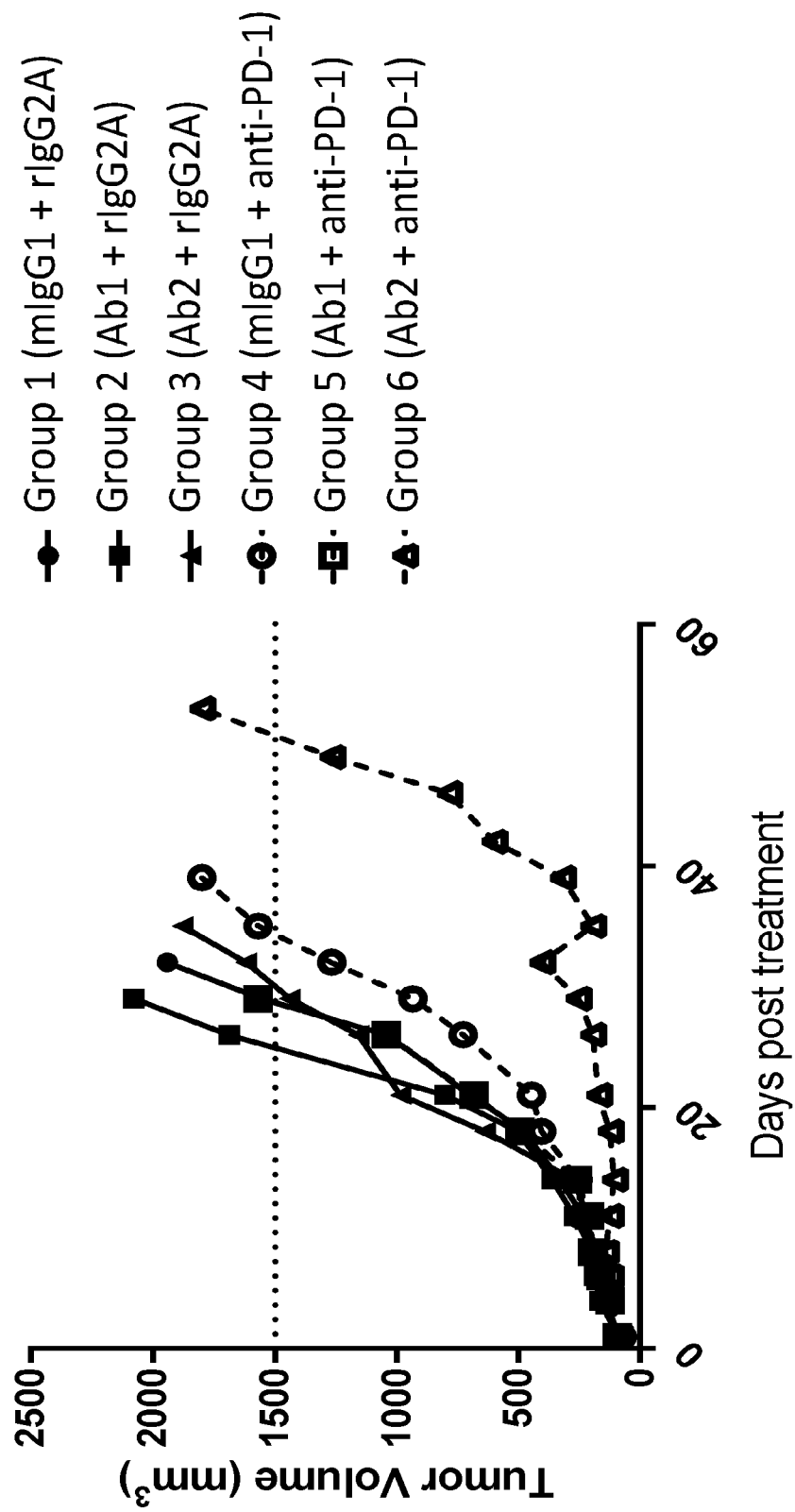
FIG. 17 depicts the median tumor volume of MC38 murine colon carcinoma syngeneic model C57/BL/6 mice that were administered either murine IgG1 isotype control antibody in combination with rat IgG2a control antibody (group 1; control); Ab1 in combination with rat IgG2a control antibody (group 2); Ab2 in combination with rat IgG2a control antibody (group 3); murine IgG1 control antibody in combination with anti-PD-1 antibody (group 4); Ab1 in combination with anti-PD-1 antibody (group 5); Ab2 in combination with anti-PD-1 antibody (group 6).

In the present study, Ab1 and Ab2 were evaluated alone and in combination with anti-PD-1 in the MC38 murine colon carcinoma C57BL/6 mouse syngeneic model. Mice that were administered Ab2 in combination with anti-PD-1 resulted in significant Day 29 TGI (P<0.05, Mann-Whitney U test), producing survival benefit that was statistically significantly different from vehicle-treated controls using logrank survival analyses (P<0.05, logrank) (see FIG. 17). Mice receiving Ab1 or Ab2 in combination with rat IgG2a control antibody had regression responses of 1 CR and 1 PR respectively. In combination with anti-PD-1 the regressions responses of Ab1 and Ab2 were 1 PR and 1 CR, and 4 CRs, respectively. Ab2 in combination with anti-PD-1 produced significant short-term efficacy on Day 29 and produced overall survival benefit in this 60-day TGD study in the MC38 murine colon carcinoma C57BL/6 mouse syngeneic model.

Example 8: Role of TGFβ1 in Muscular Dystrophy

TGFβ plays multiple roles in skeletal muscle function, including inhibition of myogenesis, regulation of inflammation and muscle repair, and promotion of fibrosis. While there is considerable interest in TGFβ inhibition as a therapy for a wide range of diseases, including muscular dystrophies, these therapies inhibit TGFβ1, TGFβ2, and TGFβ3 regardless of molecular context. The lack of specificity/ selectivity of these inhibitors may result in unwanted side effects leading to clinical doses with insufficient efficacy. While pan-TGFβ inhibitory molecules have been reported to improve muscle function and reduce fibrosis in the mdx mouse, whether those effects are due to inactivation of TGFβ1, (32, or (33 has yet to be addressed.

To that end, antibodies have been generated that specifically block the integrin-mediated activation of latent TGFβ1, while sparing TGFβ2 and (33. D2.mdx mice are treated with proTGFβ1 specific antibodies, so as to ascertain the role of TGFβ1 specifically in muscle repair in dystrophic muscle. The functional effects of TGFβ1 inhibition on protection from contraction-induced injury are assessed, as well as on recovery from the same method of injury. Histological evaluation includes whether treatment affects muscle damage, fibrosis, and inflammation. Additionally, possible toxicities may be assessed to determine whether the observed negative effects reported with pan-TGFβ inhibition in muscle (e.g., increased inflammation, long-term deficits in muscle function) are due to inhibition of TGFβ1 or TGFβ2/3. To understand whether inhibition of TGFβ1 in specific molecular contexts is more efficacious and/or has fewer negative effects (adverse effects), the efficacy of LTBP-proTGFβ1 inhibitors in this model may be assessed in order to deconvolute the role of immune cell presented TGFβ1 from that presented in the extracellular matrix (ECM), potentially leading to safer and/or more effective anti-fibrotic therapies.

Dystrophic muscle is highly susceptible to contraction-induced injury. Following injury, muscle from mdx mice shows a significant reduction in force generation and increased uptake of Evan's Blue dye, indicative of physical injury/damage to the muscle fiber, compared to WT (Lovering, R. M., et al., Arch Phys Med Rehabil, 2007. 88(5): p. 617-25). Therapeutic agents which reduce the extent of contraction-induced injury, or improve recovery following injury, would be of significant clinical benefit to muscular dystrophy patients (Bushby, K., et al., Lancet Neurol, 2010. 9(1): p. 77-93). Ab1 and Ab2 will be evaluated for their ability to i) prevent contraction-induced injury, as well as to ii) promote recovery from injury. The D2.mdx strain may be used for our experiments, as opposed to the traditional mdx strain on the B10 background. These mice, generated by crossing the mdx onto a DBA2/J background, have the non-protective variant of LTBP4 described above, and therefore exhibit disease pathology that is more severe, progressive, and similar to the human disease than the standard mdx strain (Coley, W. D., et al., Hum Mol Genet, 2016. 25(1): p. 130-45). Since the D2.mdx mice are being used, DBA2/J mice can serve as wild-type controls. Since DMD affects primarily males, the studies may focus on male mice.

To examine the ability of Ab1 and Ab2 to prevent/limit contraction-induced injury, 6 week old male D2.mdx mice (n=10) are treated with 10 mg/kg/week of either IgG control, Ab1, or Ab2 for 6 weeks. To allow for comparison to published work using a pan-TGFβ inhibitor, a fourth group is dosed with 10 mg/kg/week 1D11. All antibodies are mIgG1 isotype and this dose has previously been shown to be effective in the UUO model (FIGS. 15 & 16). A WT group dosed with the IgG control is also included. 24 hours prior to sacrifice, mice are administered 1% Evan's Blue dye (EBD) in PBS (volume 1% of body weight) to allow assessment of myofiber damage by fluorescence microscopy. At the end of treatment, mice are subjected to an in vivo eccentric contraction protocol. Eccentric injury of the gastrocnemius muscle will be may be performed with a 305B muscle lever system (Aurora Scientific) as described (Khairallah, R. J., et al., Sci Signal, 2012. 5(236): p. ra56). Briefly, 20 eccentric contractions with 1-minute pauses in between are performed, and the decrease in peak isometric force before the eccentric phase may be taken as an indication of muscle damage. The extent of force loss and the percent of EBD positive fibers may be determined. DBA2/J mice subjected to this protocol lose 30-40% of initial force after 20 eccentric contractions. In contrast, D2.mdx mice lose 80% of initial force following the same protocol, as previously described (Pratt, S. J., et al., Cell Mol Life Sci, 2015. 72(1): p. 153-64; Khairallah, R. J., et al., Sci Signal, 2012. 5(236): p. ra56). The ability of Ab1 and Ab2 to reduce force loss following injury may be assessed. Mice are sacrificed at the end of the experiment and both the injured and uninjured gastrocnemius muscles may be collected for histological analyses. EBD uptake may be assessed from both muscles. Myofiber cross-sectional area and the extent of fibrosis may be measured. For cross-sectional area determination, sections from the mid-belly of the muscle may be stained with wheat germ agglutinin conjugated to a fluorophore to visualize cell membranes. Sections may be digitized using fluorescent microscopy, cell boundary traced using predictive software and cross-sectional area determined via unbiased automated measurements. For analysis of fibrosis, sections may be stained with picrosirius red (PSR) and the area of PSR+per slide computed.

The ability of Ab1 and Ab2 to accelerate recovery from contraction-induced injury is assessed. 12 week old DBA2/J and D2.mdx mice may undergo the same eccentric contraction protocol described above. Following injury, mice are divided into treatment groups (n=10) and administered either an IgG control (for WT and D2.mdx mice), 1D11, Ab1, or Ab2 (D2.mdx only). Antibodies may be dosed at 10 mg/kg/week for the duration of the experiment. Seven and 14 days post injury, maximal peak isometric force, twitch-to-tetanic ratio, and force-frequency relationship may be measured to evaluate the effect of treatment on recovery from injury. While Ab1 and Ab2 inhibit release of TGFβ1 regardless of presenting molecule, selective release of TGFβ1 from the extracellular matrix (i.e., LTBP-presented) could have greater benefit in DMD due to the preservation of TGFβ1 driven Treg activity. To address this question, specific LTBP-proTGFβ1 inhibitory antibodies may also be assessed for both the ability to prevent contraction-induced injury and to accelerate recovery from injury.

Example 9: Role of TGFβ1 in Skeletal Muscle Regeneration Following Acute Injury

The role of TGFβ1 specifically in myofiber regeneration following muscle injury may be investigated. TGFβ1-specific antibodies may be employed in the cardiotoxin injury model to determine the role of TGFβ1 specifically during myofiber regeneration. Regeneration may be assessed histologically and functional assessments of muscle strength and quality may be conducted. Given the potential benefits of TGFβ1 inhibition for muscle regeneration, therapies which have beneficial effects without the toxicities observed with pan-TGFβ inhibition would be of great benefit. This allows an investigation of the effects of TGFβ1-specific inhibition on satellite cell function and may provide insights into satellite cell transplant studies.

As described above, TGFβ appears to have multiple effects on muscle biology, including inhibition of myoblast proliferation and differentiation, as well as promotion of atrophy and fibrosis (Allen, R. E. and L. K. Boxhorn, J Cell Physiol, 1987. 133(3): p. 567-72; Brennan, T. J., et al., Proc Natl Acad Sci USA, 1991. 88(9): p. 3822-6; Massague, J., et al., Proc Natl Acad Sci USA, 1986. 83(21): p. 8206-10; Olson, E. N., et al., J Cell Biol, 1986. 103(5): p. 1799-805; Li, Y., et al., Am J Pathol, 2004. 164(3): p. 1007-19; Mendias, C. L., et al., Muscle Nerve, 2012. 45(1): p. 55-9; Nelson, C. A., et al., Am J Pathol, 2011. 178(6): p. 2611-21). However, these studies either used recombinant TGFβ1 in culture or injected into mice which may have non-physiological results as the growth factor is removed from its molecular context. Alternatively, investigators used TGFβ inhibitors which are not selective for TGFβ1.

To evaluate isoform-specific effects of TGFβ1, multiple proTGFβ1 antibodies (e.g., Ab1 and Ab2) may be examined for their ability to affect muscle regeneration following CTX-induced injury. These antibodies are "isoform-specific" and "context-permissive" inhibitors of TGFβ1 activation, such that they specifically inhibit release of TGFβ1 (as opposed to TGFβ2 or TGFβ3) from any presenting molecule and do not bind the mature growth factors (FIG. 18A).

Muscle regeneration may be induced in male DBA2/J mice (n=10) via CTX injection into the right gastrocnemius muscle. One day prior to injury, mice may be administered 10 mg/kg IgG control, 1D11, Ab1, or Ab2. Antibodies are continued to be dosed weekly until end of study. At 7 and 14 days post injury, muscle force measurements may be measured in vivo with a 305C muscle lever system (Aurora Scientific Inc., Aurora, CAN). Briefly, for the plantarflexor muscle group, contractions are elicited by percutaneous electrical stimulation of the sciatic nerve in anaesthetized mice, and a series of stimulations is then performed at increasing frequency of stimulation (0.2 ms pulse, 500 ms train duration): 1, 10, 20, 40, 60, 80, 100, 150 Hz, followed by a final stimulation at 1 Hz. Maximal peak isometric force, twitch-to-tetanic ratio, and force-frequency relationship will be determined. Following force measurements, the injured gastrocnemius and soleus muscles are collected and prepared for histology. Myofiber cross sectional area and % PSR+area may be determined as described in Example 8 above.

Treatment with Ab1 and Ab2 may result in reduced fibrosis and improved muscle function. However, given the role of TGFβ1 in regulating immune activation, it is possible that we may observe increased inflammation with the antibodies, as has been reported with 1D11 treatment (Andreetta, F., et al., J Neuroimmunol, 2006. 175(1-2): p. 77-86). In the event increased inflammation may limit the therapeutic effects of TGFβ1 inhibition, context-specific antibodies may be subsequently evaluated to provide further degree of specificity, which may limit toxicity. For example, antibodies that inhibit release of TGFβ1 from LTBPs only may be used, using the readouts and methods described above. These antibodies may limit release of TGFβ1 only from the ECM, without affecting release from Tregs or macrophages.

Example 10: Selection of Suitable TGFβ1 Inhibitory Agents

Expression analysis of proTGFβ1 and its presenting molecules in healthy, regenerating, and diseased muscle may provide useful information to aid the selection of optimal therapeutic approach. Given the potential benefits of TGFβ1 inhibition in muscle regeneration and repair, understanding the context of proTGFβ1 presentation (e.g., in the ECM or on immune cells) in skeletal muscle under different conditions (healthy, acutely injured, and chronically injured) can help inform the therapeutic utility of antibodies, and ultimately provide insight into the degree of specificity/selectivity required to achieve both clinical efficacy and safety. The nature of TGFβ1 presentation may vary depending on the health status of the muscle and over the course of disease, which could have implications for any TGFβ1 targeted therapies. Understanding the expression profiles of these molecules will also aid in selection of appropriate time of dosing for potential therapeutic molecules. Using western blot, immunohistochemistry, and immunoprecipitation, expression of proTGFβ1 and its presenting molecules may be assessed in normal, acutely injured (cardiotoxin injury), and chronically regenerating (D2.mdx mouse) muscle. Expression of these molecules may be investigated specifically in key cell types or subset of cell types (e.g., satellite cells, macrophages, fibro-adipogenic progenitors, etc.) in the different conditions described above.

While expression of TGFβ isoforms has been examined in muscles from mdx mice, previous work focused on expression of the mature growth factors (Nelson, C. A., et al., Am J Pathol, 2011. 178(6): p. 2611-21; Zhou, L., et al., Neuromuscul Disord, 2006. 16(1): p. 32-8). Given the target specificity of the TGFβ1 antibodies described herein, it is essential that the expression patterns be examined not only for mature and proTGFβ1, but those of the presenting molecules as well, which should provide information as to the source and/or context of a pool of TGFβ1 of interest. Ideally, it is desirable to gain understanding of the expression patterns of the latent complexes, not merely of each component.

Antibodies are screened for western blot and IHC for targets of interest. Antibodies against mouse TGFβ1-LAP, LTBP1, LTBP3, and LTBP4 are commercially available. The antibody against TGFβ1-LAP (clone TW7-16B4) has been extensively characterized and is effective in both flow cytometry and western blot (Oida, T. and H. L. Weiner, PLoS One, 2010. 5(11): p. e15523). Antibodies against LTBP1 (ProteinTech #22065-1-AP) and LTBP3 (Millipore #ABT316) have been validated internally using SW480 cells transfected with LTBP1-proTGFβ1 or LTBP3-proTGFβ1 and shown to be specific for their targets. The utility of these antibodies for IHC may be determined. Muscles from healthy and D2.mdx mice are sectioned and the antibodies tested on frozen and FFPE sections. Antibodies may be validated by including conditions with 100× excess of purified target protein or complex (made in house, see FIG. 18B for example) to ensure that the signal observed is specific.

Figure 18C:
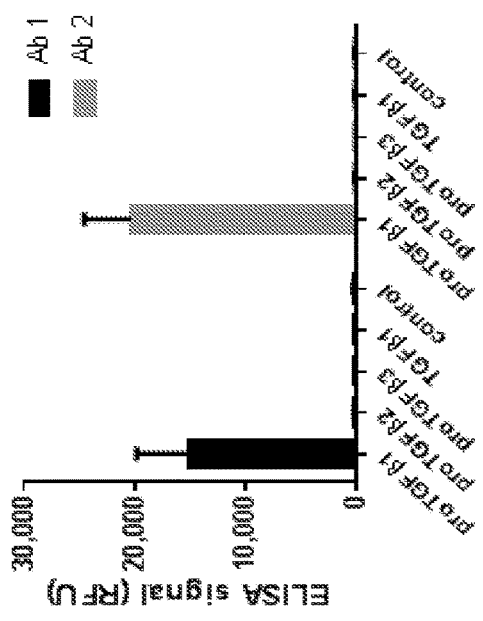
Figure 18B:
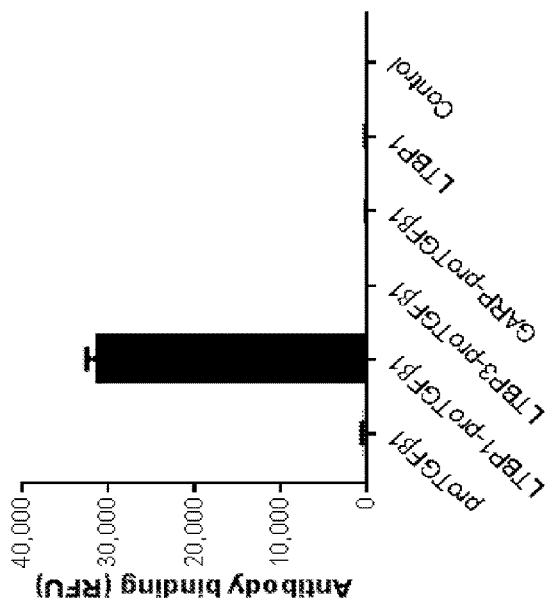

Previous work has identified antibodies which specifically bind a given latent complex but have no inhibitory activity. Antigen binding by these antibodies has been confirmed by ELISA (FIGS. 18B & 18C) and may also be evaluated for their utility in IHC (given the three-dimensional structure of these epitopes these antibodies are unlikely to be effective as western blot reagents). The presence of latent TGFβ1 complexes from bulk tissue may also be assessed by western blot or immunoprecipitation. Latent complexes can be identified by western blot by running the same sample under reducing and non-reducing conditions. Under reducing conditions, TGFβ1, LAP and the presenting molecule separate, and the three molecules can be identified on the same blot but using dual-color western blot methods. Under non-reducing conditions, the LAP:presenting molecule complex remains associated while TGFβ1 is released; the complex migrates slower than the empty presenting molecule and migrates together with TGFβ1-LAP (FIG. 18B). Various antibodies are also evaluated for their ability to immunoprecipitate latent complexes from muscle to demonstrate direct binding of TGFβ1 to specific presenting molecules.

Once appropriate antibodies have been identified, expression in healthy, regenerating, and dystrophic muscle is assessed, by western and/or IHC, depending on the antibodies available. Tibialis anterior (TA) and diaphragm muscles may be collected from DBA2/J and D2.mdx mice at 4, 8, and 12 weeks of age. For regenerating muscle, cardiotoxin may be injected into the TA of 12 week old DBA2/J mice, and muscles collected 3, 7, and 14 days post injury. Tissue from at least 4 mice may be used for each condition/time point. Co-staining experiments may also be conducted to identify cell populations expressing the various molecules (for example: CD11b for macrophages, FoxP3 for Tregs, MyoD for myogenic cells).

Example 11: Ab2 Exhibits Reduced Toxicity as Compared to the ALK5 Kinase Inhibitor LY2109761 and a Pan-TGFβ Antibody To evaluate the toxicity of Ab2, as compared to the small molecule TGF-β type I receptor (ALK5) kinase inhibitor LY2109761 and to a pan-TGFβ antibody (hIgG4), toxicity studies were performed in rats. Briefly, female F344/NHsd rats were administered either Ab2 at 3 mg/kg (1 group, n=5), at 30 mg/kg (1 group, n=5), or at 100 mg/kg (1 group, n=5); a pan-TGFβ antibody at 3 mg/kg (1 group, n=5), at 30 mg/kg (1 group, n=5), or at 100 mg/kg (1 group, n=5); LY2109761 at 200 mg/kg (1 group, n=5) or 300 mg/kg (1 group, n=5); or PBS (pH 7.4) vehicle control (1 group, n=5). Animals receiving either Ab2, the pan-TGFβ antibody, or the vehicle control were dosed once intravenously (at day 1), and the rats receiving LY2109761 were dosed by oral gavage once daily during 7 days (7 doses). Animal body weight was determined at days 1, 3, and 7 of the dosing phase. Animals were sacrificed at day 8 and necropsies performed.

Figure 19:
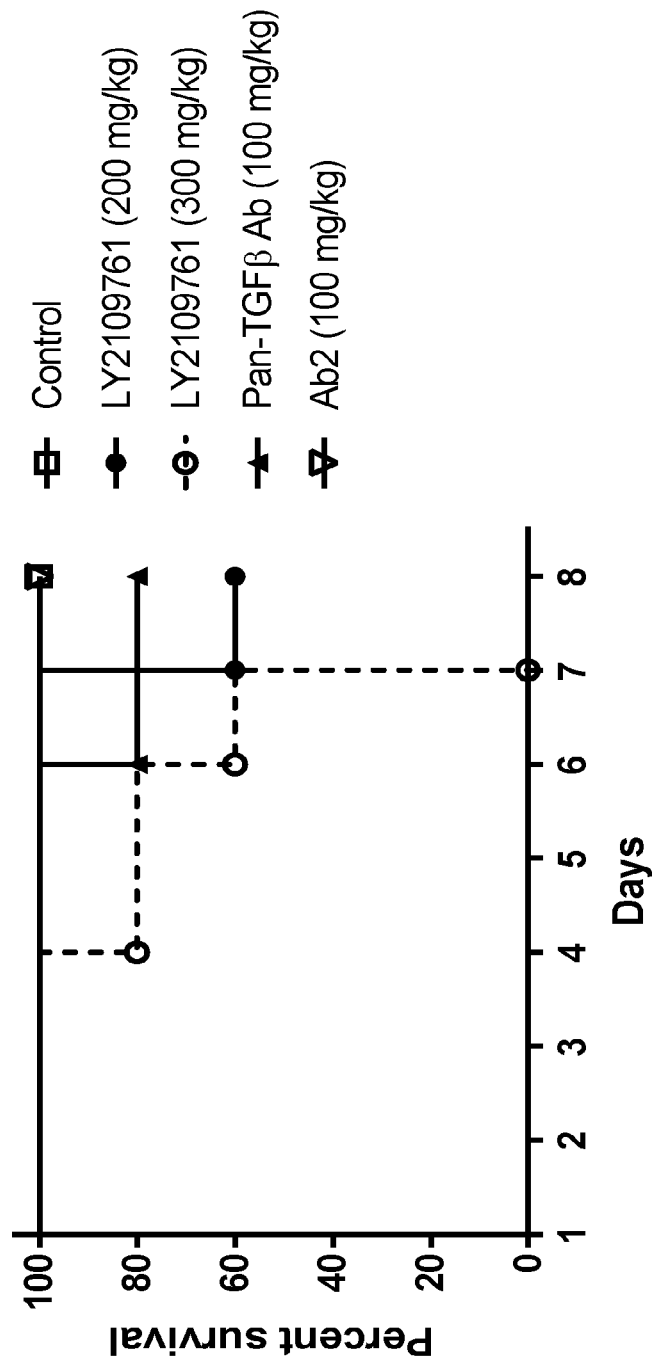
FIG. 19 depicts a survival curve of rats treated with either vehicle control (PBS; "Control"); 200 mg/kg of LY2109761; 300 mg/kg of LY2109761; 100 mg/kg of a pan-TGFβ antibody ("Pan-TGFβ Ab"); or 100 mg/kg of Ab2.
Figure 20:
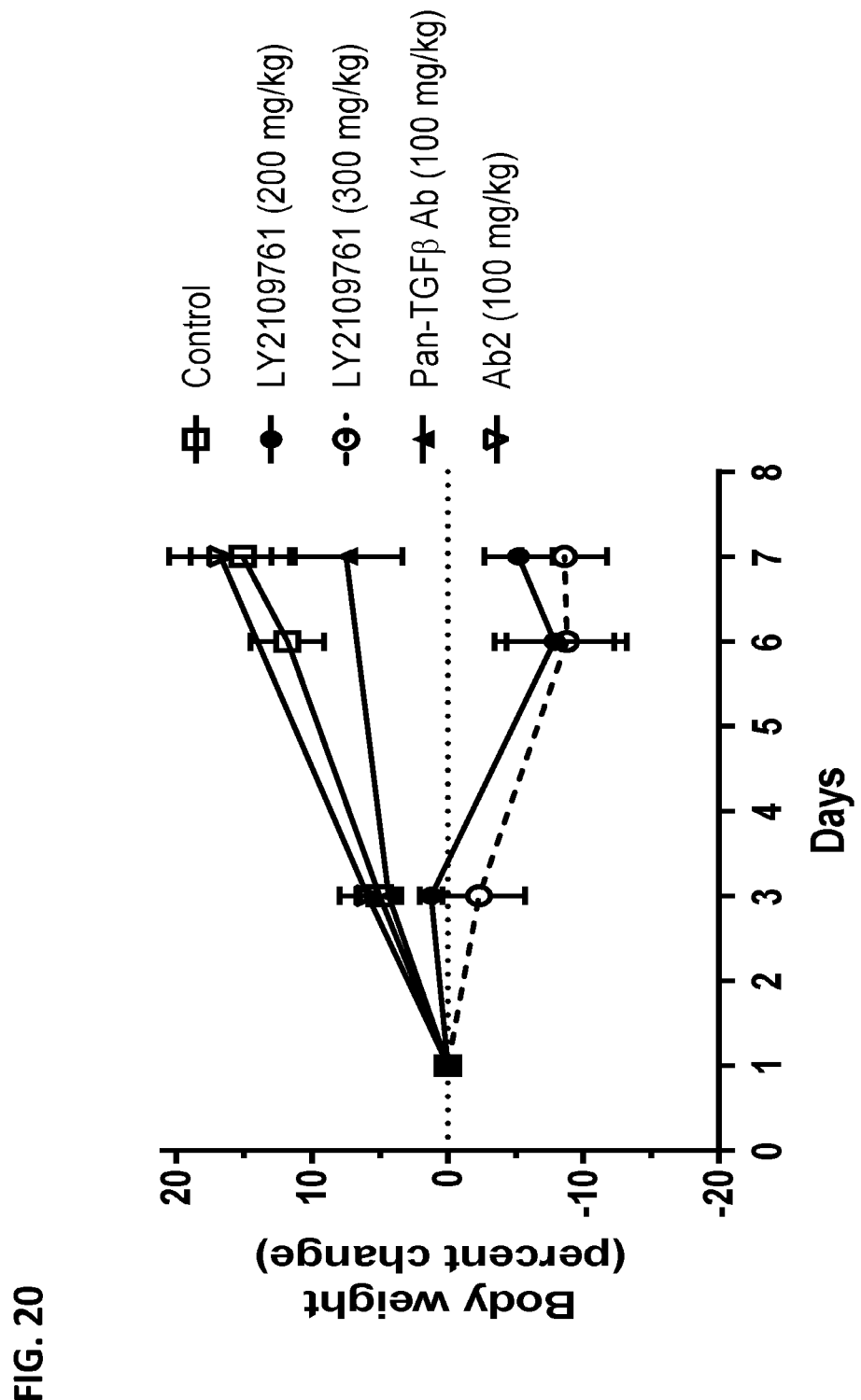
FIG. 20 depicts the body weight (mean/standard deviation) of rats treated with either vehicle control (PBS; "Control"); 200 mg/kg of LY2109761; 300 mg/kg of LY2109761; 100 mg/kg of a pan-TGFβ antibody ("Pan-TGFβ Ab"); or 100 mg/kg of Ab2.
Figure 21C:
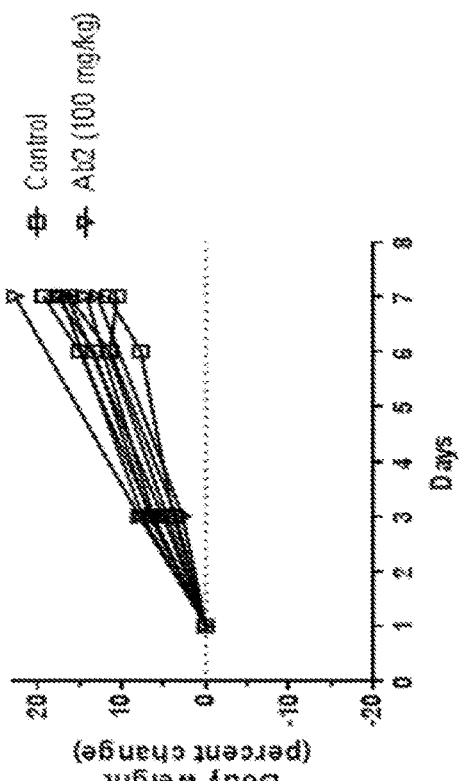
FIGS. 21A-21C depicts the body weight of individual rats treated with vehicle control (PBS; "Control"), 200 mg/kg of LY2109761, or 300 mg/kg of LY2109761 (FIG. 21A); vehicle control (PBS; "Control"), or 100 mg/kg of a pan-TGFβ antibody ("Pan-TGFβ Ab"); or vehicle control (PBS; "Control"), or 100 mg/kg of Ab2.
Figure 21A:
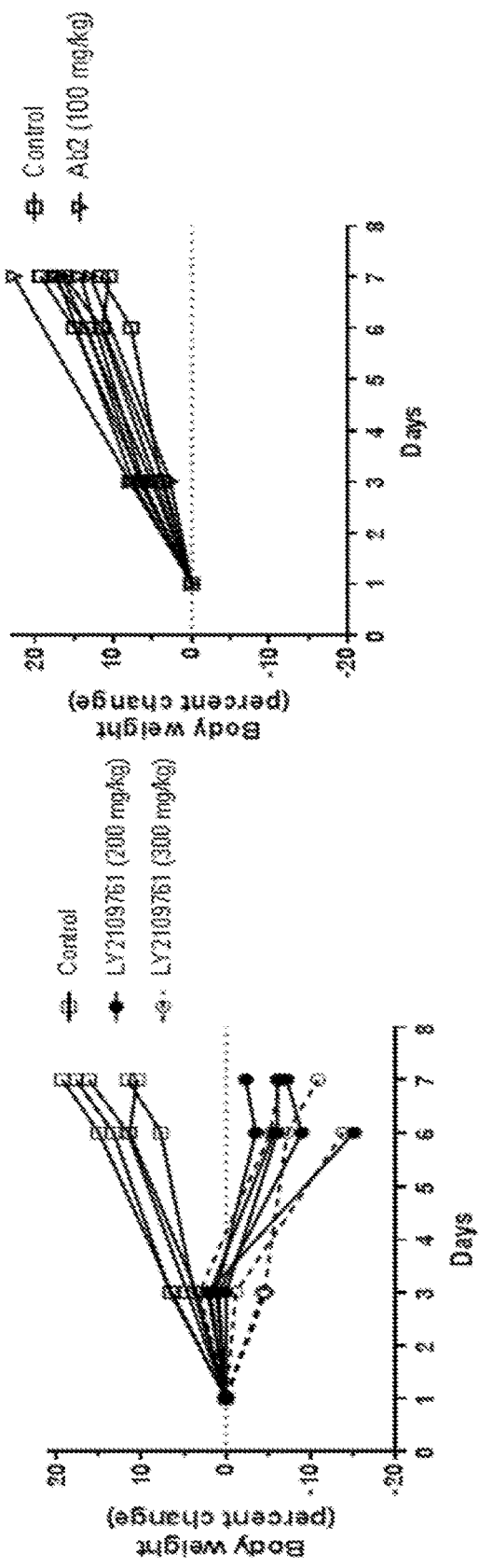
Figure 21B:
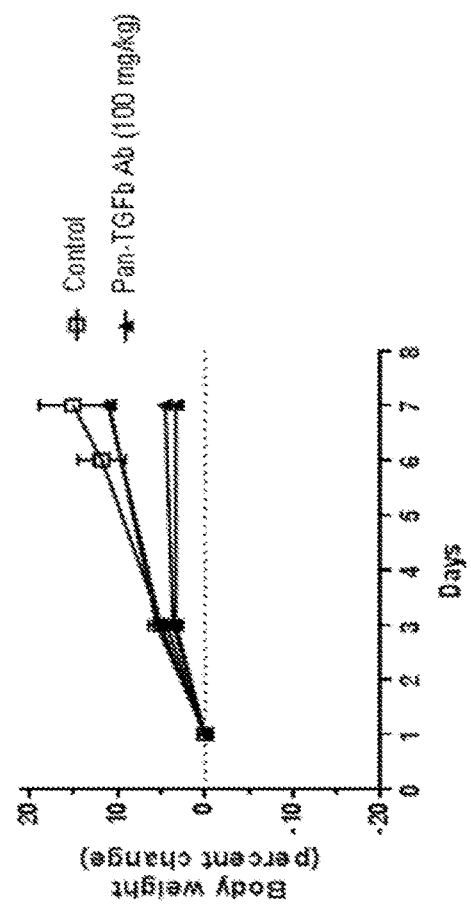

As shown in the survival data shown FIG. 19, Ab2 exhibited reduced toxicity as compared to the other treatment groups. All animals administered 300 mg/kg of the ALK5 kinase inhibitor LY2109761 were sacrificed in a moribund condition or found dead on days 3, 6, or 7 of the study. Two of the animals administered 200 mg/kg of LY2109761 were found dead at day 7 of the study. One animal administered 100 mg/kg of the pan-TGFβ antibody was found dead at day 6 of the study. All animals administered up to 100 mg/kg of Ab 2 survived until terminal sacrifice.

Further, the toxicity of the treatments was assessed by monitoring the body weights of the animals during the dosing phase. As shown in FIGS. 20 and 21A-21C, animals receiving LY2109761 at either 200 mg/kg or 300 mg/kg exhibited decreased body weight during the course of the study.

Animal organ weight was also assessed post-mortem. As shown in Table 11, Increased heart weights were observed in animals administered ≥200 mg/kg of LY2109761. Increased heart weights were also observed in animals administered ≥30 mg/kg of the pan-TGFβ antibody. No effects on organ weight were observed in animals administered upto 100 mg/kg of Ab2.

TABLE 11

Organ Weight Changes in Treatment Groups

|  | Treatment Group | | | | | |
| --- | --- | --- | --- | --- | --- | --- |
|  | Vehicle Control[a] | LY2109761 | | Pan-TGFβ Antibody | | |
| Dose Level (mg/kg/day) | 0 | 200 | 300 | 3 | 30 | 100 |
| Heart Absolute Weight (g) | 0.4084 | 112 | NE | 99 | 123 | 119 |
| Body Weight Ratio (%) | 0.3952 | 132 | NE | 96 | 122 | 122 |
| Brain Weight Ratio (%) | 26.3420 | 113 | NE | 98 | 123 | 116 |

NE = not evaluated due to early mortality.
Note:
Values for absolute weight and ratio of organ weights (relative to body or brain) for each treatment groups expressed as percentage control mean value.
[a]Vehicle control = phosphate buffered saline (PBS), pH 7.4.

While no macroscopic findings were observed in animals administered up to 100 mg/kg of Ab2 or of the pan-TGFβ antibody, abnormally-shaped sternum was observed in four animals of each treatment group receiving either 200 mg/kg or 300 mg/kg of LY2109761. 2.5 mL of clear fluid in the thoracic cavity and an enlarged thymus due to excess fluid (i.e., edema) was observed in one animal administered 300 mg/kg of LY2109761, which was found dead on Day 3 of the study.

Figure 23:
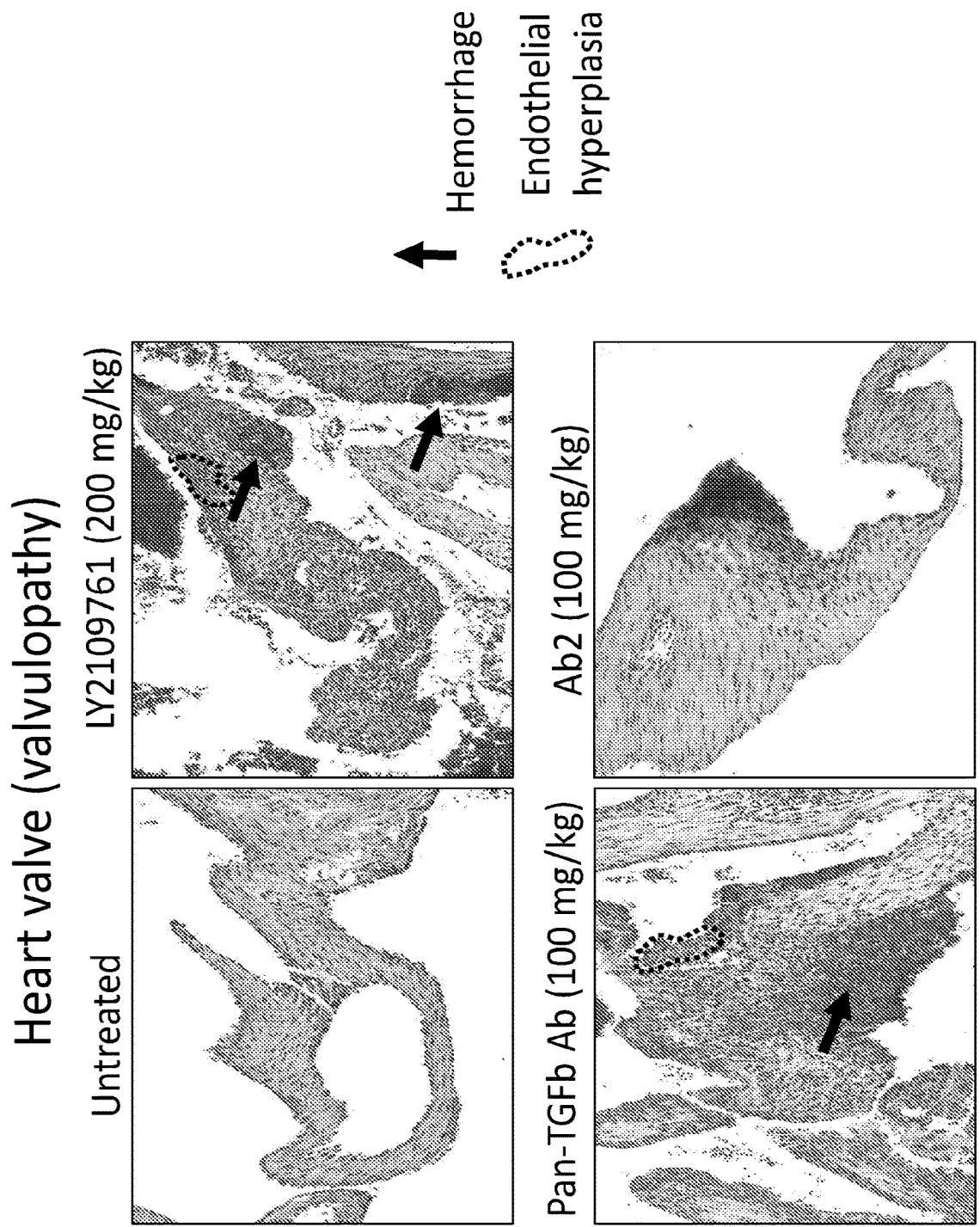
FIG. 23 depicts microscopy images of hematoxylin and eosin-stained sections from the heart valves of rats treated with either 200 mg/kg of LY2109761 (upper right panel); 100 mg/kg of a pan-TGFβ antibody ("Pan-TGFβ Ab", lower left panel); 100 mg/kg of Ab2 (lower right panel), or untreated control (upper left panel). Note: The lower right panel (Ab2) is an oblique section which stained darker due to uneven thickness.

As shown in Table 12, at the microscopic level, animals administered 200 mg/kg of LY2109761 exhibited heart valve findings (i.e., valvulopathy). Valvulopathy was characterized by heart valve thickening due to hemorrhage, endothelial hyperplasia, mixed inflammatory cell infiltrates, and/or stromal hyperplasia (see FIG. 23, upper right panel). Most animals had multiple valves affected. Additionally, atrium findings were observed including minimal to slight mixed inflammatory cell infiltrates, minimal hemorrhage, and/or minimal endothelium (endocardium) hyperplasia resulting in increased basophilic staining of the atrium in hematoxylin and eosin-stained sections. Myocardium findings were also observed mostly in the base of the heart and consisted of minimal to slight degeneration/necrosis, slight hemorrhage, and/or slight mixed inflammatory cell infiltrates. One animal administered 300 mg/kg of LY2109761 had slight necrosis with inflammation of a coronary artery. Further, two animals administered 200 mg/kg of LY2109761 had minimal mixed inflammatory cell infiltrates or hemorrhage in the aortic root.

TABLE 12

Microscopic Heart Findings in Animals Receiving LY2109761

|  |  | LY2109761 Dose Level (mg/kg/day) | | |
| --- | --- | --- | --- | --- |
| Heart |  | 0 | 200 | 300 |
| Heart valves |  |  |  |  |
| Valvulopathy | Minimal | 0 | 1 | 2 |
|  | Slight | 0 | 3 | 3 |
|  | Moderate | 0 | 1 | 0 |
| Atrium |  |  |  |  |
| Infiltrate, mixed cell | Minimal | 0 | 2 | 3 |
|  | Slight | 0 | 0 | 1 |
| Hyperplasia, endothelium | Minimal | 0 | 1 | 3 |
| Hemorrhage | Minimal | 0 | 1 | 2 |
| Myocardium |  |  |  |  |
| Degeneration/necrosis | Minimal | 0 | 0 | 1 |
|  | Slight | 0 | 1 | 1 |
| Hemorrhage | Slight | 0 | 1 | 0 |
| Infiltrate, mixed cell | Slight | 0 | 0 | 1 |
| Coronary artery |  |  |  |  |
| Necrosis with inflammation | Slight | 0 | 0 | 1 |
| Aortic root |  |  |  |  |
| Hemorrhage | Minimal | 0 | 1 | 0 |
| Infiltrate, mixed cell | Minimal | 0 | 1 | 0 |

As shown in Table 13, animals administered mg/kg of the pan-TGFβ antibody exhibited heart valve findings (i.e., valvulopathy) similar to those described in the animals administered LY2109761, as described above (see also FIG. 23, lower left panel). Animals administered ≥30 mg/kg of the pan-TGFβ antibody exhibited atrium findings similar to those described in animals administered LY2109761. Animals administered 100 mg/kg of the pan-TGFβ antibody exhibited myocardium findings similar to those described in animals administered LY2109761, and animals administered 30 mg/kg of pan-TGFβ antibody had hemorrhage in the myocardium. One animal administered 100 mg/kg of the pan-TGFβ antibody had moderate intramural necrosis with hemorrhage in a coronary artery, which was associated with slight perivascular mixed inflammatory cell infiltrates.

TABLE 13

Microscopic Heart Findings in Animals Receiving the Pan-TGFβ Antibody

|  |  | Pan-TGFβ Antibody Dose Level (mg/kg/day) | | | |
| --- | --- | --- | --- | --- | --- |
| Heart |  | 0 | 3 | 30 | 100 |
| Heart valves |  |  |  |  |  |
| Valvulopathy | Minimal | 0 | 2 | 0 | 0 |
|  | Slight | 0 | 2 | 4 | 5 |
|  | Moderate | 0 | 0 | 1 | 0 |
| Atrium |  |  |  |  |  |
| Infiltrate, mixed cell | Minimal | 0 | 0 | 1 | 2 |
|  | Slight | 0 | 0 | 1 | 1 |
| Hyperplasia, endothelium | Minimal | 0 | 0 | 3 | 1 |
| Hemorrhage | Minimal | 0 | 0 | 1 | 0 |
| Myocardium |  |  |  |  |  |
| Degeneration/necrosis | Slight | 0 | 0 | 0 | 2 |
| Hemorrhage | Minimal | 0 | 0 | 2 | 1 |
|  | Slight | 0 | 0 | 1 | 1 |
| Infiltrate, mixed cell, base | Slight | 0 | 0 | 0 | 1 |
| Coronary artery |  |  |  |  |  |
| Necrosis with hemorrhage | Moderate | 0 | 0 | 0 | 1 |
| Infiltrate, mixed cell, perivascular | Slight | 0 | 0 | 0 | 1 |

In contrast, a single animal in the treatment group administered 100 mg/kg of Ab2 had minimal mixed inflammatory cell infiltrates in a single heart valve leaflet of left atrioventricular valve (see FIG. 23, lower right panel), which was consistent with a background finding due to the single incidence and lack of concurrent valve findings. Thus, treatment with Ab2 surprisingly resulted in reduced mortality and reduced cardiotoxicity as compared to treatment with either the ALK5 kinase inhibitor LY2109761 or to treatment with the pan-TGFβ antibody.

What is claimed is:

1. A method for identifying a transforming growth factor beta 1 (TGFβ1)-specific inhibitor, wherein the TGFβ1-specific inhibitor is an antibody or antigen-binding fragment thereof, comprising:
   (i) providing an antibody or antigen-binding fragment thereof and performing a binding assay to detect isoform-specific binding to TGFβ1 and not to TGFβ2 or TGFβ3;
   (ii) contacting the antibody or antigen-binding fragment thereof with a TGFβ1 protein or a complex comprising TGFβ1 and determining relative changes in TGFβ1 activation in the presence and absence of the antibody or antigen-binding fragment thereof;
   (iii) carrying out an in vivo efficacy study to assess therapeutic effectiveness of the antibody or antigen-binding fragment thereof in an animal model, wherein the inhibitor antibody or antigen-binding fragment thereof shows efficacy when administered at a dose of about 0.1 pg/kg to about 30 mg/kg;
   (iv) carrying out an in vivo safety study to assess cardiovascular toxicity of the antibody or antigen-binding fragment thereof in an animal model, wherein the antibody or antigen-binding fragment thereof shows minimal or no cardiovascular toxicity when dosed at 100 mg/kg/week for four weeks, and wherein the cardiovascular toxicity comprises valvulopathy and/or hemorrhage in the heart;
   thereby identifying the TGFβ1-specific inhibitor.

2. The method of claim 1, wherein the animal model of step (iv) is a rat model.

3. The method of claim 1, wherein the TGFβ1-specific inhibitor shows reduced toxicity as compared to a pan TGFβ inhibitor in the in vivo safety study.

4. The method of claim 1, wherein the TGFβ1-specific inhibitor achieves reduced expression of at least one gene selected from the group consisting of: plasminogen activator inhibitor-1 (PAI-1), connective tissue growth factor (CTGF), monocyte chemotactic protein 1 (MCP-1), TGFB1, alpha-smooth muscle actin (α-SMA), Fibronectin-1, collagen type I alpha 1 (Col1a1) and collagen type III alpha 1 (Col3a1).

5. The method of claim 1, wherein the animal model of step (iii) comprises a fibrotic model.

6. The method of claim 1, wherein the animal model of step (ii) (iii) comprises a tumor model.

7. The method of claim 6, wherein the in vivo efficacy study in the tumor model further comprises administration of a checkpoint inhibitor.

8. The method of claim 7, wherein the checkpoint inhibitor is a PD-1 antagonist or a PD-L1 antagonist.

9. The method of claim 6, wherein the tumor model is a desmoplastic tumor model.

10. The method of claim 1, wherein the TGFβ1-specific inhibitor specifically binds a pro/latent complex of TGFβ1 but does not bind free mature TGFβ1 which is not associated with the pro/latent complex of TGFβ1.

11. The method of claim 10, wherein the pro/latent complex comprises glycoprotein-A repetitions predominant protein (GARP), Leucine-Rich Repeat-Containing Protein 33 (LRRC33), latent TGF-beta binding protein 1 (LTBP1), or latent TGF-beta binding protein 3 (LTBP3).

12. The method of claim 1, wherein the TGFβ1-specific inhibitor is a neutralizing antibody, or antigen-binding fragment thereof.

13. A pharmaceutical composition produced by the method of claim 1.

14. The method of claim 1, wherein the TGFβ1-specific inhibitor cross-competes with an antibody, or antigen-binding fragment thereof, comprising six complementarity determining regions (CDRs): CDRH1, CDRH2, CDRH3, CDRL1, CDRL2, and CDRL3,
  wherein CDRH1 comprises an amino acid sequence as set forth in SEQ ID NO: 1 or SEQ ID NO: 2,
  wherein CDRH2 comprises an amino acid sequence as set forth in SEQ ID NO :3 or SEQ ID NO:4,
  wherein CDRH3 comprises an amino acid sequence as set forth in SEQ ID NO: 5 or SEQ ID NO: 6,
  wherein CDRL1 comprises an amino acid sequence as set forth in SEQ ID NO: 7 or SEQ ID NO: 8,
  wherein CDRL2 comprises an amino acid sequence as set forth in SEQ ID NO: 9 or SEQ ID NO: 10,
  wherein CDRL3 comprises an amino acid sequence as set forth in SEQ ID NO: 11 or SEQ ID NO: 12.

15. The method of claim 1, further comprising a step of: selecting an antibody, or antigen-binding fragment thereof, that cross-competes with an antibody, or antigen-binding fragment thereof, comprising six complementarity determining regions (CDRs): CDRH1, CDRH2, CDRH3, CDRL1, CDRL2, and CDRL3,
  wherein CDRH1 comprises an amino acid sequence as set forth in SEQ ID NO: 2,
  wherein CDRH2 comprises an amino acid sequence as set forth in SEQ ID NO: 4,
  wherein CDRH3 comprises an amino acid sequence as set forth in SEQ ID NO: 6,
  wherein CDRL1 comprises an amino acid sequence as set forth in SEQ ID NO: 8,
  wherein CDRL2 comprises an amino acid sequence as set forth in SEQ ID NO: 10,
  wherein CDRL3 comprises an amino acid sequence as set forth in SEQ ID NO: 12.

* * * * *

UNITED STATES PATENT AND TRADEMARK OFFICE
CERTIFICATE OF CORRECTION

PATENT NO. : 11,643,459 B2
APPLICATION NO. : 16/083637
DATED : May 9, 2023
INVENTOR(S) : Thomas Schurpf et al.

Page 1 of 1

It is certified that error appears in the above-identified patent and that said Letters Patent is hereby corrected as shown below:

In the Claims

Claim 1, Column 243, Line 51, "the inhibitor antibody" should read --the antibody--.

Claim 1, Column 243, Line 53, "about 0.1 pg/kg to about 30 mg/kg:" should read --about 0.1 µg/kg to about 30 mg/kg; and--.

Claim 6, Column 244, Line 44, "step (ii) (iii) comprises" should read --step (iii) comprises--.

Signed and Sealed this
Eighth Day of August, 2023

Katherine Kelly Vidal
*Director of the United States Patent and Trademark Office*